US012685745B2

(12) United States Patent
Kennedy et al.

(10) Patent No.: US 12,685,745 B2
(45) Date of Patent: Jul. 21, 2026

(54) THERAPEUTIC CIRCULAR DNA FORMS

(71) Applicant: FLAGSHIP PIONEERING INNOVATIONS VII, LLC, Cambridge, MA (US)

(72) Inventors: Edward Matthew Kennedy, Bedford, MA (US); Camilo Ayala Breton, Andover, MA (US); Carl Wayne Brown, III, Westborough, MA (US); Brian Patrick Mead, Brookline, MA (US)

(73) Assignee: FLAGSHIP PIONEERING INNOVATIONS VII, LLC, Cambridge, MA (US)

( * ) Notice: Subject to any disclaimer, the term of this patent is extended or adjusted under 35 U.S.C. 154(b) by 0 days.

(21) Appl. No.: 19/343,405

(22) Filed: Sep. 29, 2025

(65) Prior Publication Data

US 2026/0021198 A1 Jan. 22, 2026

Related U.S. Application Data

(63) Continuation of application No. PCT/US2025/035461, filed on Jun. 26, 2025.

(60) Provisional application No. 63/800,803, filed on May 6, 2025, provisional application No. 63/763,007, filed on Feb. 25, 2025, provisional application No. 63/685,070, filed on Aug. 20, 2024, provisional application No. 63/664,455, filed on Jun. 26, 2024.

(51) Int. Cl.

| | |
|---|---|
| ***C07H 21/02*** | (2006.01) |
| ***A61K 31/713*** | (2006.01) |
| ***A61K 38/17*** | (2006.01) |
| ***A61K 48/00*** | (2006.01) |
| ***C07H 21/04*** | (2006.01) |
| ***C12N 9/00*** | (2006.01) |
| ***C12N 9/12*** | (2006.01) |
| ***C12N 9/16*** | (2006.01) |
| ***C12N 15/11*** | (2006.01) |
| ***C12P 19/34*** | (2006.01) |

(52) U.S. Cl.

CPC ........ *A61K 31/713* (2013.01); *A61K 38/1774* (2013.01); *A61K 48/0033* (2013.01); *A61K 48/005* (2013.01); *C07H 21/04* (2013.01); *C12N 9/1252* (2013.01); *C12N 9/16* (2013.01); *C12N 9/93* (2013.01); *C12N 15/11* (2013.01); *C12P 19/34* (2013.01); *C12Y 207/07007* (2013.01); *C12Y 301/21* (2013.01)

(58) Field of Classification Search

CPC .............................. A61K 31/713; C12N 15/11

See application file for complete search history.

(56) References Cited

U.S. PATENT DOCUMENTS

| | | | |
|---|---|---|---|
| 5,071,743 A | 12/1991 | Slilaty et al. | |
| 5,614,389 A | 3/1997 | Auerbach | |
| 6,063,604 A | 5/2000 | Wick et al. | |
| 6,319,906 B1 | 11/2001 | Bennett et al. | |
| 6,579,676 B1 | 6/2003 | Seed et al. | |
| 7,049,101 B1 | 5/2006 | Callen et al. | |
| 7,838,219 B2 | 11/2010 | Padgett et al. | |
| 8,541,206 B2 | 9/2013 | Wain-Hobson et al. | |
| 10,350,307 B2 | 7/2019 | Davis et al. | |
| 10,865,431 B1 * | 12/2020 | Benner | C12Q 1/6844 |
| 2002/0156261 A1 | 10/2002 | Malvy et al. | |
| 2005/0020529 A1 | 1/2005 | Dietz | |
| 2007/0020639 A1 | 1/2007 | Shapero | |
| 2011/0171287 A1 | 7/2011 | Saarma et al. | |
| 2011/0300205 A1 | 12/2011 | Geall et al. | |
| 2013/0287814 A1 | 10/2013 | Schroff et al. | |
| 2015/0167075 A1 | 6/2015 | Turner et al. | |
| 2017/0159044 A1 | 6/2017 | Toro et al. | |
| 2018/0265862 A1 | 9/2018 | Jurek et al. | |
| 2019/0062795 A1 | 2/2019 | Duthie et al. | |
| 2020/0224160 A1 | 7/2020 | Ding et al. | |
| 2020/0318122 A1 | 10/2020 | Romesberg et al. | |
| 2021/0115442 A1 | 4/2021 | Khvorova et al. | |
| 2021/0371910 A1 | 12/2021 | Yen et al. | |
| 2023/0012687 A1 | 1/2023 | Murray et al. | |
| 2023/0072532 A1 | 3/2023 | Kahvejian et al. | |
| 2023/0104113 A1 | 4/2023 | Kahvejian et al. | |
| 2023/0201333 A1 | 6/2023 | Akahata et al. | |
| 2023/0255999 A1 | 8/2023 | Sneider et al. | |
| 2023/0323343 A1 | 10/2023 | Oyarzabal Santamarina | |

(Continued)

FOREIGN PATENT DOCUMENTS

| | | |
|---|---|---|
| AU | 2021347807 A1 | 5/2023 |
| CN | 118401663 A | 7/2024 |

(Continued)

OTHER PUBLICATIONS

Luhnsdorf et al. (Anal. Biochem. 425 (2012) 47-53).*

(Continued)

*Primary Examiner* — Amy Rose Hudson

(74) *Attorney, Agent, or Firm* — K&L Gates LLP

(57) ABSTRACT

The disclosure provides, for example, double stranded DNA (dsDNA) molecules comprising one or more chemically modified nucleobases. In some embodiments, the dsDNA molecule is circular and comprises a first strand and a second strand, wherein the first strand comprises one or more chemically modified nucleobases, and the second strand is free of chemically modified nucleobases. In some embodiments, the dsDNA molecule comprises a promoter sequence and an effector sequence that encodes an effector.

22 Claims, 12 Drawing Sheets

Specification includes a Sequence Listing.

(56) References Cited

U.S. PATENT DOCUMENTS

| | | | |
|---|---|---|---|
| 2024/0285805 A1 | 8/2024 | Rubens et al. |
| 2024/0293582 A1 | 9/2024 | Rubens et al. |
| 2026/0000702 A1 | 1/2026 | Kennedy et al. |

FOREIGN PATENT DOCUMENTS

| | | | |
|---|---|---|---|
| EP | 1111069 A1 | 6/2001 |
| EP | 1281757 A1 | 2/2003 |
| EP | 3358014 A2 | 8/2018 |
| JP | H08173160 A | 7/1996 |
| JP | 2023526280 A | 6/2023 |
| PT | 2655620 E | 10/2015 |
| WO | 1998018961 A1 | 5/1998 |
| WO | 2002026757 A2 | 4/2002 |
| WO | 2014114687 A1 | 7/2014 |
| WO | 2014144942 A2 | 9/2014 |
| WO | 2015117021 A1 | 8/2015 |
| WO | 2017152149 A1 | 9/2017 |
| WO | 2019099081 A1 | 5/2019 |
| WO | 2021078947 A1 | 4/2021 |
| WO | 2021152147 A1 | 8/2021 |
| WO | 2022263807 A1 | 12/2022 |
| WO | 2023069948 A1 | 4/2023 |
| WO | 2023220729 A2 | 11/2023 |
| WO | 2024173828 A1 | 8/2024 |
| WO | 2024173836 A2 | 8/2024 |
| WO | 2025096807 A2 | 5/2025 |
| WO | 2025096970 A2 | 5/2025 |
| WO | 2026006577 A1 | 1/2026 |
| WO | 2026055543 A1 | 3/2026 |
| WO | 2026055547 A1 | 3/2026 |

OTHER PUBLICATIONS

Bilyard et al. (Current Opinion in Chemical Biology 2020, 57:1-7).*
Oliynyk et al. (Communications Biologyl (2022) 5:1393, 1-10).*
Burgess, A. et al. Targeted delivery of neural stem cells to the brain using MRI-guided focused ultrasound to disrupt the blood-brain barrier. PloS One, vol. 6,11, e27877 (2011).
Castle, J. et al. "Sonoporation for Augmenting Chemotherapy of Pancreatic Ductal Adenocarcinoma." Methods in Molecular Biology (Clifton, N.J.), vol. 2059 (2020): 191-205.
Chattaraj, R. et al. "Ultrasound Responsive Noble Gas Microbubbles for Applications in Image-Guided Gas Delivery." Advanced Healthcare Materials, vol. 9, 9, e1901721 (2020).
Chen, K. T. et al "Focused Ultrasound Combined with Microbubbles in Central Nervous System Applications." Pharmaceutics, vol. 13,7, 1084 (2021).
Choy, H. A. et al. "Activity of a phage-modified RNA polymerase at hybrid promoters. Effects of substituting thymine for hydroxymethyluracil in a phage SP01 middle promoter." Journal of Molecular Biology, vol. 191, 1 (1986): 59-73.
Cyrill, S. L. et al. "Universal Template-Assisted, Cloning-free Method for the Generation of Small RNA-Expressing Dumbbell-Shaped DNA Vectors." Molecular Therapy. Methods & Clinical Development vol. 15 (2019):149-156.
Dallas, A. et al. "Hairpin ribozyme-antisense RNA constructs can act as molecular Lassos." Nucleic Acids Research vol. 36,21 (2008): 6752-66.
Dimcevski, G. et al. "A human clinical trial using ultrasound and microbubbles to enhance gemcitabine treatment of inoperable pancreatic cancer." Journal of Controlled Release : Official Journal of the Controlled Release Society, vol. 243 (2016): 172-181.
Durham, P. G. et al. "Current clinical investigations of focused ultrasound blood-brain barrier disruption: A review." Neurotherapeutics : The Journal of the American Society for Experimental Neuro Therapeutics, vol. 21,3, e00352 (2024).
Eikrem, O. et al. "Ultrasound and Microbubbles Enhance Uptake of Doxorubicin in Murine Kidneys." Pharmaceutics, vol. 13,12 (2021): 2038.
Eisenbrey, J. R. et al. "US-triggered Microbubble Destruction for Augmenting Hepatocellular Carcinoma Response to Transarterial Radioembolization: A Randomized Pilot Clinical Trial." Radiology, vol. 298,2 (2021): 450-457.
Focused Ultrasound Foundation. "Focused Ultrasound: Overview." (2025), 3 pages, Web page printout of https://www.fusfoundation.org/the-technology/overview/.
Gerber, F. et al. "Long Lived Microbubbles for Oxygen Delivery." Artificial Cells, Blood Substitutes, and Biotechnology, vol. 35,1 (2007):119-124.
Govan, J. M. et al. "Stabilization and photochemical regulation of antisense agents through PEGylation." Bioconjugate Chemistry vol. 22,10 (2011): 2136-42.
Gracias, F. et al. "Homologues of epigenetic pyrimidines: 5-alkyl-, 5-hydroxyalkyl and 5-acyluracil and -cytosine nucleotides: synthesis, enzymatic incorporation into DNA and effect on transcription with bacterial RNA polymerase." RSC Chemical Biology, vol. 3,8 (2022): 1069-1075.
Guerniou, V. et al. "Enhancement of the in vitro transcription by T7 RNA polymerase of short DNA templates containing oxidative thymine lesions." Comptes rendus biologies, vol. 328,9 (2005): 794-801.
Harth, G. et al. "Hairpin extensions enhance the efficacy of mycolyl transferase-specific antisense oligonucleotides targeting *Mycobacterium tuberculosis*." Proceedings of the National Academy of Sciences of the United States of America vol. 104,17 (2007): 7199-204.
Hartmann, D., and M. J. Booth. "Handcuffed antisense oligonucleotides for light-controlled cell-free expression." Chemical Communications (Cambridge, England) vol. 59,38 (2023): 5685-5688.
Hersh, D. S. et al. "Emerging Applications of Therapeutic Ultrasound in Neuro-oncology: Moving Beyond Tumor Ablation." Neurosurgery, vol. 79, 5 (2016): 643-654.
Howard, M. J. et al. "Lysines in the lyase active site of DNA polymerase β destabilize nonspecific DNA binding, facilitating searching and DNA gap recognition." The Journal of Biological Chemistry vol. 295,34 (2020): 12181-12187.
Inagaki, K. et al. "The role of DNA-PKcs and artemis in opening viral DNA hairpin termini in various tissues in mice." Journal of Virology vol. 81,20 (2007): 11304-21.
International Search Report and Written Opinion in International Patent Application No. PCT/US2024/016205 mailed Jul. 10, 2024.
International Search Report and Written Opinion in International Patent Application No. PCT/US2024/053928 mailed Aug. 21, 2025.
Janoušková, M. et al. "5-(Hydroxymethyl)uracil and -cytosine as potential epigenetic marks enhancing or inhibiting transcription with bacterial RNA polymerase." Chemical Communications (Cambridge, England), vol. 53,99 (2017): 13253-13255.
Jollès, B et al. "Opening of the extraordinarily stable mini-hairpin d(GCGAAGC)." Nucleic Acids Research vol. 25,22 (1997): 4608-13.
Jordão, J. F. et al. "Antibodies targeted to the brain with image-guided focused ultrasound reduces amyloid-beta plaque load in the TgCRND8 mouse model of Alzheimer's disease." PloS One, vol. 5,5, e10549 (2010).
Kopechek, J. A. et al. "Ultrasound and Microbubble-targeted Delivery of a microRNA Inhibitor to the Heart Suppresses Cardiac Hypertrophy and Preserves Cardiac Function." Theranostics, vol. 9, 23 (2019): 7088-7098.
Kuch, D. et al. "Synthesis of DNA dumbbell based inhibitors for the human DNA methyltransferase Dnmt1." Angewandte Chemie (International ed. in English) vol. 47,8 (2008): 1515-8, and Supporting Information.
Kuznetsova, S. A. et al. "Synthesis and Properties of DNA Dumbbells Containing Chemically Active Substituted Pyrophosphate Internucleotide Groups." Nucleosides & Nucleotides vol. 15, 6, (1996): 1237-1251.
Kuznetsova, S. A. et al. "Design and synthesis of double-stranded oligonucleotides containing reactive acylphosphate internucleotide groups." FEBS Letters vol. 431,3 (1998): 453-6.
Mead, B. P., et al. "Focused Ultrasound Preconditioning for Augmented Nanoparticle Penetration and Efficacy in the Central Nervous System." Small (Weinheim an der Bergstrasse, Germany), vol. 15, 49, e1903460 (2019).

(56) References Cited

OTHER PUBLICATIONS

Mehedi Masud, M. et al. "Modified DNA bearing 5(methoxycarbonylmethyl)-2'-deoxyuridine: preparation by PCR with thermophilic DNA polymerase and postsynthetic derivatization." Chembiochem : a European Journal of Chemical Biology, vol. 4,7 (2003): 584-588.

Michalska, B. et al. "PCR synthesis of double stranded DNA labeled with 5-bromouridine. A step towards finding a bromonucleoside for clinical trials." Journal of Pharmaceutical and Biomedical Analysis vol. 56,4 (2011): 671-7.

Nawijn, C. L. et al. "High-Speed Optical Characterization of Protein-and-Nanoparticle-Stabilized Microbubbles for Ultrasound-Triggered Drug Release." Ultrasound in Medicine & Biology, vol. 50,8 (2024): 1099-1107.

O'reilly, M. A. et al. "Focused-ultrasound disruption of the blood-brain barrier using closely-timed short pulses: influence of sonication parameters and injection rate." Ultrasound in Medicine & Biology, vol. 37,4 (2011): 587-594.

Paluzzi, V. E. et al. "Near-Quantitative Preparation of Short Single-Stranded DNA Circles." Angewandte Chemie (International ed. in English) vol. 62,16 (2023): e202218443.

Rezai, A. R. et al. "Ultrasound Blood-Brain Barrier Opening and Aducanumab in Alzheimer's Disease." The New England Journal of Medicine, vol. 390,1 (2024): 55-62.

Scicchitano, D. A. "Transcription past DNA adducts derived from polycyclic aromatic hydrocarbons." Mutation Research, vol. 577,1-2 (2005): 146-154.

Song, K. H. et al. "State-of-the-art of microbubble-assisted blood-brain barrier disruption." Theranostics, vol. 8,16 (2018): 4393-4408.

Sridharan, A. et al. "Ultrasound contrast agents: microbubbles made simple for the pediatric radiologist." Pediatric Radiology, vol. 51,12 (2021): 2117-2127.

Thévenot, E. et al. "Targeted delivery of self-complementary adeno-associated virus serotype 9 to the brain, using magnetic resonance imaging-guided focused ultrasound." Human Gene Therapy, vol. 23,11 (2012):1144-1155.

Timbie, K. F. et al. "Drug and gene delivery across the blood-brain barrier with focused ultrasound." Journal of Controlled Release : Official Journal of the Controlled Release Society, 219 (2015): 61-75.

Unnikrishnan, S., & Klibanov, A. L. "Microbubbles as ultrasound contrast agents for molecular imaging: preparation and application." AJR. American Journal of Roentgenology, vol. 199,2 (2012): 292-299.

Vermeulen, A. et al. "Double-stranded regions are essential design components of potent inhibitors of RISC function." RNA (New York, N.Y.) vol. 13,5 (2007): 723-30.

Wan, L. et al. "5-Methylcytosine Substantially Enhances the Thermal Stability of DNA Minidumbbells." Chemistry (Weinheim an der Bergstrasse, Germany) vol. 27,22 (2021): 6740-6747.

Yang, Y. et al. "Cavitation dose painting for focused ultrasound-induced blood-brain barrier disruption." Scientific Reports vol. 9, 2840 (2019).

Zhang, Z. et al. "Dumbbell-Shaped Antisense Oligonucleotide Prodrugs Showed Improved Antinuclease Stability and Anticancer Efficacy." Molecular Pharmaceutics vol. 19,11 (2022): 3915-3921.

Zhou, H. et al. "Tracking of nascent deoxynucleic acids enable by incorporation of uridine variant with 2 prime azidomethyl tag and click chemistry", Tetrahedron Letters vol. 92 (2022) 153678.

Bilyard, M. K. et al. "Natural, modified DNA bases." Current Opinion in Chemical Biology vol. 57 (2020): 1-7.

International Search Report and Written Opinion in International Patent Application No. PCT/US2025/035461 mailed Oct. 29, 2025.

Lühnsdorf, B. et al. "Generation of reporter plasmids containing defined base modifications in the DNA strand of choice." Analytical Biochemistry vol. 425,1 (2012): 47-53.

* cited by examiner

THERAPEUTIC CIRCULAR DNA FORMS

RELATED APPLICATIONS

This application is a Continuation of International Patent Application No.: PCT/US2025/035461, filed Jun. 26, 2025, which claims priority to U.S. Ser. No. 63/664,455, filed Jun. 26, 2024; U.S. Ser. No. 63/685,070, filed Aug. 20, 2024; U.S. Ser. No. 63/763,007, filed Feb. 25, 2025; and U.S. Ser. No. 63/800,803, filed May 6, 2025, the entire contents of each of which are incorporated herein by reference.

SEQUENCE LISTING

The instant application contains a Sequence Listing which has been submitted electronically in XML format and is hereby incorporated by reference in its entirety. Said XML copy, created on Sep. 26, 2025, is named F2128-701920FT_SL.xml and is 35,519 bytes in size.

BACKGROUND

Novel forms of DNA therapeutics are needed.

SUMMARY OF THE INVENTION

Described herein are pharmaceutical DNA compositions comprising chemically modified nucleotides, constructs, preparations, and methods of making and using such compositions and preparations. The compositions and methods described herein have DNA stability and transcription competence, while reducing immunogenicity, and can be transcribed to cause production of therapeutic effectors (e.g., therapeutic proteins) within target cells. In some instances, the compositions may be administered in a "naked" form, without complex carriers.

Enumerated Embodiments

1. A double stranded DNA (dsDNA) molecule, wherein:
   - (a) the dsDNA molecule is circular;
   - (b) the dsDNA molecule comprises a first strand (e.g., sense strand) and a second strand (e.g., an antisense strand), wherein:
     - the first strand comprises one or more chemically modified nucleobases, and
     - the second strand is substantially free of (e.g., is free of) chemically modified nucleobases; and
   - (c) optionally, the dsDNA molecule comprises a promoter sequence and an effector sequence that encodes an effector (e.g., a therapeutic effector).
2. A double stranded DNA (dsDNA) molecule, wherein:
   - (a) the dsDNA molecule is circular;
   - (b) the dsDNA molecule comprises a first strand (e.g., sense strand) and a second strand (e.g., antisense strand), wherein:
     - the first strand comprises one or more chemically modified nucleobases, and
     - the second strand is substantially free of (e.g., is free of) chemically modified nucleobases; and
   - (c) the dsDNA molecule comprises a promoter sequence and an effector sequence that encodes an effector (e.g., a therapeutic effector).

3. A pharmaceutical composition comprising a double stranded DNA (dsDNA) molecule, wherein:
   - (a) the dsDNA molecule is circular; and
   - (b) the dsDNA molecule comprises a first strand (e.g., sense strand) and a second strand (e.g., antisense strand), wherein:
     - the first strand comprises one or more chemically modified nucleobases, and
     - the second strand is substantially free of (e.g., is free of) chemically modified nucleobases.
4. The pharmaceutical composition of embodiment 3, wherein the dsDNA molecule comprises a promoter sequence and an effector sequence that encodes an effector (e.g., a therapeutic effector).
5. The dsDNA molecule of embodiment 1 or 2 or pharmaceutical composition of embodiment 4, wherein the first strand (e.g., sense strand) of the promoter sequence comprises one or more chemically modified nucleobases.
6. The dsDNA molecule of embodiment 1 or 2 or pharmaceutical composition of embodiment 4, wherein the first strand (e.g., sense strand) of the promoter sequence is substantially free of (e.g., is free of) chemically modified nucleobases.
7. The dsDNA molecule of any of embodiments 1, 2, 5, or 6, or pharmaceutical composition of any of embodiments 3-6, wherein the dsDNA molecule comprises one or more sequences encoding a 5' untranslated region (5' UTR) that is 5' of the effector sequence and/or a 3' untranslated region (3' UTR) that is 3' of the effector sequence.
8. The dsDNA molecule or pharmaceutical composition of embodiment 7, wherein the first strand (e.g., sense strand) of said one or more sequences encoding the 5' UTR and/or 3' UTR comprises one or more chemically modified nucleobases.
9. The dsDNA molecule or pharmaceutical composition of embodiment 7, wherein the first strand (e.g., sense strand) of said one or more sequences encoding the 5' UTR and/or 3' UTR is substantially free of (e.g., is free of) chemically modified nucleobases.
10. The dsDNA molecule of any of embodiments 1, 2, or 5-9, or pharmaceutical composition of any of embodiments 3-9, wherein the dsDNA molecule comprises a sequence encoding a polyadenylation site.
11. The dsDNA molecule or pharmaceutical composition of embodiment 10, wherein the first strand (e.g., sense strand) of said sequence encoding a polyadenylation site comprises one or more chemically modified nucleobases.
12. The dsDNA molecule or pharmaceutical composition of embodiment 10, wherein the first strand (e.g., sense strand) of said sequence encoding a polyadenylation site is substantially free of (e.g., is free of) chemically modified nucleobases.
13. The dsDNA molecule of any of embodiments 1, 2, or 5-12, or pharmaceutical composition of any of embodiments 4-12, wherein the first strand (e.g., sense strand) of the effector sequence comprises one or more chemically modified nucleobases.
14. The dsDNA molecule of any of embodiments 1, 2, or 5-12, or pharmaceutical composition of any of embodiments 4-12, wherein the first strand (e.g., sense strand) of the effector sequence is substantially free of (e.g., is free of) chemically modified nucleobases.

15. The dsDNA molecule of any of embodiments 1, 2, or 5-14, or pharmaceutical composition of any of embodiments 3-14, wherein the dsDNA molecule comprises an intron sequence.
16. The dsDNA molecule or pharmaceutical composition of embodiment 15, wherein the first strand (e.g., sense strand) of said intron sequence comprises one or more chemically modified nucleobases.
17. The dsDNA molecule or pharmaceutical composition of embodiment 15, wherein the first strand (e.g., sense strand) of said intron sequence is substantially free of (e.g., is free of) chemically modified nucleobases.
18. The dsDNA molecule of any of embodiments 1, 2, or 5-17, or pharmaceutical composition of any of embodiments 3-17, wherein the dsDNA molecule comprises an enhancer sequence.
19. The dsDNA molecule or pharmaceutical composition of embodiment 18, wherein the first strand (e.g., sense strand) of said enhancer sequence comprises one or more chemically modified nucleobases.
20. The dsDNA molecule or pharmaceutical composition of embodiment 18, wherein the first strand (e.g., sense strand) of said enhancer sequence is substantially free of (e.g., is free of) chemically modified nucleobases.
21. The dsDNA molecule of any of embodiments 1, 2, or 5-20, or pharmaceutical composition of any of embodiments 3-20, wherein the first strand (e.g., sense strand) comprises one or more backbone modifications, e.g., phosphorothioate linkages.
22. The dsDNA molecule or pharmaceutical composition of embodiment 21, wherein said one or more backbone modifications of the first strand (e.g., sense strand) are situated in a stretch of adjacent nucleotides, wherein optionally the stretch of adjacent nucleotides is 4, 6, 8, 10, 12, 14, or 16 nucleotides in length.
23. The dsDNA molecule of any of embodiments 1, 2, or 5-20, or pharmaceutical composition of any of embodiments 3-22, wherein the first strand (e.g., sense strand) comprises a region that is substantially free of (e.g., is free of) backbone modifications.
24. The dsDNA molecule or pharmaceutical composition of embodiment 23, wherein the region is at least 50, at least 100, at least 200, at least 300, at least 400, at least 500, or at least 1,000 nucleotides in length.
25. The dsDNA molecule or pharmaceutical composition of embodiment 23 or 24, wherein the region is 50-100, 100-200, 200-300, 300-400, 400-500, 500-600, 600-700, 700-800, 800-900, 900-1000, 1000-1500, or 1500-2000 nucleotides in length.
26. The dsDNA molecule of any of embodiments 1, 2, or 5-25, or pharmaceutical composition of any of embodiments 3-25, wherein the second strand (e.g., antisense strand) is substantially free of (e.g., is free of) phosphorothioate linkages.
27. The dsDNA molecule of any of embodiments 1, 2, or 5-26, or pharmaceutical composition of any of embodiments 3-26, wherein the second strand (e.g., antisense strand) is substantially free of (e.g., is free of) backbone modifications.
28. The dsDNA molecule of any of embodiments 1, 2, or 5-27, or pharmaceutical composition of any of embodiments 4-27, wherein the effector is a protein, and wherein when the dsDNA molecule is introduced to a cell, the cell exhibits a level of the protein that is at least 35% of, at least 40%, at least 50% of, at least 60% of, at least 70% of, at least 80% of, at least 90% of, at least 100% of, at least 110% of, at least 120% of, or at least 125% of the level of the protein in a control cell of the same type that was contacted with an unmodified circular dsDNA molecule having the same sequence as the dsDNA molecule but comprising no chemically modified nucleobases, e.g., as measured by flow cytometry.
29. The dsDNA molecule of any of embodiments 1, 2, or 5-28, or pharmaceutical composition of any of embodiments 4-28, wherein the effector is a protein, and wherein when the dsDNA molecule is introduced to a cell, the cell exhibits a level of the protein that is 35%-40% of, 40%-50% of, 50%-60% of, 60%-70% of, 70%-80% of, 80%-90% of, 90%-100% of, 100%-110% of, 110%-120% of, or 120%-125% of the level of the protein in a control cell of the same type that was contacted with an unmodified circular dsDNA molecule having the same sequence as the dsDNA molecule but comprising no chemically modified nucleobases, e.g., as measured by flow cytometry.
30. The dsDNA molecule or pharmaceutical composition of embodiment 28 or 29, wherein the cell is a hepatocyte.
31. The dsDNA molecule of any of embodiments 1, 2, or 5-30, or pharmaceutical composition of any of embodiments 3-30, wherein when the dsDNA molecule is contacted to a human cell, the cell exhibits a level of cyclic AMP-GMP (cGAMP) that is less than 60%, less than 50%, less than 40%, less than 30%, less than 20%, less than 10%, less than 5%, or less than 1% of the level of cGAMP in a control cell of the same type that was contacted with an unmodified circular dsDNA molecule having the same sequence as the dsDNA molecule but comprising no chemically modified nucleobases, e.g., as measured using an ELISA.
32. The dsDNA molecule of any of embodiments 1, 2, or 5-31, or pharmaceutical composition of any of embodiments 3-31, wherein when the dsDNA molecule is contacted to a human cell, the cell exhibits a level of cyclic AMP-GMP (cGAMP) that is 1%-5%, 5%-10%, 10%-20%, 20%-30%, 30%-40%, 40%-50%, or 50%-60% of the level of cGAMP in a control cell of the same type that was contacted with an unmodified circular dsDNA molecule having the same sequence as the dsDNA molecule but comprising no chemically modified nucleobases, e.g., as measured using an ELISA.
33. The dsDNA molecule or pharmaceutical composition of embodiment 31 or 32, wherein the cell is a macrophage or fibroblast.
34. The dsDNA molecule of any of embodiments 1, 2, or 5-33, or pharmaceutical composition of any of embodiments 3-33, wherein at least 1%, at least 5%, at least 10%, at least 15%, at least 20%, at least 25%, at least 30%, at least 35%, at least 40%, at least 45%, or at least 50% positions in the first strand (e.g., sense strand) of the dsDNA molecule comprise chemically modified nucleobases.
35. The dsDNA molecule of any of embodiments 1, 2, or 5-34, or pharmaceutical composition of any of embodiments 3-34, wherein at least 1%, at least 5%, at least 10%, at least 15%, at least 20%, or at least 25% positions in the first strand (e.g., sense strand) of the dsDNA molecule comprise the same chemically modified nucleobase.
36. The dsDNA molecule of any of embodiments 1, 2, or 5-35, or pharmaceutical composition of any of embodiments 3-35, wherein 1%-50% (e.g., 1%-25%, 1%-5%, 5%-10%, 10%-15%, 15%-20%, 20%-25%, 25%-30%, 30%-35%, 35%-40%, 40%-45%, or 45%-50%) positions in the first strand (e.g., sense strand) of the dsDNA molecule comprise chemically modified nucleobases.

37. The dsDNA molecule of any of embodiments 1, 2, or 5-36, or pharmaceutical composition of any of embodiments 3-36, wherein 1%-25% (e.g., 1%-5%, 5%-10%, 10%-15%, 15%-20%, or 20%-25%) positions in the first strand (e.g., sense strand) of the dsDNA molecule comprise the same chemically modified nucleobase.

38. The dsDNA molecule of any of embodiments 1, 2, or 5-37, or pharmaceutical composition of any of embodiments 3-37, wherein at least 80%, at least 85%, at least 90%, at least 95%, or all the chemically modified nucleobases of the dsDNA molecule have the same chemical structure.

39. The dsDNA molecule of any of embodiments 1, 2, or 5-38, or pharmaceutical composition of any of embodiments 3-38, wherein 80%-85%, 85%-90%, 90%-95%, or 95%-100% of the chemically modified nucleobases of the dsDNA molecule have the same chemical structure.

40. The dsDNA molecule of any of embodiments 1, 2, or 5-39, or pharmaceutical composition of any of embodiments 3-39, wherein the chemically modified nucleobase comprises a uracil nucleobase.

41. The dsDNA molecule or pharmaceutical composition of embodiment 40, wherein the uracil nucleobase is a canonical uracil nucleobase or a chemically modified uracil nucleobase.

42. The dsDNA molecule or pharmaceutical composition of embodiment 40 or 41, wherein the uracil nucleobase is a canonical uracil nucleobase.

43. The dsDNA molecule or pharmaceutical composition of embodiment 40 or 41, wherein the uracil nucleobase is a chemically modified uracil nucleobase.

44. The dsDNA molecule or pharmaceutical composition of any of embodiments 40-43, wherein at least 1%, at least 5%, at least 10%, at least 15%, at least 20%, at least 25%, at least 50%, at least 75%, at least 90%, at least 95%, at least 96%, at least 97%, at least 98%, or at least 99% of thymine or uracil positions in the first strand (e.g., sense strand) of the dsDNA molecule comprise a uracil nucleobase.

45. The dsDNA molecule or pharmaceutical composition of any of embodiments 40-44, wherein 1%-100% (e.g., 1%-5%, 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, 95%-96%, 96%-97%, 97%-98%, 98%-99%, or 95%-100%) of thymine or uracil positions in the first strand (e.g., sense strand) of the dsDNA molecule comprise a uracil nucleobase.

46. The dsDNA molecule or pharmaceutical composition of any of embodiments 40-45, wherein at least 20% of thymine or uracil positions in the first strand (e.g., sense strand) of the dsDNA molecule comprise a uracil nucleobase.

47. The dsDNA molecule or pharmaceutical composition of any of embodiments 40-46, wherein at least 40% of thymine or uracil positions in the first strand (e.g., sense strand) of the dsDNA molecule comprise a uracil nucleobase.

48. The dsDNA molecule or pharmaceutical composition of any of embodiments 40-47, wherein at least 80% of thymine or uracil positions in the first strand (e.g., sense strand) of the dsDNA molecule comprise a uracil nucleobase.

49. The dsDNA molecule or pharmaceutical composition of any of embodiments 40-48, wherein every thymine or uracil position in a stretch of at least 100, at least 200, at least 300, at least 400, at least 500, at least 600, at least 700, at least 800, at least 900, at least 1000, at least 1500, or at least 2000 nucleotides in the first strand (e.g., sense strand) of the dsDNA molecule comprises a uracil nucleobase.

50. The dsDNA molecule or pharmaceutical composition of any of embodiments 40-49, wherein every thymine or uracil position in a stretch of 100-200, 200-300, 300-400, 400-500, 500-600, 600-700, 700-800, 800-900, 900-1000, 1000-1500, or 1500-2000 nucleotides in the first strand (e.g., sense strand) of the dsDNA molecule comprises a uracil nucleobase.

51. The dsDNA molecule or pharmaceutical composition of any of embodiments 41 or 43-50, wherein the chemically modified uracil nucleobase comprises 5-hydroxymethyluracil.

52. The dsDNA molecule or pharmaceutical composition of any of embodiments 41 or 43-50, wherein the chemically modified uracil nucleobase comprises 5-aminoallyluracil.

53. The dsDNA molecule or pharmaceutical composition of any of embodiments 41 or 43-50, wherein the chemically modified uracil nucleobase comprises 5-propargylaminouracil.

54. The dsDNA molecule or pharmaceutical composition of any of embodiments 41 or 43-50, wherein the chemically modified uracil nucleobase comprises N1-methylpseudouracil.

55. The dsDNA molecule or pharmaceutical composition of any of embodiments 41 or 43-50, wherein the chemically modified uracil nucleobase comprises 5-dihydroxypentyluracil.

56. The dsDNA molecule of any of embodiments 1, 2, 5-41, or 43-51, or pharmaceutical composition of any of embodiments 3-41 or 43-51, wherein at least 80%, at least 85%, at least 90%, at least 95%, or all of the chemically modified nucleobases of the dsDNA molecule comprise 5-hydroxymethyluracil.

57. The dsDNA molecule of any of embodiments 1, 2, 5-41, 43-51, or 56, or pharmaceutical composition of any of embodiments 3-41, 43-51, or 56, wherein 80%-85%, 85%-90%, 90%-95%, or 95%-100% of the chemically modified nucleobases of the dsDNA molecule comprise 5-hydroxymethyluracil.

58. The dsDNA molecule of any of embodiments 1, 2, 5-42, or 44-50, or pharmaceutical composition of any of embodiments 3-42 or 44-50, wherein at least 80%, at least 85%, at least 90%, at least 95%, or all of the chemically modified nucleobases of the dsDNA molecule comprise a canonical uracil nucleobase.

59. The dsDNA molecule of any of embodiments 1, 2, 5-42, 44-50, or 58, or pharmaceutical composition of any of embodiments 3-42, 44-50, or 58, wherein 80%-85%, 85%-90%, 90%-95%, or 95%-100% of the chemically modified nucleobases of the dsDNA molecule comprise a canonical uracil nucleobase.

60. The dsDNA molecule of any of embodiments 1, 2, 5-41, 43-50, or 52, or pharmaceutical composition of any of embodiments 3-41, 43-50, or 52, wherein at least 80%, at least 85%, at least 90%, at least 95%, or all of the chemically modified nucleobases of the dsDNA molecule comprise 5-aminoallyluracil.

61. The dsDNA molecule of any of embodiments 1, 2, 5-41, 43-50, 52, or 60, or pharmaceutical composition of any of embodiments 3-41, 43-50, 52, or 60, wherein 80%-85%, 85%-90%, 90%-95%, or 95%-100% of the chemically modified nucleobases of the dsDNA molecule comprise 5-aminoallyluracil.
62. The dsDNA molecule of any of embodiments 1, 2, 5-41, 43-50, or 53, or pharmaceutical composition of any of embodiments 3-41, 43-50, or 53, wherein at least 80%, at least 85%, at least 90%, at least 95%, or all of the chemically modified nucleobases of the dsDNA molecule comprise 5-propargylaminouracil.
63. The dsDNA molecule of any of embodiments 1, 2, 5-41, 43-50, 53, or 63, or pharmaceutical composition of any of embodiments 3-41, 43-50, 53, or 63, wherein 80%-85%, 85%-90%, 90%-95%, or 95%-100% of the chemically modified nucleobases of the dsDNA molecule comprise 5-propargylaminouracil.
64. The dsDNA molecule of any of embodiments 1, 2, 5-41, 43-50, or 54, or pharmaceutical composition of any of embodiments 3-41, 43-50, or 54, wherein at least 80%, at least 85%, at least 90%, at least 95%, or all of the chemically modified nucleobases of the dsDNA molecule comprise N1-methylpseudouracil.
65. The dsDNA molecule of any of embodiments 1, 2, 5-41, 43-50, 54, or 64, or pharmaceutical composition of any of embodiments 3-41, 43-50, 54, or 64, wherein 80%-85%, 85%-90%, 90%-95%, or 95%-100% of the chemically modified nucleobases of the dsDNA molecule comprise N1-methylpseudouracil.
66. The dsDNA molecule of any of embodiments 1, 2, 5-41, 43-50, or 55, or pharmaceutical composition of any of embodiments 3-41, 43-50, or 55, wherein at least 80%, at least 85%, at least 90%, at least 95%, or all of the chemically modified nucleobases of the dsDNA molecule comprise 5-dihydroxypentyluracil.
67. The dsDNA molecule of any of embodiments 1, 2, 5-41, 43-50, 55, or 66, or pharmaceutical composition of any of embodiments 3-41, 43-50, 55, or 66, wherein 80%-85%, 85%-90%, 90%-95%, or 95%-100% of the chemically modified nucleobases of the dsDNA molecule comprise 5-dihydroxypentyluracil.
68. The dsDNA molecule of any of embodiments 1, 2, or 5-39, or pharmaceutical composition of any of embodiments 3-39, wherein the chemically modified nucleobase comprises a chemically modified cytosine nucleobase.
69. The dsDNA molecule or pharmaceutical composition of embodiment 68, wherein at least 1%, at least 5%, at least 10%, at least 15%, at least 20%, at least 25%, at least 50%, at least 75%, at least 90%, at least 95%, at least 96%, at least 97%, at least 98%, at least 99%, or all of cytosine positions in the first strand (e.g., sense strand) of the dsDNA molecule comprise a chemically modified cytosine nucleobase.
70. The dsDNA molecule or pharmaceutical composition of embodiment 68 or 69, wherein 1%-100% (e.g., 1%-5%, 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, 95%-96%, 96%-97%, 97%-98%, 98%-99%, 99%-100%, or 95%-100%) of cytosine positions in the first strand (e.g., sense strand) of the dsDNA molecule comprise a chemically modified cytosine nucleobase.
71. The dsDNA molecule or pharmaceutical composition of any of embodiments 68-70, wherein at least 20% of cytosine positions in the first strand (e.g., sense strand) of the dsDNA molecule comprise a chemically modified cytosine nucleobase.
72. The dsDNA molecule or pharmaceutical composition of any of embodiments 68-71, wherein at least 40% of cytosine positions in the first strand (e.g., sense strand) of the dsDNA molecule comprise a chemically modified cytosine nucleobase.
73. The dsDNA molecule or pharmaceutical composition of any of embodiments 68-72, wherein at least 80% of cytosine positions in the first strand (e.g., sense strand) of the dsDNA molecule comprise a chemically modified cytosine nucleobase.
74. The dsDNA molecule or pharmaceutical composition of any of embodiments 68-73, wherein every cytosine position in a stretch of at least 100, at least 200, at least 300, at least 400, at least 500, at least 600, at least 700, at least 800, at least 900, at least 1000, at least 1500, or at least 2000 nucleotides in the first strand (e.g., sense strand) of the dsDNA molecule comprises a chemically modified cytosine nucleobase.
75. The dsDNA molecule or pharmaceutical composition of any of embodiments 68-74, wherein every cytosine position in a stretch of 100-200, 200-300, 300-400, 400-500, 500-600, 600-700, 700-800, 800-900, 900-1000, 1000-1500, or 1500-2000 nucleotides in the first strand (e.g., sense strand) of the dsDNA molecule comprises a chemically modified cytosine nucleobase.
76. The dsDNA molecule or pharmaceutical composition of any of embodiments 68-75, wherein the chemically modified cytosine nucleobase comprises 5-hydroxycytosine.
77. The dsDNA molecule or pharmaceutical composition of any of embodiments 68-76, wherein at least 80%, at least 85%, at least 90%, at least 95%, or all of the chemically modified nucleobases of the dsDNA molecule comprise 5-hydroxycytosine.
78. The dsDNA molecule of pharmaceutical composition of any of embodiments 68-77, wherein 80%-85%, 85%-90%, 90%-95%, or 95%-100% of the chemically modified nucleobases of the dsDNA molecule comprise 5-hydroxycytosine.
79. The dsDNA molecule of any of embodiments 1, 2, or 5-39, or pharmaceutical composition of any of embodiments 3-39, wherein the chemically modified nucleobase comprises a chemically modified guanine nucleobase.
80. The dsDNA molecule or pharmaceutical composition of embodiment 79, wherein at least 1%, at least 5%, at least 10%, at least 15%, at least 20%, at least 25%, at least 50%, or at least 75% of guanine positions in the first strand (e.g., sense strand) of the dsDNA molecule comprise a chemically modified guanine nucleobase.
81. The dsDNA molecule or pharmaceutical composition of embodiment 79 or 80, wherein 1%-75% (e.g., 1%-5%, 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, or 70%-75%) of guanine positions in the first strand (e.g., sense strand) of the dsDNA molecule comprise a chemically modified guanine nucleobase.
82. The dsDNA molecule or pharmaceutical composition of any of embodiments 79-81, wherein at least 40% of guanine positions in the first strand (e.g., sense strand) of the dsDNA molecule comprise a chemically modified guanine nucleobase.

83. The dsDNA molecule or pharmaceutical composition of any of embodiments 79-82, wherein every guanine position in a stretch of at least 100, at least 200, at least 300, at least 400, at least 500, at least 600, at least 700, at least 800, at least 900, at least 1000, at least 1500, or at least 2000 nucleotides in the first strand (e.g., sense strand) of the dsDNA molecule comprises a chemically modified guanine nucleobase.

84. The dsDNA molecule or pharmaceutical composition of any of embodiments 79-83, wherein every guanine position in a stretch of 100-200, 200-300, 300-400, 400-500, 500-600, 600-700, 700-800, 800-900, 900-1000, 1000-1500, or 1500-2000 nucleotides in the first strand (e.g., sense strand) of the dsDNA molecule comprises a chemically modified guanine nucleobase.

85. The dsDNA molecule or pharmaceutical composition of any of embodiments 79-84, wherein the chemically modified guanine nucleobase comprises inosine.

86. The dsDNA molecule of any of embodiments 1, 2, or 5-85, or pharmaceutical composition of any of embodiments 3-85, wherein the dsDNA molecule comprises a first type of chemically modified nucleobase and a second type of chemically modified nucleobase.

87. The dsDNA molecule or pharmaceutical composition of embodiment 86, wherein the first type of chemically modified nucleobase is a chemically modified cytosine nucleobase.

88. The dsDNA molecule or pharmaceutical composition of embodiment 87, wherein the second type of chemically modified nucleobase is a different chemically modified cytosine nucleobase, a uracil nucleobase, or a chemically modified guanine nucleobase.

89. The dsDNA molecule or pharmaceutical composition of embodiment 86, wherein the first type of chemically modified nucleobase is a uracil nucleobase.

90. The dsDNA molecule or pharmaceutical composition of embodiment 89, wherein the second type of chemically modified nucleobase is a chemically modified cytosine nucleobase, a different uracil nucleobase, or a chemically modified guanine nucleobase.

91. The dsDNA molecule or pharmaceutical composition of embodiment 86, wherein the first type of chemically modified nucleobase is a chemically modified guanine nucleobase.

92. The dsDNA molecule or pharmaceutical composition of embodiment 91, wherein the second type of chemically modified nucleobase is a chemically modified cytosine nucleobase or a uracil nucleobase.

93. The dsDNA molecule or pharmaceutical composition of any of embodiments 88 or 90-92, wherein the chemically modified guanine nucleobase comprises inosine.

94. The dsDNA molecule or pharmaceutical composition of any of embodiments 88-90, 92, or 93, wherein the uracil nucleobase comprises a canonical uracil nucleobase.

95. The dsDNA molecule or pharmaceutical composition of any of embodiments 88-90, 92, or 93, wherein the uracil nucleobase comprises 5-hydroxymethyluracil.

96. The dsDNA molecule or pharmaceutical composition of any of embodiments 87, 88, 90, or 92-95, wherein the chemically modified cytosine nucleobase comprises 5-hydroxycytosine.

97. The dsDNA molecule of any of embodiments 1, 2, or 5-96, or pharmaceutical composition of any of embodiments 3-96, wherein the longest stretch of unmodified nucleotides in the first strand (e.g., sense strand) is no more than 1000, no more than 900, no more than 800, no more than 700, no more than 600, no more than 500, no more than 400, no more than 300, no more than 200, no more than 100, no more than 50, or no more than 10 nucleotides.

98. The dsDNA molecule of any of embodiments 1, 2, or 5-97, or pharmaceutical composition of any of embodiments 3-97, wherein the longest stretch of unmodified nucleotides in the first strand (e.g., sense strand) is 10-50, 50-100, 100-200, 200-300, 300-400, 400-500, 500-600, 600-700, 700-800, 800-900, or 900-1000 nucleotides.

99. The dsDNA molecule of any of embodiments 1, 2, or 5-98, or pharmaceutical composition of any of embodiments 3-98, wherein the longest stretch of unmodified nucleobases in the first strand (e.g., sense strand) is no more than 1000, no more than 900, no more than 800, no more than 700, no more than 600, no more than 500, no more than 400, no more than 300, no more than 200, no more than 100, no more than 50, or no more than 10 nucleobases.

100. The dsDNA molecule of any of embodiments 1, 2, or 5-99, or pharmaceutical composition of any of embodiments 3-99, wherein the longest stretch of unmodified nucleobases in the first strand (e.g., sense strand) is 10-50, 50-100, 100-200, 200-300, 300-400, 400-500, 500-600, 600-700, 700-800, 800-900, or 900-1000 nucleobases.

101. The dsDNA molecule of any of embodiments 1, 2, or 5-100, or pharmaceutical composition of any of embodiments 3-100, wherein the dsDNA molecule has a length of at least 500, at least 1000, at least 2000, at least 3000, at least 4000, at least 5000, at least 6000, at least 7000, at least 8000, at least 9000, at least 10000, at least 11000, or at least 12000 nucleotides.

102. The dsDNA molecule of any of embodiments 1, 2, or 5-101, or pharmaceutical composition of any of embodiments 3-101, wherein the dsDNA molecule has a length of between 500-1000, 1000-2000, 2000-3000, 3000-4000, 4000-5000, 5000-6000, 6000-7000, 7000-8000, 8000-9000, 9000-10000, 10000-11000, or 11000-12000 nucleotides.

103. The dsDNA molecule of any of embodiments 1, 2, or 5-102, or pharmaceutical composition of any of embodiments 3-102, wherein the dsDNA molecule has a length of at least 15 nucleotides, at least 30 nucleotides, at least 50 nucleotides, at least 75 nucleotides, 100 nucleotides, at least 200 nucleotides, at least 300 nucleotides, at least 500 nucleotides, at least 750 nucleotides, at least 1,000 nucleotides, at least 2,000 nucleotides, at least 3,000 nucleotides, at least 4,000 nucleotides, at least 5,000 nucleotides, at least 6,000 nucleotides, at least 7,000 nucleotides, at least 8,000 nucleotides, at least 9,000 nucleotides, at least 10,000 nucleotides, at least 11,000 nucleotides, at least 12,000 nucleotides, at least 15,000 nucleotides, at least 20,000 nucleotides, at least 25,000 nucleotides, at least 30,000 nucleotides, at least 35,000 nucleotides, at least 40,000 nucleotides at least 45,000 nucleotides, at least 50,000 nucleotides, at least 60,000 nucleotides, or more.

104. The dsDNA molecule of any of embodiments 1, 2, or 5-103, or pharmaceutical composition of any of embodiments 3-103, wherein the dsDNA molecule has a length of between 20 and 1000 nucleotides, between 20 and 50 nucleotides, between 100 and 500 nucleotides, between 500 and 50,000 nucleotides, between 1,000 and 50,000 nucleotides, between 2,000 and 40,000 nucleotides, between 5,000 and 50,000 nucleotides, between 500 and 50,000 nucleotides, between 500 and 25,000 nucleotides, between 1,000 and 20,000 nucleotides, between 1,000 and 10,000 nucleotides, between 10,000 and 60,000 nucleotides, between 1,000 and 20,000 nucleotides, between 1,000 and 40,000 nucleotides, between 500 and 1000 nucleotides, between 1000 and 2,000 nucleotides, between 2,000 and 3,000 nucleotides, between 3,000 and 4,000 nucleotides, between 4,000 and 5,000 nucleotides, between 5,000 and 6,000 nucleotides, between 6,000 and 7,000 nucleotides, between 7,000 and 8,000 nucleotides, between 8,000 and 9,000 nucleotides, between 9,000 and 10,000 nucleotides, between 10,000 and 11,000 nucleotides, or between 11,000 and 12,000 nucleotides.

105. The dsDNA molecule of any of embodiments 1, 2, or 5-104, or pharmaceutical composition of any of embodiments 3-104, wherein the dsDNA molecule is resistant to endonuclease digestion.

106. The dsDNA molecule of any of embodiments 1, 2, or 5-105, or pharmaceutical composition of any of embodiments 3-105, wherein the dsDNA molecule is resistant to immune sensor recognition.

107. The dsDNA molecule of any of embodiments 1, 2, or 5-106, or pharmaceutical composition of any of embodiments 3-106, wherein the second strand (e.g., antisense strand) comprises no more than 10, no more than 9, no more than 8, no more than 7, no more than 6, no more than 5, no more than 4, no more than 3, no more than 2, or no more than 1 chemically modified nucleotides.

108. The dsDNA molecule of any of embodiments 1, 2, or 5-107, or pharmaceutical composition of any of embodiments 3-107, wherein the second strand (e.g., antisense strand) comprises no more than 10, no more than 9, no more than 8, no more than 7, no more than 6, no more than 5, no more than 4, no more than 3, no more than 2, or no more than 1 chemically modified nucleobases.

109. The dsDNA molecule of any of embodiments 1, 2, or 5-108, or pharmaceutical composition of any of embodiments 3-108, wherein the second strand (e.g., antisense strand) comprises no more than 10, no more than 9, no more than 8, no more than 7, no more than 6, no more than 5, no more than 4, no more than 3, no more than 2, or no more than 1 backbone modifications.

110. The dsDNA molecule of any of embodiments 1, 2, or 5-109, or pharmaceutical composition of any of embodiments 3-109, wherein the second strand (e.g., antisense strand) comprises no more than 10, no more than 9, no more than 8, no more than 7, no more than 6, no more than 5, no more than 4, no more than 3, no more than 2, or no more than 1 nucleotides having a chemically modified sugar.

111. The dsDNA molecule of any of embodiments 1, 2, or 5-110, or pharmaceutical composition of any of embodiments 3-110, wherein at least 80%, at least 85%, at least 90%, at least 95%, at least 98%, at least 99%, or 100% of the sugars of the dsDNA molecule are deoxyribose sugars.

112. The dsDNA molecule of any of embodiments 1, 2, or 5-111, or pharmaceutical composition of any of embodiments 3-111, wherein all positions in the dsDNA molecule comprise a deoxyribose sugar.

113. The dsDNA molecule of any of embodiments 1, 2, or 5-112, or pharmaceutical composition of any of embodiments 3-112, wherein all positions in the first strand (e.g., sense strand) of the dsDNA molecule comprise a deoxyribose sugar.

114. The dsDNA molecule of any of embodiments 1, 2, or 5-113, or pharmaceutical composition of any of embodiments 3-113, wherein all positions in the second strand (e.g., antisense strand) of the dsDNA molecule comprise a deoxyribose sugar.

115. The dsDNA molecule of any of embodiments 1, 2, or 5-114, or pharmaceutical composition of any of embodiments 3-114, wherein the dsDNA molecule comprises a chemical modification of a phosphate group.

116. The dsDNA molecule of any of embodiments 1, 2, or 5-115, or pharmaceutical composition of any of embodiments 3-115, wherein the dsDNA molecule comprises a chemically modified sugar, e.g., a 2'-deoxy-2'-fluoro (2'-F) nucleotide or a 2'-O-methyl (2'-O-Me) nucleotide.

117. The dsDNA molecule of any of embodiments 1, 2, or 5-116, or pharmaceutical composition of any of embodiments 3-116, wherein the dsDNA molecule further comprises one or more additional chemically modified nucleotide, wherein the additional chemically modified nucleotide comprises a modification in the backbone, sugar, or nucleobase.

118. The dsDNA molecule or pharmaceutical composition of embodiment 117, wherein one or more of the chemically modified nucleotides is conjugated to a peptide or protein.

119. The dsDNA molecule or pharmaceutical composition of embodiment 117 or 118, wherein one or more of the chemically modified nucleotides comprises a phosphorothioate linkage.

120. The dsDNA molecule or pharmaceutical composition of any of embodiments 117-119, wherein each of the first strand (e.g., sense strand) and second strand (e.g., antisense strand) of the dsDNA molecule comprises one or more chemically modified nucleotides.

121. The dsDNA molecule or pharmaceutical composition of any of embodiments 117-120, wherein each of the first strand (e.g., sense strand) and second strand (e.g., antisense strand) of the dsDNA molecule comprises one or more phosphorothioate linkages.

122. The dsDNA molecule of any of embodiments 1, 2, or 5-121, or pharmaceutical composition of any of embodiments 3-121, wherein the second strand (e.g., antisense strand) comprises an effector sequence that encodes an effector (e.g., a therapeutic effector).

123. The dsDNA molecule of any of embodiments 1, 2, or 5-122, or pharmaceutical composition of any of embodiments 3-122, wherein the second strand (e.g., antisense strand) comprises a promoter sequence, e.g., wherein the sequence that encodes an effector is operably linked to the promoter sequence.

124. The dsDNA molecule of any of embodiments 1, 2, or 5-123, or pharmaceutical composition of any of embodiments 3-123, wherein the dsDNA molecule further comprises one or more of:

i) a heterologous functional sequence, e.g., a nuclear targeting sequence or a regulatory sequence;

ii) a maintenance sequence; and/or iii) an origin of replication.

125. The dsDNA molecule or pharmaceutical composition of embodiment 124, wherein the nuclear targeting sequence comprises a CT3 sequence (e.g., a sequence of AATTCTCCTCCCCACCTTCCCCACCCTCCCCA (SEQ ID NO: 10)), or a nucleic acid sequence having at least 75%, at least 80%, at least 85%, at least 90%, at least 95%, at least 96%, at least 97%, at least 98%, or at least 99% sequence identity thereto.
126. The dsDNA molecule or pharmaceutical composition of embodiment 124, wherein the nuclear targeting sequence binds to a hnRNPK protein (e.g., a human hnRNPK protein).
127. The dsDNA molecule of any of embodiments 1, 2, or 5-126, or pharmaceutical composition of any of embodiments 4-126, wherein the effector comprises a polypeptide (e.g., a protein).
128. The dsDNA molecule of any of embodiments 1, 2, or 5-126, or pharmaceutical composition of any of embodiments 4-126, wherein the effector comprises an RNA (e.g., an mRNA, a tRNA, lncRNA, miRNA, rRNA, snRNA, microRNA, siRNA, piRNA, snoRNA, snRNA, exRNA, scaRNA, Y RNA, or hnRNA), wherein optionally the effector comprises a functional RNA (e.g., a miRNA, siRNA, or tRNA).
129. The dsDNA molecule of any of embodiments 1, 2, or 5-127, or pharmaceutical composition of any of embodiments 3-127, wherein the dsDNA molecule does not comprise a sequence encoding an RNA.
130. The dsDNA molecule of any of embodiments 1, 2, or 5-129, or pharmaceutical composition of any of embodiments 3-129, wherein the dsDNA molecule can be replicated (e.g., by a DNA polymerase native to a cell comprising the dsDNA molecule).
131. The dsDNA molecule of any of embodiments 1, 2, or 5-129, or pharmaceutical composition of any of embodiments 3-129, wherein the dsDNA molecule cannot be replicated.
132. The dsDNA molecule of any of embodiments 1, 2, or 5-131, or pharmaceutical composition of any of embodiments 4-131, wherein the effector is heterologous to a target cell.
133. The dsDNA molecule of any of embodiments 1, 2, or 5-132, or pharmaceutical composition of any of embodiments 3-132, wherein the dsDNA molecule lacks a material portion of vector backbone (e.g., plasmid backbone).
134. The dsDNA molecule of any of embodiments 1, 2, or 5-133, or pharmaceutical composition of any of embodiments 3-133, wherein the dsDNA molecule does not comprise a non-human (e.g., bacterial) origin of replication.
135. The dsDNA molecule of any of embodiments 1, 2, or 5-134, or pharmaceutical composition of any of embodiments 3-134, wherein the dsDNA molecule does not comprise an antibiotic resistance selectable marker.
136. The dsDNA molecule of any of embodiments 1, 2, or 5-135, or pharmaceutical composition of any of embodiments 3-135, wherein the dsDNA molecule is not supercoiled.
137. The dsDNA molecule of any of embodiments 1, 2, or 5-136, or pharmaceutical composition of any of embodiments 4-136, wherein the effector sequence does not encode a viral protein.
138. A method of making a dsDNA molecule, the method comprising:
(a) providing a double stranded linear DNA having a first strand and a second strand,
(b) subjecting the DNA of (a) to conditions having exonuclease activity, such that the first strand is removed,
(c) contacting the DNA of (b) with a DNA polymerase, unmodified deoxyribose nucleotides, nucleotides comprising chemically modified nucleobases, and a primer, under conditions such that a first strand comprising chemically modified nucleobases is produced,
(d) subjecting the DNA of (c) to conditions having endonuclease activity such that a sticky end at each end of the DNA is produced, and
(e) subjecting the DNA of (d) to conditions having ligase activity such that the sticky ends are ligated, thereby producing the dsDNA molecule.
139. The method of embodiment 138, wherein the chemically modified nucleobases comprise 5-hydroxymethyluracil, canonical uracil nucleobases, 5-aminoallyluracil, 5-propargylaminouracil, N1-methylpseudouracil, or 5-dihydroxypentyluracil.
140. The method of embodiment 138 or 139, wherein the chemically modified nucleobases comprise 5-hydroxymethyluracil.
141. The method of embodiment 138 or 139, wherein the chemically modified nucleobases comprise canonical uracil nucleobases.
142. The method of any of embodiments 138-141, wherein the first strand is a sense strand, and the second strand is an antisense strand.
143. The method of any of embodiments 138-142, wherein the second strand is substantially free of (e.g., is free of) chemically modified nucleobases.
144. The method of any of embodiments 138-143, wherein the second strand comprises a backbone modification that inhibits exonuclease activity, optionally wherein the backbone modification is at the 5' end of the second strand.
145. The method of embodiment 144, wherein the backbone modification that inhibits exonuclease activity comprises a phosphorothioate linkage.
146. The method of any of embodiments 138-145, wherein the DNA of (a) was produced by polymerase chain reaction (PCR).
147. The method of embodiment 146, wherein the DNA of (a) was produced by performing PCR on a composition comprising a DNA template, e.g., a plasmid, a forward primer, a reverse primer comprising one or more (e.g., 2, 3, 4, 5, 6, 7, or 8) phosphorothioate modifications, a DNA polymerase, and deoxyribose nucleotides, e.g., unmodified or chemically modified deoxyribose nucleotides, wherein optionally the unmodified deoxyribose nucleotides comprise dATP, dCTP, dTTP, and/or dGTP.
148. The method of embodiment 147, wherein the DNA polymerase comprises a KOD-Multi & Epi-polymerase, optionally wherein the KOD-Multi & Epi-polymerase is heat-activated.
149. The method of any of embodiments 138-148, wherein (b) comprises contacting the DNA of (a) with one or more exonucleases.
150. The method of embodiment 149, wherein said one or more exonucleases comprise T7 Exonuclease and/or Lambda Exonuclease.

151. The method of any of embodiments 138-150, further comprising subjecting the DNA of (b) to conditions having endonuclease activity, e.g., contacting the DNA of (b) with an endonuclease.
152. The method of embodiment 151, wherein the DNA of (b) is contacted with an endonuclease that binds dsDNA and cleaves the dsDNA to produce blunt ends.
153. The method of embodiment 151 or 152, wherein the endonuclease is a Mly1 Endonuclease.
154. The method of any of embodiments 138-153, wherein (c) comprises performing isothermal extension.
155. The method of any of embodiments 138-154, wherein (c) comprises:
    (i) contacting the DNA of (b) with the unmodified deoxyribose nucleotides, the nucleotides comprising chemically modified nucleobases, and the primer, thereby producing a composition,
    (ii) increasing the temperature of the composition of (i) to 60° C.-70° C., e.g., about 68° C., and
    (iii) contacting the composition of (i) or (ii) with the DNA polymerase, e.g., for 30-60 minutes, optionally wherein the DNA polymerase is a KOD-Multi & Epi-polymerase.
156. The method of any of embodiments 138-155, wherein the primer of (c) comprises unmodified deoxyribose nucleotides.
157. The method of any of embodiments 138-156, wherein the primer of (c) comprises no chemically modified nucleotides.
158. The method of any of embodiments 138-157, wherein the primer of (c) comprises no chemically modified nucleobases.
159. The method of any of embodiments 138-158, wherein (d) comprises incubating the DNA of (c) with a restriction enzyme that cleaves a restriction enzyme recognition sequence in the DNA of (c).
160. The method of any of embodiments 138-159, wherein (e) comprises incubating the DNA of (d) with a ligase, e.g., a T3 DNA ligase.
161. The method of any of embodiments 138-160, further comprising (f) incubating the DNA of (e) under conditions having exonuclease activity.
162. The method of embodiment 161, wherein (f) comprises incubating the DNA of (e) with an exonuclease, e.g., a T5 exonuclease.
163. The method of any of embodiments 138-162, which further comprises a step of enriching the DNA molecule (e.g., dsDNA molecule), e.g., after step (a), (b), (c), (d), (e), and/or (f).
164. The method of embodiment 163, further comprising a step (g) of measuring in the enriched DNA molecule the presence or level of one or more of: linear DNA, concatameric DNA, mono- or di-nucleotides, protein, or virus.
165. The method of embodiment 163 or 164, wherein enriching the DNA molecule (e.g., dsDNA molecule) comprises use of a DNA enrichment column or agarose gel enrichment.
166. The method of any of embodiments 138-165, which is performed in vitro, e.g., in a cell-free system.
167. The method of any of embodiments 138-166, wherein the dsDNA molecule is a dsDNA molecule of any of embodiments 1, 2, or 5-137.
168. A dsDNA molecule produced by the method of any of embodiments 138-167.
169. A composition, e.g., a pharmaceutical composition, comprising a plurality of the dsDNA molecules of any of embodiments 1, 2, 5-137, or 168, wherein the composition comprises at least 0.5 mg, at least 1 mg, at least 2 mg, at least 5 mg, at least 10 mg, at least 20 mg, or at least 50 mg of the dsDNA molecules, or wherein the composition comprises 0.5-1, 1-2, 2-5, 5-10, 10-20, 20-50, or 50-100 mg of the dsDNA molecules.
170. A plurality (e.g., a preparation) of dsDNA molecules of any of embodiments 1, 2, 5-137, or 168.
171. The plurality of dsDNA molecules of embodiment 170, wherein:
    at least 50%, at least 60%, or at least 70% of the dsDNA molecules in the plurality have substantially the same length;
    at least 50%, at least 60%, or at least 70% of the dsDNA molecules in the plurality have a length in a predetermined range; or
    at least 50%, at least 60%, or at least 70% of the dsDNA molecules in the plurality have a length of between 100, 200, 300, 400, or 500 nucleotides of each other.
172. A composition, e.g., a pharmaceutical composition, comprising a plurality of the dsDNA molecules of any of embodiments 1, 2, 5-137, or 168, or the plurality of embodiment 170 or 171.
173. The composition of embodiment 169 or 172, wherein at least 50%, at least 60%, at least 70%, at least 80%, or at least 84% by mass of total DNA in the composition is the dsDNA molecule.
174. The composition of any of embodiments 169, 172, or 173, wherein 50%-60%, 60%-70%, 70%-80%, or 80%-84% by mass of total DNA in the composition is the dsDNA molecule.
175. The composition of any of embodiments 169 or 172-174, wherein less than 30%, less than 25%, less than 20%, or less than 15% by mass of DNA in the composition is linear dsDNA.
176. The composition of any of embodiments 169 or 172-175, wherein less than 30%, less than 25%, less than 20%, or less than 15% by mass of DNA in the composition is single stranded DNA (ssDNA).
177. The composition of any of embodiments 169 or 172-176, wherein less than 30%, less than 25%, less than 20%, or less than 15% by mass of DNA in the composition is DNA having a higher molecular weight (e.g., at least 2-fold greater) than the molecular weight of the dsDNA molecule.
178. The composition of any of embodiments 169 or 172-177, wherein less than 30%, less than 25%, less than 20%, or less than 15% by mass of DNA in the composition is concatemeric DNA.
179. A pharmaceutical composition comprising the dsDNA molecule of any of embodiments 1, 2, 5-137, or 168.
180. The pharmaceutical composition of any of embodiments 3-137, 169, or 172-179, wherein the dsDNA molecule is unencapsidated.
181. The pharmaceutical composition of any of embodiments 3-137, 169, or 172-180, or the dsDNA molecule of any of embodiments 1, 2, 5-137, or 168, wherein the dsDNA molecule does not comprise a viral packaging signal.
182. The pharmaceutical composition of any of embodiments 3-137, 169, or 172-181, or the dsDNA molecule of any of embodiments 1, 2, 5-137, or 168, wherein the dsDNA molecule does not comprise a viral ITR.

183. The pharmaceutical composition of any of embodiments 3-137, 169, or 172-182, which is essentially free of viral proteins.

184. The pharmaceutical composition of any of embodiments 3-137, 169, or 172-183, wherein the dsDNA molecule is comprised in a lipid nanoparticle (LNP).

185. The pharmaceutical composition of any of embodiments 3-137, 169, or 172-184, further comprising an electroporation buffer.

186. The pharmaceutical composition of any of embodiments 3-137, 169, or 172-185, further comprising a transfection reagent.

187. A method of expressing an effector in a target cell, the method comprising:
 (i) introducing into a target cell the dsDNA molecule of any of embodiments 1, 2, 5-137, or 168; and
 (ii) maintaining (e.g., incubating) the cell under conditions suitable for expressing the effector from the dsDNA molecule;
 thereby expressing the effector in the target cell.

188. A method of delivering a dsDNA molecule to a target cell, the method comprising:
 contacting a target cell with the dsDNA molecule of any of embodiments 1, 2, 5-137, or 168, plurality of embodiment 170 or 171, or composition of any of embodiments 3-137, 169, or 172-186;
 thereby delivering the dsDNA molecule to the target cell.

189. A method of delivering an effector to a target cell, the method comprising:
 contacting a target cell with the dsDNA molecule of any of embodiments 1, 2, 5-137, or 168, plurality of embodiment 170 or 171, or composition of any of embodiments 3-137, 169, or 172-186;
 thereby delivering the effector to the target cell.

190. A method of modulating (e.g., increasing or decreasing) a biological activity in a target cell, the method comprising:
 (i) providing a target cell the dsDNA molecule of any of embodiments 1, 2, 5-137, or 168, plurality of embodiment 170 or 171, or composition of any of embodiments 3-137, 169, or 172-186, wherein the dsDNA molecule comprises a sequence encoding an effector that modulates a biological activity in the target cell; and
 (ii) maintaining (e.g., incubating) the cell under conditions suitable for expressing the effector from the dsDNA molecule;
 thereby modulating the biological activity in the target cell.

191. The method of embodiment 190, wherein the biological activity comprises cell growth, cell metabolism, cell signaling, cell movement, specialization, interactions, division, transport, homeostasis, osmosis, or diffusion.

192. The method of embodiment 190 or 191, wherein the target cell is an animal cell, e.g., a mammalian cell, e.g., a human cell.

193. A method of treating a cell, tissue, or subject in need thereof, the method comprising:
 administering to the cell, tissue, or subject the dsDNA molecule of any of embodiments 1, 2, 5-137, or 168, plurality of embodiment 170 or 171, or composition of any of embodiments 3-137, 169, or 172-186;
 thereby treating the cell, tissue, or subject.

194. The method of any of embodiments 187-193, which is performed ex vivo or in vivo.

195. A dsDNA molecule comprising N1-methylpseudouracil.

196. A dsDNA molecule comprising 5-dihydroxypentyluracil.

197. A reaction mixture comprising (i) a linear, whole or partially double stranded DNA (dsDNA), wherein one strand of the dsDNA comprises one or more chemical modifications to the backbone of the strand (e.g., phosphorothioate nucleotides) and is substantially free of (e.g., is free of) chemically modified nucleobases, wherein optionally the one or more modifications to the backbone are situated at one end (the 5 end or 3' end) of the strand, and the other strand is substantially free of (e.g., is free of) chemically modified nucleotides, and (ii) an exonuclease, e.g., lambda exonuclease.

198. A reaction mixture comprising (i) a linear single stranded DNA (ssDNA) comprising one or more chemical modifications to the backbone of the strand (e.g., phosphorothioate nucleotides) and is substantially free of (e.g., is free of) chemically modified nucleobases, wherein optionally the one or more modifications to the backbone are situated at one end (the 5 end or 3' end) of the ssDNA, and (ii) an enzyme (e.g., an endonuclease, e.g., Mly1) that preferentially cleaves dsDNA relative to ssDNA, wherein optionally the enzyme cleaves more than 100, 200, 300, 400, or 500 base pairs away from either end of the dsDNA.

199. A reaction mixture comprising (i) a linear single stranded DNA (ssDNA) that is substantially free of (e.g., is free of) chemically modified nucleobases, wherein optionally the ssDNA comprises one or more chemical modifications to the backbone of the strand (e.g., phosphorothioate nucleotides), wherein optionally the one or more modifications to the backbone are situated at one end (the 5 end or 3' end) of the ssDNA, (ii) a primer complementary to the ssDNA (e.g., complementary to the 3' end of the ssDNA), and one or both of: (iii) a plurality of nucleotides, wherein one or more of the nucleotides comprises a chemically modified nucleobase, and/or (iv) a DNA polymerase, e.g., KOD-Multi & Epi-polymerase.

200. A reaction mixture comprising (i) a linear, double stranded DNA (dsDNA), wherein the first strand of the DNA comprises one or more chemically modified nucleobases and the second strand of the DNA is substantially free of (e.g., is free of) chemically modified nucleobases, and optionally, (ii) a restriction endonuclease (e.g., BsaI v2-HF) that cleaves a site at each end of the dsDNA (optionally, wherein the restriction endonuclease cleaves no more than two sites in the dsDNA), wherein optionally the restriction endonuclease generates two sticky ends, and further optionally wherein restriction endonuclease cleavage removes phosphorothioate nucleotides from the dsDNA.

201. A reaction mixture comprising (i) a linear, double stranded DNA (dsDNA), wherein the first strand of the DNA comprises one or more chemically modified nucleobases and the second strand of the DNA is substantially free of (e.g., is free of) chemically modified nucleobases, and wherein the DNA comprises two compatible sticky ends, and optionally, (ii) a DNA ligase (e.g., T3 DNA ligase).

202. A reaction mixture comprising (i) a circular, double stranded DNA (dsDNA), wherein the first strand of the DNA comprises one or more chemically modified nucleobases and the second strand of the DNA is substantially free of (e.g., is free of) chemically modified nucleobases, and optionally, (ii) a nuclease (e.g., an exonuclease, e.g., T5 exonuclease) that preferentially cleaves linear DNA compared to circular DNA.

203. A double stranded DNA (dsDNA) molecule, comprising:
- a promoter region that comprises: i) a bidirectional promoter sequence, or ii) a first promoter sequence and a second promoter sequence that are oriented to drive transcription in opposite directions,
- a first effector sequence situated on one side of the promoter region, wherein the first effector sequence has a first strand (e.g., sense strand) that comprises one or more chemically modified nucleobases, and a second strand (e.g., antisense strand) that is substantially free of chemically modified nucleobases, and wherein the first effector sequence encodes a first effector; and
- a second effector sequence situated on the other side of the promoter region, wherein the second effector sequence has a first strand (e.g., sense strand) that comprises one or more chemically modified nucleobases, and a second strand (e.g., antisense strand) that is substantially free of chemically modified nucleobases, and wherein the second effector sequence encodes a second effector; and
- wherein the bidirectional promoter sequence is operably linked to the first effector sequence and the second effector sequence, or wherein the first promoter sequence is operably linked to the first effector sequence and the second promoter sequence is operably linked to the second effector sequence.

204. The dsDNA molecule of embodiment 203, which is a circular, dsDNA molecule.

205. The dsDNA molecule of embodiment 203, which comprises:
- a) a first DNA end form;
- b) a double stranded region that comprises the promoter region, the first effector sequence, and the second effector sequence; and
- c) a second DNA end form.

206. A circular dsDNA molecule, comprising:
- a first strand of the dsDNA molecule and a second strand of the dsDNA molecule, wherein:
  - the first strand of the dsDNA molecule comprises, in a 5' to 3' direction:
    - optionally, a promoter region;
    - a first strand of a first effector sequence (e.g., a sense strand of the first effector sequence), wherein the first strand of the first effector sequence comprises one or more chemically modified nucleobases, and
    - a second strand of a second effector sequence (e.g., an antisense strand of the second effector sequence), wherein the second strand of the second effector sequence is substantially free of chemically modified nucleobases; and the second strand comprises, in a 5' to 3' direction:
    - optionally, the promoter region,
    - a first strand of the second effector sequence (e.g., a sense strand of the second effector sequence), wherein the first strand of the second effector sequence comprises one or more chemically modified nucleobases; and
    - a second strand of the first effector sequence (e.g., an antisense strand of the first effector sequence), wherein the second strand of the first effector sequence is substantially free of chemically modified nucleobases,
- wherein the first effector sequence encodes a first effector and the second effector sequence encodes a second effector.

207. A dsDNA molecule comprising:
- a) a first DNA end form;
- b) a double stranded region comprising a first strand and a second strand; and
- c) a second DNA end form,
- wherein the first strand of the dsDNA molecule comprises, in a 5' to 3' direction:
  - a second strand of a first effector sequence (e.g., an antisense strand of the first effector sequence), wherein the second strand of the first effector sequence is substantially free of chemically modified nucleobases;
  - optionally, a promoter region; and
  - a first strand of a second effector sequence (e.g., a sense strand of the second effector sequence), wherein the first strand of the second effector sequence comprises one or more chemically modified nucleobases; and
- wherein the second strand of the dsDNA molecule comprises, in a 5' to 3' direction:
  - a second strand of the second effector sequence (e.g., an antisense strand of the second effector sequence), wherein the second strand of the second effector sequence is substantially free of chemically modified nucleobases;
  - optionally, the promoter region, and
  - a first strand of the first effector sequence (e.g., a sense strand of the first effector sequence), wherein the first strand of the first effector sequence comprises one or more chemically modified nucleobases,
- wherein the first effector sequence encodes a first effector and the second effector sequence encodes a second effector.

208. The dsDNA molecule of embodiment 206 or 207, wherein the promoter region comprises: i) a bidirectional promoter sequence, or ii) a first promoter sequence and a second promoter sequence that are oriented to drive transcription in opposite directions.

209. The dsDNA molecule of any of embodiments 203-208, wherein the promoter region and the first effector sequence are directly adjacent or are separated by no more than 200, 100, 50, 40, 30, 20, or 10 base pairs.

210. The dsDNA molecule of any of embodiments 203-209, wherein the promoter region and the second effector sequence are directly adjacent or are separated by no more than 200, 100, 50, 40, 30, 20, or 10 base pairs.

211. The dsDNA molecule of any of embodiments 203-205 or 208-210, wherein the first promoter sequence and the second promoter sequence are directly adjacent or are separated by no more than 600, 500, 400, 300, 200, 100, 50, 40, 30, 20, or 10 base pairs.

212. The dsDNA molecule of any of embodiments 203-211, wherein the downstream end of the first effector sequence and the downstream end of the second effector sequence are separated by no more than 200, 100, 50, 40, 30, 20, or 10 base pairs.

213. The dsDNA molecule of any of embodiments 203-212, wherein the dsDNA molecule comprises, downstream of the first effector sequence, a sequence encoding a polyadenylation site.

214. The dsDNA molecule of any of embodiments 203-213, wherein the dsDNA molecule comprises, downstream of the second effector sequence, a sequence encoding a polyadenylation site.

215. The dsDNA molecule of any of embodiments 203-214, wherein the dsDNA molecule comprises, between the first effector sequence and the promoter region, a sequence encoding a 5' UTR.

216. The dsDNA molecule of any of embodiments 203-215, wherein the dsDNA molecule comprises, between the second effector sequence and the promoter region, a sequence encoding a 5' UTR.

217. The dsDNA molecule of any of embodiments 203-216, wherein the dsDNA molecule comprises, downstream of the first effector sequence, a sequence encoding a 3' UTR.

218. The dsDNA molecule of any of embodiments 203-217, wherein the dsDNA molecule comprises, downstream of the second effector sequence, a sequence encoding a 3' UTR.

219. The dsDNA molecule of any of embodiments 203-218, wherein the longest stretch of base pairs in the dsDNA molecule that is substantially free of chemically modified nucleobases is no longer than 50, no longer than 40, no longer than 30, no longer than 20, or no longer than 10 base pairs.

220. The dsDNA molecule of any of embodiments 203-219, wherein the longest stretch of base pairs in the dsDNA molecule that is substantially free of chemically modified nucleobases is 10-20, 20-30, 30-40, or 40-50 base pairs.

221. The dsDNA molecule of any of embodiments 203-220, wherein the longest stretch of unmodified nucleobases in the first strand of the first effector sequence (e.g., the sense strand of the first effector sequence) and/or the first strand of the second effector sequence (e.g., the sense strand of the second effector sequence) is no more than 50, no more than 40, no more than 30, no more than 20, or no more than 10 nucleobases.

222. The dsDNA molecule of any of embodiments 203-221, wherein the longest stretch of unmodified nucleobases in the first strand of the first effector sequence (e.g., the sense strand of the first effector sequence) and/or the first strand of the second effector sequence (e.g., the sense strand of the second effector sequence) is 10-20, 20-30, 30-40, or 40-50 nucleobases.

223. The dsDNA molecule of any of embodiments 203-222, wherein the promoter region is substantially free of chemically modified nucleobases.

224. The dsDNA molecule of any of embodiments 203-222, wherein the promoter region comprises one or more chemically modified nucleobases.

225. The dsDNA molecule of any of embodiments 203-222 or 224, wherein the promoter region comprises a first strand and a second strand, wherein the first strand of the promoter region comprises one or more chemically modified nucleobases and the second strand of the promoter region is substantially free of chemically modified nucleobases.

226. The dsDNA molecule of any of embodiments 203-222 or 224, wherein the promoter region comprises a first strand and a second strand, wherein the first strand of the promoter region comprises one or more chemically modified nucleobases and the second strand of the promoter region comprises one or more chemically modified nucleobases.

227. The dsDNA molecule of any of embodiments 203-226, wherein the promoter region is at least 50, at least 100, at least 150, at least 200, at least 300, at least 400, at least 500, at least 600, at least 700, at least 800, at least 900, at least 1000, or at least 1200 base pairs in length.

228. The dsDNA molecule of any of embodiments 203-227, wherein the promoter region is 50-100, 100-150, 200-300, 300-400, 400-500, 500-600, 600-700, 700-800, 800-900, 900-1000, or 1000-1200 base pairs in length.

229. The dsDNA molecule of any of embodiments 203-228, wherein the first effector sequence and the second effector sequence have the same nucleotide sequence.

230. The dsDNA molecule of any of embodiments 203-228, wherein the first effector sequence and the second effector sequence have different nucleotide sequences.

231. The dsDNA molecule of any of embodiments 203-230, wherein the first effector and the second effector form a complex.

232. The dsDNA molecule of any of embodiments 203-231, wherein the first effector and the second effector are in the same biological pathway.

233. The dsDNA molecule of any of embodiments 203-232, wherein the first effector is a therapeutic effector and the second effector increases the level or activity of the first effector.

234. The dsDNA molecule of any of embodiments 203-233, wherein the first effector sequence and/or the second effector sequence each independently encodes a therapeutic effector.

235. The dsDNA molecule of any of embodiments 203-205 or 208-234, wherein the bidirectional promoter sequence is a viral promoter sequence.

236. The dsDNA molecule of any of embodiments 203-205 or 208-235, wherein the bidirectional promoter sequence is a naturally occurring promoter sequence.

237. The dsDNA molecule of any of embodiments 203-205 or 208-235, wherein the bidirectional promoter sequence is a non-naturally occurring promoter sequence.

238. The dsDNA molecule of any of embodiments 203-205 or 208-237, wherein the bidirectional promoter sequence comprises a CAG promoter sequence, a PGK promoter sequence, a DAS1-DAS2 promoter sequence, a RPBSA synthetic promoter sequence, a Rpl13a-based promoter sequence, an EF1-α promoter sequence, an LMP2/TAP1 promoter sequence, or a fragment or derivative thereof.

239. The dsDNA molecule of any of embodiments 203-238, further comprising an intron sequence.

240. The dsDNA molecule of any of embodiments 203-239, further comprising an enhancer sequence.

241. The dsDNA molecule of any of embodiments 203-240, wherein the chemically modified nucleobase(s) of the first effector sequence have a different chemical structure from the chemically modified nucleobase(s) of the second effector sequence.

242. The dsDNA molecule of any of embodiments 203-240, wherein the chemically modified nucleobase(s) of the first effector sequence have the same chemical structure as the chemically modified nucleobase(s) of the second effector sequence.

243. The dsDNA molecule of any of embodiments 203-242, further comprising one or more backbone modifications.

244. The dsDNA molecule of embodiment 243, wherein the one or more backbone modifications are phosphorothioate linkages.
245. The dsDNA molecule of any of embodiments 203-244, wherein the dsDNA molecule, when contacted to human cells, results in a level at least the level of expression of the first effector and/or the second effector compared to an unmodified control DNA molecule, wherein the unmodified control DNA molecule comprises the same sequence and structure as the dsDNA molecule, but comprises no chemically modified nucleobases.
246. The dsDNA molecule of any of embodiments 203-245, wherein the dsDNA molecule, when contacted to human cells, results in expression of the first effector and/or the second effector at a level at least the level of expression of a modified control DNA molecule, wherein the modified control DNA molecule comprises the same sequence, same structure, and same degree of first strand (e.g., sense strand) nucleobase modification as the dsDNA molecule, but comprises second strand (e.g., antisense strand) nucleobase modification at the same degree as first strand (e.g., sense strand) nucleobase modification.
247. The dsDNA molecule of any of embodiments 203-246, wherein the dsDNA molecule, when contacted to human cells, results in a lower level of IL6 or CXCL10 mRNA compared to a control DNA molecule, wherein the control DNA molecule comprises the same sequence and same structure as the dsDNA molecule, but comprises no chemically modified nucleobases.
248. The dsDNA molecule of any of embodiments 203-247, wherein the chemically modified nucleobase is a chemically modified cytosine nucleobase.
249. The dsDNA molecule of embodiment 248, wherein at least 1%, at least 5%, at least 10%, at least 15%, at least 20%, at least 25%, at least 50%, at least 75%, at least 90%, or at least 99% of cytosine positions in the first strand of the first effector sequence (e.g., the sense strand of the first effector sequence) and/or the first strand of the second effector sequence (e.g., the sense strand of the second effector sequence) comprise a chemically modified cytosine nucleobase.
250. The dsDNA molecule of embodiment 248 or 249, wherein 1%-100% (e.g., 1%-5%, 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%) of cytosine positions in the first strand of the first effector sequence (e.g., the sense strand of the first effector sequence) and/or the first strand of the second effector sequence (e.g., the sense strand of the second effector sequence) comprise a chemically modified cytosine nucleobase.
251. The dsDNA molecule of any of embodiments 203-247, wherein the chemically modified nucleobase is a uracil nucleobase.
252. The dsDNA molecule of embodiment 251, wherein the uracil nucleobase is a canonical uracil nucleobase or a chemically modified uracil nucleobase.
253. The dsDNA molecule of embodiment 252, wherein the chemically modified uracil nucleobase comprises 5-hydroxymethyluracil.
254. The dsDNA molecule of any of embodiments 251-253, wherein at least 1%, at least 5%, at least 10%, at least 15%, at least 20%, at least 25%, at least 50%, at least 75%, at least 90%, or at least 99% of thymine or uracil positions in the first strand of the first effector sequence (e.g., the sense strand of the first effector sequence) and/or the first strand of the second effector sequence (e.g., the sense strand of the second effector sequence) comprise a uracil nucleobase.
255. The dsDNA molecule of any of embodiments 251-254, wherein 1%-100% (e.g., 1%-5%, 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%) of thymine and uracil positions in the first strand of the first effector sequence (e.g., the sense strand of the first effector sequence) and/or the first strand of the second effector sequence (e.g., the sense strand of the second effector sequence) comprise a uracil nucleobase.
256. The dsDNA molecule of any of embodiments 251, 252, 254, or 255, wherein at least 1%, at least 5%, at least 10%, at least 15%, at least 20%, at least 25%, at least 50%, at least 75%, at least 90%, or at least 99% of thymine or uracil positions in the first strand of the first effector sequence (e.g., the sense strand of the first effector sequence) and/or the first strand of the second effector sequence (e.g., the sense strand of the second effector sequence) comprise a canonical uracil nucleobase.
257. The dsDNA molecule of any of embodiments 251, 252, or 254-256, wherein 1%-100% (e.g., 1%-5%, 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%) of thymine and uracil positions in the first strand of the first effector sequence (e.g., the sense strand of the first effector sequence) and/or the first strand of the second effector sequence (e.g., the sense strand of the second effector sequence) comprise a canonical uracil nucleobase.
258. The dsDNA molecule of any of embodiment 251-255, wherein at least 1%, at least 5%, at least 10%, at least 15%, at least 20%, at least 25%, at least 50%, at least 75%, at least 90%, or at least 99% of thymine or uracil positions in the first strand of the first effector sequence (e.g., the sense strand of the first effector sequence) and/or the first strand of the second effector sequence (e.g., the sense strand of the second effector sequence) comprise a chemically modified uracil nucleobase.
259. The dsDNA molecule of any of embodiments 251-255 or 258, wherein 1%-100% (e.g., 1%-5%, 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%) of thymine and uracil positions in the first strand of the first effector sequence (e.g., the sense strand of the first effector sequence) and/or the first strand of the second effector sequence (e.g., the sense strand of the second effector sequence) comprise a chemically modified uracil nucleobase.
260. The dsDNA molecule of any of embodiments 251-255, 258, or 259, wherein at least 1%, at least 5%, at least 10%, at least 15%, at least 20%, at least 25%, at least 50%, at least 75%, at least 90%, or at least 99% of thymine or uracil positions in the first strand of the first effector sequence (e.g., the sense strand of the first effector sequence) and/or the first strand of the second effector sequence (e.g., the sense strand of the second effector sequence) comprise 5-hydroxymethyluracil.

261. The dsDNA molecule of any of embodiments 251-255 or 258-260, wherein 1%-100% (e.g., 1%-5%, 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%) of thymine and uracil positions in the first strand of the first effector sequence (e.g., the sense strand of the first effector sequence) and/or the first strand of the second effector sequence (e.g., the sense strand of the second effector) sequence comprise 5-hydroxymethyluracil.

262. The dsDNA molecule of any of embodiments 205 or 207-261, wherein one or both of the first DNA end form and second DNA end form are blunt ends.

263. The dsDNA molecule of any of embodiments 205 or 207-262, wherein one or both of the first DNA end form and second DNA end form have an overhang.

264. The dsDNA molecule of any of embodiments 205 or 207-263, wherein the first DNA end form comprises a first restriction site and the second DNA end form comprises a second restriction site.

265. The dsDNA molecule of embodiment 264, wherein the first restriction site and the second restriction site have the same sequence.

266. The dsDNA molecule of any of embodiments 205 or 207-265, wherein one or both of the first DNA end form and second DNA end form are closed ends.

267. The dsDNA molecule of any of embodiments 205 or 207-266, wherein one or both of the first DNA end form and second DNA end form comprise a loop.

268. The dsDNA molecule of any of embodiments 203-261 or 264-267, wherein every nucleotide of the dsDNA molecule binds another nucleotide in the dsDNA molecule.

269. The dsDNA molecule of any of embodiments 205 or 207-268, wherein one or both of the first DNA end form and second DNA end form comprise a protelomerase sequence.

270. The dsDNA molecule of any of embodiments 205 or 207-269, wherein one or both of the first DNA end form and second DNA end form do not comprise a protelomerase sequence.

271. The dsDNA molecule of any of embodiments 203-270, wherein the dsDNA molecule has a length of at least 500, at least 1000, at least 2000, at least 3000, at least 4000, at least 5000, at least 6000, at least 7000, at least 8000, at least 9000, at least 10000, at least 11000, or at least 12000 base pairs.

272. The dsDNA molecule of any of embodiments 203-271, wherein the dsDNA molecule has a length of between 500-1000, 1000-2000, 2000-3000, 3000-4000, 4000-5000, 5000-6000, 6000-7000, 7000-8000, 8000-9000, 9000-10000, 10000-11000, or 11000-12000 base pairs.

273. The dsDNA molecule of any of embodiments 203-272, wherein the dsDNA molecule has a length of at least 15, at least 30, at least 50, at least 75, at least 100, at least 200, at least 300, at least 500, at least 750, at least 1,000, at least 2,000, at least 3,000, at least 4,000, at least 5,000, at least 6,000, at least 7,000, at least 8,000, at least 9,000, at least 10,000, at least 11,000, at least 12,000, at least 15,000, at least 20,000, at least 25,000, at least 30,000, at least 35,000, at least 40,000 at least 45,000, at least 50,000, at least 60,000 base pairs or more.

274. The dsDNA molecule of any of embodiments 203-273, wherein the dsDNA molecule has a length of between 20 and 1000, between 20 and 50, between 100 and 500, between 500 and 50,000, between 1,000 and 50,000, between 2,000 and 40,000, between 5,000 and 50,000, between 500 and 50,000, between 500 and 25,000, between 1,000 and 20,000, between 1,000 and 10,000, between 10,000 and 60,000, between 1,000 and 20,000, between 1,000 and 40,000, between 500 and 1000, between 1000 and 2,000, between 2,000 and 3,000, between 3,000 and 4,000, between 4,000 and 5,000, between 5,000 and 6,000, between 6,000 and 7,000, between 7,000 and 8,000, between 8,000 and 9,000, between 9,000 and 10,000, between 10,000 and 11,000, between 11,000 and 12,000, between 12,000 and 15,000, between 15,000 and 20,000, between 20,000 and 25,000, between 25,000 and 30,000, between 30,000 and 35,000, between 35,000 and 40,000, between 40,000 and 45,000, between 45,000 and 50,000, or between 50,000 and 60,000 base pairs.

275. The dsDNA molecule of any of embodiments 203-274, wherein the dsDNA molecule is resistant to endonuclease digestion.

276. The dsDNA molecule of any of embodiments 203-275, wherein the dsDNA molecule is resistant to immune sensor recognition.

277. The dsDNA molecule of any of embodiments 203-276, wherein the second strand (e.g., antisense strand) of the first effector sequence and/or the second strand (e.g., antisense strand) of the second effector sequence comprises no more than 10, no more than 9, no more than 8, no more than 7, no more than 6, no more than 5, no more than 4, no more than 3, no more than 2, or no more than 1 chemically modified nucleobases.

278. The dsDNA molecule of any of embodiments 203-277, wherein the dsDNA molecule comprises no more than 10, no more than 9, no more than 8, no more than 7, no more than 6, no more than 5, no more than 4, no more than 3, no more than 2, or no more than 1 backbone modifications.

279. The dsDNA molecule of any of embodiments 203-278, wherein the second strand (e.g., antisense strand) of the first effector sequence and/or the second strand (e.g., antisense strand) of the second effector sequence comprises no more than 10, no more than 9, no more than 8, no more than 7, no more than 6, no more than 5, no more than 4, no more than 3, no more than 2, or no more than 1 backbone modifications.

280. The dsDNA molecule of any of embodiments 203-279, wherein the first strand of the first effector sequence (e.g., the sense strand of the first effector sequence) and/or the first strand of the second effector sequence (e.g., the sense strand of the second effector sequence) comprises no more than 10, no more than 9, no more than 8, no more than 7, no more than 6, no more than 5, no more than 4, no more than 3, no more than 2, or no more than 1 backbone modifications.

281. The dsDNA molecule of any of embodiments 203-280, wherein the second strand of the first effector sequence (e.g., the antisense strand of the first effector sequence) and/or the second strand of the second effector sequence (e.g., the antisense strand of the second effector sequence) comprises no more than 10, no more than 9, no more than 8, no more than 7, no more than 6, no more than 5, no more than 4, no more than 3, no more than 2, or no more than 1 nucleotides having a chemically modified sugar.

282. The dsDNA molecule of any of embodiments 203-281, wherein at least 80%, at least 85%, at least 90%, at least 95%, at least 98%, at least 99%, or 100% of the sugars of the dsDNA molecule are deoxyribose sugars.

283. The dsDNA molecule of any of embodiments 203-282, wherein all positions in the dsDNA molecule comprise a deoxyribose sugar.

284. The dsDNA molecule of any of embodiments 203-283, which comprises a chemical modification of a phosphate group.

285. The dsDNA molecule of any of embodiments 203-284, wherein one or more of the chemically modified nucleobases is conjugated to a peptide or protein.

286. The dsDNA molecule of any of embodiments 203-285, wherein the first effector and/or the second effector are each independently a polypeptide (e.g., a protein).

287. The dsDNA molecule of any of embodiments 203-285, wherein the first effector and/or the second effector are each independently an RNA (e.g., an mRNA, a tRNA, lncRNA, miRNA, rRNA, snRNA, microRNA, siRNA, piRNA, snoRNA, snRNA, exRNA, scaRNA, Y RNA, or hnRNA), wherein optionally the RNA is a functional RNA (e.g., a miRNA, siRNA, or tRNA).

288. The dsDNA molecule of any of embodiments 203-285, wherein the first effector is a polypeptide (e.g., a protein) and the second effector is an RNA (e.g., an mRNA, a tRNA, lncRNA, miRNA, rRNA, snRNA, microRNA, siRNA, piRNA, snoRNA, snRNA, exRNA, scaRNA, Y RNA, or hnRNA), wherein optionally the RNA is a functional RNA (e.g., a miRNA, siRNA, or tRNA).

289. The dsDNA molecule of any of embodiments 203-286, wherein the dsDNA molecule does not comprise a sequence encoding an RNA.

290. The dsDNA molecule of any of embodiments 203-289, wherein the first effector and/or the second effector are each independently heterologous to a target cell.

291. The dsDNA molecule of any of embodiments 203-290, wherein the dsDNA molecule comprises one or more of:

i) a heterologous functional sequence, e.g., a nuclear targeting sequence or a regulatory sequence;

ii) a maintenance sequence; and/or iii) an origin of replication.

292. The dsDNA molecule of embodiment 291, which comprises:

i, ii, and iii;

i and ii;

i and iii; or ii and iii.

293. The dsDNA molecule of any of embodiments 203-292, wherein the dsDNA molecule lacks a material portion of vector backbone (e.g., plasmid backbone).

294. The dsDNA molecule of any of embodiments 203-293, wherein the dsDNA molecule does not comprise a non-human (e.g., bacterial) origin of replication.

295. The dsDNA molecule of any of embodiments 203-294, wherein the dsDNA molecule does not comprise an antibiotic resistance selectable marker.

296. The dsDNA molecule of any of embodiments 203-295, wherein the dsDNA molecule is not supercoiled.

297. The dsDNA molecule of any of embodiments 203-296, wherein the first effector sequence and/or the second effector sequence does not encode a viral protein.

298. A population comprising a plurality of the dsDNA molecule of any of embodiments 203-297.

299. A pharmaceutical composition comprising the dsDNA molecule of any of embodiments 203-297 or the population of embodiment 298.

300. The pharmaceutical composition of embodiment 299, wherein the dsDNA molecule is unencapsidated.

301. The pharmaceutical composition of embodiment 299 or 300 or the dsDNA molecule of any of embodiments 203-297, wherein the dsDNA molecule does not comprise a viral ITR.

302. The pharmaceutical composition of any of embodiments 299-301, which is essentially free of (e.g., is free of) viral proteins.

303. The pharmaceutical composition of any of embodiments 299-302, wherein the dsDNA molecule is comprised in a lipid nanoparticle (LNP).

304. The pharmaceutical composition of any of embodiments 299-303, further comprising an electroporation buffer.

305. The pharmaceutical composition of any of embodiments 299-304, further comprising a transfection reagent.

306. A method of making DNA, the method comprising:

(a) providing a DNA strand comprising a second strand of a first effector sequence (e.g., an antisense strand of a first effector sequence), which is substantially free of chemically modified nucleotides, (b) providing a DNA strand comprising a second strand of a second effector sequence (e.g., an antisense strand of a second effector sequence), which is substantially free of chemically modified nucleotides, and (c) contacting the DNA strands of (a) and (b) with a DNA polymerase, chemically modified dNTPs, and optionally also canonical dNTPs under conditions allowing for production of first and second double stranded effector sequences.

307. The method of embodiment 306, wherein providing the DNA strands of (a) and (b) comprises:

(i) providing DNA that comprises a first effector sequence and a second effector sequence, wherein optionally the DNA further comprises a promoter region, (ii) performing two PCR reactions, wherein performing each PCR reaction comprises: contacting the DNA of (i) with a DNA polymerase, canonical deoxynucleoside triphosphates (dNTPs), and two primers, optionally wherein one of the primers is exonuclease-resistant (e.g., comprises phosphorothioate), and the other primer is exonuclease-sensitive (e.g., comprises canonical nucleotides), under conditions such that a first PCR amplicon comprising the first effector sequence is produced, and a second PCR amplicon comprising the second effector sequence is produced, and wherein each PCR amplicon comprises a second strand (e.g., antisense strand) optionally having an exonuclease-resistant end (e.g., a 5' exonuclease-resistant end) and a first strand (e.g., sense strand) optionally having exonuclease-sensitive ends, and wherein further optionally the first and second PCR amplicons have a region complementary (e.g., perfectly complementary) to each other; and (iii) isolating the second strand of each PCR amplicon (e.g., antisense strand of each PCR amplicon), e.g., by subjecting the first and second PCR amplicon of (ii) to conditions having exonuclease activity (e.g., with a 5' to 3' exonuclease), such that the first strand of each PCR amplicon is digested and the second strand of each PCR amplicon remains.

308. The method of embodiment 306 or 307, which further comprises converting the first and second double stranded effector sequences of (c) into a circular dsDNA.

309. The method of embodiment 308, wherein converting the first and second double stranded effector sequences into circular dsDNA comprises:

contacting the first and second double stranded effector sequences of (c) with a restriction enzyme under conditions that allow for production of compatible ends (e.g., compatible sticky ends), allowing for production of a digested first and second double stranded effector sequence, and contacting the digested first and second double stranded effector sequences with a ligase under conditions that allow for ligation of the compatible ends.

310. The method of any of embodiments 307-309, wherein the DNA of (i) is a plasmid.

311. The method of any of embodiments 307-310, wherein the DNA of (i) comprises a DNA molecule comprising the first effector sequence, the second effector sequence, and optionally a promoter region, wherein the first effector sequence and the second effector sequence are oriented to be transcribed in opposite directions.

312. The method of any of embodiments 307-311, wherein the promoter region is situated between the first effector sequence and the second effector sequence.

313. The method of any of embodiments 307-310, wherein the DNA of (i) comprises:

a first DNA molecule comprising the first effector sequence, and optionally a promoter region or a first promoter sequence and a second DNA molecule comprising the second effector sequence, and optionally a promoter region or a second promoter sequence.

314. The method of any of embodiments 307-313, wherein the exonuclease is a lambda exonuclease.

315. The method of any of embodiments 307-314, wherein the first primer that is exonuclease-resistant forms part of the DNA strand of (a).

316. The method of any of embodiments 307-315, wherein the second primer that is exonuclease-resistant forms part of the DNA strand of (b).

317. The method of any of embodiments 306-316, wherein the method comprises combining the DNA strand of (a) with the DNA strand of (b) under conditions that allow the strands to anneal to each other, thereby producing a DNA molecule comprising a double stranded region and two single stranded regions, prior to step (c).

318. The method of embodiment 317, wherein the double stranded region is a spacer region.

319. The method of embodiment 317, wherein the double stranded region is a promoter region.

320. The method of any of embodiments 306-319, wherein the first double stranded effector sequence produced in step (c) is part of the same DNA molecule as the second double stranded effector sequence produced in step (c).

321. The method of any of embodiments 306-316, wherein the first double stranded effector sequence produced in step (c) is a different DNA molecule from the second double stranded effector sequence produced in step (c).

322. The method of embodiment 321, wherein the method further comprises, after step (c), covalently linking the first double stranded effector sequence to the second double stranded effector sequence such that the first effector sequence and second effector sequence are oriented to be transcribed in opposite directions.

323. The method of embodiment 322, wherein covalently linking the first double stranded effector sequence to the second double stranded effector sequence comprises:

contacting each of the first double stranded effector sequence and the second double stranded effector sequence with one or two restriction enzymes under conditions that allow for production of a first digested double stranded effector sequence that comprises an upstream sticky end and a downstream sticky end, and a second digested double stranded effector sequence that comprises an upstream sticky end and a downstream sticky end, wherein the upstream sticky ends of the first and second double stranded effector sequences are compatible with each other, and wherein the downstream sticky ends of the first and second double stranded effector sequences are compatible with each other, but the upstream sticky ends are not compatible with the downstream sticky ends; and contacting the first digested double stranded effector sequence with the second digested double stranded effector sequence and with a ligase, under conditions that allow for ligation of the upstream sticky ends with each other, and ligation of the downstream sticky ends with each other.

324. The method of embodiment 320, wherein the method further comprises covalently linking a first closed end and a second closed end to the DNA molecule comprising the first double stranded effector sequence and the second double stranded effector sequence.

325. The method of embodiment 321 or 322, wherein the method further comprises covalently linking a first closed end to the DNA molecule comprising the first double stranded effector sequence, and a second closed end to the DNA molecule comprising the second double stranded effector sequence.

326. The method of embodiment 324, wherein the covalently linking comprises:

contacting each of: the DNA molecule comprising the first double stranded effector sequence and the second double stranded effector sequence, a first hairpin molecule, and a second hairpin molecule with one or two restriction enzymes under conditions that allow for production of a digested linear dsDNA and two digested hairpin molecules, wherein the digested linear dsDNA comprises a first sticky end and a second sticky end that is not compatible with the first sticky end, the first digested hairpin molecule comprises a third sticky end compatible with the first sticky end, the second digested hairpin molecule comprises a fourth sticky end compatible with the second sticky end, and contacting the digested linear dsDNA with the first and second digested hairpin molecules and with a ligase, under conditions that allow for ligation of the digested linear dsDNA to both hairpin molecules.

327. The method of embodiment 325, wherein the covalently linking comprises:

contacting each of: the DNA molecule comprising the first double stranded effector sequence, the DNA molecule comprising the second double stranded effector sequence, a first hairpin molecule, and a second hairpin molecule with one, two, or three restriction enzymes under conditions that allow for production of a first and second digested linear dsDNA molecules and two digested hairpin molecules, wherein:

the first digested linear dsDNA molecule comprises a first sticky end and a second sticky end that is not compatible with the first sticky end, the second digested linear dsDNA molecule comprises a third sticky end that is compatible with the second sticky end, and a fourth sticky end that is not compatible with the third sticky end, the first digested hairpin molecule comprises a fifth sticky end compatible with the first sticky end, and the second digested hairpin molecule comprises a sixth sticky end compatible with the fourth sticky end;

contacting the first digested linear dsDNA molecule with the second digested linear dsDNA molecule, the first digested hairpin molecule, and the second digested hairpin molecule and with a ligase, under conditions that allow for ligation of the first linear dsDNA molecule, the second digested linear dsDNA molecule, and both digested hairpin molecules.

328. The method of embodiment 326 or 327, wherein each hairpin molecule comprises a first stem sequence, a loop sequence, and a second stem sequence complementary to the first stem sequence.

329. The method of embodiment 324, wherein the covalently linking comprises:

contacting the molecule comprising the first double stranded effector sequence and the second double stranded effector sequence with one or two restriction enzymes under conditions that allow for production of a digested linear dsDNA that comprises a first sticky end and a second sticky end that is not compatible with the first sticky end, combining the digested linear dsDNA with a first hairpin molecule and a second hairpin molecule, wherein the first hairpin molecule comprises a first single-stranded region which is complementary to the first sticky end, and the second hairpin molecule comprises a second single-stranded region which is complementary to the second sticky end, and contacting the digested linear dsDNA and the first and second hairpin molecules with a ligase, under conditions that allow for ligation of the first sticky end with the first single-stranded region of the first hairpin molecule, and ligation of the second sticky end with the second single-stranded region of the second hairpin molecule.

330. The method of embodiment 325, wherein the covalently linking comprises:

contacting each of: the DNA molecule comprising the first double stranded effector sequence and the DNA molecule comprising the second double stranded effector sequence with one, two, or three restriction enzymes under conditions that allow for production of a first and second digested linear dsDNA molecule, wherein:

the first digested linear dsDNA molecule comprises a first sticky end and a second sticky end that is not compatible with the first sticky end, and the second digested linear dsDNA molecule comprises a third sticky end that is compatible with the second sticky end, and a fourth sticky end that is not compatible with the third sticky end, and combining the first digested linear dsDNA molecule with a first hairpin molecule and a second hairpin molecule, wherein the first hairpin molecule comprises a first single-stranded region which is complementary to the first sticky end, and the second hairpin molecule comprises a second single-stranded region which is complementary to the fourth sticky end, and contacting the first digested linear dsDNA molecule with the second digested linear dsDNA molecule, the first hairpin molecule, and the second hairpin molecule and with a ligase, under conditions that allow for ligation of the first sticky end with the first single-stranded region of the first hairpin molecule, ligation of the third sticky end with the second sticky end, and ligation of the fourth sticky end with the second single-stranded region of the second hairpin molecule.

331. The method of any of embodiments 309-330, wherein at least one (e.g., one, two, or three) of the restriction enzymes is a Type IIS restriction enzyme.

332. The method of any of embodiments 309-331, wherein at least one (e.g., one, two, or three) of the restriction enzymes is a Type II restriction enzyme other than a Type IIS restriction enzyme.

333. The method of any of embodiments 306-332, wherein the DNA strand of (a) further comprises a region that is not transcribed, e.g., a promoter region or a spacer region.

334. The method of any of embodiments 306-333, wherein the DNA strand of (b) further comprises a region that is not transcribed, e.g., a promoter region or a spacer region.

335. The method of any of embodiments 306-334, wherein the resulting DNA is a dsDNA molecule according to any of embodiments 203-297.

336. A composition comprising:

a first linear dsDNA molecule comprising a first effector sequence, wherein the first effector sequence has a first strand (e.g., a sense strand) that comprises one or more chemically modified nucleobases, and a second strand (e.g., an antisense strand) that is substantially free of chemically modified nucleobases, and wherein the first effector sequence encodes a first effector; and a second, separate linear dsDNA molecule comprising a second effector sequence, wherein the second effector sequence has a first strand (e.g., sense strand) that comprises one or more chemically modified nucleobases, and a second strand (e.g., antisense strand) that is substantially free of chemically modified nucleobases, and wherein the second effector sequence encodes a second effector.

337. The composition of embodiment 336, wherein the first linear dsDNA molecule comprises a first restriction site and a second restriction site at opposite ends, wherein the first and second restriction sites are not complementary to each other.
338. The composition of embodiment 336 or 337, wherein the second linear dsDNA molecule comprises a third restriction site and a fourth restriction site at opposite ends, wherein the third and fourth restriction sites are not complementary to each other, and wherein the first restriction site is complementary to the third restriction site, and the second restriction site is complementary to the fourth restriction site.
339. A method of expressing a first effector and/or a second effector in a target cell, the method comprising:
(i) introducing into a target cell the dsDNA molecule, population, or composition (e.g., pharmaceutical composition) of any of embodiments 203-305, or a dsDNA molecule made by the method of any of embodiments 306-335; and
(ii) maintaining (e.g., incubating) the cell under conditions suitable for expressing the first effector and/or the second effector from the dsDNA molecule;
thereby expressing the first effector and/or the second effector in the target cell.
340. A method of delivering a dsDNA molecule in a target cell, the method comprising:
contacting a target cell with the dsDNA molecule, population, or composition (e.g., pharmaceutical composition) of any of embodiments 203-305, or a dsDNA molecule made by the method of any of embodiments 306-335;
thereby delivering the dsDNA molecule to the target cell.
341. A method of delivering a first effector and/or a second effector in a target cell, the method comprising:
contacting a target cell with the dsDNA molecule, population, or composition (e.g., pharmaceutical composition) of any of embodiments 203-305, or a dsDNA molecule made by the method of any of 306-335;
thereby delivering the first effector and/or the second effector to the target cell.
342. A method of modulating (e.g., increasing or decreasing) a biological activity in a target cell, the method comprising:
(i) providing a target cell comprising the dsDNA molecule, population, or composition (e.g., pharmaceutical composition) of any of embodiments 203-305, or a dsDNA molecule made by the method of any of embodiments 306-335;
(ii) maintaining (e.g., incubating) the cell under conditions suitable for expression the first effector and/or the second effector from the dsDNA molecule;
thereby modulating the biological activity in the target cell.
343. The method of embodiment 342, wherein the first effector and/or the second effector increases the biological activity in the target cell.
344. The method of embodiment 342, wherein the first effector and/or the second effector decreases the biological activity in the target cell.
345. The method of any of any of embodiments 342-344, wherein the biological activity comprises cell growth, cell metabolism, cell signaling, cell movement, specialization, interactions, division, transport, homeostasis, osmosis, or diffusion.
346. The method of any of embodiments 339-345, wherein the target cell is an animal cell, e.g., a mammalian cell, e.g., a human cell.
347. A method of treating a cell, tissue, or subject in need thereof, the method comprising:
administering to the cell, tissue, or subject the dsDNA molecule, population, or composition (e.g., pharmaceutical composition) of any of embodiments 203-305, or a dsDNA molecule made by the method of any of embodiments 306-335;
thereby treating the cell, tissue, or subject.
348. The method of any of embodiments 339-347, which is performed ex vivo or in vivo.
349. The method of any of embodiments 187-194 or 339-348, which further comprises administering to the subject a plurality of bubbles having an average diameter less than 10 m.
350. The method of any of embodiments 187-194 or 339-349, which further comprises performing ultrasound, e.g., focused ultrasound (FUS), on a tissue in the subject.
351. A method of delivering a DNA molecule into a target cell of a tissue in a subject, the method comprising, in combination:
a) administering to the subject a DNA molecule, wherein the DNA molecule:
comprises a first strand (e.g., sense strand) and a second strand (e.g., antisense strand), and wherein
the first strand comprises one or more chemically modified nucleobases, and
the second strand is substantially free of (e.g., is free of) chemically modified nucleobases;
b) administering to the subject a plurality of bubbles having an average diameter less than 10 μm; and
c) performing ultrasound, e.g., focused ultrasound (FUS), on the tissue;
thereby delivering the DNA molecule into the target cell.
352. A method of delivering a DNA molecule into a target cell of a tissue in a subject, the method comprising, in combination:
a) administering to the subject the DNA molecule (e.g., dsDNA molecule), composition (e.g., pharmaceutical composition), plurality, or population of any of embodiments 1-137, 168-186, 195, 196, or 203-305;
b) administering to the subject a plurality of bubbles having an average diameter less than 10 μm; and
c) performing ultrasound (e.g., FUS) on the tissue;
thereby delivering the DNA molecule into the target cell.
353. A composition comprising:
a) a DNA molecule, wherein the DNA molecule:
comprises a first strand (e.g., sense strand) and a second strand (e.g., antisense strand), and wherein
the first strand comprises one or more chemically modified nucleobases, and
the second strand is substantially free of (e.g., is free of) chemically modified nucleobases; and
b) a plurality of bubbles having an average diameter of 10 m or less.
354. A composition comprising:
a) the DNA molecule (e.g., dsDNA molecule), composition (e.g., pharmaceutical composition), plurality, or population of any of embodiments 1-137, 168-186, 195, 196, or 203-305; and
b) a plurality of bubbles having an average diameter less than 10 m.

355. A kit comprising:
a) a DNA molecule, wherein the DNA molecule:
comprises a first strand (e.g., sense strand) and a second strand (e.g., antisense strand), and wherein the first strand comprises one or more chemically modified nucleobases, and
the second strand is substantially free of (e.g., is free of) chemically modified nucleobases; and
b) a plurality of bubbles having an average diameter of 10 m or less.

356. A kit comprising:
a) a DNA molecule, wherein the DNA molecule:
comprises a first strand (e.g., sense strand) and a second strand (e.g., antisense strand), and wherein the first strand comprises one or more chemically modified nucleobases, and
the second strand is substantially free of (e.g., is free of) chemically modified nucleobases; and
b) a means for performing ultrasound (e.g., FUS).

357. A kit comprising:
a) the DNA molecule (e.g., dsDNA molecule), composition (e.g., pharmaceutical composition), plurality, or population of any of embodiments 1-137, 168-186, 195, 196, or 203-305; and
b) a plurality of bubbles having an average diameter less than 10 m.

358. The method, composition, or kit of any of embodiments 351-357, wherein the DNA molecule comprises:
a) an upstream DNA end form which is a closed end;
b) a double stranded region comprising a first strand (e.g., sense strand) and a second strand (e.g., antisense strand); and
c) a downstream DNA end form which is a closed end.

359. The method, composition, or kit of embodiment 358, wherein the first strand (e.g., sense strand) comprises one or more (e.g., at least 3) backbone modifications, e.g., phosphorothioate linkages.

360. The method, composition, or kit of embodiment 359, wherein:
the one or more backbone modifications are situated between the 2, 3, 4, 5, 6, 7, 8, 9, or 10 nucleotides adjacent to the upstream DNA end form; and/or
the one or more backbone modifications are situated between the 2, 3, 4, 5, 6, 7, 8, 9, or 10 nucleotides adjacent to the downstream DNA end form.

361. The method, composition, or kit of any of embodiments 351-357, wherein the DNA molecule is circular and double stranded.

362. The method, composition, or kit of any of embodiments 351-361, wherein the DNA molecule comprises a promoter sequence and an effector sequence that encodes an effector (e.g., a therapeutic effector).

363. The method, composition, or kit of embodiment 362, wherein the effector is an exogenous agent.

364. The method of any of embodiments 351, 352, or 358-363, wherein step b) is performed after step a), and step c) is performed after step b).

365. The method of any of embodiments 351, 352, or 358-363, wherein step a) is performed after step b), and step c) is performed after step a).

366. The method of any of embodiments 351, 352, or 358-363, wherein steps a) and b) are performed concurrently, e.g., simultaneously, and wherein step c) is performed after steps a) and b).

367. The method of any of embodiments 351, 352, or 358-363, wherein steps a), b), and c) are performed concurrently, e.g., simultaneously.

368. The method of any of embodiments 351, 352, or 358-363, wherein steps b) and c) are performed concurrently, e.g., simultaneously, and wherein steps b) and c) are performed after step a).

369. The method of any of embodiments 351, 352, or 358-363, wherein steps a) and c) are performed concurrently, e.g., simultaneously, and wherein steps a) and c) are performed after step b).

370. The method of any of embodiments 351, 352, or 358-369, wherein step c) is initiated less than 70 minutes after step a) is initiated, e.g., less than 1 second, less than 5 seconds, less than 10 seconds, less than 20 seconds, less than 30 seconds, less than 1 minute, less than 2 minutes, less than 3 minutes, less than 4 minutes, less than 5 minutes, less than 6 minutes, less than 7 minutes, less than 8 minutes, less than 9 minutes, less than 10 minutes, less than 15 minutes, less than 20 minutes, less than 25 minutes, less than 30 minutes, less than 35 minutes, less than 40 minutes, less than 45 minutes, less than 50 minutes, less than 55 minutes, less than 60 minutes, or less than 65 minutes after step a) is initiated.

371. The method of any of embodiments 351, 352, or 358-370, wherein step c) is initiated between 0 seconds and 5 seconds, between 5 seconds and 10 seconds, between 10 seconds and 20 seconds, between 20 seconds and 30 seconds, between 30 seconds and 1 minute, between 1 minute and 5 minutes, between 5 minutes and 10 minutes, between 10 minutes and 20 minutes, between 20 minutes and 30 minutes, between 30 minutes and 40 minutes, between 40 minutes and 50 minutes, between 50 minutes and 60 minutes, between 60 minutes and 70 minutes, between 0 seconds and 30 seconds, between 0 seconds and 5 minutes, or between 0 seconds and 10 minutes after step a) is initiated.

372. The method of any of embodiments 351, 352, or 358-371, wherein step c) is initiated less than 70 minutes after step b) is initiated, e.g., less than 1 second, less than 5 seconds, less than 10 seconds, less than 20 seconds, less than 30 seconds, less than 1 minute, less than 2 minutes, less than 3 minutes, less than 4 minutes, less than 5 minutes, less than 6 minutes, less than 7 minutes, less than 8 minutes, less than 9 minutes, less than 10 minutes, less than 15 minutes, less than 20 minutes, less than 25 minutes, less than 30 minutes, less than 35 minutes, less than 40 minutes, less than 45 minutes, less than 50 minutes, less than 55 minutes, less than 60 minutes, or less than 65 minutes after step b) is initiated.

373. The method of any of embodiments 351, 352, or 358-372, wherein step c) is initiated between 0 seconds and 5 seconds, between 5 seconds and 10 seconds, between 10 seconds and 20 seconds, between 20 seconds and 30 seconds, between 30 seconds and 1 minute, between 1 minute and 5 minutes, between 5 minutes and 10 minutes, between 10 minutes and 20 minutes, between 20 minutes and 30 minutes, between 30 minutes and 40 minutes, between 40 minutes and 50 minutes, between 50 minutes and 60 minutes, between 60 minutes and 70 minutes, between 0 seconds and 30 seconds, between 0 seconds and 5 minutes, or between 0 seconds and 10 minutes after step b) is initiated.

374. The method of any of embodiments 351, 352, or 358-373, wherein step c) is initiated less than 70 minutes after step a) and step b) are initiated, e.g., less than 1 second, less than 5 seconds, less than 10 seconds, less than 20 seconds, less than 30 seconds, less than 1 minute, less than 2 minutes, less than 3 minutes, less than 4 minutes, less than 5 minutes, less than 6 minutes, less than 7 minutes, less than 8 minutes, less than 9 minutes, less than 10 minutes, less than 15 minutes, less than 20 minutes, less than 25 minutes, less than 30 minutes, less than 35 minutes, less than 40 minutes, less than 45 minutes, less than 50 minutes, less than 55 minutes, less than 60 minutes, or less than 65 minutes after step a) and step b) are initiated.

375. The method of any of embodiments 351, 352, or 358-374, wherein step c) is initiated between 0 seconds and 5 seconds, between 5 seconds and 10 seconds, between 10 seconds and 20 seconds, between 20 seconds and 30 seconds, between 30 seconds and 1 minute, between 1 minute and 5 minutes, between 5 minutes and 10 minutes, between 10 minutes and 20 minutes, between 20 minutes and 30 minutes, between 30 minutes and 40 minutes, between 40 minutes and 50 minutes, between 50 minutes and 60 minutes, between 60 minutes and 70 minutes, between 0 seconds and 30 seconds, between 0 seconds and 5 minutes, or between 0 seconds and 10 minutes after step a) and step b) are initiated.

376. The method of any of embodiments 351, 352, 358-364, 366-368, or 370-375, wherein step b) is initiated less than 85 minutes after step a), e.g., less than 1 second, less than 5 seconds, less than 10 seconds, less than 20 seconds, less than 30 seconds, less than 1 minute, less than 2 minutes, less than 3 minutes, less than 4 minutes, less than 5 minutes, less than 6 minutes, less than 7 minutes, less than 8 minutes, less than 9 minutes, less than 10 minutes, less than 15 minutes, less than 20 minutes, less than 25 minutes, less than 30 minutes, less than 35 minutes, less than 40 minutes, less than 45 minutes, less than 50 minutes, less than 55 minutes, less than 60 minutes, less than 65 minutes, less than 70 minutes, less than 75 minutes, or less than 80 minutes after step a) is initiated.

377. The method of any of embodiments 351, 352, 358-364, 366-368, or 370-376, wherein step b) is initiated between 0 seconds and 5 seconds, between 5 seconds and 10 seconds, between 10 seconds and 20 seconds, between 20 seconds and 30 seconds, between 30 seconds and 1 minute, between 1 minute and 5 minutes, between 5 minutes and 10 minutes, between 10 minutes and 20 minutes, between 20 minutes and 30 minutes, between 30 minutes and 40 minutes, between 40 minutes and 50 minutes, between 50 minutes and 60 minutes, between 60 minutes and 70 minutes, between 0 seconds and 30 seconds, between 0 seconds and 5 minutes, or between 0 seconds and 10 minutes after step a) is initiated.

378. The method of any of embodiments 351, 352, 358-363, 365-367, or 369-375, wherein step a) is initiated less than 85 minutes after step b), e.g., less than 1 second, less than 5 seconds, less than 10 seconds, less than 20 seconds, less than 30 seconds, less than 1 minute, less than 2 minutes, less than 3 minutes, less than 4 minutes, less than 5 minutes, less than 6 minutes, less than 7 minutes, less than 8 minutes, less than 9 minutes, less than 10 minutes, less than 15 minutes, less than 20 minutes, less than 25 minutes, less than 30 minutes, less than 35 minutes, less than 40 minutes, less than 45 minutes, less than 50 minutes, less than 55 minutes, less than 60 minutes, less than 65 minutes, less than 70 minutes, less than 75 minutes, or less than 80 minutes after step b) is initiated.

379. The method of any of embodiments 351, 352, 358-363, 365-367, 369-375, or 378, wherein step a) is initiated between 0 seconds and 5 seconds, between 5 seconds and 10 seconds, between 10 seconds and 20 seconds, between 20 seconds and 30 seconds, between 30 seconds and 1 minute, between 1 minute and 5 minutes, between 5 minutes and 10 minutes, between 10 minutes and 20 minutes, between 20 minutes and 30 minutes, between 30 minutes and 40 minutes, between 40 minutes and 50 minutes, between 50 minutes and 60 minutes, between 60 minutes and 70 minutes, between 0 seconds and 30 seconds, between 0 seconds and 5 minutes, or between 0 seconds and 10 minutes after step b) is initiated.

380. The method of any of embodiments 349-379, wherein the DNA molecule is delivered into a plurality of target cells of the tissue.

381. The method or kit of any of embodiments 349-352 or 355-380, wherein the DNA molecule and the plurality of bubbles are present in the same volume.

382. The method or kit of any of embodiments 349-352 or 355-380, wherein the DNA molecule in a first volume, and the plurality of bubbles is present in a second volume.

383. The method, composition, or kit of any of embodiments 349-382, wherein the bubbles comprise a gas comprising octafluoropropane, sulfur hexafluoride, perfluorobutane, perfluoropentane, perfluorohexane, nitrogen, a noble gas (e.g., xenon, helium, or argon), or air.

384. The method, composition, or kit of any of embodiments 349-383, wherein the bubbles comprise an exterior layer comprising a lipid (e.g., phospholipid), albumin (e.g., human albumin or bovine albumin), palmitic acid, lysozyme, casein, or PEG (polyethylene glycol).

385. The method, composition, or kit of embodiment 384, wherein the exterior layer comprises DPPC, 1,2-Dipalmitoyl-sn-glycero-3-phosphate (DPPA), DPPE-methoxyPEG5000 (DPPE-MPEG5000), DSPC, DPPG-Na, hydrogenated egg yolk phosphatidylserine, DSPG, DSPE, or DSPE-PEG2000.

386. The method, composition, or kit of any of embodiments 349-385, wherein the bubbles are situated in a solvent, e.g., a biocompatible solvent.

387. The method of any of embodiments 351, 352, or 358-386, wherein step c) comprises performing FUS on the tissue.

388. The method of any of embodiments 350-352 or 358-387, wherein the ultrasound (e.g., focused ultrasound) is performed at a frequency of 0.2-3 MHz.

389. The method of any of embodiments 350-352 or 358-387, wherein the ultrasound (e.g., focused ultrasound) is performed at a frequency of about 2 MHz to about 40 MHz (e.g., about 20 MHz).

390. The method of embodiment 388, wherein the ultrasound (e.g., focused ultrasound) is performed at a frequency of 0.2 to 0.5 MHz, 0.5 to 1.0 MHz, 1.0 to 1.5 MHz, 1.5 to 2.0 MHz, 2.0 to 2.5 MHZ, or 2.5 to 3.0 MHz.

391. The method of any of embodiments 350-352 or 358-390, wherein the ultrasound is performed with a focused ultrasound transducer.

392. The method of any of embodiments 350-352 or 358-391, wherein the ultrasound (e.g., focused ultrasound) is performed at 5 μs to 0.5 s, e.g., 100 μs to 0.5 s, e.g., 5 ms to 20 ms, e.g., 10 ms, bursts.

393. The method of any of embodiments 350-352 or 358-392, wherein the ultrasound (e.g., focused ultrasound) is performed at a pulse repetition frequency of 0.1 to 10 Hz, e.g., 0.1 to 1.0 Hz, e.g., 0.5 Hz.

394. The method of any of embodiments 350-352 or 358-393, wherein the ultrasound (e.g., focused ultrasound) is performed at a peak negative pressure of 0.1 to 2.0 MPa.

395. The method of any of embodiments 350-352 or 358-394, wherein the ultrasound (e.g., focused ultrasound) is performed at a peak negative pressure of 0.1 to 0.5 MPa, 0.5 to 1.0 MPa, 1.0 to 1.5 MPa, or 1.5 to 2.0 MPa.

396. The method of any of embodiments 350-352 or 358-395, wherein the ultrasound (e.g., focused ultrasound) is performed for 1 minute to 10 minutes, e.g., 1 minute to 3 minutes, 3 minutes to 5 minutes, or 5 minutes to 10 minutes, e.g., about 2 minutes.

397. The method of any of embodiments 350-352 or 358-396, wherein the DNA molecule is delivered into the nucleus of the target cell.

398. The method of any of embodiments 350-352 or 358-397, wherein the target cell is a non-dividing cell.

399. The method of any of embodiments 350-352 or 358-397, wherein the target cell is a dividing cell.

400. The method of any of embodiments 350-352 or 358-399, wherein the target cell is a hepatocyte, immune cell, neuron, glial cell, ependymal cell, pancreatic islet cell (e.g., alpha, beta, or delta cell), cardiomyocyte, skeletal myocyte, skeletal satellite cell, podocytes, tubular epithelial cell, endothelial cell, fibroblast, or tumor cell.

401. The method of any of embodiments 350-352 or 358-400, wherein the tissue is liver tissue, spleen tissue, brain tissue, pancreatic tissue, heart tissue, skeletal muscle tissue, kidney tissue, tumor tissue, breast tissue, or skin tissue.

402. The method, composition, or kit of any of embodiments 349-401, wherein the DNA molecule is comprised in a lipid nanoparticle (LNP).

403. The method, composition, or kit of any of embodiments 349-401, wherein the DNA molecule is not comprised in an LNP.

404. The method of any of embodiments 349-352 or 358-403, wherein the bubbles are administered to the subject at a concentration of $10^7$ bubbles/mL solvent to $10^{10}$ bubbles/mL solvent, e.g., about $10^9$ bubbles/mL solvent.

405. The method of any of embodiments 349-352 or 358-404, wherein the bubbles are administered to the subject at a volume of about 0.5 mL to about 5 mL.

406. The method of any of embodiments 349-352 or 358-405, wherein the bubbles are administered to the subject at a final concentration of $1\times10^4$ bubbles/g to $1\times10^7$ bubbles/g.

407. The method of any of embodiments 349-352 or 358-406, wherein the DNA molecule and bubbles are administered to the subject at a ratio of between $10^5$:1 to $10^{10}$:1 DNA molecules:microbubbles.

408. The method, composition, or kit of any of embodiments 349-407, wherein the plurality of bubbles have an average diameter of 50 nm to 10 m, 50 nm to 100 nm, or 1 m to 10 m.

409. The method of any of embodiments 349-352 or 358-408, which further comprises performing an imaging step.

410. The method of embodiment 409, wherein the imaging step comprises magnetic resonance imaging (MRI).

411. The method of any of embodiments 349-352 or 358-410, wherein the DNA molecule and/or the plurality of bubbles are administered intravenously.

412. The method of any of embodiments 349-352 or 358-411, wherein the DNA molecule and/or the plurality of bubbles are administered to the tissue via intravenous (IV) infusion or IV bolus.

413. The method of any of embodiments 351, 352, or 358-412, wherein step (a) comprises intravenously injecting the DNA molecule such that the DNA molecule reaches the tissue.

414. The method of any of embodiments 349-352 or 358-410, wherein the DNA molecule is administered by injection into the tissue.

415. The method of any of embodiments 349-352, 358-410, or 414, wherein the DNA molecule is administered intramuscularly or intratumorally.

416. The method of any of embodiments 351, 352, or 358-415, wherein step c) is performed on a volume of the tissue of between 10-50,000 $mm^3$.

417. The dsDNA molecule, pharmaceutical composition, method, composition, plurality, or kit of any of embodiments 1-141, 143-194, or 349-416, wherein the first strand is a sense strand and the second strand is an antisense strand.

418. The dsDNA molecule, pharmaceutical composition, method, composition, plurality, or kit of any of embodiments 1-141, 143-194, or 349-416, wherein the first strand is an antisense strand and the second strand is a sense strand.

419. The dsDNA molecule, population, pharmaceutical composition, method, composition, or kit of any of embodiments 203-350, 352, 354, or 357-416, wherein the first strand of the first effector sequence is a sense strand, the second strand of the first effector sequence is an antisense strand, the first strand of the second effector sequence is a sense strand, and the second strand of the second effector sequence is an antisense strand.

420. The dsDNA molecule, population, pharmaceutical composition, method, composition, or kit of any of embodiments 203-350, 352, 354, or 357-416, wherein the first strand of the first effector sequence is an antisense strand, the second strand of the first effector sequence is a sense strand, the first strand of the second effector sequence is an antisense strand, and the second strand of the second effector sequence is a sense strand.

421. The pharmaceutical composition of any of embodiments 3-137, 169, 172-183, 185, 186, 299-302, 304, 305, or 417-420, which is substantially free of (e.g., is free of) lipids.

422. The method of any of embodiments 187-194, 339-352, or 358-420, which further comprises administering or delivering a protein or a second nucleic acid molecule encoding the protein.

423. The method of embodiment 422, wherein the protein is an enzyme, a DNA-binding protein, an RNA-binding protein, a nuclear protein, a cytoplasmic protein, a kinase, a phosphatase, a structural protein, an antigen, or an antibody.

424. The method of embodiment 422 or 423, wherein the second nucleic acid molecule is RNA (e.g., mRNA or circular RNA) or DNA.

425. The method of any of embodiments 422-424, which further comprises administering or delivering a third nucleic acid molecule (e.g., an RNA or DNA).

426. The pharmaceutical composition of any of embodiments 3-137, 169, 172-186, 299-305, 417, 418, or 421, which further comprises a protein or a second nucleic acid molecule encoding the protein.
427. The pharmaceutical composition of embodiment 426, wherein the protein is an enzyme, a DNA-binding protein, an RNA-binding protein, a nuclear protein, a cytoplasmic protein, a kinase, a phosphatase, a structural protein, an antigen, or an antibody.
428. The pharmaceutical composition of embodiment 426 or 427, wherein the second nucleic acid molecule is RNA (e.g., mRNA or circular RNA) or DNA.
429. The pharmaceutical composition of any of embodiments 426-428, which further comprises a third nucleic acid molecule (e.g., an RNA or DNA).
430. A dsDNA molecule produced by the method of any of embodiments 306-335.

Definitions

As used herein, the term "5' untranslated region" (5' UTR) refers to a region of an mRNA or pre-mRNA that is transcribed but not translated, and is 5' of the coding region. Similarly, the term "3' untranslated region" (3' UTR) refers to a region of an mRNA or pre-mRNA that is transcribed but not translated, and is 3' of the coding region.

As used herein the term "polyadenylation site" refers to a segment of an mRNA or pre-mRNA that recruits polyadenylation machinery. A polyadenylation site typically includes one or more AAUAAA polyadenylation signals. A polyadenylation site may also include a GU-rich region. An exemplary polyadenylation is the Bovine growth hormone PolyA sequence of SEQ ID NO: 3.

As used herein, a first nucleotide being "adjacent" to a second nucleotide means that there are no nucleotides situated between the first and second nucleotide. The two nucleotides may be connected by, for instance, a phosphate linkage or a phosphorothioate linkage. When a plurality of nucleotides is described as being adjacent to a given nucleotide, it is understood that one nucleotide of the plurality (either the 5' most or the 3' most nucleotide of the plurality) is adjacent to the given nucleotide, and that each nucleotide of the plurality is adjacent to at least one other nucleotide in the plurality.

As used herein, the term "antibody" refers to a molecule that specifically binds to, or is immunologically reactive with, a particular antigen and includes at least the variable domain of a heavy chain, and normally includes at least the variable domains of a heavy chain and of a light chain of an immunoglobulin. Antibodies and antigen-binding fragments, variants, or derivatives thereof include, but are not limited to, polyclonal, monoclonal, multispecific, human, humanized, primatized, or chimeric antibodies, heteroconjugate antibodies (e.g., bi- tri- and quad-specific antibodies, diabodies, triabodies, and tetrabodies), single-domain antibodies (sdAb), epitope-binding fragments, e.g., Fab, Fab' and F(ab').sub.2, Fd, Fvs, single-chain Fvs (scFv), rlgG, single-chain antibodies, disulfide-linked Fvs (sdFv), nanobody, fragments including either a VL or VH domain, fragments produced by an Fab expression library, and anti-idiotypic (anti-Id) antibodies. Antibodies described herein can be of any type (e.g., IgG, IgE, IgM, IgD, IgA, and IgY), class (e.g., IgG1, IgG2, IgG3, IgG4, IgAQ1 and IgA2) or subclass of immunoglobulin molecule. Moreover, unless otherwise indicated, the term "monoclonal antibody" (mAb) is meant to include both intact molecules as well as antibody fragments (such as, for example, Fab and F(ab')2 fragments) that are capable of specifically binding to a target protein. Fab and F(ab')2 fragments lack the Fc fragment of an intact antibody.

As used herein, the term "backbone modification" refers to a chemical modification to the backbone of a DNA molecule. In some embodiments, the backbone modification is a chemical modification to a phosphate group, e.g., phosphorothioate. In some embodiments, the backbone modification is a chemical modification to deoxyribose.

As used herein, the term "carrier" means a compound, composition, reagent, or molecule that facilitates or promotes the transport or delivery of a composition (e.g., a dsDNA molecule described herein) into a cell. For example, a carrier may be a partially or completely encapsulating agent.

As used herein, the term "chemically modified nucleotide" as used herein with respect to DNAs, refers to a nucleotide comprising one or more structural differences relative to the canonical deoxyribonucleotides (i.e., G, T, C, and A). A chemically modified nucleotide may have (relative to a canonical nucleotide) a chemically modified nucleobase, a chemically modified sugar, a chemically modified phosphodiester linkage, or a combination thereof. No particular process of making is implied; for instance, a chemically modified nucleotide can be produced directly by chemical synthesis, or by covalently modifying a canonical nucleotide.

As used herein, the term "chemically modified nucleobase" as used herein with respect to DNAs, refers to a nucleobase comprising one or more structural differences relative to the canonical nucleobases (i.e., guanine, thymine, cytosine, and adenine). No particular process of making is implied; for instance, a chemically modified nucleobase can be produced directly by chemical synthesis, or by covalently modifying a canonical nucleobase. A canonical uracil present in DNA is considered a chemically modified nucleobase under this definition.

As used herein, the term "chemically modified cytosine nucleobase," as used herein with respect to DNAs, refers to a chemically modified nucleobase wherein the nucleobase comprises a monocyclic 6-member ring in which carbon 4 is covalently bound to a nitrogen that is not one of the six members of the ring, wherein the nucleobase comprises one or more structural differences relative to canonical cytosine nucleobase. In some embodiments, the C-5 position of the nucleobase can have a substitution other than H. For example, the C-5 position of the nucleobase can have a substitution of —OH; -aldehyde; -carboxylic acid; -alkyl; $—(CH_2)_mOR_3$, m=1-3 and $R_3$=H or a sugar molecule; or -propargylamino. No particular process of making is implied.

As used herein, the term "chemically modified uracil nucleobase" as used herein with respect to DNAs, refers to a chemically modified nucleobase wherein the nucleobase comprises a monocyclic 6-member ring in which carbon 4 is covalently bound to an oxygen through a double bond, and wherein the nucleobase comprises one or more structural differences relative to canonical uracil and thymine nucleobases. In some embodiments, the C-5 position of the nucleobase can have a substitution other than H or a methyl group. For example, the C-5 position of the nucleobase can have a substitution of $CH_2OH$; -aminoallyl; -propargylamino; or -dihydroxypentyl. No particular process of making is implied.

As used herein, the term "uracil nucleobase" encompasses both canonical uracil nucleobases and chemically modified uracil nucleobases.

As used herein the term "circular" in reference to a dsDNA described herein, means a dsDNA that lacks a free end. A circular dsDNA may be covalently closed. The term circular does not imply that the DNA would appear as a perfect geometric circle under a microscope; for instance, a circular dsDNA may be supercoiled. In some embodiments, the circular dsDNA comprises a first strand that is circular and lacks a free end, and a second strand that is circular and lacks a free end, and the first strand and second strand hybridize with each other.

Administered or performed "in combination", as used herein, means that two or more different compositions (e.g., a DNA molecule as described herein or a plurality of bubbles) and/or treatments (e.g., ultrasound, e.g., FUS) are administered to and/or performed on a subject such that a tissue in the subject is in contact with or exposed to both or all of the compositions and/or treatments for a period of time. In some embodiments, the administration of one composition or performance of one treatment is still occurring when the administration or performance of a second composition or treatment begins, so that there is overlap in terms of administration or performance. In some embodiments, the administration of a composition ends before the performance of a treatment or administration of a second composition begins; however the tissue is still in contact with the first-administered composition when the treatment is performed or when the tissue is in contact with the second-administered composition. In some embodiments, the treatment or composition is more effective because of combined performance or administration. For example, one of the treatments or compositions is more effective, e.g., an equivalent effect is seen with less of the treatment or composition, or the treatment or composition reduces symptoms to a greater extent, than would be seen if the treatment or composition were performed or administered in the absence of at least one of the other treatments or compositions. In some embodiments, administration or performance is such that the reduction in a symptom, or other parameter related to a disorder is greater than what would be observed with one treatment performed or composition administered in the absence of at least one of the other treatments or compositions. The effect of the two treatments or compositions can be partially additive, wholly additive, or greater than additive. The administration or performance can be such that an effect of the first composition administered is still detectable when a treatment is performed or administration of a second composition is administered.

As used herein, the term "free end" in reference to a DNA described herein, refers to an end of a DNA strand where the terminal nucleotide is covalently bound to exactly one other nucleotide.

As used herein, the term "closed end" refers to a portion of a DNA molecule positioned at one end of a double-stranded region, in which all nucleotides within the portion of the DNA molecule are covalently attached to adjacent nucleotides on either side. A closed end may, in some embodiments, include a loop comprising one or more nucleotides that are not hybridized to another nucleotide. In some embodiments, every nucleotide of the closed end is hybridized to another nucleotide. In some embodiments, a dsDNA molecule comprises a first closed end (e.g., upstream of a heterologous object sequence) and a second closed end (e.g., downstream of a heterologous object sequence).

As used herein, the term "DNA" refers to any compound and/or substance that comprises at least two (e.g., at least 10, at least 20, at least 50, at least 100) covalently linked deoxyribonucleotides. In some embodiments, the DNA is a single oligonucleotide chain, while in other embodiments, the DNA comprises a plurality of oligonucleotide chains, while in yet other embodiments the DNA is a portion of an oligonucleotide chain. In some embodiments, DNA is a compound and/or substance that is or can be incorporated into an oligonucleotide chain via a phosphodiester linkage. In some embodiments, the DNA comprises solely canonical nucleotides. In some embodiments, the DNA comprises one or more chemically modified nucleotides. In some embodiments, at least 80%, at least 85%, at least 90%, at least 95%, at least 98%, at least 99%, or 100% of the sugars of the DNA are deoxyribose sugars. In some embodiments, the DNA was prepared by one or more of: isolation from a natural source, enzymatic synthesis by polymerization based on a complementary template (in vivo or in vitro), reproduction in a recombinant cell or system, and chemical synthesis.

As used herein, the term "effector sequence" refers to the part of a DNA molecule that exerts a function on a cell, either directly (wherein the effector sequence is a functional DNA sequence) or by encoding a functional RNA or protein. The encoded functional RNA or protein is referred to as the "effector".

As used herein, the term "heterologous", when used to describe a first element in reference to a second element means that the first element and second element do not exist in nature disposed as described. For example, a heterologous polypeptide, nucleic acid molecule, construct or sequence refers to (a) a polypeptide, nucleic acid molecule or portion of a polypeptide or nucleic acid molecule sequence that is not native to a cell in which it is expressed, (b) a polypeptide or nucleic acid molecule or portion of a polypeptide or nucleic acid molecule that has been altered or mutated relative to its native state, or (c) a polypeptide or nucleic acid molecule with an altered expression as compared to the native expression levels under similar conditions. For example, a heterologous regulatory sequence (e.g., promoter, enhancer) may be used to regulate expression of a gene or a nucleic acid molecule in a way that is different than the gene or a nucleic acid molecule is normally expressed in nature. In another example, a heterologous domain of a polypeptide or nucleic acid sequence (e.g., a DNA binding domain of a polypeptide or nucleic acid encoding a DNA binding domain of a polypeptide) may be disposed relative to other domains or may be a different sequence or from a different source, relative to other domains or portions of a polypeptide or its encoding nucleic acid. In certain embodiments, a heterologous nucleic acid molecule may exist in a native host cell genome, but may have an altered expression level or have a different sequence or both. In other embodiments, heterologous nucleic acid molecules may not be endogenous to a host cell or host genome but instead may have been introduced into a host cell by transformation (e.g., transfection, electroporation), wherein the added molecule may integrate into the host genome or can exist as extra-chromosomal genetic material either transiently (e.g., mRNA) or semi-stably for more than one generation (e.g., episomal viral vector, plasmid or other self-replicating vector).

As used herein, the term "heterologous functional sequence" refers to a nucleic acid sequence that is heterologous to a nearby (e.g., adjacent) nucleic acid sequence and has one or more biological function. In some embodiments, the biological function comprises targeting to an organelle, e.g., nuclear targeting. In some embodiments, the heterologous functional sequence comprises a nuclear targeting sequence or a regulatory sequence.

As used herein, the terms "increasing" and "decreasing" refer to modulating resulting in, respectively, greater or lesser amounts, of function, expression, or activity of a metric relative to a reference. For example, subsequent to administration of a dsDNA molecule in a method described herein, the amount of the metric described herein (e.g., the level of gene expression, or a marker of innate immunity) may be increased or decreased in a subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 98% relative to the amount of the marker prior to administration, or relative to administration of a control dsDNA molecule, such as a dsDNA molecule comprising chemically modified nucleotides compared to a control dsDNA molecule having only unmodified nucleotides. Generally, the metric is measured subsequent to administration at a time that the administration has had the recited effect, e.g., at least one day, one week, one month, 3 months, or 6 months, after a treatment regimen has begun.

As used herein, the term "maintenance sequence" is a DNA sequence or motif that enables or facilitates retention of a DNA molecule in the nucleus through cell division. A maintenance sequence typically enables replication and/or transcription of DNA in the nucleus by interacting with proteins that facilitate chromatin looping. An example of a maintenance sequence is a scaffold/matrix attached region (S/MAR element).

As used herein, a "nuclear targeting sequence" is a DNA sequence that enables or facilitates DNA entry into a target cell nucleus.

As used herein, a "pharmaceutical composition" or "pharmaceutical preparation" is a composition or preparation which is indicated for animal, e.g., human or veterinary pharmaceutical use, for example, non-human animal or human prophylactic or therapeutic use. A pharmaceutical preparation comprises an active agent having a biological effect on a cell or tissue of a subject, e.g., having pharmacological activity or an effect in the mitigation, treatment, or prevention of disease, in combination with a pharmaceutically acceptable excipient or diluent. A pharmaceutical composition also means a finished dosage form or formulation of a prophylactic or therapeutic composition.

As used herein, the terms "peptide," "polypeptide," and "protein" are used interchangeably and refer to a compound comprising amino acid residues covalently linked by peptide bonds, or by means other than peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds or by means other than peptide bonds. As used herein, the term refers to both short chains, which also commonly are referred to in the art as peptides, oligopeptides and oligomers, for example, and to longer chains, which generally are referred to in the art as proteins, of which there are many types. In some embodiments, a polypeptide comprises a non-canonical amino acid residue.

As used herein, a "sense strand" of a dsDNA is a strand which has the same sequence as an mRNA or pre-mRNA which encodes for a functional protein, and does not serve as a template for transcription of the protein. It is understood that a DNA having the same sequence as an mRNA or pre-mRNA may comprise a T in place of a U at one or more positions in the mRNA or pre-mRNA. An "antisense strand" of a dsDNA is a strand that has a sequence complementary to an mRNA or pre-mRNA which encodes for a functional protein and/or can serve as a template for transcription.

As used herein, the term "double stranded DNA molecule" or dsDNA molecule means a DNA composition comprising two complementary chains of deoxyribonucleotides that base pair to each other. The two complementary strands may have perfect complementarity or may have one or more mismatches, e.g., forming bulges. Either of the two strands may, in some embodiments, have paired regions of self-complementarity that form intramolecular/intrastrand double stranded motifs in a folded configuration, for example, may form hairpin loops, junctions, bulges or internal loops. In some embodiments, the dsDNA molecule is circular or linear. In some embodiments, the dsDNA molecule comprises one or two closed ends. In some embodiments (e.g., in a dsDNA molecule with closed ends), the two complementary chains of deoxyribonucleotides are covalently linked.

As used herein, "treatment" and "treating" refer to the medical management of a subject with the intent to improve, ameliorate, stabilize (i.e., not worsen), prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

BRIEF DESCRIPTION OF THE DRAWINGS

FIG. 1A depicts production of a single stranded DNA (ssDNA) intermediate (e.g., precursor) in which a dsDNA molecule comprising a first strand (e.g., sense strand) and a second strand (e.g., antisense strand) comprising phosphorothioate linkages (represented by S in circles) is synthesized (e.g., by PCR) and subsequently incubated with one or more exonucleases to remove the first strand. The ssDNA intermediates can be enriched through treatment of a restriction enzyme, e.g., Mly1 endonuclease, to remove residual linear dsDNA molecules. FIG. 1B depicts production of a circular hemi-modified dsDNA in which the ssDNA intermediate is contacted with chemically modified nucleotides, a polymerase (e.g., KME polymerase), and a primer (wherein the primer optionally comprises unmodified nucleotides) in an isothermal extension reaction. The resulting dsDNA molecule is digested using a restriction enzyme and ligated to form a circular hemi-modified dsDNA. The circular hemi-modified dsDNA may be enriched through incubation with an exonuclease, e.g., T5 exonuclease, to remove unligated DNA.

FIG. 10A shows the % EGFP+ of live cells 48 hours post-transfection, and FIG. 10B shows the relative median fluorescence intensity (MedFI) of live cells 48 hours post-transfection.

DETAILED DESCRIPTION

This disclosure relates to compositions and methods for providing an effector sequence to a cell, tissue or subject, e.g., in vivo or in vitro. The effector may be a DNA sequence. In some embodiments, the effector sequence encodes a polypeptide, e.g., a therapeutic protein. In some embodiments, the effector sequence encodes an RNA, e.g., a regulatory RNA or an mRNA.

While many of the embodiments herein refer to a sense strand having a first chemical structure and an antisense strand having a second chemical structure, it is understood that the application also provides a first strand (e.g., sense or antisense strand) having the first chemical structure and a second strand (e.g., sense or antisense strand) having the second chemical structure.

Chemically Modified (e.g., Hemi-Modified) DNA Molecules

In some aspects, the present disclosure provides a dsDNA molecule, wherein (a) the dsDNA molecule is circular; (b) the dsDNA molecule comprises a sense strand and an antisense strand, wherein the sense strand comprises one or more chemically modified nucleobases, and the antisense strand is substantially free of (e.g., is free of) chemically modified nucleobases; and (c) the dsDNA molecule comprises a promoter sequence and an effector sequence that encodes an effector (e.g., a therapeutic effector).

In some aspects, the present disclosure provides a pharmaceutical composition comprising a dsDNA molecule, wherein (a) the dsDNA molecule is circular; and (b) the dsDNA molecule comprises a sense strand and an antisense strand, wherein the sense strand comprises one or more chemically modified nucleobases, and the antisense strand is substantially free of (e.g., is free of) chemically modified nucleobases.

Figure 1A:
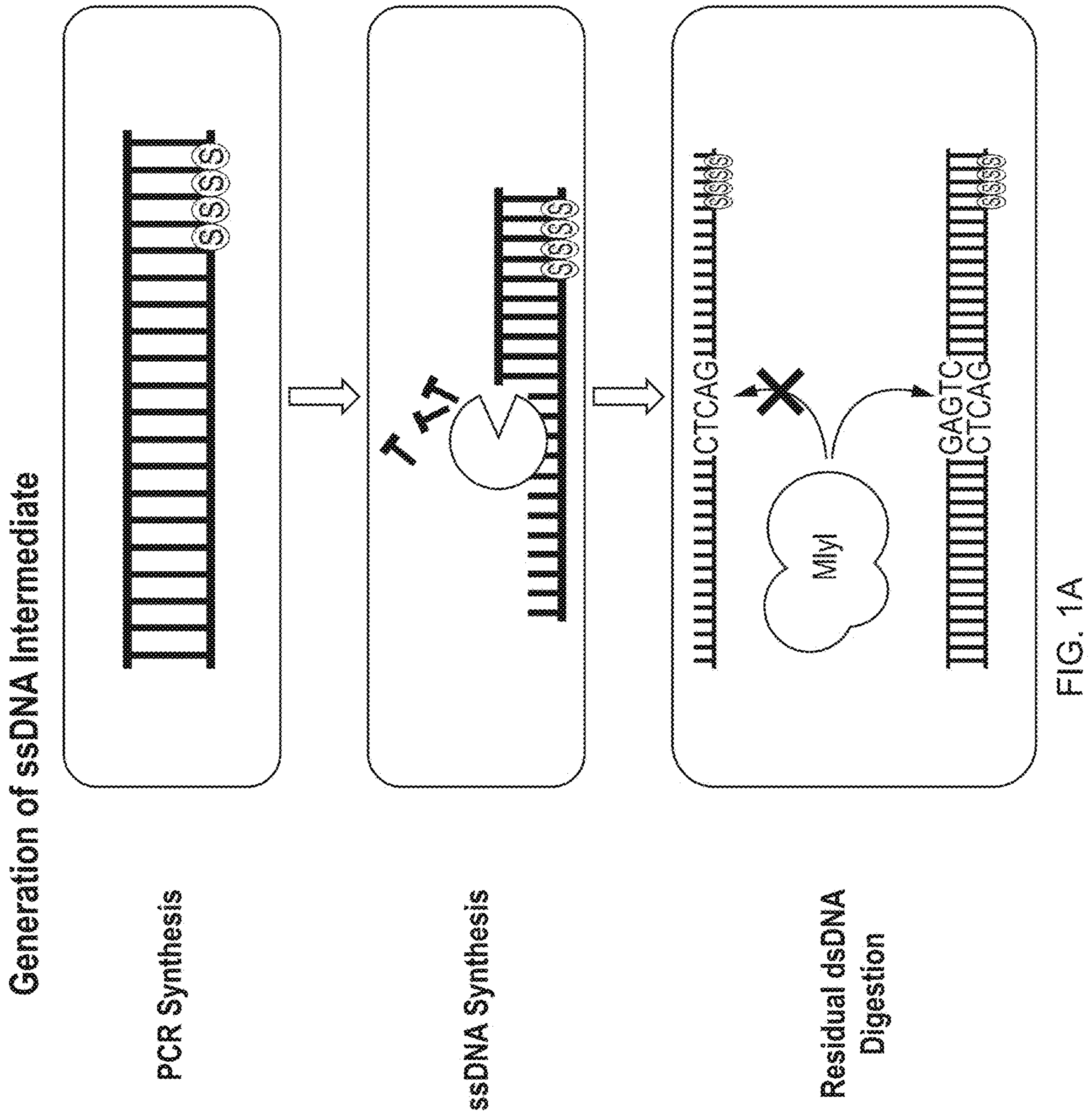
FIGS. 1A-1B illustrate an exemplary method of making a circular hemi-modified dsDNA molecule (cheDNA).
Figure 1B:
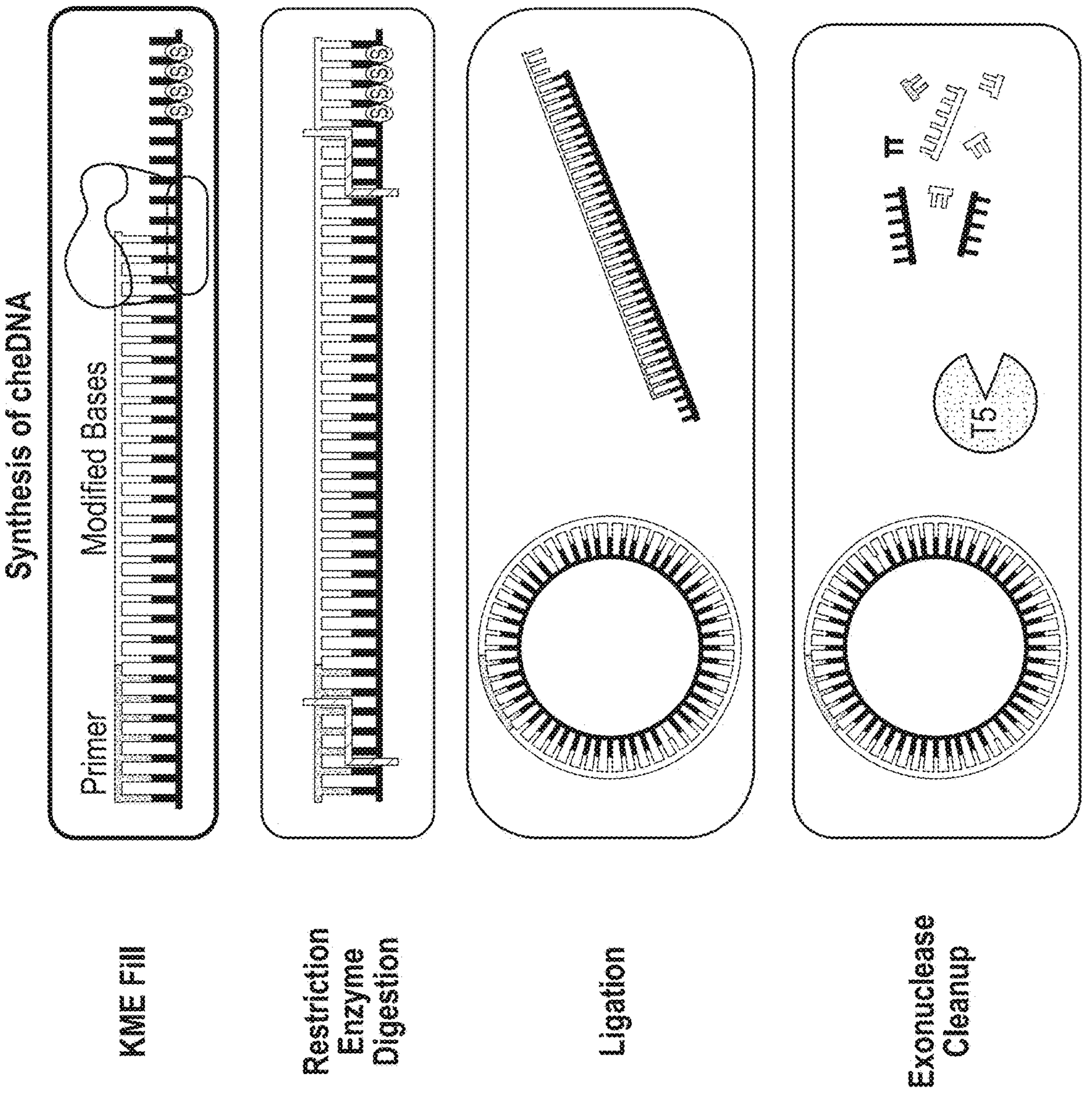

The dsDNA molecules described herein may have chemical modifications of the nucleobases, sugars, and/or the phosphate backbone (e.g., as shown in FIG. 1B). While not wishing to be bound by theory, such modifications can be useful for protecting a DNA from degradation (e.g., from exonucleases) or from the immune system of a host tissue or subject. In general, a chemically modified nucleotide has the same base-pairing specificity as the unmodified nucleotide, e.g., a uracil nucleobase can base-pair with adenine "A". In certain embodiments, chemical modifications (e.g., one or more modifications) are present in each of the sugar and the internucleoside linkage.

A nucleobase comprising 5-hydroxymethyluracil is shown below as Formula I.

Formula I

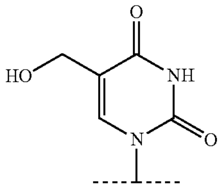

A nucleobase comprising a canonical uracil nucleobase is shown below as Formula II.

Formula II

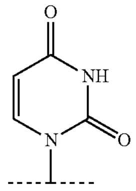

A nucleobase comprising 5-aminoallyluracil is shown below as Formula III.

Formula III

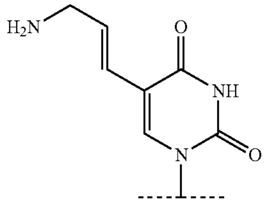

A nucleobase comprising 5-propargylaminouracil is shown below as Formula VI.

Formula VI

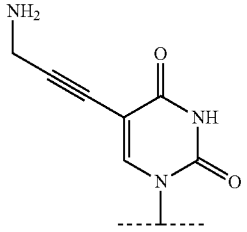

A nucleobase comprising N1-methylpseudouracil is shown below as Formula V.

Formula V

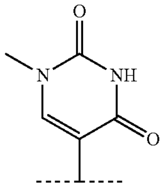

A nucleobase comprising 5-dihydroxypentyluracil is shown below as Formula VI.

Formula VI

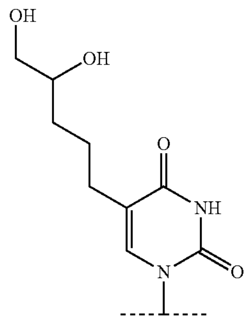

Examples of chemical modifications to DNA useful in the methods described herein include, e.g., phosphorothioate; or S and R phosphorothioate linkages. See, e.g., Pu et al. 2020. *An in-vitro DNA phosphorothioate modification reaction. Mol Microbiol.* 113: 452-463; Zheng & Sheng. 2021.

In some embodiments, a dsDNA molecule as described herein may comprise a phosphorothioate-modified nucleotide. In some embodiments, the dsDNA molecules described herein may include S and R phosphorothioate modified nucleotide linkages. In one embodiment, the phosphorothioate linkages are made according to Iwamoto et al, 2017, Nature Biotechnology, Volume 35:845-851. Briefly, monomers of nucleoside 3'-oxazaphospholidine derivates undergo stereocontrolled oligonucleotide synthesis with iterative capping and sulfurization to create stereocontrolled phosphorothioate linkages. The final sample is analyzed by reverse-phase high-performance liquid chromatography (RP-HPLC) and Ultraperformance liquid chromatography mass spectrometry (UPLC/MS) to determine stereochemistry of the modification. Nucleic acids containing phosphorothioate linkages are also commercially available.

In embodiments, a dsDNA molecule described herein, or one strand (e.g., the sense strand or the antisense strand) of the dsDNA molecule, comprises between 1-100% chemically modified nucleotides, between 1%-90% chemically modified nucleotides, between 1%-80% chemically modified nucleotides, between 1%-70% chemically modified nucleotides, between 1%-60% chemically modified nucleotides, between 1%-50% chemically modified nucleotides, between 1%-40% chemically modified nucleotides, between 1%-30% chemically modified nucleotides, between 1%-20% chemically modified nucleotides, between 1%-15% chemically modified nucleotides, between 1%-10% chemically modified nucleotides, between 20%-90% chemically modified nucleotides, between 20%-80% chemically modified nucleotides, between 80%-99% chemically modified nucleotides, or between 90%-99% chemically modified nucleotides. In embodiments, a dsDNA molecule described herein, or one strand (e.g., the sense strand or the antisense strand) of the dsDNA molecule, comprises at least 1% chemically modified nucleotides, at least 5% chemically modified nucleotides; at least 10% chemically modified nucleotides; at least 15% chemically modified nucleotides; at least 20% chemically modified nucleotides; at least 25% chemically modified nucleotides; at least 30% chemically modified nucleotides; at least 40% chemically modified nucleotides; at least 50% chemically modified nucleotides; at least 60% chemically modified nucleotides; at least 70% chemically modified nucleotides; at least 80% chemically modified nucleotides; at least 85% chemically modified nucleotides; at least 90% chemically modified nucleotides; at least 92% chemically modified nucleotides; at least 95% chemically modified nucleotides; at least 97% chemically modified nucleotides, at least 98% chemically modified nucleotides, or at least 99% chemically modified nucleotides.

In embodiments, a dsDNA molecule described herein, or one strand (e.g., the sense strand or the antisense strand) of the dsDNA molecule, comprises between 1-100% chemically modified nucleobases, between 1%-90% chemically modified nucleobases, between 1%-80% chemically modified nucleobases, between 1%-70% chemically modified nucleobases, between 1%-60% chemically modified nucleobases, between 1%-50% chemically modified nucleobases, between 1%-40% chemically modified nucleobases, between 1%-30% chemically modified nucleobases, between 1%-20% chemically modified nucleobases, between 1%-15% chemically modified nucleobases, between 1%-10% chemically modified nucleobases, between 20%-90% chemically modified nucleobases, between 20%-80% chemically modified nucleobases, between 80%-99% chemically modified nucleobases, or between 90%-99% chemically modified nucleobases. In embodiments, a dsDNA molecule described herein, or one strand (e.g., the sense strand or the antisense strand) of the dsDNA molecule, comprises at least 1% chemically modified nucleobases, at least 5% chemically modified nucleobases; at least 10% chemically modified nucleobases; at least 15% chemically modified nucleobases; at least 20% chemically modified nucleobases; at least 25% chemically modified nucleobases; at least 30% chemically modified nucleobases; at least 40% chemically modified nucleobases; at least 50% chemically modified nucleobases; at least 60% chemically modified nucleobases; at least 70% chemically modified nucleobases; at least 80% chemically modified nucleobases; at least 85% chemically modified nucleobases; at least 90% chemically modified nucleobases; at least 92% chemically modified nucleobases; at least 95% chemically modified nucleobases; at least 97% chemically modified nucleobases, at least 98% chemically modified nucleobases, or at least 99% chemically modified nucleobases.

In embodiments, chemically modified nucleotides, e.g., modifications described herein, can be introduced in the dsDNA molecules described herein throughout the entire sequence; within an element of a sequence, e.g., an element described herein; at a 5'- or 3'-end; and/or between the last 10, 8, 6, 5, 4, 3, or 2 nucleotides at the 5'- or 3'-end.

In some embodiments, a dsDNA molecule as described herein comprises chemically modified nucleobases on only one strand (e.g., as shown in FIG. 1B). Such asymmetrically modified dsDNA molecules may be called "hemi-modified." Note that, in some embodiments, the hemi-modified DNA may be completely free of chemically modified nucleotides on the antisense strand, and in other embodiments, the hemi-modified DNA may comprise a few chemical modifications (such as backbone modifications) on the antisense strand. In some embodiments, a dsDNA molecule as described herein comprises chemically modified nucleotides on the antisense strand. In some embodiments, a dsDNA molecule as described herein comprises chemically modified nucleotides on the sense strand.

In some embodiments, a chemically modified dsDNA molecule described herein exhibits decreased recognition by DNA sensors in a cell, host tissue, or subject compared to an unmodified dsDNA molecule of the same sequence, e.g., at least 10%, at least 20%, at least 30%, at least 40%, at least 50%, at least 60%, at least 70%, at least 80%, at least 90%, at least 95%, or at least 99% decreased recognition by DNA sensors in a cell, host tissue, or subject compared to an unmodified dsDNA molecule of the same sequence. In some embodiments, recognition by DNA sensors is measured by an assay for cyclic AMP-GMP (cGAMP) levels, e.g., using an ELISA. Without wishing to be bound by theory, increased level of cGAMP levels in a cell may be an indicator for activation of the cGAS-STING pathway in response to presence of dsDNA.

In some embodiments, a chemically modified dsDNA molecule described herein exhibits decreased degradation by DNA nucleases compared to an unmodified dsDNA molecule of the same sequence, e.g., at least 10%, at least 20%, at least 30%, at least 40%, at least 50%, at least 60%, at least 70%, at least 80%, at least 90%, or at least 95% decreased degradation by DNA nucleases in a host tissue or subject compared to an unmodified dsDNA molecule. In some embodiments, a chemically modified dsDNA molecule described herein shows decreased activation of the innate immune system in a target/host tissue or subject compared to an unmodified dsDNA molecule of the same sequence, e.g., at least 10%, at least 20%, at least 30%, at least 40%, at least 50%, at least 60%, at least 70%, at least 80%, at least 90%, at least 95%, or at least 99% decreased activation of the innate immune system in a target/host tissue or subject compared to an unmodified dsDNA molecule of the same sequence.

In some embodiments, a dsDNA molecule comprising chemically modified nucleotides described herein exhibits any of the following properties in a target/host tissue or subject compared to dsDNA of the same sequence that does not comprise chemically modified nucleotides (unmodified dsDNA): increased integration of exogenous construct in a genome of a target cell; increased retention in a target cell through replication; reduced secondary or tertiary structure formation; reduced interaction with innate immune sensors; reduced interaction with nucleases; enhanced stability; enhanced longevity; reduced toxicity; enhanced delivery; increased expression; increased transport across membranes; increased binding to DNA binding moieties such as nuclear DNA binding proteins, transcription factors, chaperones, or DNA polymerases. In embodiments, any of the above listed properties is modulated by at least 10%, at least 20%, at least 30%, at least 40%, at least 50%, at least 60%, at least 70%, at least 80%, at least 90%, or at least 95% in a target/host tissue or subject compared to an unmodified dsDNA of the same sequence.

In some embodiments, a dsDNA molecule described herein comprises a chemically modified cytosine nucleobase. In some embodiments, the chemically modified cytosine nucleobase comprises a substitution other than hydrogen at the carbon 5 (C-5) position of the nucleobase. In some embodiments, the chemically modified cytosine nucleobase comprises the structure of Formula VII:

Formula VII

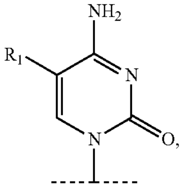

wherein $R_1$ is selected from the group consisting of —OH; -aldehyde; -carboxylic acid; -alkyl; —$(CH_2)_mOR_2$, m=1-3 and $R_2$=H or a sugar molecule; and -propargylamino. In some embodiments, $R_1$ is selected from the group consisting of —OH; —CHO; —COOH; -alkyl; —$(CH_2)_mOR_2$, m=1-3 and $R_2$=H or a sugar molecule; and -propargylamino, wherein the alkyl group includes one to six carbons. In some embodiments, $R_1$ is selected from the group consisting of —OH; —CHO; —COOH; —$CH_2OR_3$, $R_3$=H or glucose; -methyl; and -propargylamino. In some embodiments, the chemically modified cytosine nucleobase comprises 5-formylcytosine, 5-hydroxycytosine, 5-carboxycytosine, 5-propargylaminocytosine, 5-methylcytosine, 5-hydroxymethylcytosine, or glucosyl-5-hydroxymethylcytosine. Chemically modified cytosine nucleobases are further described in International Application WO/2024/173836, which is herein incorporated by reference in its entirety.

In some embodiments, a dsDNA molecule described herein comprises a chemically modified uracil nucleobase. In some embodiments, the chemically modified uracil nucleobase comprises a substitution other than hydrogen or a methyl group at the carbon 5 (C-5) position of the nucleobase. In some embodiments, the chemically modified uracil nucleobase comprises the structure of Formula VIII:

Formula VIII

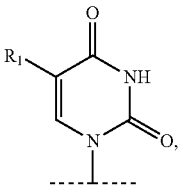

wherein $R_1$ is selected from the group consisting of —$(CH_2)_mOH$, m=1-10; -halogen; —$(CH_2)_n$—CHO, n=0-10; —$(CH_2)_pCOOH$, p=0-10; -aminoallyl; —S—$(C_1$-$C_6)$alkyl; and -propargylamino. In some embodiments, $R_1$ is selected from the group consisting of —$(CH_2)_mOH$, m=1-6; -halogen; —$(CH_2)_n$—CHO, n=0-6; —$(CH_2)_pCOOH$, p=0-6; -aminoallyl; —S—$(C_1$-$C_3)$alkyl; and -propargylamino. In some embodiments, $R_1$ is selected from the group consisting of —$(CH_2)OH$; —I; —Br; —CHO; —COOH; -aminoallyl; —S-methyl; and -propargylamino. In some embodiments, the chemically modified uracil nucleobase comprises 5-hydroxymethyluracil, 5-aminoallyluracil, 5-bromouracil, 5-iodouracil, 5-propargylaminouracil, 5-formyluracil, 5-carboxyuracil, 5-methylthiouracil, or 5-dihydroxypentyluracil. Chemically modified uracil nucleobases are further described in International Application WO/2024/173828, which is herein incorporated by reference in its entirety.

In some embodiments, a dsDNA molecule described herein comprises a first type of chemically modified nucleobase and a second type of chemically modified nucleobase. In some embodiments, the first type of chemically modified nucleobase is a chemically modified cytosine nucleobase and the second type of chemically modified nucleobase is a chemically modified uracil nucleobase. In some embodiments, the first type of chemically modified nucleobase is a chemically modified cytosine nucleobase and the second type of chemically modified nucleobase is a different chemically modified cytosine nucleobase. In some embodiments, the first type of chemically modified nucleobase is a chemically modified uracil nucleobase and the second type of chemically modified nucleobase is a different chemically modified uracil nucleobase.

In some embodiments, at least 10% of positions in the sense strand of the DNA molecule comprise chemically modified nucleobases, and the antisense strand is free of chemically modified nucleobases. In some embodiments, at least 20% of positions in the sense strand of the DNA molecule comprise chemically modified nucleobases, and the antisense strand is free of chemically modified nucleobases. In some embodiments, at least 30% of positions in the sense strand of the DNA molecule comprise chemically modified nucleobases, and the antisense strand is free of chemically modified nucleobases. In some embodiments, at least 40% of positions in the sense strand of the DNA molecule comprise chemically modified nucleobases, and the antisense strand is free of chemically modified nucleobases. In some embodiments, 10%-20% of positions in the sense strand of the DNA molecule comprise chemically modified nucleobases, and the antisense strand is free of chemically modified nucleobases. In some embodiments, 20%-30% of positions in the sense strand of the DNA molecule comprise chemically modified nucleobases, and the antisense strand is free of chemically modified nucleobases. In some embodiments, 30%-50% of positions in the sense strand of the DNA molecule comprise chemically modified nucleobases, and the antisense strand is free of chemically modified nucleobases.

In some embodiments, at least 20% of thymine or uracil positions in the sense strand of the DNA molecule comprise a uracil nucleobase, and the antisense strand is free of chemically modified nucleobases. In some embodiments, at least 40% of thymine or uracil positions in the sense strand of the DNA molecule comprise a uracil nucleobase, and the antisense strand is free of chemically modified nucleobases. In some embodiments, at least 80% of thymine or uracil positions in the sense strand of the DNA molecule comprise a uracil nucleobase, and the antisense strand is free of chemically modified nucleobases. In some embodiments, the uracil nucleobase is a canonical uracil nucleobase. In some embodiments, the uracil nucleobase is a chemically modified uracil nucleobase. In some embodiments, the chemically modified uracil nucleobase comprises 5-hydroxymethyluracil.

In some embodiments, at least 20% of cytosine positions in the sense strand of the DNA molecule comprise a chemically modified cytosine nucleobase, and the antisense strand is free of chemically modified nucleobases. In some embodiments, at least 40% of cytosine positions in the sense strand of the DNA molecule comprise a chemically modified cytosine nucleobase, and the antisense strand is free of chemically modified nucleobases. In some embodiments, at least 80% of cytosine positions in the sense strand of the DNA molecule comprise a chemically modified cytosine nucleobase, and the antisense strand is free of chemically modified nucleobases.

In some embodiments, the sense strand comprises a chemically modified guanine nucleobase. In some embodiments, at least 1%, at least 5%, at least 10%, at least 15%, at least 20%, at least 25%, at least 50%, or at least 75% of guanine positions in the sense strand of the DNA molecule comprise a chemically modified guanine nucleobase. In some embodiments, at least 40% of guanine positions in the sense strand of the DNA molecule comprise a chemically modified guanine nucleobase, and the antisense strand is free of chemically modified nucleobases. In some embodiments, 1%-75% (e.g., 1%-5%, 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, or 70%-75%) of guanine positions in the sense strand of the DNA molecule comprise a chemically modified guanine nucleobase. In some embodiments, every guanine position in a stretch of at least 100, at least 200, at least 300, at least 400, at least 500, at least 600, at least 700, at least 800, at least 900, at least 1000, at least 1500, or at least 2000 nucleotides in the sense strand of the DNA molecule comprises a chemically modified guanine nucleobase. In some embodiments, every guanine position in a stretch of 100-200, 200-300, 300-400, 400-500, 500-600, 600-700, 700-800, 800-900, 900-1000, 1000-1500, or 1500-2000 nucleotides in the sense strand of the DNA molecule comprises a chemically modified guanine nucleobase. In some embodiments, the chemically modified guanine nucleobase comprises inosine.

Other Chemically Modified (e.g., Substantially or Fully Modified) DNA Molecules

While many of the DNA molecules described herein are hemi-modified, other configurations are also contemplated. For instance, in some embodiments, a dsDNA comprises chemically modified nucleotides on both strands. In some embodiments, each of the sense strand and the antisense strand comprises some chemically modified nucleotides and other nucleotides that are not chemically modified.

In some embodiments, a dsDNA molecule as described herein comprises chemically modified nucleotides on both strands. In certain embodiments, both strands comprise chemical modifications at the same positions (e.g., chemically modified nucleotides on one strand are base-paired with chemically modified nucleotides on the opposite strand, and/or non-chemically modified nucleotides on one strand are base-paired with non-chemically modified nucleotides on the opposite strand). In embodiments, the entirety of both strands are composed of chemically modified nucleotides. In other embodiments, the two strands of a dsDNA molecule as described herein comprise different chemical modification patterns (e.g., one or more chemically modified nucleotides on one strand are base-paired with non-chemically modified nucleotides on the other strand). In embodiments, a dsDNA molecule as described herein comprises one or more double-stranded regions in which both strands are chemically modified, and/or one or more double-stranded regions in which neither strand is chemically modified. In embodiments, a dsDNA molecule as described herein comprises one or more double-stranded regions in which one strand is chemically modified and the other is not.

dsDNA Molecules Comprising N1-methylpseudouracil or 5-dihydroxypentyluracil

In some aspects, the present disclosure provides a double stranded DNA (dsDNA) molecule comprising a chemically modified uracil nucleobase, wherein the chemically modified uracil nucleobase comprises N1-methylpseudouracil. In some aspects, the present disclosure provides a dsDNA molecule comprising a chemically modified uracil nucleobase, wherein the chemically modified uracil nucleobase comprises 5-dihydroxypentyluracil.

In some embodiments, at least 1%, at least 5%, at least 10%, at least 15%, at least 20%, at least 25%, at least 50%, at least 75%, at least 90%, at least 95%, or at least 99% of uracil and thymine positions in the dsDNA molecule comprise the chemically modified uracil nucleobase. In some embodiments, 1%-100% (e.g., 1-5%, 5-10%, 10-15%, 15-20%, 20-25%, 25-30%, 30-35%, 35-40%, 40-45%, 45-50%, 50%-55%, 55-60%, 60-65%, 65-70%, 70-75%, 75-80%, 80-85%, 85-90%, 90-95%, or 95%-100%) of uracil and thymine positions in the dsDNA molecule comprise the chemically modified uracil nucleobase.

In some embodiments, the dsDNA molecule is circular. In some embodiments, the dsDNA molecule is linear. In some embodiments, the dsDNA molecule is linear and comprises a closed end at each end of the dsDNA molecule.

In some embodiments, the dsDNA molecule comprises a sense strand and an antisense strand, wherein both the sense strand and the antisense strand comprise the chemically modified uracil nucleobase.

In some embodiments, the dsDNA molecule comprises a sense strand and an antisense strand, wherein one strand comprises the chemically modified uracil nucleobase, and the other strand is substantially free of (e.g., is free of) chemically modified uracil nucleobases. In some embodiments, the sense strand of the dsDNA molecule comprises a chemically modified uracil nucleobase, and the antisense strand is substantially free of, e.g., is free of, chemically modified uracil nucleobases. In some embodiments, at least 1%, at least 5%, at least 10%, at least 15%, at least 20%, at least 25%, at least 50%, at least 75%, at least 90%, at least 95%, or at least 99% of uracil and thymine positions in the sense strand of the dsDNA molecule comprise the chemically modified uracil nucleobase. In some embodiments, 1%-100% (e.g., 1%-5%, 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%) of uracil and thymine positions in the sense strand of the dsDNA molecule comprise the chemically modified uracil nucleobase.

In some embodiments, the dsDNA molecule comprises one or more of an effector sequence, a promoter sequence, a sequence encoding a 5' UTR, a sequence encoding a 3' UTR, a sequence encoding a polyadenylation site, an intron sequence, or an enhancer sequence. In some embodiments, the sense strand of one or more of said sequences comprises a chemically modified uracil nucleobase. In some embodiments, both the sense strand and antisense strand of one or more of said sequences are substantially free of (e.g., are free of) chemically modified uracil nucleobases.

In some embodiments, at least 80%, at least 85%, at least 90%, at least 95%, at least 98%, at least 99%, or 100% of the sugars of the dsDNA molecule are deoxyribose sugars. In some embodiments, at least 80%, at least 85%, at least 90%, at least 95%, at least 98%, at least 99%, or 100% of the sugars of the chemically modified uracil nucleobases of the dsDNA molecule are deoxyribose sugars. In some embodiments, all positions in the dsDNA molecule comprise a deoxyribose sugar.

In some embodiments, the dsDNA molecule has at least 15 nucleotides, at least 30 nucleotides, at least 50 nucleotides, at least 75 nucleotides, 100 nucleotides, at least 200 nucleotides, at least 300 nucleotides, at least 500 nucleotides, at least 750 nucleotides, at least 1,000 nucleotides, at least 2,000 nucleotides, at least 3,000 nucleotides, at least 4,000 nucleotides, at least 5,000 nucleotides, at least 6,000 nucleotides, at least 7,000 nucleotides, at least 8,000 nucleotides, at least 9,000 nucleotides, at least 10,000 nucleotides, at least 11,000 nucleotides, at least 12,000 nucleotides, at least 15,000 nucleotides, at least 20,000 nucleotides, at least 25,000 nucleotides, at least 30,000 nucleotides, at least 35,000 nucleotides, at least 40,000 nucleotides at least 45,000 nucleotides, at least 50,000 nucleotides, at least 60,000 nucleotides, or more.

In some embodiments, the dsDNA molecule has between 20 and 1000 nucleotides, between 20 and 50 nucleotides, between 100 and 500 nucleotides, between 500 and 50,000 nucleotides, between 1,000 and 50,000 nucleotides, between 2,000 and 40,000 nucleotides, between 5,000 and 50,000 nucleotides, between 500 and 50,000 nucleotides, between 500 and 25,000 nucleotides, between 1,000 and 20,000 nucleotides, between 1,000 and 10,000 nucleotides, between 10,000 and 60,000 nucleotides, between 1,000 and 20,000 nucleotides, between 1,000 and 40,000 nucleotides, between 500 and 1000 nucleotides, between 1000 and 2,000 nucleotides, between 2,000 and 3,000 nucleotides, between 3,000 and 4,000 nucleotides, between 4,000 and 5,000 nucleotides, between 5,000 and 6,000 nucleotides, between 6,000 and 7,000 nucleotides, between 7,000 and 8,000 nucleotides, between 8,000 and 9,000 nucleotides, between 9,000 and 10,000 nucleotides, between 10,000 and 11,000 nucleotides, or between 11,000 and 12,000 nucleotides.

Elements of DNA Constructs

The dsDNA molecules or nucleic acids comprising dsDNA described herein may contain elements sufficient to deliver an effector sequence to a target cell, tissue or subject. In some embodiments, the effector sequence is a DNA sequence. In some embodiments, the dsDNA molecule drives expression of an effector, e.g., comprises a promoter and a sequence encoding an RNA (e.g., a therapeutic RNA) or polypeptide. In some embodiments, the DNA constructs described herein further contain one or both of: a nuclear targeting sequence and a maintenance sequence.

Promoters and Other Regulatory Sequences

The dsDNA molecule described herein may contain a promoter (a DNA sequence at which RNA polymerase and transcription factors bind to, directly or indirectly, to initiate transcription) operably linked to an effector sequence. A promoter may be found in nature operably linked to the effector sequence, or may be heterologous to the effector sequence. A promoter described herein may be native to the target cell or tissue, or heterologous to the target cell or tissue. A promoter may be constitutive, inducible and/or tissue-specific.

Examples of constitutive promoters include the ubiquitin C (UBC) promoter, retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985), the SV40 promoter, the dihydrofolate reductase promoter, the beta-actin promoter, the phosphoglycerol kinase (PGK) promoter, and the EF1alpha promoter.

Inducible promoters allow regulation of expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of sources. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769

(1995), see also Harvey et al, Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)).

In some embodiments, the native promoter for the sequence encoding the effector can be used.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a alpha-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptoralpha.-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be known to the skilled artisan.

Examples of tissue/cell specific promoters are listed in Table 1:

TABLE 1

Tissue or cell specific promoters

| Tissue/Cell | Promoter | Accession Number; Human Genome Coordinate (hg38) |
|---|---|---|
| Skeletal muscle | ACTA1 | NM_001100; chr1: 229,439,090-229,432,090 |
| Melanoma | TYR | NM_000372; chr11: 89,300,750-89,293,750 |
| Hepatoma | a-fetoprotein | NM_001354717; chr4: 73,461,175-73,454,175 |
| Mammary carcinoma | Mucin 1 | NM_001371720; chr1: 155,197,900-155,190,900 |
| Prostate Cancer | KLK3 | NM_001648; chr19: 50,865,760-50,858,760 |
| Neuronal cells | ENO2 | NM_001975; chr12: 6,928,700-6,921,700 |
| Response to Hypoxia | HIF-1alpha | NM_001530; chr14: 61,753,200-61,746,200 |
| Retinoblastoma | E2F1 | NM_005225; chr20: 33,691,380-33,684,380 |
| Ionizing radiation | EGR-1 | NM_001964; chr5: 138,474,303-138,467,303 |
| Oncogene | ErbB2 | NM_004448; chr17: 39,735,530-39,728,530 |
| Endothelial cells | vWF | NM_000552; chr12: 6,129,670-6,122,670 |
| Endothelial cells | FLT-1 | NM_002019; chr13: 28,500,100-28,493,100 |

TABLE 1-continued

Tissue or cell specific promoters

| Tissue/Cell | Promoter | Accession Number; Human Genome Coordinate (hg38) |
|---|---|---|
| Endothelial cells | ICAM-2 | NM_001099786; chr17: 64,025,630-64,018,630 |
| Retinal pigment epithelium | VMD2 | NM_004183; chr11: 61,972,630-61,965,630 |
| Rod cells | RHO | NM_000539; chr3: 129,540,350-129,533,350 |
| Cone cells | Red/green opsin (OPN1LW) | NM_020061; chrX: 154,164,030-154,157,030 |
| Ganglion cells | Thymocyte antigen (Thy1) | NM_006288; chr11: 119,428,150-119,421,150 |
| T cells | TIM3 | NM_032782; chr5: 157,114,050-157,107,050 |
| T cells | FOXP3 | NM_014009; chrX: 49,269,700-49,262,700 |
| PBMCs | Vβ6.7 | ENST00000390373.2; chr7: 142,493,295-142,486,295 |
| Cell cycle | Cdk1 | NM_001786; chr10: 60,799,850-60,792,850 |

The dsDNA molecules described herein may also include other native or heterologous expression control elements, such as enhancer elements, polyadenylation sites or Kozak consensus sequences. The dsDNA molecules described herein may include a 5' untranslated region (UTR) and/or a 3' UTR flanking the coding region of the effector sequence, such that, in some embodiments, transcription of the dsDNA molecule produces an mRNA comprising a 5' UTR, coding region of the effector sequence, and 3' UTR. The dsDNA molecules described herein may include a sequence encoding a polyadenylation site, e.g., a Bovine growth hormone polyadenylation site. The dsDNA molecules described herein may include an enhancer element, e.g., an SV40 enhancer. The dsDNA molecules described herein may include an intron sequence, e.g., a chimeric intron. As will be clear from context, an "intron sequence" in a DNA molecule corresponds to the transcribed pre-mRNA that will be removed by splicing. An "intron" in an RNA molecule refers to a portion of the pre-mRNA that will be removed by splicing. In some embodiments, a DNA molecule described herein comprises a sequence encoding a UBC intron. The dsDNA molecules described herein may include a post-transcriptional regulatory element, e.g., a Woodchuck hepatitis virus post transcriptional element (WPRE).

Bidirectional Promoters

In some aspects, the present disclosure provides double stranded DNA (dsDNA) molecules comprising bidirectional promoters. Bidirectional promoters are typically employed to control or regulate transcription of two effector sequences that are present on opposite strands (e.g., a first strand and a second strand) of the dsDNA molecule. The bidirectional promoter may be used to drive transcription in opposite directions. In embodiments, the bidirectional promoter is used to express one or more effectors, e.g., a first effector encoded by a first effector sequence and/or a second effector encoded by a second effector sequence.

In some embodiments, the bidirectional promoter is a naturally occurring promoter. In some embodiments, the bidirectional promoter is a viral promoter. In some embodiments, the bidirectional promoter naturally occurs in a mammalian genome, e.g., a human genome. In some embodiments, the bidirectional promoter is one that, in its native context, regulates expression of a housekeeping gene, a DNA repair gene, or an oncogene. In some embodiments, the bidirectional promoter is a non-naturally occurring promoter. In some embodiments, the non-naturally occurring promoter is an engineered promoter that has been modified relative to a naturally occurring promoter. In some embodiments, an engineered promoter has one or more (e.g., 1 or more, 5 or more, 10 or more, 50 or more, 100 or more, 200 or more, 400 or more, or 500 or more) nucleotide differences relative to the corresponding naturally occurring promoter. In some embodiments, the non-naturally occurring promoter is a synthetic promoter that comprises a sequence that has been designed de novo, e.g., a sequence that is not known to occur in nature and/or is not derived from a naturally occurring sequence. In some embodiments, the synthetic promoter comprises entirely de novo sequences. In some embodiments, only a portion of the synthetic promoter is a de novo sequence. In some embodiments, the bidirectional promoter comprises a CAG promoter, a PGK promoter, a DAS1-DAS2 promoter, a RPBSA synthetic promoter, a Rpl13a-based promoter, an EF1-α promoter, an LMP2/TAP1 promoter, or a fragment or derivative thereof. In some embodiments, the bidirectional promoter comprises a functional fragment or derivative of a CAG promoter, a PGK promoter, a DAS1-DAS2 promoter, a RPBSA synthetic promoter, a Rpl13a-based promoter, an EF1-α promoter, an LMP2/TAP1 promoter.

In some embodiments, the bidirectional promoter is substantially free of (e.g., is free of) a TATA box. In some embodiments, the bidirectional promoter comprises one or more CpG islands. In some embodiments, the bidirectional promoter comprises a midpoint equidistant from the ends of the promoter, and comprises a sequence having more than 50% Cs and As on one side of the midpoint, and more than 50% Gs and Ts on the other side of the midpoint. In some embodiments, the bidirectional promoter comprises the nucleotide sequence TCTCGCGAGA (SEQ ID NO: 11) or a nucleotide sequence that differs by 1, by 2, or by 3 nucleotides therefrom. In some embodiments, the bidirectional promoter comprises one or more CCAAT boxes (e.g., the sequence CCAAT or the sequence GGCCAATCT). In some embodiments, the bidirectional promoter comprises a motif that is overrepresented in bidirectional promoters, e.g., binding sites for GABPA, MYC, E2F1, E2F4, NRF-1, YY1, or the sequence CCAAT, ACTACAnnTCC, or ACTAYRnnnCCCR (SEQ ID NO: 19), wherein the symbol "n" represents any nucleotide, the symbol "Y" represents C or T, and the symbol "R" represents G or A. In some embodiments, the bidirectional promoter has a high GC content. In some embodiments, the bidirectional promoter has a GC content of more than 55%, more than 60%, more than 65%, more than 70%, more than 75%, or more than 80%. In some embodiments, the bidirectional promoter has a GC content of 55%-60%, 60%-65%, 65%-70%, 70%-75%, or 75%-80%.

In some embodiments, the bidirectional promoter is inducible, e.g., through an environmental or chemical stimulus. For instance, the stimulus may regulate transcription from the promoter in one or both directions. In some embodiments, the bidirectional promoter asymmetrically regulates transcription (and thus expression) of multiple effectors. For instance, a first effector encoded by a first effector sequence operably linked to a bidirectional promoter can be preferentially transcribed relative to a second effector encoded by a second effector sequence that is also operably linked to the bidirectional promoter.

In some embodiments, the bidirectional promoter comprises a first strand comprising one or more chemically modified nucleobases. In some embodiments, the bidirectional promoter comprises a second strand comprising one or more chemically modified nucleobases. In some embodiments, the first strand of the bidirectional promoter comprises one or more chemically modified nucleobases and the second strand of the bidirectional promoter is substantially free of (e.g., is free of) chemically modified nucleobases. In some embodiments, the second strand of the bidirectional promoter comprises one or more chemically modified nucleobases and the first strand of the bidirectional promoter is substantially free of (e.g., is free of) chemically modified nucleobases.

In some embodiments, the bidirectional promoter is at least 50, at least 100, at least 150, at least 200, at least 300, at least 400, at least 500, at least 600, at least 700, at least 800, at least 900, at least 1000, or at least 1200 base pairs in length. In some embodiments, the bidirectional promoter is 50-100, 100-150, 150-200, 200-300, 300-400, 400-500, 500-600, 600-700, 700-800, 800-900, 900-1000, or 1000-1200 base pairs in length.

In some embodiments, a double stranded effector sequence described herein has an upstream sticky end on the side of the promoter and a downstream sticky end on the side of the polyadenylation site. When two double stranded effector sequences are joined by their upstream sticky ends, the first and second effector sequences may be oriented to be transcribed in opposite directions.

Effector Sequence

The effector sequence of a dsDNA molecule described herein may be, e.g., a functional DNA sequence, e.g., a therapeutically functional DNA sequence; a DNA sequence encoding a therapeutic peptide, polypeptide or protein; or a DNA sequence encoding a therapeutic RNA (e.g., a non-coding RNA).

DNA Effector Sequences:

A therapeutically functional DNA sequence may be a DNA sequence that forms a functional structure, e.g., a DNA sequence comprising a DNA aptamer, DNAzyme or allele-specific oligonucleotide (a DNA ASO). A therapeutically functional DNA sequence may lack a promoter operably linked. In embodiments, a dsDNA molecule described herein may include one or a plurality of functional DNA sequences, e.g., 2, 3, 4, 5, 6, or more sequences, which may be the same or different.

Polypeptide Effectors:

A DNA sequence encoding a therapeutic polypeptide may be a DNA sequence encoding one or more effector which is a peptide, protein, or combinations thereof. For example, the DNA sequence encodes an mRNA. The peptide or protein may be: a DNA binding protein; an RNA binding protein; a transporter; a transcription factor; a translation factor; a ribosomal protein; a chromatin remodeling factor; an epigenetic modifying factor; an antigen; a hormone; an enzyme (such as a nuclease, e.g., an endonuclease, e.g., a nuclease element of a CRISPR system, e.g., a Cas9, dCas9, aCas9-nickase, Cpf/Cas12a); a Crispr-linked enzyme, e.g. a base editor or prime editor; a mobile genetic element protein (e.g., a transposase, a retrotransposase, a recombinase, an integrase); a gene writer; a polymerase; a methylase; a demethylase; an acetylase; a deacetylase; a kinase; a phosphatase; a ligase; a deubiquitinase; a protease; an integrase; a recombinase; a topoisomerase; a gyrase; a helicase; a lysosomal acid hydrolase); an antibody (e.g., an intact antibody, a fragment thereof, or a nanobody); a signaling peptide; a receptor ligand; a receptor (e.g., a chimeric antigen receptor (CAR) or a T cell receptor); a clotting factor; a coagulation factor; a structural protein; a caspase; a membrane protein; a mitochondrial protein; a nuclear protein; or an engineered binder such as a centyrin, darpin, or adnectin. See, e.g., Gebauer & Skerra. 2020. Annual Review of Pharmacology and Toxicology 60:1, 391-415. In some embodiments, the DNA sequence encodes a protein comprising one or more polypeptides; for instance, an antibody which comprises a heavy chain and a light chain.

In embodiments, a dsDNA molecule described herein may include one or a plurality of sequences encoding a polypeptide, e.g., 2, 3, 4, 5, 6, or more sequences encoding a polypeptide. Each of the plurality may encode the same or different protein. For example, a dsDNA molecule described herein may include multiple sequences encoding multiple proteins, e.g., a plurality of proteins in a biological pathway.

In some embodiments, a dsDNA molecule may include a plurality of sequences encoding a polypeptide, e.g., 2, 3, 4, 5, 6, or more sequences encoding a polypeptide, separated by a self-cleaving peptide, e.g., P2A, T2A, E2A or F2A. Self-cleaving peptides are typically 18-22 amino acids long, and can induce ribosomal skipping during protein translation so that two polypeptides can be encoded in the same transcript. Each of the polypeptides may have the same or different protein sequence. In one embodiment, a dsDNA molecule may include a promoter followed by a sequence encoding a first polypeptide of interest, a sequence encoding a 2A self-cleaving peptide, a sequence encoding a second polypeptide of interest, and a polyA site. In another embodiment, a dsDNA molecule may include a promoter followed by a sequence encoding the first polypeptide of interest, a first 2A self-cleaving peptide, a second polypeptide of interest, a sequence encoding a second 2A self-cleaving peptide, a sequence encoding a third polypeptide of interest, and a polyA site.

In some embodiments, the effector comprises a cell penetrating polypeptide. In some embodiments, the effector is a fusion protein that comprises a cell penetrating polypeptide and a second amino acid sequence.

RNA Effectors:

An effector sequence may be a DNA sequence encoding a non-coding RNA, e.g., one or more of a short interfering RNA (siRNA), a microRNA (miRNA), long non-coding RNA, a piwi-interacting RNA (piRNA), a small nucleolar RNA (snoRNA), a small Cajal body-specific RNA (scaRNA), a transfer RNA (tRNA), a ribosomal RNA (rRNA), an RNA aptamer, and a small nuclear RNA (snRNA).

In some embodiments, the dsDNA molecule disclosed herein comprises one or more expression sequences that encode a regulatory RNA, e.g., an RNA that modifies expression of an endogenous gene and/or an exogenous gene. In some embodiments, the dsDNA molecule or sequence disclosed herein can comprise a sequence that is antisense to a regulatory nucleic acid like a non-coding RNA, such as, but not limited to, tRNA, lncRNA, miRNA, rRNA, snRNA, microRNA, siRNA, piRNA, snoRNA, snRNA, exRNA, scaRNA, Y RNA, and hnRNA. In one embodiment, the regulatory nucleic acid targets a host gene. A regulatory nucleic acid may include, but is not limited to, a nucleic acid that hybridizes to an endogenous gene, e.g., an antisense RNA, a guide RNA, a nucleic acid that hybridizes to an exogenous nucleic acid such as a viral DNA or RNA, nucleic acid that hybridizes to an RNA, nucleic acid that interferes with gene transcription, nucleic acid that interferes with RNA translation, nucleic acid that stabilizes RNA or destabilizes RNA such as through targeting for degradation, and nucleic acid that modulates a DNA or RNA binding factor. In one embodiment, the sequence is an miRNA. In some embodiments, the regulatory nucleic acid targets a sense strand of a host gene. In some embodiments, the regulatory nucleic acid targets an antisense strand of a host gene.

In some embodiments, the dsDNA molecule encodes a guide RNA. Guide RNA sequences are generally designed to have a sequence having a length of between 15-30 nucleotides (e.g., 17, 19, 20, 21, 24 nucleotides) that is complementary to the targeted nucleic acid sequence, and a region that facilitates complex formation (e.g., with a tracrRNA or a nuclease). Custom gRNA generators and algorithms are available commercially for use in the design of effective guide RNAs. Gene editing has also been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al. (2015) Nature Biotechnol., 985-991. The gRNA may recognize specific DNA sequences (e.g., sequences adjacent to or within a promoter, enhancer, silencer, or repressor of a gene). In one embodiment, the gRNA is used as part of a CRISPR system for gene editing. For the purposes of gene editing, the dsDNA molecule or sequence disclosed herein may be designed to include one or multiple sequences encoding guide RNA sequences corresponding to a desired target DNA sequence; see, for example, Cong et al. (2013) Science, 339:819-823; Ran et al. (2013) Nature Protocols, 8:2281-2308.

A dsDNA molecule or sequence disclosed herein may encode certain regulatory nucleic acids that can inhibit gene expression through the biological process of RNA interference (RNAi). RNAi molecules comprise RNA or RNA-like structures typically containing 15-50 base pairs (such as about 18-25 base pairs) and having a nucleobase sequence identical (complementary) or nearly identical (substantially complementary) to a coding sequence in an expressed target gene within the cell. Such RNAi molecules include, but are not limited to: short interfering RNAs (siRNAs), double-stranded RNAs (dsRNA), micro RNAs (miRNAs), short hairpin RNAs (shRNA), meroduplexes, dicer substrates (U.S. Pat. Nos. 8,084,599; 8,349,809; and 8,513,207), or RNA antisense oligonucleotides (RNA ASOs).

In one embodiment, the dsDNA molecule or sequence disclosed herein comprises a sequence comprising a sense strand of a lncRNA. In one embodiment, the dsDNA molecule or sequence disclosed herein comprises a sequence encoding an antisense strand of a lncRNA.

The dsDNA molecule or sequence disclosed herein may encode a regulatory nucleic acid substantially complementary, or fully complementary, to a fragment of an endogenous gene or gene product (e.g., mRNA). The regulatory nucleic acids may complement sequences at the boundary between introns and exons, in between exons, or adjacent to exons, to prevent the maturation of newly-generated nuclear RNA transcripts of specific genes into mRNA for transcription. The regulatory nucleic acids that are complementary to specific genes can hybridize with the mRNA for that gene and prevent its translation. The antisense regulatory nucleic acid can be DNA, RNA, or a derivative or hybrid thereof. In some embodiments, the regulatory nucleic acid comprises a protein-binding site that can bind to a protein that participates in regulation of expression of an endogenous gene or an exogenous gene.

The length of a dsDNA molecule or sequence disclosed herein that may encode a regulatory nucleic acid that hybridizes to a transcript of interest and may be, for instance, between about 5 to 30 nucleotides, between about 10 to 30 nucleotides, or about 11, 12, 13, 14, 15, 16, 17, 18, 19, 20, 21, 22, 23, 24, 25, 26, 27, 28, 29, 30 or more nucleotides. The degree of identity of the regulatory nucleic acid to the targeted transcript should be at least 75%, at least 80%, at least 85%, at least 90%, or at least 95%.

A dsDNA molecule or sequence disclosed herein may encode a micro-RNA (miRNA) molecule identical to about 5 to about 30 contiguous nucleotides of a target gene. In some embodiments, the miRNA sequence targets a mRNA and commences with the dinucleotide AA, comprises a GC-content of about 30%-70% (about 30%-60%, about 40%-60%, or about 45%-55%), and does not have a high percentage identity to any nucleotide sequence other than the target in the genome of the mammal in which it is to be introduced, for example as determined by standard BLAST search. In some embodiments, the dsDNA molecule or sequence disclosed herein encodes at least one miRNA, e.g., 2, 3, 4, 5, 6, or more. In some embodiments, the dsDNA molecule or sequence disclosed herein comprises a sequence that encodes an miRNA having at least 50%, at least 60%, at least 70%, at least 75%, at least 80%, at least 85%, at least 90%, at least 95%, at least 96%, at least 97%, or at least 99% nucleotide sequence identity to any one of the nucleotide sequences or a sequence that is complementary to a target sequence. Lists of known miRNA sequences can be found in databases maintained by research organizations, such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed by technologies known in the art. In addition, there are computational tools that increase the chance of finding effective and specific sequence motifs (see, e.g., Lagana et al., Methods Mol. Bio., 2015, 1269: 393-412).

The dsDNA molecule or sequence disclosed herein may modulate expression of RNA encoded by a gene. Because multiple genes can share some degree of sequence homology with each other, in some embodiments, the dsDNA molecule or sequence disclosed herein can be designed to target a class of genes with sufficient sequence homology. In some embodiments, the dsDNA molecule or sequence disclosed herein can contain a sequence that has complementarity to sequences that are shared amongst different gene targets or are unique for a specific gene target. In some embodiments, the dsDNA molecule or sequence disclosed herein can be designed to target conserved regions of an RNA sequence having homology between several genes thereby targeting several genes in a gene family (e.g., different gene isoforms, splice variants, mutant genes, etc.). In some embodiments, the dsDNA molecule or sequence disclosed herein can be designed to target a sequence that is unique to a specific RNA sequence of a single gene.

In some embodiments, the effector sequence encoding a regulatory RNA has a length less than 5000 bps (e.g., less than about 5000 bps, less than about 4000 bps, less than about 3000 bps, less than about 2000 bps, less than about 1000 bps, less than about 900 bps, less than about 800 bps, less than about 700 bps, less than about 600 bps, less than about 500 bps, less than about 400 bps, less than about 300 bps, less than about 200 bps, less than about 100 bps, less than about 50 bps, less than about 40 bps, less than about 30 bps, less than about 20 bps, less than about 10 bps, or less). In some embodiments, the effector sequence has, independently or in addition to, a length greater than 10 bps (e.g., at least 10 bps, at least 20 bps, at least 30 bps, at least 40 bps, at least 50 bps, at least 60 bps, at least 70 bps, at least 80 bps, at least 90 bps, at least 100 bps, at least 200 bps, at least 300 bps, at least 400 bps, at least 500 bps, at least 600 bps, at least 700 bps, at least 800 bps, at least 900 bps, at least 1000 kb, at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4 kb, at least 4.1 kb, at least 4.2 kb, at least 4.3 kb, at least 4.4 kb, at least 4.5 kb, at least 4.6 kb, at least 4.7 kb, at least 4.8 kb, at least 4.9 kb, or at least 5 kb or greater).

In some embodiments, a dsDNA molecule or sequence disclosed herein comprises one or more of the features described hereinabove, e.g., one or more structural DNA sequence, a sequence encoding one or more peptides or proteins, a sequence encoding one or more regulatory element, a sequence encoding one or more regulatory nucleic acids, e.g., one or more non-coding RNAs, other expression sequences, and any combination of the aforementioned. A construct described herein may have one or a plurality of effector sequences, e.g., 2, 3, 4, 5 or more effector sequences. In the case of a plurality of effector sequences in a single construct, the effector sequences may be the same or different. In some embodiments, a dsDNA molecule can include an effector sequence that is a structural DNA and a second effector sequence that is a DNA sequence encoding a functional RNA or polypeptide.

In one embodiment, the dsDNA molecule includes a therapeutically functional, structural DNA sequence. In one embodiment, the dsDNA molecule includes a promoter and a sequence encoding a therapeutic peptide, polypeptide, or protein described herein. In one embodiment, the dsDNA molecule includes a promoter and a sequence encoding a regulatory RNA described herein.

In some embodiments, the effector sequence that encodes a polypeptide or protein is codon optimized, e.g., codon optimized for expression in a mammal, e.g., a human. In general, codon optimization means modifying a nucleic acid sequence for enhanced expression in the host cells of interest by replacing at least one codon (e.g., one or more, e.g., 1, 2, 3, 4, 5, 10, 15, 20, 25, 50, or more codons; e.g., at least 1%, at least 5%, at least 10%, at least 20%, at least 25%, at least 50%, at least 60%, at least 70%, at least 80%, at least 90% or 100%) of the native sequence with codons that are more frequently or most frequently used in the genes of that host cell while maintaining the native amino acid sequence. Codon usage tables are available, for example, at the "Codon Usage Database" available at www.kazusa.or.jp/codon/. These tables can be adapted in a number of ways, see, e.g., Nakamura et al., 2000, Nucl. Acids Res. 28:292. Computer algorithms for codon optimizing a particular sequence for expression in a particular host cell are also available, such as Gene Forge.

Nuclear Targeting Sequences (NTS)

A dsDNA molecule or nucleic acid comprising dsDNA (e.g., as disclosed herein) may include a nuclear targeting sequence (NTS) that facilitates transport of DNA from the cytoplasm into the nucleus of a cell. An NTS includes binding sites to proteins (e.g., transcription factors, chaperones, etc.) which bind to importin which transports cargo into the nucleus via the nuclear pore complex. In embodiments, an NTS may function generally (e.g. SV40 enhancer NTS). In other embodiments, NTS's may be cell or tissue specific, e.g., containing binding sites for transcription factors expressed in unique cell types that may target a dsDNA molecule described herein to the nucleus in a cell-specific manner (e.g., SRF, Nkx3). An NTS can be functional in multiple locations in a dsDNA molecule described herein, e.g., before the promoter and/or after the effector sequence.

An NTS may be viral or non-viral derived. NTS's are described, e.g., in Le Guen et al. 2021. Nucleic Acids Vol. 24: 477-486. Examples of NTS's are disclosed in Table 2:

TABLE 2

Exemplary nuclear targeting sequences

| Viral/ Non-viral | Name | Sequence |
|---|---|---|
| Viral | SV40 | 5'-cccaagaagaagaggaaagtc-3' (SEQ ID NO: 12) |
| Non-viral | 3NF | 5'-ctggggactttccagcctggggac tttccagctgggactttccagg-3' (SEQ ID NO: 13) |

In some embodiments, the NTS has a sequence according to Table 2, or a functional sequence having at least 80%, at least 90%, at least 95%, at least 96%, at least 97%, at least 98%, or at least 99% identity thereto.

Nuclear Import Proteins

In some embodiments, a dsDNA molecule is capable of being imported into the nucleus, e.g., by a nuclear import protein. In some embodiments, the dsDNA molecule can be bound by a nuclear import protein. In some embodiments, a dsDNA molecule comprises a recognition sequence for a nuclear import protein.

Exemplary import proteins include, e.g., basic helix-loop-helix (bHLH) proteins, heterogeneous nuclear ribonucleoprotein (hnRNP) isoforms, or nuclear factor I (NFI) proteins. In some embodiments, the import protein comprises an importin.

In some embodiments, the import protein comprises a Ran binding protein. In some embodiments, the import protein comprises a homeobox transcription factor. In some embodiments, the import factor specifically binds an E-box, a DTS, a promoter, a telomere, an ATTT motif, a cell cycle regulatory unit (CCRU), a CT3 sequence, an S/MAR, a topoisomerase II consensus sequence, an ARS consensus sequence, a 3NF, or a viral ori.

Maintenance Sequence

A dsDNA molecule disclosed herein may include a maintenance sequence that supports or enables sustained gene expression through successive rounds of cell division and/or progenitor differentiation in a host cell for a dsDNA molecule of the invention. In embodiments, a maintenance sequence is a nuclear scaffold/matrix attachment region (S/MAR). S/MAR elements are diverse, AT-rich sequences ranging from 60-500 bp that are conserved across species, thought to anchor chromatin to nuclear matrix proteins during interphase (Bode et al. 2003. Chromosome Res 11, 435-445). An S/MAR can be incorporated into a dsDNA molecule described herein to facilitate long-term transgene expression and extra-chromosomal maintenance. In one embodiment, the maintenance sequence is human interferon-beta MAR (5'tataattcactggaattttttgtgtgtatggtatgacatatgggttccttttattttttacatataaatatatttccctgtttttctaaaaaagaaaaagatcatcattttcccattgtaaaatgccatatttttttcataggtcacttacata-3' (SEQ ID NO: 9)), or a functional sequence having at least 80%, at least 90%, at least 95%, or at least 98% identity thereto. In embodiments, S/MARs useful in the constructs described herein can be found by searching the MARome on the world wide web at bioinfo.net.in/MARome, described also by Narwade et al. 2019. Nucleic Acids Research. Volume 47, Issue 14: 7247-7261.

In embodiments, a dsDNA molecule described herein is capable of replicating in a mammalian cell, e.g., human cell. In some embodiments, a dsDNA molecule described herein is maintained in a host cell, tissue or subject through at least one cell division. For example, a dsDNA molecule described herein is maintained in a host cell, tissue or subject through at least 2, at least 3, at least 4, at least 5, at least 6, at least 7, at least 8, at least 10, at least 15, at least 20, at least 40, or at least 50 cell divisions. In vitro, cell division may be tracked by flow cytometry or microscopy. In vivo, cell division may be tracked by intravital microscopy.

Other Elements

A dsDNA molecule disclosed herein may also include other control elements operably linked to the effector sequence, e.g., the sequence encoding an effector, in a manner which permits its transport, localization, transcription, translation and/or expression in a target cell, or which promotes its degradation or repression of expression in a non-target cell. As used herein, "operably linked" sequences include both expression control sequences that are contiguous with the sequence encoding the effector and expression control sequences that act in trans or at a distance to control the sequence encoding the effector. The precise nature of regulatory sequences needed for gene expression in host cells may vary between species, tissues or cell types, but in general may include, as necessary, 5' non-transcribed and 5' non-translated sequences involved with the initiation of transcription and translation respectively, such as a TATA box, capping sequence, CAAT sequence, enhancer elements and the like. Regulatory sequences may also include enhancer sequences or upstream activator sequences as desired. The constructs described herein may optionally include 5' leader or signal sequences.

Structure of DNA Constructs

In some embodiments, the dsDNA molecule disclosed herein is at least about 20 nucleotides, at least about 30 nucleotides, at least about 40 nucleotides, at least about 50 nucleotides, at least about 75 nucleotides, at least about 100 nucleotides, at least about 200 nucleotides, at least about 300 nucleotides, at least about 500 nucleotides, at least about 1000 nucleotides, at least about 2000 nucleotides, at least about 3000 nucleotides, at least about 4000 nucleotides, at least about 5000 nucleotides, at least about 6000 nucleotides, at least about 7000 nucleotides, at least about 8000 nucleotides, at least about 9000 nucleotides, at least about 10,000 nucleotides, at least about 20,000 nucleotides, at least about 30,000 nucleotides, at least about 40,000 nucleotides, or at least about 50,000 nucleotides in length. In some embodiments, the dsDNA molecule disclosed herein is between 20-30, 30-40, 40-50, 50-75, 75-100, 100-200, 200-300, 300-500, 500-1000, 1000-2000, 2000-3000, 3000-4000, 4000-5000, 5000-6000, 6000-7000, 7000-8000, 8000-9000, 9000-10,000, 10,000-20,000, 20,000-30,000, 30,000-40,000, or 40,000-50,000 nucleotides in length. In some embodiments, the size of a dsDNA molecule disclosed herein is a length sufficient to encode useful polypeptides or RNAs.

A sense strand as described herein may be a sense strand of a particular stretch of DNA, e.g., an effector sequence. An antisense strand as described herein may be an antisense strand of a particular stretch of DNA, e.g., an effector sequence. A sense strand as described herein or an antisense strand as described herein does not necessarily refer to the entire strand of the DNA molecule. For example, the sense strand of one effector sequence may be on the other strand of the DNA molecule from the sense strand of a second effector sequence on the same DNA molecule.

A first strand as described herein may be a first strand of a particular stretch of DNA, e.g., a promoter region or effector sequence. A second strand as described herein may be a second strand of a particular stretch of DNA, e.g., a promoter region or effector sequence. For example, when referring to a first strand of a promoter region or a second strand of a promoter region, this does not necessarily refer to the entire strand of the DNA molecule which comprises the first or second strand of the promoter region. For instance, a first strand of a first promoter sequence may be on the same strand of the DNA molecule as a second strand of a second promoter sequence. Further, a first strand of a first effector sequence may be on the same strand of the DNA molecule as a second strand of a second effector sequence.

Production

In some embodiments, a circular hemi-modified dsDNA molecule may be produced as follows. First, a linear dsDNA molecule comprising a first strand (e.g., a sense strand) and a second strand (e.g., antisense strand) is provided, e.g., using routine methods. The second strand may comprise a backbone modification that is resistant to exonuclease activity, e.g., one or more (e.g., two, three, four, five, six, seven, or eight) phosphorothioate linkages. The backbone modifications may be placed at one end of the second strand, in order to protect that strand from exonuclease degradation starting from that end. The linear dsDNA molecule may be incubated with one or more nucleases, e.g., one or more exonucleases, e.g., an exonuclease that acts in a 5' to 3' direction (e.g., T7 exonuclease or Lambda Exonuclease) or an exonuclease that acts in a 3' to 5' direction, to remove the first strand, thereby producing a single stranded DNA (ssDNA) intermediate. Without wishing to be bound by theory, the backbone modifications on the second strand may protect the second strand from exonuclease degradation, e.g., modification at the 5' end would protect the strand from an exonuclease that acts in a 5' to 3' direction. The ssDNA intermediate may be enriched through treatment of a restriction enzyme, e.g., Mly1 endonuclease, to remove residual linear dsDNA molecules. The ssDNA intermediate may be used to produce a linear, hemi-modified dsDNA in an isothermal extension reaction, e.g., the ssDNA intermediate may be contacted with a polymerase (e.g., a heat activated KME polymerase), unmodified deoxyribose triphosphates, chemically modified nucleotides, and a primer optionally comprising unmodified nucleotides, thereby producing a linear, hemi-modified dsDNA in which the first strand comprises chemically modified nucleotides. The linear, hemi-modified dsDNA may be digested using a restriction enzyme and ligated (e.g., through incubation with a DNA ligase, e.g., T3 Ligase) to produce circular, hemi-modified dsDNA. The circular hemi-modified dsDNA may be enriched through incubation with an exonuclease, e.g., T5 exonuclease, to remove unligated DNA.

In some aspects, the present disclosure provides a method of enriching single stranded DNA (ssDNA) in a composition. The method may comprise providing a composition comprising ssDNA and dsDNA, wherein the dsDNA comprises a site recognized a restriction endonuclease. The method may further comprise contacting the composition with the restriction endonuclease under conditions that allow for cleavage of the dsDNA. In some embodiments, the restriction endonuclease is an endonuclease that binds dsDNA and cleaves the dsDNA to produce blunt ends. In some embodiments, the restriction endonuclease is a Mly1 endonuclease.

In some embodiments, a dsDNA molecule as described herein is produced from a plasmid assembled to contain the desired elements described herein. The plasmid template can be assembled, for example, using Golden Gate cloning for assembly of multiple DNA fragments in a defined linear order in a recipient vector using a one-pot assembly procedure. Golden Gate cloning is described in Marillonnet & Grutzner, 2020, *Synthetic DNA assembly using golden gate cloning and the hierarchical modular cloning pipeline*, Current Protocols in Molecular Biology, 130:e115. In some embodiments, a plasmid template is linearized, for example, by digestion with a nuclease (e.g., a restriction endonuclease) or by PCR amplification of a linear nucleic acid sequence from the plasmid template.

In some embodiments, the method further comprises formulating the enriched dsDNA molecule for pharmaceutical use, e.g., formulating the dsDNA molecule with a pharmaceutically acceptable excipient and/or with a carrier, e.g., an LNP. In some embodiments, the method comprises contacting a dsDNA molecule described herein, or a population of dsDNA molecules described herein, with a lipid. In some embodiments, the method comprises diluting the dsDNA molecules in a buffer (e.g., a citrate buffer, e.g., a citrate buffer at pH 4.0) to make a dsDNA composition, and diluting a lipid composition (e.g., a lipid composition comprising a commercially available ionizable lipid, DSPC, cholesterol and DMG-PEG2000), e.g., in ethanol. In some embodiments, the dsDNA composition and the lipid composition are mixed, e.g., at a ratio of about 3:1 dsDNA composition:lipid composition (vol:vol). In some embodiments the resulting LNPs are washed and concentrated, e.g., using a centrifugal filter.

In some embodiments, a method described herein comprises enriching the dsDNA molecule. In some embodiments, the enriching includes substantially removing from the dsDNA molecule one or more impurity selected from: endotoxin, process impurities such as mononucleotides, chemically modified mononucleotides, single stranded DNA, DNA fragments or truncations, and proteins (e.g., enzymes, e.g., ligases, restriction enzymes). In the case of circular dsDNA molecules, the enriching may include substantially removing linear dsDNA molecules. In some embodiments, the enriching may include substantially removing concatemeric DNA. In some embodiments, the enriching may include substantially removing DNA with a higher molecular weight (e.g., at least 2-fold greater) than the dsDNA molecule.

The dsDNA molecule may be enriched from impurities or byproducts selected from the group consisting of: endotoxin, process impurities such as mononucleotides, chemically modified mononucleotides, single stranded DNA, proteins (e.g., enzymes, e.g., ligases, restriction enzymes), DNA fragments or truncations. In some embodiments, the enriched dsDNA molecule is substantially free of process byproducts and impurities, e.g., process byproducts or impurities described herein. In embodiments, a composition comprising a circular dsDNA molecule described herein is substantially free of impurities or process byproducts, e.g., selected from the group consisting of: endotoxin, mononucleotides, chemically modified mononucleotides, DNA fragments or truncations, and proteins (e.g., enzymes, e.g., ligases, restriction enzymes). In some embodiments, a composition comprising a circular dsDNA molecule described herein is substantially free of (e.g., is free of) linear DNA and/or ssDNA.

In some embodiments, enrichment involves a partial reduction of one or more contaminants.

Enrichment of the dsDNA molecule may be assessed using routine methods. In some embodiments, enrichment of the dsDNA molecule may be assessed using an electrophoresis method, e.g., a Fragment Analyzer or a 4200 Tapestation system (G2991BA, Agilent).

In some embodiments, a dsDNA molecule is formulated with a lipid based carrier, e.g., a lipid nanoparticle (LNP), e.g., as described in Example 1.

The dsDNA molecule may be sequenced to confirm the desired, designed sequence. In embodiments, other structural analysis of the dsDNA molecule (e.g., restriction enzyme analysis) may be performed to confirm or verify its sequence.

A chemically modified dsDNA molecule described herein may be produced by a number of methods, including methods routine in the art. For instance, a chemically modified dsDNA molecule can be produced by performing polymerase chain reaction on a DNA template in the presence of unmodified and chemically modified nucleotides and a suitable polymerase. A wide variety of polymerases are available, e.g., from commercial sources. Various polymerases can be used so long as they incorporate chemically modified nucleotides with a sufficiently high efficiency.

A chemically modified dsDNA molecule may also be produced by a method that does not comprise performing polymerase chain reaction. For instance, direct chemical synthesis may be used.

A chemically modified dsDNA molecule may be produced by providing a dsDNA molecule and chemically modifying nucleotides of the dsDNA molecule. For instance, a dsDNA molecule may be contacted with an enzyme, resulting in a chemically modified dsDNA molecule. In some embodiments, the enzyme converts an unmodified nucleotide into a chemically modified nucleotide. In some embodiments, the enzyme converts a chemically modified nucleotide into a differently modified nucleotide.

Enrichment

A composition described herein is typically enriched to remove process impurities and/or contaminants. In some embodiments, a composition comprising a circular dsDNA molecule described herein is enriched. For instance, in some embodiments, at least 60%, at least 65%, at least 70%, at least 75%, at least 80%, or at least 84% by mass of total DNA in the composition may be the circular dsDNA molecule. As an example, the composition may also comprise linear dsDNA, e.g., as a process impurity. As an example, the composition may also comprise ssDNA such as linear ssDNA, e.g., as a process impurity. As an example, the composition may also comprise DNA having a higher molecular weight (e.g., at least 2-fold greater) than the molecular weight of a desired circular dsDNA molecule, e.g., as a contaminant. As an example, the composition may also comprise concatemeric DNA, e.g., as a process impurity. As an example, the composition may comprise a contaminant, such as bacterial or viral or fungal agents.

In some embodiments, a composition described herein (e.g., a composition comprising circular dsDNA, e.g., a pharmaceutical composition comprising circular dsDNA or a manufacturing intermediate comprising linear ssDNA or linear dsDNA) is free of or is substantially free of one or more process impurity or contaminant, e.g., as described in this section. In some embodiments, a method described herein (e.g., a method of making circular dsDNA) results in a composition that is free of or is substantially free of one or more process impurity or contaminant, e.g., as described in this section. In some embodiments, a method described herein (e.g., a method of making circular dsDNA) comprises a step of assaying for one or more process impurity or contaminant, e.g., as described in this section. In some embodiments, the method comprises approving or releasing a batch if the batch is free of or substantially free of the process impurity or contaminant or meets a release criterion for that process impurity or contaminant.

In some embodiments, the process impurity comprises a nonhuman animal serum (e.g., fetal bovine serum); an enzyme, e.g., a ligase, a polymerase, or a digestive enzyme (e.g., a trypsin, a collagenase, a DNase, a RNase, an exonuclease, or an endonuclease, e.g., a restriction endonuclease); a growth factor; a cytokine; an antibody (e.g., a monoclonal antibody); a bead (e.g., an antibody-coated bead); an antibiotic; a cell culture medium; a component of a cell culture medium; a detergent; a protein, e.g., a host cell protein; an extraneous nucleic acid sequence (e.g., a mononucleotide (e.g., a modified mononucleotide), or a DNA fragment or truncation; helper virus contaminant (e.g., infectious virus, viral DNA, or viral proteins); or a solvent; a cellular debris; a cell; a pyrogen; a fungus; or any combination thereof, or a portion of any of the foregoing. In some embodiments, the contaminant was a component introduced during a manufacturing process. In some embodiments, the contaminant comprises a viral protein.

In some embodiments, the contaminant comprises an agent for transmissible spongiform encephalopathy (TSE). In some embodiments, a test for this contaminant is performed on a composition for which an bovine material, was used in manufacturing.

In some embodiments, the contaminant comprises a zoonotic virus, a porcine circovirus 1, a porcine circovirus 2, or a porcine parvovirus; or any combination thereof, or a portion of any of the foregoing. In some embodiments, a test for this contaminant is performed on a composition for which non-human animal material, e.g., a porcine material was used in manufacturing.

In some embodiments, the contaminant comprises a virus or portion thereof, e.g., a human virus; human immunodeficiency virus (HIV); HIV-1; HIV-2; hepatitis B virus (HBV); hepatitis C virus (HCV); human TSE, including Creutzfeldt-Jakob disease (CJD); variant CJD (vCJD); *Treponema pallidum* (syphilis); human T-lymphotropic virus (HTLV), HTLV-1, HTLV-2; or cytomegalovirus, human herpesvirus (e.g.,—human herpesvirus-6, -7 or -8 (HHV-6, -7& -8)), JC virus, BK virus, Epstein-Barr virus (EBV), human parvovirus B19, human papillomavirus (HPV); an adenovirus, e.g., adenovirus E1; SV40 Large T antigen sequence; HPV E6 or E7 DNA; or any combination thereof, or a portion of any of the foregoing. In some embodiments, a test for this contaminant is performed on a composition for which human donor cells (e.g., leukocyte-rich cells) were used in manufacturing. In some embodiments, a test for this contaminant is performed on a cell bank.

In some embodiments, the contaminant comprises a microbe or a portion thereof, a bacterium (e.g., a Gram-negative bacterium); *mycoplasma*; spiroplasma (e.g., when insect cells are used); bacterial toxin (e.g., endotoxin); or an adventitious agent, e.g., an adventitious viral agent or a non-viral adventitious agent, or any combination thereof, or a portion of any of the foregoing. In some embodiments, the contaminant comprises a simian virus, e.g., simian polyomavirus SV40 or simian retrovirus, or any combination thereof, or a portion of any of the foregoing. In some embodiments, the contaminant comprises an arbovirus. In some embodiments, the contaminant comprises a bacteriophage. In some embodiments, a test for this contaminant is performed on a cell bank, e.g., a cell bank of bacterial cells.

In some embodiments, the contaminant or process impurity comprises DNA from a host cell, e.g., wherein the host cell is a non-tumorigenic cell. In some embodiments, the DNA is present at a level of less than 10 ng/dose. In some embodiments, the DNA size is below about 200 nucleotides in length.

In some embodiments, the contaminant is an endotoxin. In some embodiments, a level of the endotoxin is less than 5 Endotoxin Unit (EU)/kg body weight/hour, e.g., wherein the composition is formulated for parenteral administration. In some embodiments, a level of the endotoxin is less than 0.2 EU/kg body weight/hour, e.g., wherein the composition is formulated for intrathecal administration. In some embodiments, a level of the endotoxin is not more than 2.0 EU/dose/eye, e.g., wherein the composition is formulated for injection or implantation into the eye, or not more than 0.5 EU/mL, e.g., wherein the composition is formulated for intraocular administration.

In some embodiments, a process impurity comprises an organic solvent, e.g., an aromatic organic solvent, e.g., phenol or chloroform.

In some embodiments, the contaminant or process impurity is described in *Chemistry, Manufacturing, and Control (CMC) Information for Human Gene Therapy Investigational New Drug Applications (INDs)—Guidance for Industry* (U.S. Department of Health and Human Services, Food and Drug Administration, Center for Biologics Evaluation and Research, January 2020), which is herein incorporated by reference in its entirety.

In some embodiments, the composition is substantially free of (e.g., is free of) a polymerase. In some embodiments, the composition is substantially free of (e.g., is free of) lipids, e.g., LNPs. In some embodiments, the composition is substantially free of (e.g., is free of) nanoparticles.

In some embodiments, the composition is substantially free of (e.g., is free of) agarose. In some embodiments, the composition is substantially free of (e.g., is free of) acrylamide.

In some embodiments, the composition is substantially free of (e.g., is free of) polypeptides.

In some embodiments, the ratio of the number of molecules of the circular dsDNA (e.g., circular, hemi-modified dsDNA described herein) to other DNA molecules (e.g., linear dsDNA and/or ssDNA) in the composition is at least 10:1, at least 20:1, at least 50:1, at least 80:1, at least 90:1, at least 100:1, at least 200:1, at least 500:1, or at least 1000:1. In some embodiments, the composition is substantially free of DNA from a host cell, e.g., DNA from a host cell is present at a level of less than 10 ng/dose. In some embodiments, the composition is substantially free of DNA having a size of below about 200 nucleotides in length. In some embodiments, the composition is substantially free of individual nucleotides. In some embodiments, at least 50%, at least 60%, at least 70%, at least 80%, or at least 84% of dsDNA by mass (or by copy number) in the composition is full length. In some embodiments, at least 50%, at least 60%, at least 70%, at least 80%, or at least 84% by mass of total DNA in the composition is the circular dsDNA. In some embodiments, less than 30%, less than 25%, less than 20%, or less than 15% by mass of DNA in the composition is linear dsDNA. In some embodiments, less than 30%, less than 25%, less than 20%, or less than 15% by mass of DNA in the composition is ssDNA. In some embodiments, less than 30%, less than 25%, less than 20%, or less than 15% by mass of DNA in the composition is DNA having a higher molecular weight (e.g., at least 2-fold greater) than the molecular weight of a desired circular dsDNA molecule. In some embodiments, less than 30%, less than 25%, less than 20%, or less than 15% by mass of DNA in the composition is concatemeric DNA.

In some embodiments, the level of contaminant DNA in a composition is measured by a gel electrophoresis method, e.g., a Fragment Analyzer or a 4200 Tapestation system (G2991BA, Agilent).

Pharmaceutical Compositions

The present disclosure includes a dsDNA molecule and related compositions in combination with one or more pharmaceutically acceptable excipients and/or carriers.

Pharmaceutical compositions may optionally comprise one or more additional active substances, e.g., therapeutically and/or prophylactically active substances. Pharmaceutical compositions of the present invention are generally sterile and/or pyrogen-free.

A dsDNA molecule described herein may be formulated without a carrier, e.g., the dsDNA molecule described herein may be administered to a host cell, tissue or subject "naked". A naked formulation may include pharmaceutical excipients or diluents but lacks a carrier.

Pharmaceutically acceptable excipients or diluents may comprise an inactive substance that serves as a vehicle or medium for the compositions described herein, such as any one of the inactive ingredients approved by the United States Food and Drug Administration (FDA) and listed in the Inactive Ingredient Database, which is incorporated by reference herein. Non-limiting examples of pharmaceutically acceptable excipients or diluents include solvents, aqueous solvents, non-aqueous solvents, tonicity agents, dispersion media, cryoprotectants, diluents, suspension aids, surface active agents, isotonic agents, thickening agents, emulsifying agents, preservatives, hyaluronidases, dispersing agents, preservatives, lubricants, granulating agents, disintegrating agents, binding agents, antioxidants, buffering agents (e.g., phosphate buffered saline (PBS)), lubricating agents, oils, and mixtures thereof.

General considerations in the formulation and/or manufacture of pharmaceutical agents may be found, for example, in Remington: The Science and Practice of Pharmacy 21st ed., Lippincott Williams & Wilkins, 2005 (incorporated herein by reference).

Carriers

A dsDNA molecule described herein may also be formulated, or included, with a carrier. General considerations of carriers and delivery of pharmaceutical agents may be found, for example, in *Delivery Technologies for Biopharmaceuticals: Peptides, Proteins, Nucleic Acids and Vaccines* (Lene Jorgensen and Hanne Morck Nielson, Eds.) Wiley; 1st edition (Dec. 21, 2009); and Vargason et al. 2021. Nat Biomed Eng 5, 951-967.

Non-limiting examples of carriers include carbohydrate carriers (e.g., an anhydride-modified phytoglycogen or glycogen-type material, GalNAc), nanoparticles (e.g., a nanoparticle that encapsulates or is covalently linked to the dsDNA molecule, gold nanoparticles, silica nanoparticles), lipid particles (e.g., liposomes, lipid nanoparticles), cationic carriers (e.g., a cationic lipopolymer or transfection reagent), fusosomes, non-nucleated cells (e.g., ex vivo differentiated reticulocytes), nucleated cells, exosomes, protein carriers (e.g., a protein covalently linked to the dsDNA molecule), peptides (e.g., cell-penetrating peptides), materials (e.g., graphene oxide), single pure lipids (e.g., cholesterol), or DNA origami (e.g., DNA tetrahedron).

In some embodiments, the dsDNA molecule compositions, constructs and systems described herein can be formulated in liposomes or other similar vesicles. Liposomes are spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Vesicles can be made from several different types of lipids; however, phospholipids are most commonly used to generate liposomes as drug carriers. Methods for preparation of multilamellar vesicle lipids are known in the art (see for example U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

Exosomes can also be used as drug delivery vehicles for the compositions and systems described herein. For a review, see Ha et al. July 2016. Acta Pharmaceutica *Sinica* B. Volume 6, Issue 4, Pages 287-296; https://doi.org/10.1016/j.apsb.2016.02.001.

Ex vivo differentiated red blood cells can also be used as a carrier for an agent (e.g., a dsDNA molecule) described herein. See, e.g., WO2015073587; WO2017123646; WO2017123644; WO2018102740; WO2016183482; WO2015153102; WO2018151829; WO2018009838; Shi et al. 2014. Proc Natl Acad Sci USA. 111(28): 10131-10136; U.S. Pat. No. 9,644,180; Huang et al. 2017. Nature Communications 8: 423; Shi et al. 2014. Proc Natl Acad Sci USA. 111(28): 10131-10136.

Fusosome compositions, e.g., as described in WO2018208728, can also be used as carriers to deliver the dsDNA molecules described herein.

Lipid Nanoformulations Lipid-Based Carriers

In some embodiments, compositions described herein are formulated into a lipid-based carrier (or lipid nanoformulation). In some embodiments, the lipid-based carrier (or lipid nanoformulation) is a liposome or a lipid nanoparticle (LNP). In some embodiments, the lipid-based carrier is an LNP.

In some embodiments, the lipid-based carrier (or lipid nanoformulation) comprises a cationic lipid (e.g., an ionizable lipid), a non-cationic lipid (e.g., phospholipid), a structural lipid (e.g., cholesterol), and a PEG-modified lipid. In some embodiments, the lipid-based carrier (or lipid nanoformulation) contains one or more compounds described herein, or a pharmaceutically acceptable salt thereof.

As described herein, suitable compositions to be used in the lipid-based carrier (or lipid nanoformulation) include all the isomers and isotopes of the compositions described above, as well as all the pharmaceutically acceptable salts, solvates, or hydrates thereof, and all crystal forms, crystal form mixtures, and anhydrides or hydrates.

In addition to one or more compositions described herein, the lipid-based carrier (or lipid nanoformulation) may further include a second lipid. In some embodiments, the second lipid is a cationic lipid, a non-cationic (e.g., neutral, anionic, or zwitterionic) lipid, or an ionizable lipid.

One or more naturally occurring and/or synthetic lipid compounds may be used in the preparation of the lipid-based carrier (or lipid nanoformulation).

The lipid-based carrier (or lipid nanoformulation) may contain positively charged (cationic) lipids, neutral lipids, negatively charged (anionic) lipids, or a combination thereof.

Cationic Lipids (Positively Charged) and Ionizable Lipids

In some embodiments, the lipid-based carrier (or lipid nanoformulation) comprises one or more cationic lipids, e.g., a cationic lipid that can exist in a positively charged or neutral form depending on pH, or an amine-containing lipid that can be readily protonated. In some embodiments, the cationic lipid is a lipid capable of being positively charged, e.g., under physiological conditions.

Exemplary cationic lipids include one or more amine group(s) which bear the positive charge. Examples of positively charged (cationic) lipids include, but are not limited to, N,N'-dimethyl-N,N'-dioctacyl ammonium bromide (DDAB) and chloride DDAC), N-(1-(2,3-dioleyloxy)propyl)-N,N,N-trimethylammonium chloride (DOTMA), 3β-[N—(N',N'-dimethylaminoethyl)carbamoyl) cholesterol (DC-chol), 1,2-dioleoyloxy-3-[trimethylammonio]-propane (DOTAP), 1,2-dioctadecyloxy-3-[trimethylammonio]-propane (DSTAP), and 1,2-dioleoyloxypropyl-3-dimethyl-hydroxy ethyl ammonium chloride (DORI), N,N-dioleyl-N,N-dimethylammonium chloride (DODAC), N,N-dimethyl-2,3-dioleyloxy)propylamine (DODMA), 1,2-Dioleoyl-3-Dimethylammonium-propane (DODAP), 1,2-Dioleoylcarbamyl-3-Dimethylammonium-propane (DOCDAP), 1,2-Dilineoyl-3-Dimethylammonium-propane (DLINDAP), 3-Dimethylamino-2-(Cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',12'-octadecadienoxy)propane (CpLin DMA), N,N-Dimethyl-3,4-dioleyloxybenzylamine (DMOBA), and the cationic lipids described in e.g. Martin et al., *Current Pharmaceutical Design*, pages 1-394, which is herein incorporated by reference in its entirety. In some embodiments, the lipid-based carrier (or lipid nanoformulation) comprises more than one cationic lipid.

In some embodiments, the lipid-based carrier (or lipid nanoformulation) comprises a cationic lipid having an effective pKa over 6.0. In some embodiments, the lipid-based carrier (or lipid nanoformulation) further comprises a second cationic lipid having a different effective pKa (e.g., greater than the first effective pKa) than the first cationic lipid.

In some embodiments, cationic lipids that can be used in the lipid-based carrier (or lipid nanoformulation) include, for example those described in Table 4 of WO 2019/217941, which is incorporated by reference.

In some embodiments, the cationic lipid is an ionizable lipid (e.g., a lipid that is protonated at low pH, but that remains neutral at physiological pH). In some embodiments, the lipid-based carrier (or lipid nanoformulation) may comprise one or more additional ionizable lipids, different than the ionizable lipids described herein. Exemplary ionizable lipids include, but are not limited to,
(LP01)
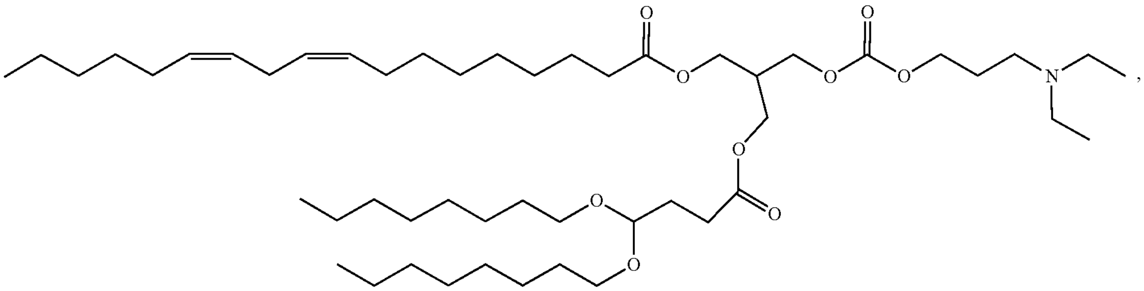
,
(SM-086)
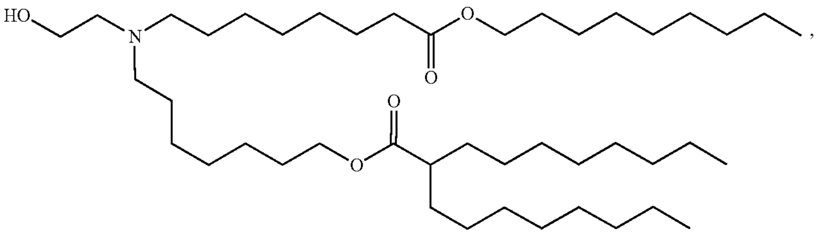
,
(SM-102)
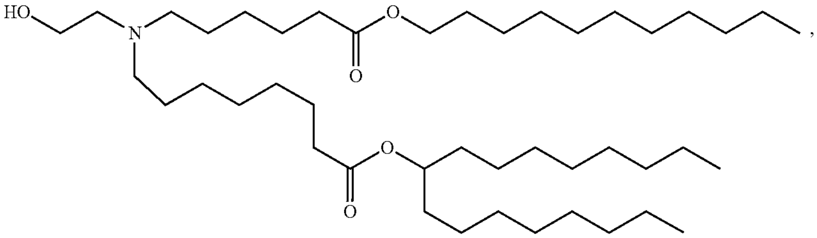
,
(ALC-0315)
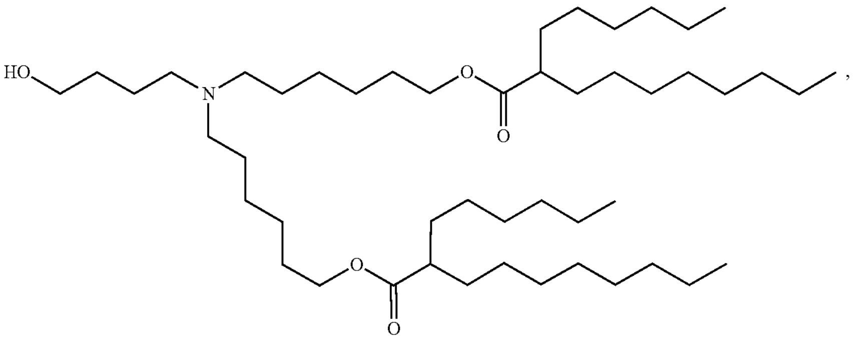
,
(Lipid 10)
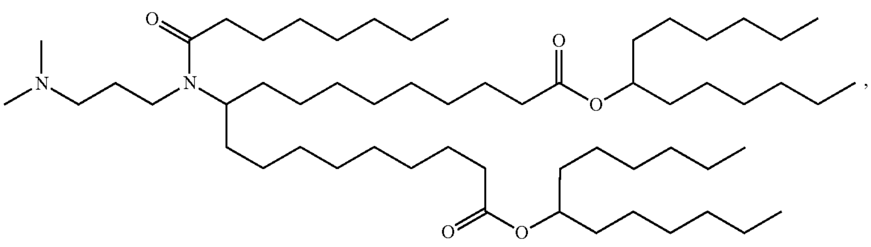
, -continued (Lipid A9)

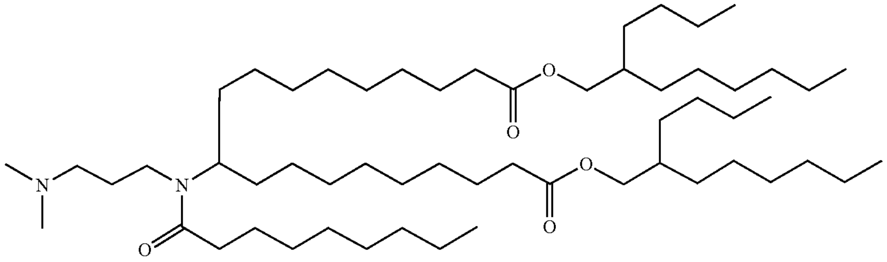

, and (DLin-MC3-DMA)

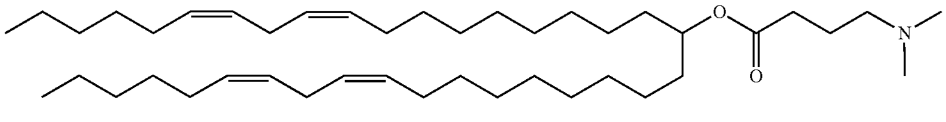

, (see WO 2017/004143A1, which is incorporated herein by reference in its entirety).

In some embodiments, the lipid-based carrier (or lipid nanoformulation) further comprises one or more compounds described by WO 2021/113777 (e.g., a lipid of Formula (3) such as a lipid of Table 3 of WO 2021/113777), which is incorporated herein by reference in its entirety.

In one embodiment, the ionizable lipid is a lipid disclosed in Hou, X., et al. Nat Rev Mater 6, 1078-1094 (2021). https://doi.org/10.1038/s41578-021-00358-0 (e.g., L319, C12-200, and DLin-MC3-DMA), (which is incorporated by reference herein in its entirety).

Examples of other ionizable lipids that can be used in lipid-based carrier (or lipid nanoformulation) include, without limitation, one or more of the following formulas: X of US 2016/0311759; I of US 20150376115 or in US 2016/0376224; Compound 5 or Compound 6 in US 2016/0376224; I, IA, or II of U.S. Pat. No. 9,867,888; I, II or III of US 2016/0151284; I, IA, II, or IIA of US 2017/0210967; I-c of US 2015/0140070; A of US 2013/0178541; I of US 2013/0303587 or US 2013/0123338; I of US 2015/0141678; II, III, IV, or V of US 2015/0239926; I of US 2017/0119904; I or II of WO 2017/117528; A of US 2012/0149894; A of US 2015/0057373; A of WO 2013/116126; A of US 2013/0090372; A of US 2013/0274523; A of US 2013/0274504; A of US 2013/0053572; A of WO 2013/016058; A of WO 2012/162210; I of US 2008/042973; I, II, III, or IV of US 2012/01287670; I or II of US 2014/0200257; I, II, or III of US 2015/0203446; I or III of US 2015/0005363; I, IA, IB, IC, ID, II, IIA, IIB, IIC, IID, or III-XXIV of US 2014/0308304; of US 2013/0338210; I, II, III, or IV of WO 2009/132131; A of US 2012/01011478; I or XXXV of US 2012/0027796; XIV or XVII of US 2012/0058144; of US 2013/0323269; I of US 2011/0117125; I, II, or III of US 2011/0256175; I, II, III, IV, V, VI, VII, VIII, IX, X, XI, XII of US 2012/0202871; I, II, III, IV, V, VI, VII, VIII, X, XII, XIII, XIV, XV, or XVI of US 2011/0076335; I or II of US 2006/008378; I of WO2015/074085 (e.g., ATX-002); I of US 2013/0123338; I or X-A-Y—Z of US 2015/0064242; XVI, XVII, or XVIII of US 2013/0022649; I, II, or III of US 2013/0116307; I, II, or III of US 2013/0116307; I or II of US 2010/0062967; I-X of US 2013/0189351; I of US 2014/0039032; V of US 2018/0028664; I of US 2016/0317458; I of US 2013/0195920; 5, 6, or 10 of U.S. Pat. No. 10,221,127; 111-3 of WO 2018/081480; I-5 or I-8 of WO 2020/081938; I of WO 2015/199952 (e.g., compound 6 or 22) and Table 1 therein; 18 or 25 of U.S. Pat. No. 9,867,888; A of US 2019/0136231; II of WO 2020/219876; 1 of US 2012/0027803; OF-02 of US 2019/0240349; 23 of U.S. Pat. No. 10,086,013; cKK-E12/A6 of Miao et al (2020); C12-200 of WO 2010/053572; 7C1 of Dahlman et al (2017); 304-O13 or 503-O13 of Whitehead et al; TS-P4C2 of U.S. Pat. No. 9,708,628; I of WO 2020/106946; I of WO 2020/106946; (1), (2), (3), or (4) of WO 2021/113777; and any one of Tables 1-16 of WO 2021/113777, all of which are incorporated herein by reference in their entirety.

In some embodiments, the lipid-based carrier (or lipid nanoformulation) further includes biodegradable ionizable lipids, for instance, (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate). See, e.g., lipids of WO 2019/067992, WO 2017/173054, WO 2015/095340, and WO 2014/136086, which are incorporated herein by reference in their entirety.

Non-Cationic Lipids (e.g., Phospholipids)

In some embodiments, the lipid-based carrier (or lipid nanoformulation) further comprises one or more non-cationic lipids. In some embodiments, the non-cationic lipid is a phospholipid. In some embodiments, the non-cationic lipid is a phospholipid substitute or replacement. In some embodiments, the non-cationic lipid is a negatively charged (anionic) lipid.

Exemplary non-cationic lipids include, but are not limited to, distearoyl-sn-glycero-phosphoethanolamine, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleyolphosphatidylglycerol (POPG), dielaidoyl-phosphatidylethanolamine (DEPE), 1,2-dilauroyl-sn-glycero-3-phosphocholine (DLPC), Sodium 1,2-ditetradecanoyl-sn-glycero-3-phosphate (DMPA), phosphatidylcholine (lecithin), phosphatidylethanolamine, lysolecithin, lysophosphatidylethanolamine, phosphatidylserine, phosphatidylinositol, sphingomyelin, egg sphingomyelin (ESM), phosphatidylethanolamine (cephalin), cardiolipin, phosphatidic acid, cerebrosides, dicetylphosphate, lysophosphatidylcholine, dilinoleoylphosphatidylcholine, or mixtures thereof. It is understood that other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, paimitoyl, stearoyl, or oleoyl. Additional exemplary lipids, in certain embodiments, include, without limitation, those described in Kim et al. (2020) dx.doi.org/10.1021/acs.nanolett.0c01386, which is incorporated herein by reference. Such lipids include, in some embodiments, plant lipids found to improve liver transfection with mRNA (e.g., DGTS).

In some embodiments, the lipid-based carrier (or lipid nanoformulation) may comprise a combination of distearoylphosphatidylcholine/cholesterol, dipalmitoylphosphatidylcholine/cholesterol, dimyrystoylphosphatidylcholine/cholesterol, 1,2-Dioleoyl-sn-glycero-3-phosphocholine (DOPC)/cholesterol, or egg sphingomyelin/cholesterol.

Other examples of suitable non-cationic lipids include, without limitation, nonphosphorous lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyl dimethyl ammonium bromide, ceramide, sphingomyelin, and the like. Other non-cationic lipids are described in WO 2017/099823 or US 2018/0028664, which are incorporated herein by reference in their entirety.

In one embodiment, the lipid-based carrier (or lipid nanoformulation) further comprises one or more non-cationic lipid that is oleic acid or a compound of Formula I, II, or IV of US 2018/0028664, which is incorporated herein by reference in its entirety.

The non-cationic lipid content can be, for example, 0-30% (mol) of the total lipid components present. In some embodiments, the non-cationic lipid content is 5-20% (mol) or 10-15% (mol) of the total lipid components present.

In some embodiments, the lipid-based carrier (or lipid nanoformulation) further comprises a neutral lipid, and the molar ratio of an ionizable lipid to a neutral lipid ranges from about 2:1 to about 8:1 (e.g., about 2:1, 3:1, 4:1, 5:1, 6:1, 7:1, or 8:1).

In some embodiments, the lipid-based carrier (or lipid nanoformulation) does not include any phospholipids.

In some embodiments, the lipid-based carrier (or lipid nanoformulation) can further include one or more phospholipids, and optionally one or more additional molecules of similar molecular shape and dimensions having both a hydrophobic moiety and a hydrophilic moiety (e.g., cholesterol).

Structural Lipids

The lipid-based carrier (or lipid nanoformulation) described herein may further comprise one or more structural lipids. As used herein, the term “structural lipid” refers to sterols (e.g., cholesterol) and also to lipids containing sterol moieties.

Incorporation of structural lipids in the lipid nanoparticle may help mitigate aggregation of other lipid in the particle. Structural lipids can be selected from the group including but not limited to, cholesterol or cholesterol derivative, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

In some embodiments, structural lipids may be incorporated into the lipid-based carrier at molar ratios ranging from about 0.1 to 1.0 (cholesterol phospholipid).

In some embodiments, sterols, when present, can include one or more of cholesterol or cholesterol derivatives, such as those described in WO 2009/127060 or US 2010/0130588, which are incorporated herein by reference in their entirety. Additional exemplary sterols include phytosterols, including those described in Eygeris et al. (2020), Nano Lett. 2020; 20(6):4543-4549, incorporated herein by reference.

In some embodiments, the structural lipid is a cholesterol derivative. Non-limiting examples of cholesterol derivatives include polar analogues such as 5a-cholestanol, 53-coprostanol, cholesteryl-(2'-hydroxy)-ethyl ether, cholesteryl-(4'-hydroxy)-butyl ether, and 6-ketocholestanol; non-polar analogues such as 5a-cholestane, cholestenone, 5a-cholestanone, 5p-cholestanone, and cholesteryl decanoate; and mixtures thereof. In some embodiments, the cholesterol derivative is a polar analogue, e.g., cholesteryl-(4'-hydroxy)-butyl ether. Exemplary cholesterol derivatives are described in WO 2009/127060 and US 2010/0130588, each of which is incorporated herein by reference in its entirety.

In some embodiments, the lipid-based carrier (or lipid nanoformulation) further comprises sterol in an amount of 0-50 mol % (e.g., 0-10 mol %, 10-20 mol %, 20-50 mol %, 20-30 mol %, 30-40 mol %, or 40-50 mol %) of the total lipid components.

Polymers and Polyethylene Glycol (PEG)—Lipids

In some embodiments, the lipid-based carrier (or lipid nanoformulation) may include one or more polymers or co-polymers, e.g., poly(lactic-co-glycolic acid) (PFAG) nanoparticles.

In some embodiments, the lipid-based carrier (or lipid nanoformulation) may include one or more polyethylene glycol (PEG) lipid. Examples of useful PEG-lipids include, but are not limited to, 1,2-Diacyl-sn-Glycero-3-Phosphoethanolamine-N-[Methoxy(Polyethylene glycol)-350] (mPEG 350 PE); 1,2-Diacyl-sn-Glycero-3-Phosphoethanolamine-N-[Methoxy(Polyethylene glycol)-550](mPEG 550 PE); 1,2-Diacyl-sn-Glycero-3-Phosphoethanolamine-N-[Methoxy(Polyethylene glycol)-750](mPEG 750 PE); 1,2-Diacyl-sn-Glycero-3-Phosphoethanolamine-N-[Methoxy(Polyethylene glycol)-1000](mPEG 1000 PE); 1,2-Diacyl-sn-Glycero-3-Phosphoethanolamine-N-[Methoxy(Polyethylene glycol)-2000](mPEG 2000 PE); 1,2-Diacyl-sn-Glycero-3-Phosphoethanolamine-N—[Methoxy(Polyethylene glycol)-3000](mPEG 3000 PE); 1,2-Diacyl-sn-Glycero-3-Phosphoethanolamine-N-[Methoxy(Polyethylene glycol)-5000](mPEG 5000 PE); N-Acyl-Sphingosine-1-[Succinyl(Methoxy Polyethylene Glycol) 750](mPEG 750 Ceramide); N-Acyl-Sphingosine-1-[Succinyl(Methoxy Polyethylene Glycol) 2000](mPEG 2000 Ceramide); and N-Acyl-Sphingosine-1-[Succinyl (Methoxy Polyethylene Glycol) 5000](mPEG 5000 Ceramide). In some embodiments, the PEG lipid is a polyethyleneglycol-diacylglycerol (i.e., polyethyleneglycol diacylglycerol (PEG-DAG), PEG-cholesterol, or PEG-DMB) conjugate.

In some embodiments, the lipid-based carrier (or nanoformulation) includes one or more conjugated lipids (such as PEG-conjugated lipids or lipids conjugated to polymers described in Table 5 of WO 2019/217941, which is incorporated herein by reference in its entirety). In some embodiments, the one or more conjugated lipids is formulated with one or more ionic lipids (e.g., non-cationic lipid such as a neutral or anionic, or zwitterionic lipid); and one or more sterols (e.g., cholesterol).

The PEG conjugate can comprise a PEG-dilaurylglycerol (C12), a PEG-dimyristylglycerol (C14), a PEG-dipalmitoylglycerol (C16), a PEG-disterylglycerol (C18), PEG-dilaurylglycamide (C12), PEG-dimyristylglycamide (C14), PEG-dipalmitoylglycamide (C16), and PEG-disterylglycamide (C18).

In some embodiments, conjugated lipids, when present, can include one or more of PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanoloamine (PEG-PE), PEG succinate diacylglycerol (PEGS-DAG) (such as 4-O-(2',3'-di(tetradecanoyloxy)propyl-1-O-(w-methoxy(polyethoxy)ethyl) butanedioate (PEG-S-DMG)), PEG dialkoxypropylcarbam, N-(carbonyl-methoxypolyethylene glycol 2000)-1,2-distearoyl-sn-glycero-3-phosphoethanolamine sodium salt, and those described in Table 2 of WO 2019/051289 (which is herein incorporated by reference in its entirety), and combinations of the foregoing.

Additional exemplary PEG-lipid conjugates are described, for example, in U.S. Pat. Nos. 5,885,613, 6,287,591, US 2003/0077829, US 2003/0077829, US 2005/0175682, US 2008/0020058, US 2011/0117125, US 2010/0130588, US 2016/0376224, US 2017/0119904, US 2018/0028664, and WO 2017/099823, all of which are incorporated herein by reference in their entirety.

In some embodiments, the PEG-lipid is a compound of Formula III, III-a-I, III-a-2, III-b-1, III-b-2, or V of US 2018/0028664, which is incorporated herein by reference in its entirety. In some embodiments, the PEG-lipid is of Formula II of US 2015/0376115 or US 2016/0376224, both of which are incorporated herein by reference in their entirety. In some embodiments, the PEG-DAA conjugate can be, for example, PEG-dilauryloxypropyl, PEG-dimyristyloxypropyl, PEG-dipalmityloxypropyl, or PEG-distearyloxypropyl. In some embodiments, the PEG-lipid includes one of the following:

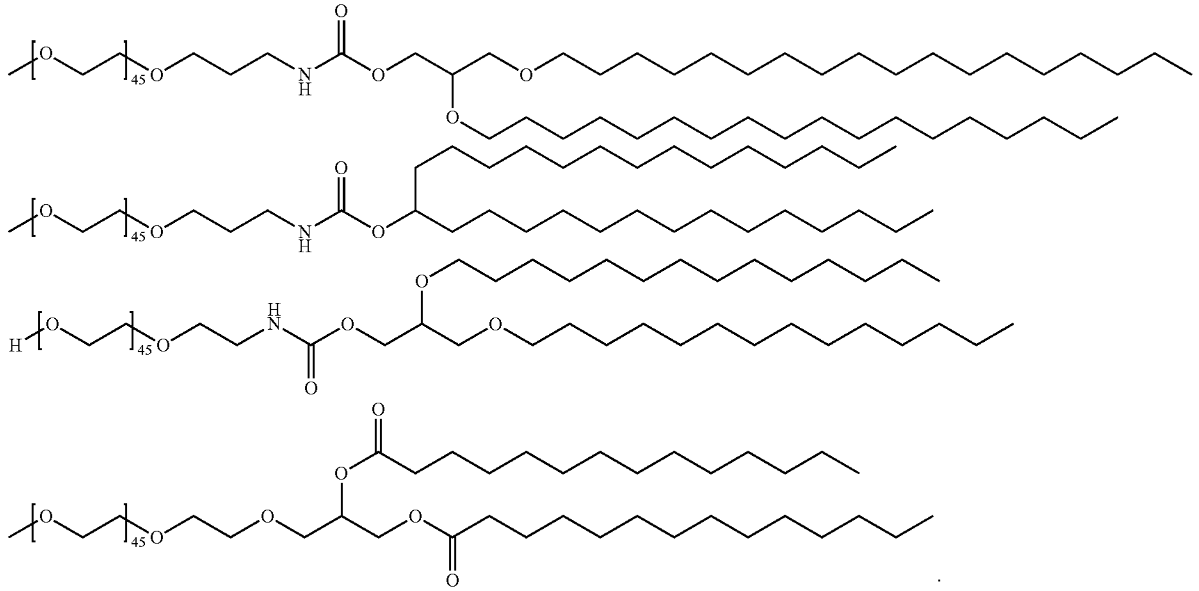

In some embodiments, lipids conjugated with a molecule other than a PEG can also be used in place of PEG-lipid. For example, polyoxazoline (POZ)-lipid conjugates, polyamide-lipid conjugates (such as ATTA-lipid conjugates), and cationic-polymer lipid (GPL) conjugates can be used in place of or in addition to the PEG-lipid.

Exemplary conjugated lipids, e.g., PEG-lipids, (POZ)-lipid conjugates, ATTA-lipid conjugates and cationic polymer-lipids, include those described in Table 2 of WO 2019/051289A9, which is incorporated herein by reference in its entirety.

In some embodiments, the conjugated lipid (e.g., the PEGylated lipid) can be present in an amount of 0-20 mol % of the total lipid components present in the lipid-based carrier (or lipid nanoformulation). In some embodiments, the conjugated lipid (e.g., the PEGylated lipid) content is 0.5-10 mol % or 2-5 mol % of the total lipid components.

When needed, the lipid-based carrier (or lipid nanoformulation) described herein may be coated with a polymer layer to enhance stability in vivo (e.g., sterically stabilized LNPs).

Examples of suitable polymers include, but are not limited to, poly(ethylene glycol), which may form a hydrophilic surface layer that improves the circulation half-life of liposomes and enhances the amount of lipid nanoformulations (e.g., liposomes or LNPs) that reach therapeutic targets. See, e.g., Working et al. *J Pharmacol Exp Ther,* 289: 1128-1133 (1999); Gabizon et al., *J Controlled Release* 53: 275-279 (1998); Adlakha Hutcheon et al., *Nat Biotechnol* 17: 775-779 (1999); and Koning et al., *Biochim Biophys Acta* 1420: 153-167 (1999), which are incorporated herein by reference in their entirety.

Percentages of Lipid Nanoformulation Components

In some embodiments, the lipid-based carrier (or lipid nanoformulation) comprises one of more of the compounds described herein, optionally a non-cationic lipid (e.g., a phospholipid), a sterol, a neutral lipid, and optionally conjugated lipid (e.g., a PEGylated lipid) that inhibits aggregation of particles. In some embodiments, the lipid-based carrier (or lipid nanoformulation) further comprises a payload (e.g., a DNA molecule described herein). The amounts of these components can be varied independently and to achieve desired properties. For example, in some embodiments, the ionizable lipid including the lipid compounds described herein is present in an amount from about 20 mol % to about 100 mol % (e.g., 20-90 mol %, 20-80 mol %, 20-70 mol %, 25-100 mol %, 30-70 mol %, 30-60 mol %, 30-40 mol %, 40-50 mol %, or 50-90 mol %) of the total lipid components; a non-cationic lipid (e.g., phospholipid) is present in an amount from about 0 mol % to about 50 mol % (e.g., 0-40 mol %, 0-30 mol %, 5-50 mol %, 5-40 mol %, 5-30 mol %, or 5-10 mol %) of the total lipid components, a conjugated lipid (e.g., a PEGylated lipid) in an amount from about 0.5 mol % to about 20 mol % (e.g., 1-10 mol % or 5-10%) of the total lipid components, and a sterol in an amount from about 0 mol % to about 60 mol % (e.g., 0-50 mol %, 10-60 mol %, 10-50 mol %, 15-60 mol %, 15-50 mol %, 20-50 mol %, 20-40 mol %) of the total lipid components, provided that the total mol % of the lipid component does not exceed 100%.

In some embodiments, the lipid-based carrier (or lipid nanoformulation) comprises about 25-100 mol % of the ionizable lipid including the lipid compounds described herein, about 0-50 mol % phospholipid, about 0-50 mol % sterol, and about 0-10 mol % PEGylated lipid.

In some embodiments, the lipid-based carrier comprises a payload (e.g., a DNA molecule described herein) that is formulated in a lipid nanoparticle, wherein the lipid nanoparticle comprises about 25-100 mol % of the ionizable lipid including the lipid compounds described herein, about 0-50 mol % phospholipid, about 0-50 mol % sterol, and about 0-10 mol % PEGylated lipid. In some embodiments, the encapsulation efficiency of the payload may be at least 70%.

In one embodiment, the lipid-based carrier (or lipid nanoformulation) comprises about 25-100 mol % of the ionizable lipid including the lipid compounds described herein; about 0-40 mol % phospholipid (e.g., DSPC), about 0-50 mol % sterol (e.g., cholesterol), and about 0-10 mol % PEGylated lipid.

In some embodiments, the lipid-based carrier comprises a payload (e.g., a DNA molecule described herein) that is formulated in a lipid nanoparticle, wherein the lipid nanoparticle comprises about 25-100 mol % of the ionizable lipid including the lipid compounds described herein; about 0-40 mol % phospholipid (e.g., DSPC), about 0-50 mol % sterol (e.g., cholesterol), and about 0-10 mol % PEGylated lipid. In some embodiments, the encapsulation efficiency of the payload may be at least 70%.

In some embodiments, the lipid-based carrier (or lipid nanoformulation) comprises about 30-60 mol % (e.g., about 35-55 mol %, or about 40-50 mol %) of the ionizable lipid including the lipid compounds described herein, about 0-30 mol % (e.g., 5-25 mol %, or 10-20 mol %) phospholipid, about 15-50 mol % (e.g., 18.5-48.5 mol %, or 30-40 mol %) sterol, and about 0-10 mol % (e.g., 1-5 mol %, or 1.5-2.5 mol %) PEGylated lipid.

In some embodiments, the lipid-based carrier comprises a payload (e.g., a DNA molecule described herein) that is formulated in a lipid nanoparticle, wherein the lipid nanoparticle comprises about 30-60 mol % (e.g., about 35-55 mol %, or about 40-50 mol %) of the ionizable lipid including the lipid compounds described herein, about 0-30 mol % (e.g., 5-25 mol %, or 10-20 mol %) phospholipid, about 15-50 mol % (e.g., 18.5-48.5 mol %, or 30-40 mol %) sterol, and about 0-10 mol % (e.g., 1-5 mol %, or 1.5-2.5 mol %) PEGylated lipid. In some embodiments, the encapsulation efficiency of the payload may be at least 70%.

In some embodiments, molar ratios of ionizable lipid/sterol/phospholipid (or another structural lipid)/PEG-lipid/additional components is varied in the following ranges: ionizable lipid (25-100%); phospholipid (DSPC) (0-40%); sterol (0-50%); and PEG lipid (0-5%).

In some embodiments, the lipid-based carrier comprises a payload (e.g., a DNA molecule described herein) that is formulated in a lipid nanoparticle, wherein the lipid nanoparticle comprises molar ratios of ionizable lipid/sterol/phospholipid (or another structural lipid)/PEG-lipid/additional components in the following ranges: ionizable lipid (25-100%); phospholipid (DSPC) (0-40%); sterol (0-50%); and PEG lipid (0-5%). In some embodiments, the encapsulation efficiency of the payload may be at least 70%.

In some embodiments, the lipid-based carrier (or lipid nanoformulation) comprises, by mol % or wt % of the total lipid components, 50-75% ionizable lipid (including the lipid compound as described herein), 20-40% sterol (e.g., cholesterol or derivative), 0 to 10% non-cationic-lipid, and 1-10% conjugated lipid (e.g., the PEGylated lipid).

In some embodiments, the lipid-based carrier comprises a payload (e.g., a DNA molecule described herein) that is formulated in a lipid nanoparticle, wherein the lipid nanoparticle comprises, by mol % or wt % of the total lipid components, 50-75% ionizable lipid (including the lipid compound as described herein), 20-40% sterol (e.g., cholesterol or derivative), 0 to 10% non-cationic-lipid, and 1-10% conjugated lipid (e.g., the PEGylated lipid). In some embodiments, the encapsulation efficiency of the payload may be at least 70%.

In some embodiments, the lipid-based carrier (or lipid nanoformulation) comprises (i) a DNA molecule described herein; (ii) a cationic lipid comprising from 50 mol % to 65 mol % of the total lipid present in the lipid-based carrier; (iii) a non-cationic lipid comprising a mixture of a phospholipid and a cholesterol derivative thereof, wherein the phospholipid comprises from 3 mol % to 15 mol % of the total lipid present in the lipid-based carrier and the cholesterol or derivative thereof comprises from 30 mol % to 40 mol % of the total lipid present in the lipid-based carrier; and (iv) a conjugated lipid comprising 0.5 mol % to 2 mol % of the total lipid present in the particle.

In some embodiments, the lipid-based carrier (or lipid nanoformulation) comprises (i) a DNA molecule described herein; (ii) a cationic lipid comprising from 50 mol % to 85 mol % of the total lipid present in the lipid-based carrier; (iii) a non-cationic lipid comprising from 13 mol % to 49.5 mol % of the total lipid present in the lipid-based carrier; and (d) a conjugated lipid comprising from 0.5 mol % to 2 mol % of the total lipid present in the lipid-based carrier.

In some embodiments, the phospholipid component in the mixture may be present from 2 mol % to 20 mol %, from 2 mol % to 15 mol %, from 2 mol % to 12 mol %, from 4 mol % to 15 mol %, from 4 mol % to 10 mol %, from 5 mol % to 10 mol %, (or any fraction of these ranges) of the total lipid components. In some embodiments, the lipid-based carrier (or lipid nanoformulation) is phospholipid-free.

In some embodiments, the sterol component (e.g. cholesterol or derivative) in the mixture may comprise from 25 mol % to 45 mol %, from 25 mol % to 40 mol %, from 25 mol % to 35 mol %, from 25 mol % to 30 mol %, from 30 mol % to 45 mol %, from 30 mol % to 40 mol %, from 30 mol % to 35 mol %, from 35 mol % to 40 mol %, from 27 mol % to 37 mol %, or from 27 mol % to 35 mol % (or any fraction of these ranges) of the total lipid components.

In some embodiments, the non-ionizable lipid components in the lipid-based carrier (or lipid nanoformulation) may be present from 5 mol % to 90 mol %, from 10 mol % to 85 mol %, or from 20 mol % to 80 mol % (or any fraction of these ranges) of the total lipid components.

The ratio of total lipid components to the payload (e.g., an encapsulated therapeutic agent such as a DNA molecule described herein can be varied as desired. For example, the total lipid components to the payload (mass or weight) ratio can be from about 10:1 to about 30:1. In some embodiments, the total lipid components to the payload ratio (mass/mass ratio; w/w ratio) can be in the range of from about 1:1 to about 25:1, from about 10:1 to about 14:1, from about 3:1 to about 15:1, from about 4:1 to about 10:1, from about 5:1 to about 9:1, or about 6:1 to about 9:1. The amounts of total lipid components and the payload can be adjusted to provide a desired N/P ratio, for example, N/P ratio of 3, 4, 5, 6, 7, 8, 9, 10, 11, 12, 13, 14, 15, 16, 17, 18, 19, 20, 21, 22, 23, 24, 25, 26, 27, 28, 29, 30, or higher. Generally, the lipid-based carrier (or lipid nanoformulation's) overall lipid content can range from about 5 mg/ml to about 30 mg/mL. Nitrogen: phosphate ratios (N:P ratio) is evaluated at values between 0.1 and 100.

The efficiency of encapsulation of a payload such as a protein and/or nucleic acid, describes the amount of protein and/or nucleic acid that is encapsulated or otherwise associated with a lipid nanoformulation (e.g., liposome or LNP) after preparation, relative to the initial amount provided. The encapsulation efficiency is desirably high (e.g., at least 70%, at least 80%, at least 90%, at least 95%, or close to 100%). The encapsulation efficiency may be measured, for example, by comparing the amount of protein or nucleic acid in a solution containing the liposome or LNP before and after breaking up the liposome or LNP with one or more organic solvents or detergents. An anion exchange resin may be used to measure the amount of free protein or nucleic acid (e.g., RNA) in a solution. Fluorescence may be used to measure the amount of free protein and/or nucleic acid (e.g., RNA) in a solution. For the lipid-based carrier (or lipid nanoformulation) described herein, the encapsulation efficiency of a protein and/or nucleic acid may be at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In some embodiments, the encapsulation efficiency may be at least 70%. In some embodiments, the encapsulation efficiency may be at least 80%. In some embodiments, the encapsulation efficiency may be at least 90%. In some embodiments, the encapsulation efficiency may be at least 95%.

Route of Administration

A dsDNA molecule described herein is introduced into a cell, tissue or subject by any suitable route.

Administration to a target cell or tissue (e.g., ex vivo) may be by methods known in the art such as transfection, e.g., transient or stable transfection using reagents (e.g., liposomal, calcium phosphate) or physical means (e.g., electroporation, gene gun, microinjection, microfluidic fluid shear, cell squeezing). Other methods are described, e.g., in Rad et al. 2021. Adv. Mater. 33:2005363, which is incorporated herein by reference.

Administration to a subject, e.g., a mammal, e.g., a human subject, may be by parenteral (e.g., intravenous, intramuscular, intraperitoneal, subcutaneous, or intracranial) route; by topical administration, transdermal administration or transcutaneous administration. Other suitable routes include oral, rectal, transmucosal, intranasal, inhalation (e.g., via an aerosol), buccal (e.g., sublingual), vaginal, intrathecal, intraocular, transdermal, intraendothelial, in utero (or in ovo), intrapleural, intracerebral, intraarticular, topical, intralymphatic. Also included is direct tissue or organ injection (e.g., to liver, eye, skeletal muscle, cardiac muscle, diaphragm, muscle or brain).

Ultrasound

In some aspects, the present disclosure provides a method of performing ultrasound (e.g., focused ultrasound (FUS)), e.g., for delivery of a DNA molecule described herein. Without wishing to be bound by theory, ultrasound is typically performed as a non-invasive technique that comprises administering ultrasound waves (e.g., sound waves with frequencies greater than 20 kHz) to a subject or a tissue of interest. In some embodiments, the ultrasound that is performed is focused ultrasound (FUS). In some embodiments, the ultrasound that is performed is unfocused ultrasound. In some embodiments, performing ultrasound comprises performing FUS to focus the ultrasound waves to target a precise area. In some embodiments, when combined with the use of bubbles (e.g., microbubbles or nanobubbles), ultrasound allows for delivery of a DNA molecule into a target cell of a tissue, e.g., through enhanced tissue permeabilization. Without wishing to be bound by theory, performing ultrasound on the tissue may induce oscillations of the bubbles, which may result in disruptions to the tight junctions of cells. In some embodiments, the tight junctions of capillary epithelial cells may be disrupted, which may allow for increased delivery of the DNA molecule across an endothelial barrier. In some embodiments, ultrasound is used to permeabilize a nuclear membrane of a target cell. In some embodiments, ultrasound is used to deliver a DNA molecule described herein to a liver tissue, spleen tissue, brain tissue, pancreatic tissue, heart tissue, skeletal muscle tissue, kidney tissue, or tumor tissue. In some embodiments, ultrasound and bubbles may be used to disrupt a blood-brain barrier to deliver the DNA molecule to brain tissue. In some embodiments, ultrasound is used to deliver a DNA molecule described herein to central nervous system (CNS) tissue, spinal cord tissue, dorsal root ganglia, trigeminal ganglia, or lymphatic vessels (e.g., meningeal lymphatic vessels). In some embodiments, ultrasound is used to deliver a DNA molecule described herein to a vascular endothelium. In some embodiments, ultrasound is performed concurrently with, before, or after an imaging step. In some embodiments, ultrasound is performed concurrently with the imaging step. The imaging step may comprise, e.g., magnetic resonance imaging (MRI) or ultrasound (e.g., medical or diagnostic ultrasound).

Devices for Ultrasound

In some embodiments, a device for performing ultrasound (e.g., FUS) comprises an ultrasound transducer (e.g., a piezoelectric ultrasound transducer). The ultrasound transducer may be used to deliver the ultrasound waves to a tissue. In some embodiments, the ultrasound transducer is a concave focusing transducer. The concave focusing transducer may comprise a fixed aperture and focal length. In some embodiments, the ultrasound transducer is a phase array transducer. In embodiments, the phase array transducer comprises one or more piston transducers that are arranged on a truncated surface of a spherical bowl. In some embodiments, the ultrasound transducer is a flat transducer, otherwise known as a fully populated phase array. In some embodiments, a device for performing ultrasound comprises an acoustic lens. While not wishing to be bound by theory, it is believed that the acoustic lens concentrates multiple ultrasound waves to a targeted area. In some embodiments, a device for administering ultrasound comprises one or more of (e.g., all of) a transducer (e.g., an ultrasound transducer, e.g., a piezoelectric ultrasound transducer), a crystal, an array, an electrode, a control, a power generator, a probe, a sensor, a Piezo ceramic, an amplifiers (e.g., a power amplifier), a transformer, a cable, a coupler, a filter, an accessory, a hydrophone, a phantom, or an acoustic intensity measurement system. In some embodiments, a device for performing ultrasound comprises a single-element transducer, e.g., a single-element FUS transducer. In some embodiments, a device for performing ultrasound comprises an image guidance system. In some embodiments, the image guidance system is used to perform magnetic resonance interference (MRI). In some embodiments, the image guidance system is used to perform ultrasound (e.g., medical or diagnostic ultrasound). In some embodiments, ultrasound is performed in a water tank (e.g., a degassed water tank). In some embodiments, one or more components in the device for performing ultrasound (e.g., a transducer) is placed inside a water tank (e.g., a degassed water tank).

Bubbles

In some aspects, a method described herein, e.g., a method of delivering a DNA molecule described herein, comprises administering a plurality of bubbles and performing ultrasound (e.g., FUS) on a tissue. In some embodiments, the bubbles have an average diameter less than 10 μm. In some embodiments, the bubbles have an average diameter of 50 nm to 10 μm. In some embodiments, the bubbles have an average diameter of 50 nm to 100 nm. In some embodiments, the bubbles have an average diameter of 1 μm to 10 μm.

In some embodiments, the bubbles comprise a gas comprising octafluoroproprane, also known as perflutren. In some embodiments, the bubbles comprise a gas comprising sulfur hexafluoride. In some embodiments, the bubbles comprise a gas comprising perfluorobutane, also known as perflubutane. In some embodiments, the bubbles comprise a gas comprising perfluopentane, also known as perflenapent. In some embodiments, the bubbles comprise a gas comprising perfluorohexane, also known as perflexane. In some embodiments, the bubbles comprise an inert gas. In some embodiments, the bubbles comprise a noble gas, e.g., Xe gas, He gas, or Ar gas. In some embodiments, the bubbles comprise a gas comprising one or more of (e.g., all of) air, nitrogen gas, sulfur hexafluoride gas, perfluorocarbon gas, or fluorocarbon gases.

In some embodiments, the bubbles comprise an exterior layer, also known as a shell. In some embodiments, the exterior layer of the bubbles comprises one or more of, e.g., all of, lipids, proteins, surfactants, or polymers. In some embodiments, the bubbles comprise albumin (e.g., human serum albumin, bovine serum albumin), lysozyme, avidin, or casein. In some embodiments, the proteins comprised in the exterior layer of the bubbles are denatured, e.g., denatured via heating or denatured via sonication, prior to assembly of the bubbles. In some embodiments, the bubbles comprise an exterior layer comprising a phospholipid. In some embodiments, the bubbles comprise an exterior layer comprising distearoylphosphatidylcholine (DSPC), dipalmitoylphosphatidylcholine (DPPC), 1,2-distearoyl-sn-glycero-3-phosphoglycerol (DSPG), distearoylphosphatidylethanolamine (DSPE), distearoylphosphatidylethanolamine-polyethyleneglycol molecular weight 2000 (DSPE-PEG2000), or polyethyleneglycol (PEG). In some embodiments, the exterior layer of the bubbles comprise polylactide-derived or cyanoacrylate polymers. In some embodiments, the bubbles comprise a monolayer lipid shell. In some embodiments, the monolayer lipid shell comprises lipids wherein the hydrophobic tails face toward the gas phase of the bubbles.

Bubbles may be provided as part of a kit or may be formed by the user of a kit. In some embodiments, a kit herein comprises, or a method herein involves the use of, a container that is suitable for making bubbles for use with ultrasound, e.g., FUS. In some embodiments, the container comprises a gas, e.g., octafluoropropane or any gas described herein. In some embodiments, the container comprises a component of a shell (e.g., a lipid and/or a protein). In some embodiments, the container also comprises a solvent, e.g., a biocompatible solvent, e.g., saline. In some embodiments, the container comprises a gas, solvent, and lipid. In some embodiments, mechanically agitating the container promotes formation of bubbles within the container; this is sometimes referred to as activation. In some embodiments, the components of the shell are provided in lyophilized form in the container. In some embodiments, re-suspension of the components of the shell results in a formation of bubbles. In some embodiments, the kit further comprises a dsDNA molecule described herein.

Tissues and Cells for Targeting

In some aspects, a method described herein comprising performing ultrasound (e.g., FUS) to deliver a DNA molecule described herein into a target cell of a tissue of interest. In some embodiments, ultrasound is used to deliver the DNA molecule into non-dividing cells or dividing cells. In some embodiments, ultrasound is used to deliver the DNA molecule into a hepatocyte, immune cell, neuron, glial cell, ependymal cell, pancreatic islet cell (e.g., alpha, beta, or delta cell), cardiomyocyte, skeletal myocyte, skeletal satellite cell, podocyte, tubular epithelial cell, endothelial cell, or fibroblast. In some embodiments, ultrasound is used to deliver the DNA molecule into the nucleus of a cell. In some embodiments, ultrasound is used to permeabilize a nuclear membrane of a target cell. In some embodiments, ultrasound is used to temporarily permeabilize the blood vessel wall of a capillary (e.g., a capillary of a subject, e.g., a human subject). In some embodiments, performing ultrasound enlarges an extracellular space or a perivascular space of a tissue. In some embodiments, performing ultrasound enhances interstitial flow in a brain or a tumor. In some embodiments, ultrasound is used to deliver the DNA molecule to brain tissue. In some embodiments, ultrasound is used to deliver the DNA molecule into a central nervous system (CNS) cell. In some embodiments, ultrasound is used to mediate delivery of a DNA molecule into a tumor. In some embodiments, the tumor comprises a hepatocellular carcinoma, brain tumor, pancreatic cancer, sarcoma, renal cancer, breast cancer, or skin cancer (e.g., a melanoma). In some embodiments, ultrasound is used to mediate delivery of a DNA molecule into a liver tissue, a spleen tissue, a brain tissue, a pancreas tissue, a heart tissue, a skeletal muscle tissue, kidney tissue, tumor tissue, breast tissue, or skin tissue. In some embodiments, ultrasound is performed on a volume of about 1 $mm^3$ to about 50 $cm^3$.

Administration

In some embodiments, a device used for performing ultrasound (e.g., FUS) may be used concurrently with a device used to perform MRI (e.g., an MRI scanner). In some embodiments, a device used to perform ultrasound can also perform MRI. In some embodiments, a plurality of bubbles or a DNA molecule (e.g., a DNA molecule described herein) is administered to a subject (e.g., a human subject) intravenously. In some embodiments, the plurality of bubbles or the DNA molecule is administered via intravenous (IV) infusion or IV bolus. In some embodiments, the DNA molecule is injected intravenously such that the DNA molecule reaches a tissue (e.g., the tissue that is targeted by ultrasound). In some embodiments, the plurality of bubbles or the DNA molecule is administered by injection (e.g., direct injection into the tissue of interest). In some embodiments, the plurality of bubbles and the DNA molecule are administered via different modes of administration. In some embodiments, the plurality of bubbles is administered intravenously, and the DNA molecule is administered to the tissue of interest by injection into the tissue. In some embodiments, the DNA molecule is administered intramuscularly or intratumorally.

In some embodiments, the DNA molecule is formulated, or included, with a carrier. In some embodiments, the DNA molecule is comprised in a nanoparticle (e.g., a nanoparticle that encapsulates or is covalently linked to the DNA molecule, gold nanoparticles, silica nanoparticles). In some embodiments, the DNA molecule is comprised in a lipid nanoparticle (LNP). In some embodiments, the DNA molecule is not comprised in an LNP. In some embodiments, the DNA molecule is comprised in a polymer nanoparticle. In some embodiments, the DNA molecule is comprised in a lipid particle. In some embodiments, the DNA molecule is comprised in a liposome. In some embodiments, the carrier is a cationic carrier (e.g., a cationic lipopolymer or transfection reagent), a fusosome, a non-nucleated cell (e.g., an ex vivo differentiated reticulocyte), a nucleated cell, an exosome, a protein carrier (e.g., a protein covalently linked to the DNA molecule), a peptide (e.g., a cell-penetrating peptide), a material (e.g., graphene oxide), a single pure lipid (e.g., cholesterol), or a DNA origami (e.g., DNA tetrahedron).

In some embodiments, the plurality of bubbles is administered to the subject at a concentration of $10^7$ bubbles/mL solvent to $10^{10}$ bubbles/mL solvent, e.g., about $10^9$ bubbles/mL solvent. In some embodiments, the solvent comprises a biocompatible solvent. In some embodiments, a subject is administered DEFINITY® perflutren lipid microsphere solution. In some embodiments, the plurality of bubbles is administered to a subject at a final concentration of $1\times10^4$ bubbles/g to $1\times10^7$ bubbles/g. In some embodiments, the DNA molecule and the bubbles are administered to the subject at a ratio of 105:1 to $10^{10}$:1 DNA molecules: microbubbles. In some embodiments, ultrasound is performed at a frequency of 0.2-3 MHz (e.g., 0.2-0.5 MHz, 0.5-1.0 MHz, 1.0-1.5 MHz, 1.5-2 MHz, 2-2.5 MHz, or 2.5-3 MHz). In some embodiments, ultrasound is performed at a frequency of about 2 MHz to about 40 MHz (e.g., about 20 MHz). In some embodiments, ultrasound is performed with an ultrasound transducer, e.g., an ultrasound transducer as described herein, e.g., a focused ultrasound transducer. In some embodiments, ultrasound is performed at 5 μs to 0.5 s bursts, e.g., at 5 ms to 20 ms, e.g., at 10 ms bursts. In some embodiments, ultrasound is performed at a pulse repetition frequency of 0.1 to 10 Hz, e.g., about 0.5 Hz. In some embodiments, ultrasound is performed at a peak negative pressure of 0.1 to 2.0 (e.g., 0.1-0.5 MPa, 0.5-1.0 MPa, 1.0 to 1.5 MPa, or 1.5 to 2.0 MPa). In some embodiments, ultrasound is performed for a duration of 1 minute to 10 minutes, e.g., 1 minute to 5 minutes, 1 minute to 3 minutes, 3 minutes to 5 minutes, or 5 minutes to 10 minutes, e.g., about 2 minutes.

In some embodiments, a method described herein comprises administering a plurality of bubbles, administering a DNA molecule (e.g., an DNA molecule described herein), and performing ultrasound. In some embodiments, the plurality of bubbles is administered after the DNA molecule is administered, and ultrasound is performed after the plurality of bubbles is administered. In some embodiments, the DNA molecule is administered after the plurality of bubbles is administered, and ultrasound is performed after the DNA molecule is administered. In some embodiments, the plurality of bubbles is administered concurrently (e.g., simultaneously) with the DNA molecule. In some embodiments, the plurality of bubbles and the DNA molecule are administered concurrently (e.g., simultaneously) with ultrasound being performed.

In some embodiments, the plurality of bubbles is administered concurrently (e.g., simultaneously) with ultrasound being performed. In some embodiments, the DNA molecule is administered first, and then the plurality of bubbles is administered concurrently (e.g., simultaneously) with ultrasound being performed. In some embodiments, the DNA molecule is administered concurrently (e.g., simultaneously) with ultrasound being performed. In some embodiments, the plurality of bubbles is administered first, and then the DNA molecule is administered concurrently (e.g., simultaneously) with ultrasound being performed.

In some embodiments, ultrasound is initiated less than 70 minutes (e.g., less than 1 second, less than 5 seconds, less than 10 seconds, less than 20 seconds, less than 30 seconds, less than 1 minute, less than 2 minutes, less than 3 minutes, less than 4 minutes, less than 5 minutes, less than 6 minutes, less than 7 minutes, less than 8 minutes, less than 9 minutes, less than 10 minutes, less than 15 minutes, less than 20 minutes, less than 25 minutes, less than 30 minutes, less than 35 minutes, less than 40 minutes, less than 45 minutes, less than 50 minutes, less than 55 minutes, less than 60 minutes, or less than 65 minutes) after the administration of the plurality of bubbles is initiated. In some embodiments, ultrasound is initiated less than 70 minutes (e.g., less than 1 second, less than 5 seconds, less than 10 seconds, less than 20 seconds, less than 30 seconds, less than 1 minute, less than 2 minutes, less than 3 minutes, less than 4 minutes, less than 5 minutes, less than 6 minutes, less than 7 minutes, less than 8 minutes, less than 9 minutes, less than 10 minutes, less than 15 minutes, less than 20 minutes, less than 25 minutes, less than 30 minutes, less than 35 minutes, less than 40 minutes, less than 45 minutes, less than 50 minutes, less than 55 minutes, less than 60 minutes, or less than 65 minutes) after administration of the DNA molecule is initiated.

In some embodiments, administration of a plurality of bubbles is initiated less than 85 minutes (e.g., less than 1 second, less than 5 seconds, less than 10 seconds, less than 20 seconds, less than 30 seconds, less than 1 minute, less than 2 minutes, less than 3 minutes, less than 4 minutes, less than 5 minutes, less than 6 minutes, less than 7 minutes, less than 8 minutes, less than 9 minutes, less than 10 minutes, less than 15 minutes, less than 20 minutes, less than 25 minutes, less than 30 minutes, less than 35 minutes, less than 40 minutes, less than 45 minutes, less than 50 minutes, less than 55 minutes, less than 60 minutes, less than 65 minutes, less than 70 minutes, less than 75 minutes, or less than 80 minutes) after administration of the DNA molecule is initiated. In some embodiments, administration of the DNA molecule is initiated less than 85 minutes (e.g., less than 1 second, less than 5 seconds, less than 10 seconds, less than 20 seconds, less than 30 seconds, less than 1 minute, less than 2 minutes, less than 3 minutes, less than 4 minutes, less than 5 minutes, less than 6 minutes, less than 7 minutes, less than 8 minutes, less than 9 minutes, less than 10 minutes, less than 15 minutes, less than 20 minutes, less than 25 minutes, less than 30 minutes, less than 35 minutes, less than 40 minutes, less than 45 minutes, less than 50 minutes, less than 55 minutes, less than 60 minutes, less than 65 minutes, less than 70 minutes, less than 75 minutes, or less than 80 minutes) after administration of the plurality of bubbles is initiated.

In some embodiments, a method described herein comprises a first step (e.g., administration of a composition or performing ultrasound) and a second step (e.g., administration of a second composition or performing ultrasound) wherein the first step is begun, then the second step is begun such that there is overlap in time of the first step and second step. In some embodiments, the first step may end before the second step ends. In some embodiments, the second step may end before the first step ends. In some embodiments, the first step and the second step end at the same time. In some embodiments, the first step and the second step begin at the same time, but end at different times. In some embodiments, the first step and the second step begin at different times and end at the same time. In some embodiments, the first step and the second step begin at different times and end at different times.

In some embodiments, the method comprises two or more steps, wherein the two or more steps are being performed at the same time, and wherein the start and end of each step are not necessarily at the same time. In some embodiments, the method comprises a first step, a second step, and a third step, such that there is overlap in time of all of the first step, second step, and third step. In some embodiments, the start and end of each step are at the same time. In some embodiments, the start and end of each step are at different times. In some embodiments, there is a period of time of at least 3 seconds (e.g., at least 5 seconds, at least 10 seconds, at least 30 seconds, at least 1 minute, at least 5 minutes, at least 10 minutes, at least 30 minutes, at least 60 minutes) where two or more of the steps overlap.

In some embodiments, when a first step and second step are being performed concurrently, the first step starts at least 3 seconds (e.g., at least 5 seconds, at least 10 seconds, at least 30 seconds, at least 1 minute, at least 5 minutes, at least 10 minutes, at least 30 minutes, at least 60 minutes) before the second step starts. In some embodiments, when a first step and second step are being performed concurrently, the first step starts at least 3 seconds (e.g., at least 5 seconds, at least 10 seconds, at least 30 seconds, at least 1 minute, at least 5 minutes, at least 10 minutes, at least 30 minutes, at least 60 minutes) after the second step starts. In some embodiments, when a first step and second step are being performed concurrently, the first step ends at least 3 seconds (e.g., at least 5 seconds, at least 10 seconds, at least 30 seconds, at least 1 minute, at least 5 minutes, at least 10 minutes, at least 30 minutes, at least 60 minutes) before the second step ends. In some embodiments, when a first step and second step are being performed concurrently, the first step ends at least 3 seconds (e.g., at least 5 seconds, at least 10 seconds, at least 30 seconds, at least 1 minute, at least 5 minutes, at least 10 minutes, at least 30 minutes, at least 60 minutes) after the second step ends.

In some embodiments, a method described herein comprises a first step (e.g., administration of a composition or performing ultrasound) and a second step (e.g., administration of a second composition or performing ultrasound), wherein the first step and second step are simultaneous. In some embodiments, the first step and the second step start at the same time and end at the same time. In some embodiments, the method comprises two or more steps, wherein the two or more steps start at the same time and end at the same time. In some embodiments, the method comprises a first step, a second step, and a third step, wherein the first step, second step, and third step all start at the same time and end at the same time.

In some embodiments, a user chooses a target cell and then delivers DNA to that cell using a method of delivery described herein. In other embodiments, a user delivers DNA to a target cell in a tissue without specifically choosing the target cell beforehand. For example, if a user delivers DNA to a target tissue, and 10 cells in the target tissue take up the DNA, those 10 cells are target cells even if the user did not specifically choose those 10 cells over other cells in the tissue. A target cell may come into contact with or receive a DNA molecule described herein. A target cell may be a cell of a type to which it is desired to receive one or all of a DNA molecule as described herein, a plurality of bubbles, or ultrasound. The combination of administering a DNA molecule, administering a plurality of bubbles, and performing ultrasound may lead to preferential delivery of the DNA molecule to a target cell compared to a non-target cell. In some embodiments, a cell of the same type of the target cell or in the same tissue as the target cell does not receive one or all of a DNA molecule as described herein, a plurality of bubbles, or ultrasound.

Applications

The dsDNA molecule described herein can be used in any applications where an effector is beneficially administered to a subject, e.g., therapeutic or health applications for a subject, e.g., a human or non-human animal. Although the descriptions of pharmaceutical compositions provided herein are principally directed to pharmaceutical compositions which are suitable for administration to humans, it will be understood by the skilled artisan that such compositions are generally suitable for administration to any other animal. The subject can be any animal, e.g., a mammal, e.g., a human or non-human mammal. In embodiments, the subject is a vertebrate animal (e.g., mammal, bird, fish, reptile, or amphibian). In embodiments, the subject is a human. In embodiments, the method subject is a non-human mammal. In embodiments, the subject is a non-human mammal is such as a non-human primate (e.g., monkeys, apes), ungulate (e.g., cattle, buffalo, sheep, goat, pig, camel, llama, alpaca, deer, horses, donkeys), carnivore (e.g., dog, cat), rodent (e.g., rat, mouse), or lagomorph (e.g., rabbit). In embodiments, the subject is a bird, such as a member of the avian taxa Galliformes (e.g., chickens, turkeys, pheasants, quail), Anseriformes (e.g., ducks, geese), Paleaognathae (e.g., ostriches, emus), Columbiformes (e.g., pigeons, doves), or Psittaciformes (e.g., parrots). In embodiments, the subject is an invertebrate such as an arthropod (e.g., insects, arachnids, crustaceans), a nematode, an annelid, a helminth, or a mollusk.

In some embodiments, a dsDNA molecule described herein is provided at a dose of about 0.1-100 mg/kg of the DNA.

In some embodiments, a dsDNA molecule described herein imparts a biological effect of the effector, e.g., expression of a therapeutic polypeptide, on a host cell, tissue or subject over a time period of at least 2, at least 3, at least 4, at least 5, at least 6 days or at least a week; at least 8, at least 9, at least 10, at least 12, at least 14 days or at least two weeks; at least 16, at least 18, at least 20 days or at least 3 weeks; at least 22, at least 24, at least 25, at least 27, at least 28 days or at least a month; at least 2 months, 3 months, 4 months, 5 months, 6 months or more; between one week and 6 months, between 1 month to 6 months, or between 3 months to 6 months.

In some embodiments, a dsDNA molecule described herein imparts a biological effect of the effector, e.g., expression of a therapeutic polypeptide, on a host cell, tissue or subject over a time period of at least 1 cell divisions of the host cell.

In embodiments, a dsDNA molecule described herein can be used to deliver an effector, e.g., an effector described herein, to a cell, tissue or subject.

In embodiments, a dsDNA molecule described herein can be used to modulate (e.g., increase or decrease) a biological parameter in a cell, tissue or subject. The biological parameter may be an increase or decrease in gene expression of a subject gene in a target cell, tissue or subject.

In embodiments, a dsDNA molecule described herein can be used to treat a cell, tissue or subject in need thereof by administering a dsDNA molecule described herein to such cell, tissue or subject. In an embodiment, the subject has or has been diagnosed with a condition that can be treated with an effector encoded in the dsDNA.

In some embodiments, the present disclosure provides a method of modulating (e.g., increasing or decreasing) a biological activity in a target cell, the method comprising: (i) providing a target cell comprising a dsDNA molecule as described herein, wherein the dsDNA molecule encodes an effector that modulates a biological activity in the target cell; and (ii) maintaining (e.g., incubating) the cell under conditions suitable for expressing the effector from the dsDNA molecule; thereby modulating the biological activity in the target cell.

In some embodiments, the present disclosure provides a method of administering a dsDNA molecule to a subject, e.g., a mammal, wherein the dsDNA molecule comprises a sense strand and an antisense strand, wherein the sense strand comprises one or more chemically modified nucleobases, and wherein the antisense strand is substantially free of (e.g., is free of) chemically modified nucleobases. In some embodiments, administration of the dsDNA molecule results in a weight change in the subject of less than 12%, less than 10%, or less than 8%, as compared to the initial weight of the subject prior to administration of the dsDNA molecule. In some embodiments, the subject does not lose weight after administration of the dsDNA molecule. In some embodiments, the weight loss is less than 12%, less than 10%, or less than 8%, as compared to the initial weight of the subject prior to administration of the dsDNA molecule. In some embodiments, a subject administered a dsDNA molecule comprising a sense strand and an antisense strand, wherein the sense strand comprises one or more chemically modified nucleobases, and wherein the antisense strand is substantially free of (e.g., is free of) chemically modified nucleobases, exhibits less weight loss (e.g., 1.5-fold, 2-fold, 2.5-fold, or 3-fold less weight loss) relative to a subject administered a dsDNA molecule that does not comprise chemically modified nucleobases. In some embodiments, the weight change is measured at 1 day, 2 days, 3 days, 4 days, 5 days, 6 days, or 7 days following administration of the dsDNA molecule.

EXAMPLES

Table of Contents

Example 1: Formulation of a dsDNA molecule with LNP
Example 2: Design and assembly of a plasmid template for production of double-stranded DNA (dsDNA) molecules
Example 3: Production of single-stranded DNA molecules as precursors to circular hemi-modified dsDNA molecules
Example 4: Production of circular hemi-modified double-stranded DNA molecules
Example 5: Assessment of reporter gene expression in vitro
Example 6: Assessment of innate immune response in cells in vitro
Example 7: Production of lipid nanoparticles (LNPs) comprising circular hemi-modified double-stranded DNA molecules
Example 8: Assessment of tolerability and effector expression following in vivo administration of cheDNA molecules
Example 9: Preparation of double-stranded DNA incorporating chemically modified DNA nucleobases on one strand (hemi-modified) in a bidirectional format
Example 10: Alternative method of preparation of double-stranded DNA incorporating chemically modified DNA nucleobases on one strand (hemi-modified) in a bidirectional format
Example 11: Delivery of naked DNA molecules
Example 12: Production of lipid nanoparticle-encapsulated DNA molecules
Example 13: Delivery of lipid nanoparticle-encapsulated DNA molecules
Example 14: Design and assembly of a plasmid template for production of double-stranded DNA (dsDNA) molecules
Example 15: Production of single-stranded DNA molecules as precursors to circular hemi-modified dsDNA molecules
Example 16: Production of circular hemi-modified double-stranded DNA molecules containing modified nucleobases in sense or antisense strands
Example 17: Assessment of reporter gene expression in vitro
Example 18: Assessment of innate immune response in cells in vitro

Example 1: Formulation of a dsDNA Molecule with LNP

This example describes how to formulate the dsDNA molecules made as described herein with a lipid nanoparticle (LNP).

Nucleic acid molecules are combined with lipid components via microfluidic devices according to the method of Chen et al. 2012. J Am Chem Soc. Volume 134, Issue 16:6948-6951. Briefly, the microfluidic devices are fabricated in polydimethylsiloxane (PDMS) according to standard lithographic procedures (McDonald & Whitesides. 2002. Accounts Chem Res Volume 35, Issue 7:491-499). The lipid components, typically containing cationic lipids, cholesterol, helper lipids, polyethylene glycol modified lipids, and lipids facilitating targeting moiety conjugation (optional), are combined and solubilized in 90% ethanol. The nucleic acid molecules are dissolved in buffer. The nucleic acid solution, the lipid solution, and phosphate buffer saline (PBS) are injected into the microfluidic device. The freshly prepared LNPs are dialyzed against PBS buffer using membranes with MWCO of 3.5 kD to remove ethanol and exchange buffer.

The LNPs are characterized in terms of effective diameter, polydispersity, and zeta potential using dynamic light scattering (DLS) (ZetaPALS, Brookhaven Instruments, NY, 15-mW laser, incident beam 676 nm); and total nucleic acid concentration is determined by lysing the particles and using Quant-iT™ 1×dsDNA Assay Kits, High Sensitivity (HS) and Broad Range (BR) (ThermoFisher Scientific, Q33232).

Example 2: Design and Assembly of a Plasmid Template for Production of Double-Stranded DNA (dsDNA) Molecules This example describes production of a plasmid template for a dsDNA molecule. In this example, a construct template was designed with the following specific sequence components.

Promoter UBC:

(SEQ ID NO: 1)

```
5'ggcctccgcgccgggttttggcgcctcccgcgggcgcccccctcgtcacggcgagcgctgccacgtcagacgaagggcg
caggagcgtcctgatccttccgcccggacgctcaggacagcggcccgctgctcataagactcggccttagaaccccagtatca
gcagaaggacattttaggacgggacttgggtgactctagggcactggttttctttccagagagcggaacaggcgaggaaaagta
gtcccttctcggcgattctgcggagggatctccgtggggcggtgaacgccgatgattatataaggacgcgccgggtgtggcac
agctagttccgtcgcagccgggatttgggtcgcggttcttgtttgtggatcgctgtgatcgtcacttggtgagtagcgggctgctgg
gctggccggggctttcgtggccgccgggccgctcggtgggacggaagcgtgtggagagattgccaagggctgtagtctgggt
ccgcgagcaaggttgccctgaactgggggttggggggagcgcagcaaaatggcggctgttcccgagtcttgaatggaagacg
cttgtgaggcgggctgtgaggtcgttgaaacaaggtgggggggcatggtgggcggcaagaacccaaggtcttgagcccttcgct
aatgcgggaaagctcttattcgggtgagatgggctgggcaccatctggggaccctgacgtgaagtttgtcactgactggagaac
tcggtttgtcgtctgttgcgggggcggcagttatggcggtgccgttgggcagtgcacccgtacctttgggagcgcgcgccctcgt
cgtgtcgtgacgtcacccgttctgttggcttataatgcagggtggggccacctgccggtaggtgtgcggtaggcttttctccgtcg
caggacgcagggttcgggcctagggtaggctctcctgaatcgacaggcgccggacctctggtgaggggagggataagtgag
gcgtcagtttctttggtcggttttatgtacctatcttcttaagtagctgaagctccggttttgaactatgcgctcggggttggcgagtgt
gttttgtgaagttttttaggcaccttttgaaatgtaatcatttgggtcaatatgtaattttcagtgttagacttgtaaattgtccgctaaattc
tggccgtttttggctttttgttagaca3'
```

Effector sequence (in this case exemplified by a reporter protein) encoding a dual reporter protein cassette (FLuc/T2A/eGFP/Double Stop):

(SEQ ID NO: 2)

```
5'atggaggacgccaagaacatcaagaagggcccgcccccttctacccccctggaggacggcaccgccggcgagcagctg
cacaaggccatgaagcggtacgccctggtgcccggcaccatcgccttcaccgacgcccacatcgaggtggacatcacctacg
ccgagtacttcgagatgagcgtgcggctggccgaggccatgaagcggtacggcctgaacaccaaccaccggatcgtggtgtg
cagcgagaacagcctgcagttcttcatgcccgtgctgggcgccctgttcatcggcgtggccgtggccccgccaacgacatcta
caacgagcgggagctgctgaacagcatgggcatcagccagcccaccgtggtgttcgtgagcaagaagggcctgcagaagat
cctgaacgtgcagaagaagctgcccatcatccagaagatcatcatcatggacagcaagaccgactaccagggcttccagagca
tgtacaccttcgtgaccagccacctgcccccggcttcaacgagtacgacttcgtgcccgagagcttcgaccgggacaagacc
atcgccctgatcatgaacagcagcggcagcaccggcctgcccaagggcgtggccctgccccaccggaccgcctgcgtgcgg
ttcagccacgcccgggaccccatcttcggcaaccagatcatccccgacaccgccatcctgagcgtggtgcccttccaccacgg
cttcggcatgttcaccaccctgggctacctgatctgcggcttccgggtggtgctgatgtaccggttcgaggaggagctgttcctgc
ggagcctgcaggactacaagatccagagcgccctgctggtgcccaccctgttcagcttcttcgccaagagcaccctgatcgaca
agtacgacctgagcaacctgcacgagatcgccagcggcggcgcccccctgagcaaggaggtgggcgaggccgtggccaa
gcggttccacctgcccggcatccggcagggctacggcctgaccgaaaccaccagcgccatcctgatcacccccgagggcga
cgacaagcccggcgccgtgggcaaggtggtgcccttcttcgaggccaaggtggtggacctggacaccggcaagaccctggg
cgtgaaccagcggggcgagctgtgcgtgcggggccccatgatcatgagcggctacgtgaacaaccccgaggccaccaacg
ccctgatcgacaaggacggctggctgcacagcggcgacatcgcctactgggacgaggacgagcacttcttcatcgtggaccg
gctgaagagcctgatcaagtacaagggctaccaggtggcccccgccgagctggagagcatcctgctgcagcaccccaacatc
ttcgacgccggcgtggccggcctgcccgacgacgacgccggcgagctgcccgccgccgtggtggtgctggagcacggcaa
gaccatgaccgagaaggagatcgtggactacgtggccagccaggtgaccaccgccaagaagctgcggggcggcgtggtgtt
cgtggacgaggtgcccaagggcctgaccggcaagctggacgcccggaagatccgggagatcctgatcaaggccaagaagg
gcggcaagatcgccgtgggctccggcgagggcagaggaagtcttctaacatgcggtgacgtggaggagaatcccggccctg
tgagcaagggcgaggagctgttcaccggggtggtgcccatcctggtcgagctggacggcgacgtaaacggccacaagttcag
cgtgtccggcgagggcgagggcgatgccacctacggcaagctgaccctgaagttcatctgcaccaccggcaagctgcccgtg
ccctggcccaccctcgtgaccaccctgacctacggcgtgcagtgcttcagccgctaccccgaccacatgaagcagcacgactt
cttcaagtccgccatgcccgaaggctacgtccaggagcgcaccatcttcttcaaggacgacggcaactacaagacccgcgccg
aggtgaagttcgagggcgacaccctggtgaaccgcatcgagctgaagggcatcgacttcaaggaggacggcaacatcctgg
ggcacaagctggagtacaactacaacagccacaacgtctatatcatggccgacaagcagaagaacggcatcaaggtgaacttc
aagatccgccacaacatcgaggacggcagcgtgcagctcgccgaccactaccagcagaacacccccatcggcgacggccc
cgtgctgctgcccgacaaccactacctgagcacccagtccgccctgagcaaagaccccaacgagaagcgcgatcacatggtc
ctgctggagttcgtgaccgccgccgggatcactctcggcatggacgagctgtacaagtgatga3'
```

Bovine growth hormone PolyA:

(SEQ ID NO: 3)

```
5'ctgtgccttctagttgccagccatctgttgtttgcccctcccccgtgccttccttgaccctggaaggtgccactcccactgtccttt
cctaataaaatgaggaaattgcatcgcattgtctgagtaggtgtcattctattctggggggtggggggggcaggacagcaaggg
ggaggattgggaagacaatagcaggcatgctggggatgcggtgggctctatgg3'
```

-continued

```
Optional:
SV40 enhancer sequence:
                                                        (SEQ ID NO: 4)
5'-ggtgtggaaagtccccaggctccccagcaggcagaagtatgcaaagcatgcatctcaattagtcagcaacca-3'

Chimeric intron:
                                                        (SEQ ID NO: 5)
5'gtaagtatcaaggttacaagacaggtttaaggaaaccaatagaaactgggcttgtcgagacagagaagactcttgcgtttctg
ataggcacctattggtcttactgacatccactttgcctttctctccacag-3'

Woodchuck hepatitis virus post transcriptional element (WPRE)
                                                        (SEQ ID NO: 6)
5'aatcaacctctggattacaaaatttgtgaaagattgactggtattcttaactatgttgctccttttacgctatgtggatacgctgcttt
aatgcctttgtatcatgctattgcttcccgtatggctttcattttctcctccttgtataaatcctggttgctgtctctttatgaggagttgtgg
cccgttgtcaggcaacgtggcgtggtgtgcactgtgtttgctgacgcaacccccactggttggggcattgccaccacctgtcagc
tcctttccgggactttcgctttccccctccctattgccacggcggaactcatcgccgcctgccttgcccgctgctggacaggggct
cggctgttgggcactgacaattccgtggtgttgtcggggaaatcatcgtcctttccttggctgctcgcctgtgttgccacctggattc
tgcgcgggacgtccttctgctacgtcccttcggccctcaatccagcggaccttccttcccgcggcctgctgccggctctgcggcc
tcttccgcgtcttcgccttcgccctcagacgagtcggatctccctttgggccgcctccccgc-3'
```

A plasmid template was designed with these elements using standard DNA design manipulation software. Once designed, plasmids were prepared according to standard methods for use as a template in PCR amplification.

Example 3: Production of Single-Stranded DNA Molecules as Precursors to Circular Hemi-Modified dsDNA Molecules This example demonstrates preparation of single stranded DNA (ssDNA) molecules, illustrated in FIG. 1A, which can be used as precursor material for production of circular, hemi-modified double stranded DNA. To generate the ssDNA precursor, plasmid DNA (2 ng/100 ul PCR reaction), e.g., as described in Example 2, was used as a template for PCR amplification using KOD-Multi & Epi-polymerase (TYB-KME-101, Diagnocine). Other commercially available polymerases such as KOD One (TYB-KMM-101, Diagnocine) or KOD Xtreme (Millipore Sigma) may also be used. PCR reaction conditions include:

a. PCR Buffer for KOD FX (TYB-KFX-1B, Diagnocine) at a 1× concentration.
b. Forward and reverse primers at a final concentration of 300 μM.
c. 2 units of KOD-Multi & Epi-polymerase/100 ul PCR reaction For the synthesis of dsDNA molecules by PCR, in addition to containing sequences complementary to the plasmid, primers contained additional sequences useful in downstream processes:

a. Restriction enzyme recognition sequence (e.g. BsaI), used to create sticky ends in the DNA after restriction enzyme digestion and facilitate adapter ligation; and
b. Additional bases (e.g., 5'-GGTCCTTC-3') to increase restriction enzyme digestion efficiency.
c. Phosphorothioate modifications to block 5'->3' exonuclease activity.

The following primers were used for PCR amplification:

```
FWD:
                                        (SEQ ID NO: 7)
/5Phos/GCGCGGTCCTTCGGTCTCAGAAGgctgcttcgcgatgtacggg
ccag

REV:
                                        (SEQ ID NO: 8)
C*A*C*A*C*G*T*C*CCGAGGTCTCACTTCgccatagagcccaccgcat
ccccag
```

In these sequences, the bases specific for the template are in lower case, the additional bases to create the sticky ends, including the BsaI recognition site, are shown in UPPER CASE, and the phosphorothioate linkages between nucleosides are shown as *.

Thermocycling was performed. For KOD-Multi & Epi-polymerase, the following reaction conditions were used: 1 cycle at 94° C. for 2 minutes, and 40 repeats of the following cycles: 10 seconds at 98° C., 10 seconds at 63° C., and 30 seconds/kb at 68° C., with a final hold at 4° C. The PCR was enriched first through treatment with 2.4 U of Thermolabile Proteinase K (P8111, New England Biolabs) per 1 mL of PCR, incubated at 37° C. for 15-30 minutes, followed by a heat inactivation of 10-30 minutes at 55-80° C. The solution was 0.22 micron filtered and enriched by tangential flow filtration on the Pulse system (Formulatrix) using a 100 kD cutoff chip with 14× diavolumes. The PCR DNA was then quantified by Nanodrop (Thermo Scientific).

To generate the single-stranded DNA precursor, PCR DNA containing the 8× phosphorothioate modifications on the 5' side of the reverse primer was digested overnight (~14 hours) at 37° C. in 1×NEB4 buffer (B7004S, New England Biolabs), with 1 U/μg of both T7 Exonuclease (M0263, New England Biolabs) and Lambda Exonuclease (M0262, New England Biolabs). To remove residual PCR DNA, the DNA was incubated with Mly1 endonuclease, then enriched using standard DNA enrichment techniques. The enrichment of the ssDNA precursor was assessed by Agilent UPLC, using a weak anion exchange column.

Example 4: Production of Circular Hemi-Modified Double-Stranded DNA Molecules This example demonstrates preparation of circular "hemi-modified" dsDNA molecules (cheDNA), i.e., circular dsDNA molecules containing chemically modified nucleobases on a single strand, using ssDNA precursors from Example 3 (as illustrated in FIG. 1B).

KOD-Multi & Epi-polymerase was first heat-activated by incubation at 94° C. for two minutes. Thereafter, 5' second-strand synthesis reactions were set up, consisting of 0.25-2 units of heat-activated KOD-Multi & Epi-polymerase per 250 ng of ssDNA, 25 ng/μL ssDNA, the forward primer from PCR at 300 M, dNTPs to a final concentration of 0.2 mM each, and KOD FX polymerase buffer (1× final concentration). Modified deoxynucleoside triphosphates were added at various ratios with their cognate dNTP, summing to a total of 200 M. Table 3 includes the modified deoxynucleoside triphosphates that were incorporated into the second strand (e.g., sense strand) of the DNA molecule. For instance, the cognate dNTP of 5-hydroxymethyl-2'-dUTP, 2'-dUTP, 5-aminoallyl-2'-dUTP, 5-propargylamino-2'-dUTP, N1-methylpseudo-dUTP, and 5-dihydroxypentyl-2'-dUTP is dTTP. A reaction designed for 25% incorporation into the second strand of the DNA would be 50 μM chemically modified dNTP and 150 μM cognate dNTP, whereas a reaction designed for 75% incorporation into the second strand of the DNA would be 150 μM chemically modified dNTP and 50 μM cognate dNTP. 100% incorporation into the second strand of the DNA, as denoted in Table 3, entails complete replacement of the cognate dNTP with the chemically modified dNTP during the second-strand synthesis reactions. In instances where the primer contains canonical nucleobases, the resulting strand may have less than 100% chemically modified nucleobases, e.g., at least 98% or 99% chemically modified nucleobases, even when 100% incorporation takes place during the second-strand synthesis reaction.

TABLE 3

Exemplary chemically modified deoxynucleoside triphosphates, cognate dNTP, and percent incorporation into circular hemi-modified dsDNA.

| Chemically Modified Deoxynucleoside Triphosphate | Modification Abbreviation | Cognate dNTP | Percent incorporation into the second strand |
|---|---|---|---|
| 5-aminoallyl-2'-dUTP | 5aaU | dTTP | 100% |
| N1-methylpseudo-dUTP | nmpU | dTTP | 100% |
| 5-dihydroxypentyl-2'-dUTP | 5hpU | dTTP | 100% |
| 5-propargylamino-2'-dUTP | 5paU | dTTP | 100% |
| 5-hydroxymethyl-2'dUTP | 5hmU | dTTP | 100% |
| 2'-dUTP | dU | dTTP | 100% |

Production of the linear, hemi-modified dsDNA entailed isothermal extension of DNA from a primer, not a thermocycling process akin to polymerase chain reaction. To polymerize DNA starting from the primer, reaction mixtures (without the heat-activated KOD-Multi & Epi-polymerase) were brought up to 68° C., at which time the heat-activated KOD-Multi & Epi-polymerase was added to the reaction and the entire solution was thoroughly mixed via tube inversion and shaking. The reaction was then incubated for 30-60 minutes at 68° C. DNA was enriched using standard DNA enrichment columns. Second strand synthesis was confirmed via the Invitrogen E-gel system with 1% EX gels (G401001, Invitrogen). An alternative method of assessing DNA enrichment was determined by the 4200 Tapestation (G2991BA, Agilent) using the Genomic DNA screentape (5067-5366; 5067-5365). Samples were run according to the manufacturer's protocol. Enrichment was determined by automated software detection of the target peak, calculated as a percentage of the total area of all peaks detected by the software.

To generate circular, hemi-modified double-stranded DNA (cheDNA), the linear, hemi-modified double stranded DNA was digested at 80 ng/μL by BsaI v2-HF (R3733, New England Biolabs) at 2.5 U/μg in 1× rCutsmart buffer at 37° C. for >1 hr to create sticky ends. The solution was then diluted to 16 ng/μL in 1× T4 Ligase buffer (B0202, New England Biolabs), and ligated with T3 DNA Ligase (M0317, New England Biolabs) at 300 U/μg at 20° C. for >1 hr. Ligation was confirmed via the Invitrogen E-gel system with 1% EX gels (G401001, Invitrogen). The enzymes were then heat inactivated at >65° C. for 20 minutes and allowed to cool to room temperature. To remove unligated DNA, T5 exonuclease (M0663, New England Biolabs) was added to the solution at 2.5 U/μg and incubated at 37° C. for 75-120 minutes. The persistence of the desired product was confirmed via the Invitrogen E-gel system with 1% EX gels (G401001, Invitrogen). The solution was then run through standard silica DNA enrichment columns to enrich for cheDNA. The cheDNA enrichment was assessed by the 4200 Tapestation (G2991BA, Agilent) using the Genomic DNA screentape (5067-5366; 5067-5365). Samples were run according to the manufacturer's protocol. Enrichment was determined by automated software detection of the target peak, calculated as a percentage of the total area of all peaks detected by the software. The circularization percentage of the cheDNA was calculated by first digesting the cheDNA with a single cutter restriction enzyme, at 80 U/μg at 37° C. for 15 minutes. 50 ng of the digestion and undigested samples were run on the 4200 Tapestation (G2991BA, Agilent) using the Genomic DNA screentape (5067-5366; 5067-5365). Samples were run according to the manufacturer's protocol. Enrichment of the cheDNA was determined by automated software detection of the target peak, calculated as a percentage of the total area of the target peak and digested fragment peak (which runs at a lower molecular weight if the product is linear instead of circular), as detected by the software. About 84% of DNA (84.4% for circular unmodified dsDNA comprising no chemically modified nucleobases, 84.4% for circular hemi-modified dsDNA produced in a polymerization reaction designed for 100% incorporation of canonical uracil nucleobase into the sense strand, and 84.2% for circular hemi-modified dsDNA produced in a polymerization reaction designed for 100% incorporation of 5-hydroxymethyluracil into the sense strand) migrated to a position corresponding to circular dsDNA.

Example 5: Assessment of Reporter Gene Expression In Vitro

This example demonstrates detection and quantification of gene expression using circular hemi-modified dsDNA molecules.

Circular hemi-modified dsDNA molecules comprising chemically modified nucleobases in the sense strand were prepared as described in Examples 3-4 above, e.g., produced in a reaction with the modified deoxynucleoside triphosphates and percent incorporation listed in Table 3. Control circular, unmodified dsDNA molecules (denoted "che-UM" in FIGS. 2A-3B), were prepared as in Examples 3-4 above, except that the isothermal extension reaction comprised unmodified dNTPs (and no chemically modified dNTPs). The circular hemi-modified dsDNA molecules and controls were administered via lipid transfection (lipofection) into Fa2N and AML12 cells. Briefly, 8.4 μL OptiMEM (31985062, Thermo Fisher), 1 μL of DNA, 0.17 μL TransIT mRNA BOOST reagent, and 0.17 μL TransIT mRNA reagent (MIR2225, Mirus Bio) were mixed in order and incubated at room temperature for 3-5 minutes. The mixture was then added to cells in a 96 well plate and incubated at 37 degrees Celsius for 4-6 hours. After incubation, the mixture was removed and cell media was replaced.

To determine expression of constructs encoding the reporter protein firefly luciferease (Fluc), cells were washed once with 1× phoshphate buffered saline, 20-50 μL of 1× passive lysis buffer (E1941, Promega) were added to cells, 20 μL of the cell lysate were added to a well of an opaque 96 well plate, 100 μL of luciferase reagent (E1483, Promega) were added to each well of lysate, and the mixture was read on the GloMax plate reader (GM3500, Promega) at 0.1 integrations/second. Expression of the reporter protein was measured 48 hours post-transfection.

Figure 2A:
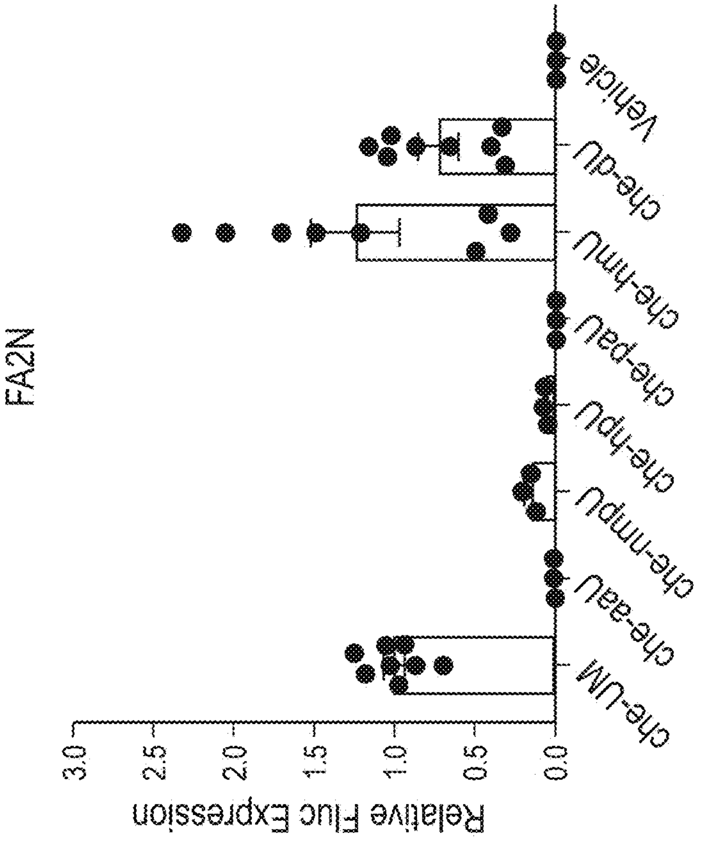
FIGS. 2A-2B are graphs showing the relative expression of a reporter gene (firefly luciferase; FLuc), in FA2N (FIG. 2A) or AML12 (FIG. 2B) cells following transfection of circular hemi-modified dsDNA molecules containing chemically modified nucleobases in the sense strand, compared to circular dsDNA molecules without chemically modified nucleobases ("che-UM"). The circular hemi-modified dsDNA molecules were produced in a polymerization reaction designed for 100% incorporation of 5-aminoallyluracil ("che-aaU"), N1-methylpseudouracil ("che-nmpU"), 5-dihydroxypentyluracil ("che-hpU"), 5-propargylaminouracil ("che-paU"), 5-hydroxymethyluracil ("che-hmU"), or canonical uracil nucleobase ("che-dU") into the newly polymerized sense strand. "Vehicle" represents cells treated with transfection reagent only.
Figure 2B:
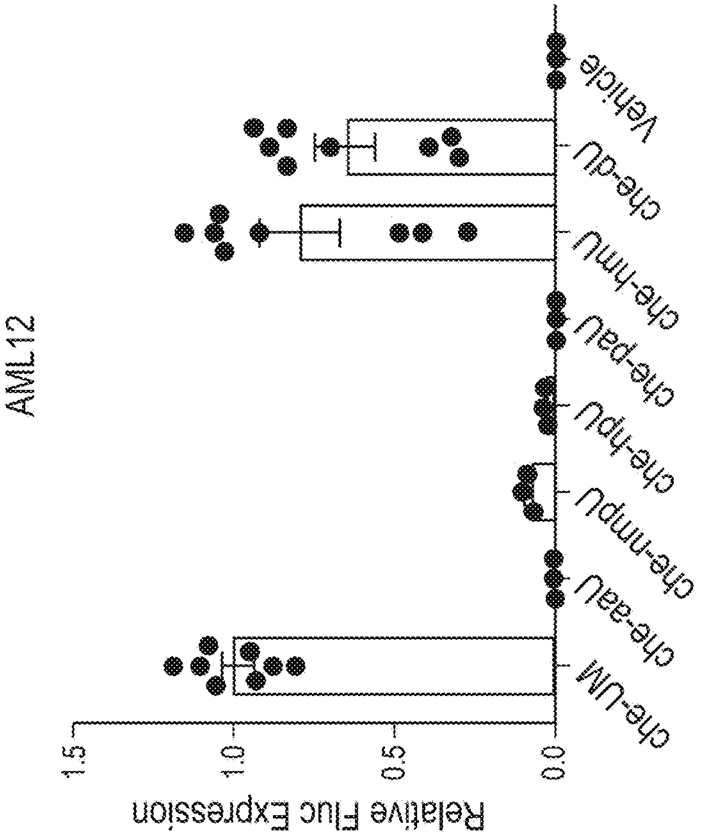

FIGS. 2A-2B show that circular hemi-modified dsDNA molecules comprising various chemically modified nucleobases were functional with detectable expression of the reporter protein luciferase. For example, in FA2N cells, circular hemi-modified dsDNA molecules comprising 5-hydroxymethyluracil in the sense strand (produced in a polymerization reaction designed for 100% incorporation of 5-hydroxymethyluracil into the sense strand) yielded successful luciferase expression at a level of more than 100% of that of control circular unmodified dsDNA. As another example, in FA2N cells, circular hemi-modified dsDNA molecules comprising canonical uracil nucleobase in the sense strand (produced in a polymerization reaction designed for 100% incorporation of canonical uracil nucleobase into the sense strand) yielded successful luciferase expression at a level of more than 50% of that of control circular unmodified dsDNA.

These results demonstrate that circular hemi-modified DNAs comprising various chemically modified nucleobases can be efficiently transcribed and ultimately yield a protein product in cells.

Example 6: Assessment of Innate Immune Response in Cells In Vitro

This example demonstrates that circular hemi-modified dsDNA molecules with various chemical modifications can reduce the innate immune response of cultured cells compared to control dsDNA.

Circular, hemi-modified dsDNA molecules were prepared as in Examples 3-4 above, e.g., produced in a reaction with the modified deoxynucleoside triphosphates listed in Table 3, and administered to macrophages or fibroblast cells using the transfection procedures as described in Example 5 above. 24 hours after administration to cells, cGAMP levels were measured using the 2'3'-cyclic GAMP ELISA Kit (Invitrogen, EIAGAMP).

Figure 3A:
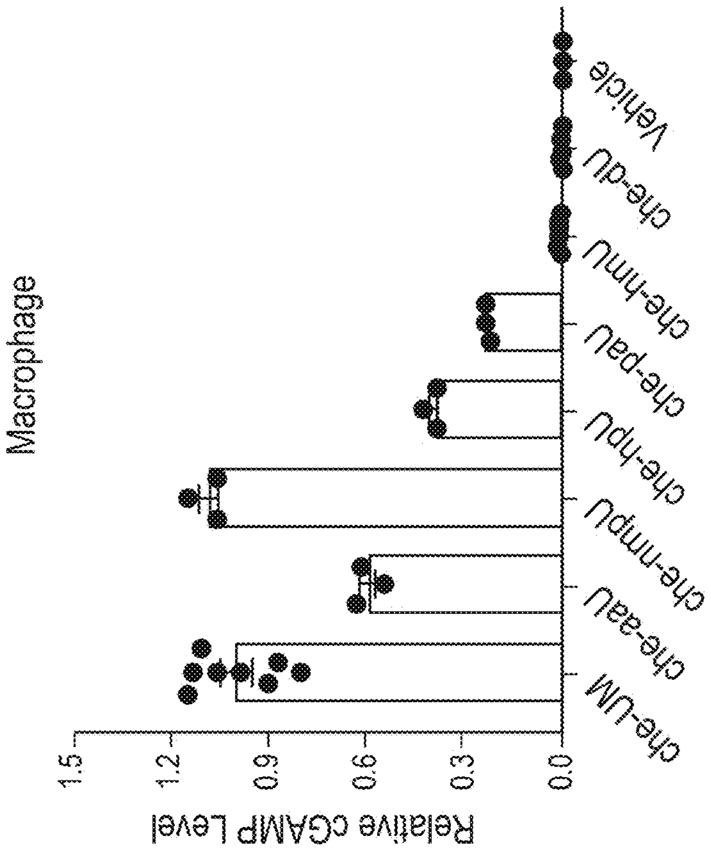
FIGS. 3A-3B are graphs showing the relative cGAMP levels of macrophages (FIG. 3A) or fibroblasts (FIG. 3B) following transfection of circular hemi-modified dsDNA molecules containing chemically modified nucleobases in the sense strand, compared to circular dsDNA molecules without chemically modified nucleobases ("che-UM"). Macrophages were transfected with circular hemi-modified dsDNA molecules produced in a polymerization reaction designed for 100% incorporation of 5-aminoallyluracil ("che-aaU"), N1-methylpseudouracil ("che-nmpU"), 5-dihydroxypentyluracil ("che-hpU"), 5-propargylaminouracil ("che-paU"), 5-hydroxymethyluracil ("che-hmU"), or canonical uracil nucleobase ("che-dU") into the newly polymerized sense strand. Fibroblasts were transfected with circular hemi-modified dsDNA molecules produced in a polymerization reaction designed for 100% incorporation of 5-hydroxymethyluracil ("che-hmU") or canonical uracil nucleobase ("che-dU") into the newly polymerized sense strand. "Vehicle" represents cells treated with transfection reagent only.
Figure 3B:
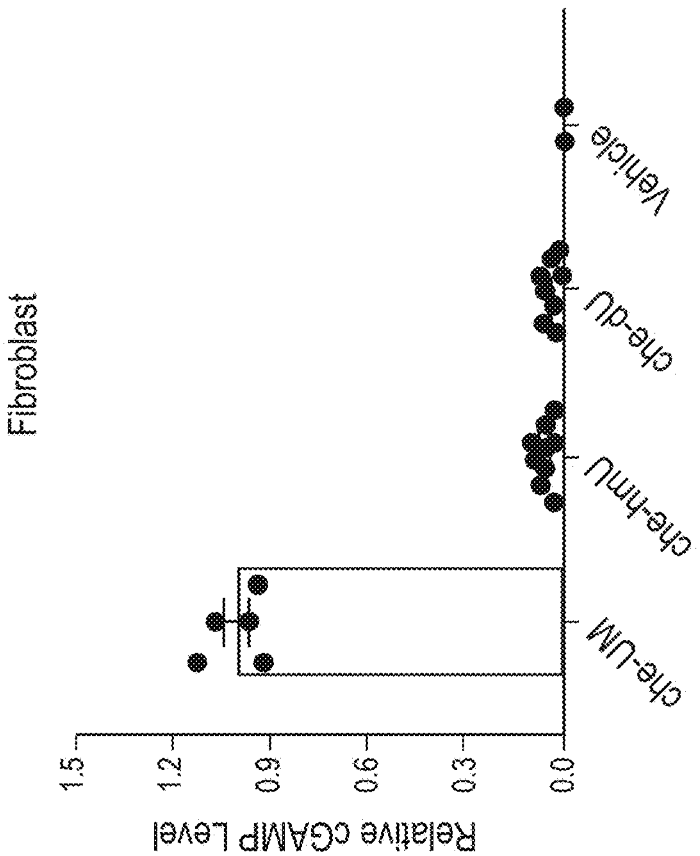

FIGS. 3A-3B show that circular hemi-modified dsDNA molecules with chemically modified nucleobases led to reduced innate immune response relative to control circular dsDNA comprising unmodified DNA. For instance, circular hemi-modified dsDNA molecules comprising 5-hydroxymethyluracil in the sense strand (produced in a polymerization reaction designed for 100% incorporation of 5-hydroxymethyluracil into the sense strand), and circular hemi-modified dsDNA molecules comprising canonical uracil nucleobase in the sense strand (produced in a polymerization reaction designed for 100% incorporation of canonical uracil nucleobase into the sense strand), yielded lower cGAMP levels as compared to control unmodified circular dsDNA, indicating that incorporation of modified nucleobases in the sense strand of the circular dsDNA molecules abrogates cGAS-STING detection.

These results indicate that incorporation of chemically modified nucleobases into the sense strand of circular dsDNA can reduce the immunogenicity of dsDNA while retaining the capacity to encode a functional protein product.

Example 7: Production of Lipid Nanoparticles (LNPs) Comprising Circular Hemi-Modified Double-Stranded DNA Molecules This example demonstrates the encapsulation of circular "hemi-modified" DNA molecules (cheDNA), i.e., circular dsDNA molecules containing chemically modified nucleobases on a single strand, in lipid nanoparticles (LNPs).

LNPs were formulated by encapsulating either unmodified circular double stranded DNA (as a control) or cheDNA (containing chemically modified nucleobases on the sense strand, where at least 98% of the thymine or uracil positions in the sense strand comprise a uracil nucleobase) comprising a sequence encoding a Nano-Luciferase reporter, a UBC promoter sequence, a sequence encoding a UBC intron, a sequence encoding a 5' UTR, a sequence encoding a 3' UTR, and a sequence encoding a bGH polyA signal. In brief, the DNA molecules were diluted into citrate buffer (pH 4.0), and a lipid mix (a commercially available ionizable lipid, DSPC, Cholesterol and DMG-PEG2000) was dissolved into ethanol. The resulting DNA and lipid solutions were mixed rapidly at a ratio of 3:1 DNA:lipids (vol:vol). The LNPs were washed and concentrated using Amicon centrifugal filter units (100 kDa, UFC8100, Millipore).

Example 8: Assessment of Tolerability and Effector Expression Following In Vivo Administration of cheDNA Molecules This example demonstrates the tolerability and expression of an effector following cheDNA/LNP dosing in a mouse model.

The unmodified DNA/LNP and cheDNA/LNP test articles were produced as described in Example 7, prepared to a final concentration of 0.45 mg/mL in PBS, and loaded into a sterile syringe. Test articles were dosed via bolus intravenous administration to a final dose of 1.5 mg/kg of DNA (3.3 mL/kg) into the lateral tail vein of female C57Bl/6 mice. Mice were 11-13 weeks of age at the time of dosing. Mice were monitored for weight change, clinical signs and other phenotypic indications of adverse events throughout the course of the study.

Six hours after test article dosing, blood was collected via non-terminal submandibular bleeds into K2EDTA tubes (BD 365974). Cells were separated from whole blood by centrifuging for 10 minutes at 2000×g using a refrigerated (4° C.) centrifuge. The resulting supernatant was transferred to a clean polypropylene tube and immediately frozen at −80° C.

Seven days after test article dosing, mice were sacrificed and key organs, including liver, were collected, frozen on liquid nitrogen, and stored at −80° C. Frozen tissues were pulverized using dry tissue pulverizer (CP02, Corvaris). Following tissue lysis with Glo Lysis Buffer (Promega E2661), total protein content was measured with a BCA protein assay (23225, Invitrogen) and luciferase activity was measured with the Nano-Glo Luciferase Assay System (Promega E2510) according to manufacturer instructions. Data is represented as relative light units (RLU) per milligram of total protein.

Figure 4:
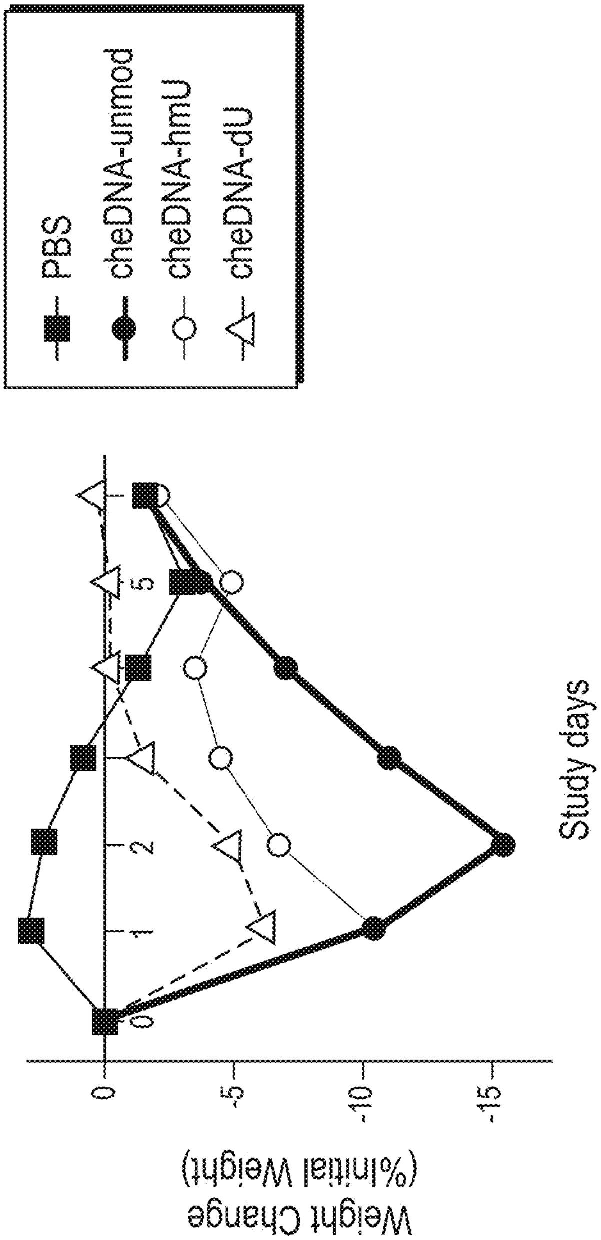
FIG. 4 is a graph showing the body weight change ((weight−initial weight)/initial weight) of mice following dosing of the unmodified circular dsDNA ("cheDNA-unmod"), or cheDNA comprising either 5-hydroxymethyluracil ("cheDNA-hmU") or canonical uracil nucleobase ("cheDNA-dU") in the sense strand. Weights were measured daily for seven days following dosing.
Figure 5:
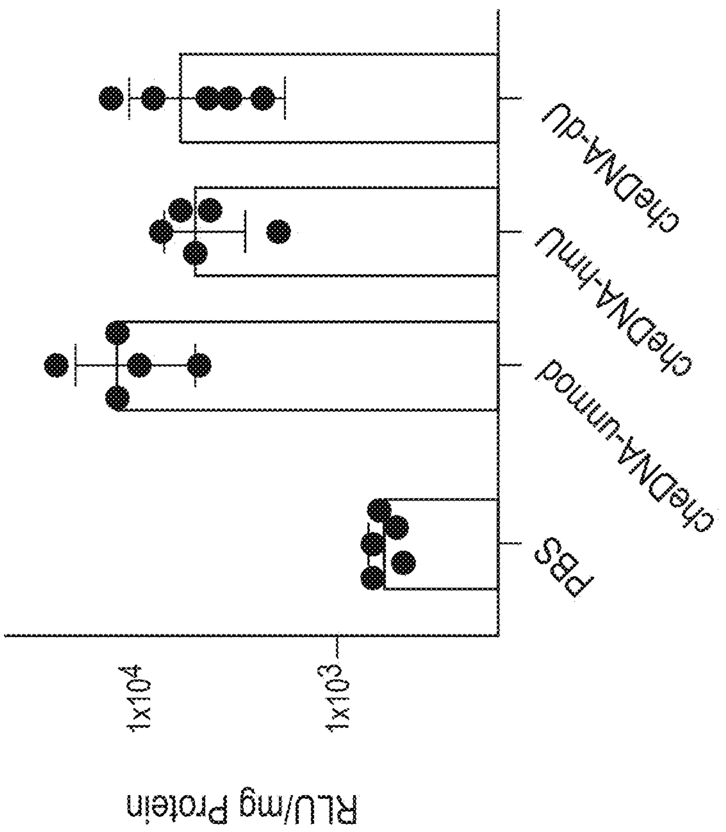
FIG. 5 is a bar graph showing bioluminescence relative light units (RLU) activity normalized to total protein resulting from liver tissue collected from mice administered unmodified circular dsDNA ("cheDNA-unmod"), or cheDNA comprising either 5-hydroxymethyluracil ("cheDNA-hmU") or canonical uracil nucleobase ("cheDNA-dU") in the sense strand. Tissue was collected 7 days following test article dosing.

As shown in FIG. 4, mice administered with cheDNA comprising either 5hmU or dU in the sense strand demonstrated decreased weight loss, as compared to mice administered with unmodified circular dsDNA. Further, as shown in FIG. 5, luciferase activity was detected from liver samples of mice administered with cheDNA comprising either 5hmU or dU in the sense strand.

Collectively, these data demonstrate that in vivo administration of LNPs encapsulating cheDNA molecules (comprising chemically modified nucleobases in the sense strand) is tolerable, with decreased weight loss as compared to administration of unmodified circular double stranded DNA.

Furthermore, following in vivo administration of the LNPs, the cheDNA molecules can be transcribed to successfully yield a protein product.

Example 9: Preparation of Double-Stranded DNA Incorporating Chemically Modified DNA Nucleobases on One Strand (Hemi-Modified) in a Bidirectional Format This example describes the preparation of circular or linear end-closed dsDNA comprising a first promoter sequence operably linked to a first effector sequence that comprises chemically modified nucleobases on the sense strand of the first effector sequence. The dsDNA also comprises a second promoter sequence, which is oriented to drive transcription in the opposite direction of the first promoter sequence, operably linked to a second effector sequence that comprises chemically modified nucleobases on the sense strand of the second effector sequence. The first promoter sequence and the second promoter sequence are both comprised in a promoter region.

Figure 6:
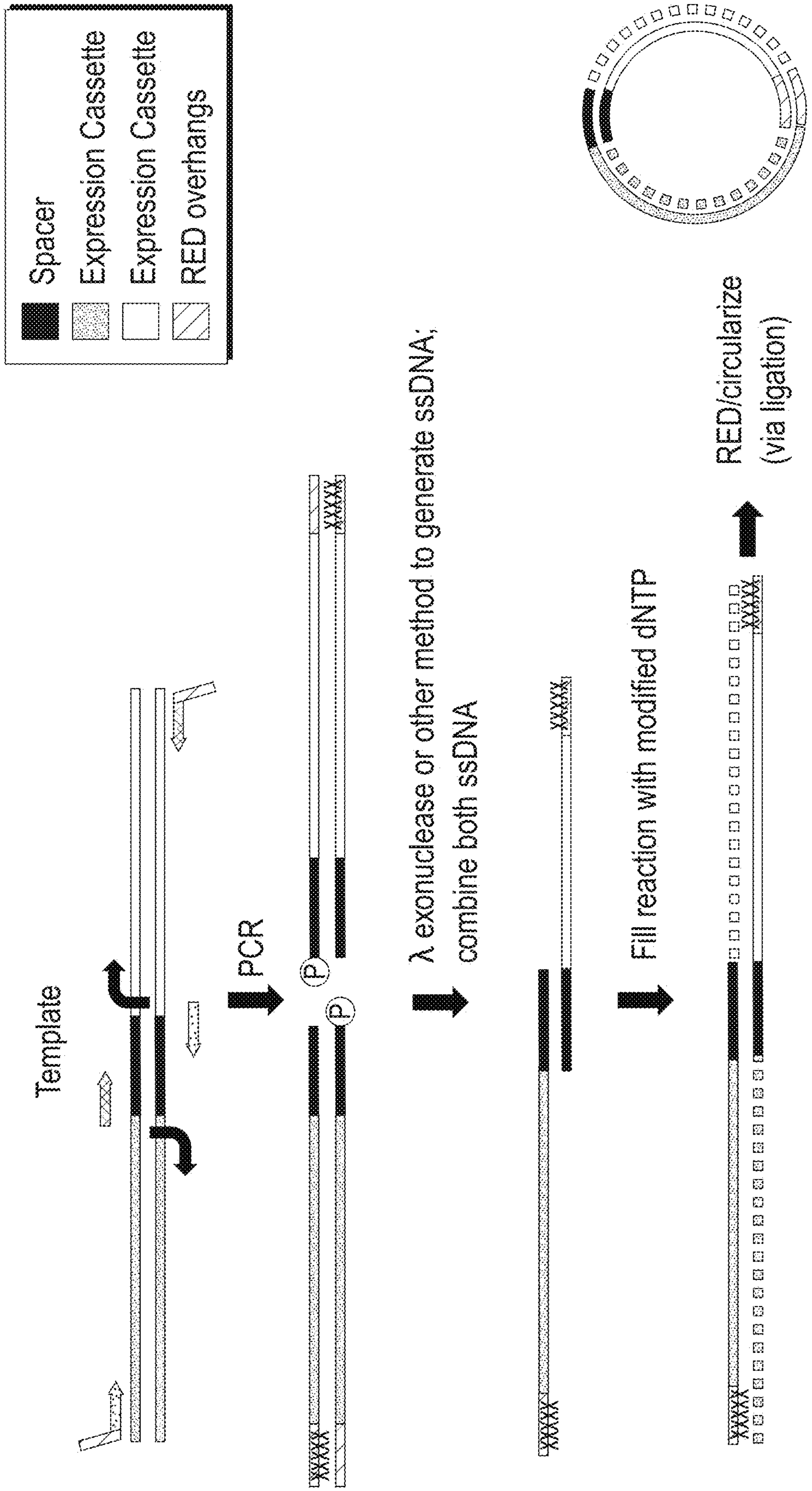
FIG. 6 shows an exemplary method for producing a dsDNA molecule having asymmetrical modification as described herein, using a single restriction enzyme. The template may contain both effector sequences on one DNA molecule or may contain each effector sequence on separate DNA molecules. Restriction enzyme digest (RED) overhangs are shown with the pattern indicated in the legend. Primers for PCR amplification of the template are shown with arrows. The curved black arrows indicate promoter sequences, and the direction that these arrows point indicates the direction in which transcription is oriented to occur. The solid lines of the DNA molecules indicate a portion of the DNA molecule which is substantially free of chemically modified nucleobases, while the dotted lines of the DNA molecules indicate a portion of the DNA molecule which contains chemically modified nucleobases. The "X"s present on certain DNA strands represent a region of the DNA strand where phosphorothioate bonds are present in the backbone. In brief, the method comprises performing PCR on the template, isolating antisense strands using lambda exonuclease, annealing the two antisense strands to each other, filling in the single stranded region with DNA comprising chemically modified nucleotides, digesting with a restriction enzyme, and then ligating to form circular dsDNA. This process is described in more detail in Example 9.

The methods in this example are illustrated in FIG. 6.

Plasmid DNA, at a concentration of 10 ng/50 μl PCR reaction, is used as a template for PCR amplification, and contains a promoter region (comprising a first promoter sequence and a second promoter sequence, where the second promoter sequence is oriented to drive transcription in the opposite direction of the first promoter sequence), a first effector sequence on one side of the promoter region, a second effector sequence on the other side of the promoter region, and a sequence encoding a polyadenylation site downstream of each of the first and second effector sequences. In the promoter region, the first promoter sequence and the second promoter sequence are separated by 40-500 base pairs, and this region is referred to as the spacer region.

As an alternative to using a single plasmid as in the paragraph above, two separate plasmids can be used. The first plasmid comprises the first promoter sequence, the first effector sequence, and a sequence encoding a polyadenylation site, and the second plasmid comprises the second promoter sequence, the second effector sequence, and a sequence encoding a polyadenylation. Each plasmid comprises an identical 40-500 nucleotide sequence upstream of the promoter sequence.

In both cases above, the promoter sequence, the effector sequence, and the sequences encoding a polyadenylation site are comprised within an expression cassette. In other words, the first expression cassette comprises the first promoter sequence, the first effector sequence, and a sequence encoding a polyadenylation site, and the second expression cassette comprises the second promoter sequence, the second effector sequence, and a sequence encoding a polyadenylation site.

PCR amplification is performed on each of the two expression cassettes using KOD One polymerase (KMM-101, TOYOBO) or KOD Multi-Epi polymerase (KME-101, TOYOBO). Other commercially available polymerases suitable for PCR may also be used. Canonical dNTPs (dATP, dGTP, dCTP, dTTP) are used for the PCR reactions. PCR reaction conditions for each enzyme include:

a. For the KOD One polymerase, a 2× mastermix is used. For the KME polymerase, 2 U/50 μL PCR is used, along with a 5× reaction buffer diluted to 1×.
b. For the KME polymerase, 100 mM dNTP solution set (N0446, New England Biolabs) is used, at a final concentration of 200 μM.
c. Forward and reverse primers are used at a final concentration of 300 μM.

For the synthesis of circular DNA, in addition to containing sequences complementary to the plasmid to allow for PCR amplification, the primers contain additional sequences useful in downstream processes:

a. Restriction enzyme recognition sequence (e.g., BsaI v2-HF, SalI-HF, or EcoRI-HF, New England Biolabs) which are used to create sticky-ends in the DNA after restriction enzyme digestion and facilitate DNA circularization; and
b. Additional bases (e.g., 5'-TATATATATA-3' (SEQ ID NO: 14)) to increase Lambda exonuclease digestion efficiency; and
c. The primer on the strand to contain chemically modified nucleobases (the strand of the DNA molecule that contains the sense strand of the first or second effector sequence) has a 5' phosphate group, whereas the primer with the other strand (the antisense strand) comprises phosphorothioate modifications on the first eight bases of the 5' side.

For the synthesis of linear, end-closed DNA, primers include the same sequences as above, and include non-complementary restriction enzyme sequences, either with different Type IIS cleavage site sequences or two different restriction enzymes, which are used to create two non-compatible sticky-ends in the DNA after restriction enzyme digestion and facilitate DNA ligation to hairpin molecules containing a complementary overhang region.

The PCR amplicons are cleaned using Nucleospin Maxi columns (4-6 columns/plate of PCR; 740610.20, Takara Bio) using manufacturer recommended conditions. Alternatively, PCR amplicons are cleaned by first incubating with 0.24 U/mL of Thermolabile Proteinase K (P8111S, New England Biolabs) at 37° C. for 1-16 hrs. The Proteinase K is inactivated by incubating the reaction mixture at 80° C. for 25 minutes, and then the reaction mixture is cooled to room temperature. The PCR amplicons are then enriched from the solutions.

Next, single-stranded DNA (ssDNA) precursors are prepared from the PCR amplicons. The PCR amplicons are first digested at 150 ng/μL with 5 U/μg Lambda exonuclease (M0262, New England Biolabs) in Lambda exonuclease buffer, with 0-10% DMSO as an additive. The reaction proceeds at 37° C. for 16 hours, and the enzymes are then inactivated by incubating the solution at 80° C. for 25-30 minutes. The exonuclease digestion results in the antisense strand comprising phosphorothioate modifications being preserved, while the sense strand is digested. A blunt end restriction enzyme (e.g. DraI, New England Biolabs) is used to digest residual dsDNA, with 0.5 U/μg at 37° C. for 1 hr. The ssDNA precursors are then enriched from the solution.

Each expression cassette is produced as a ssDNA precursor as described above. The ssDNA precursors for each expression cassette are mixed together at a 1:1 ratio, ensuring that the spacer regions are complementary to and hybridize to each other. Next, a “fill” reaction is performed to produce a strand comprising chemically modified nucleobases that is complementary to the strand that lacks chemically modified nucleobases. Each of the DNA molecules is added at a final concentration of 12.5 ng/μL in a reaction solution containing DNA polymerase (e.g., KME polymerase) and dNTPs, with one of the cognate dNTPs replaced by a modified dNTP. The reaction solution containing the KME polymerase is then incubated at 94° C. for 2 min, and then the reaction is allowed to run at 68° C. for 1 hour. The resulting product is run on a 1% E-gel EX (G401001, Thermo Scientific) to verify the conversion from ssDNA to linear dsDNA. The linear dsDNA molecules are then enriched from the reaction solution using Nucleospin Maxi columns.

To convert the linear dsDNA molecules prepared as described above to circular dsDNA molecules, the linear dsDNA molecules are digested by the restriction enzyme specific to the recognition sequence incorporated on the primer overhangs. Digested DNA molecules are circularized using T3 DNA ligase (M0317, New England Biolabs) for 1-16 hours at 23-26° C. Non-circularized DNA molecules are degraded by incubating the reaction solution with T5 exonuclease (M0663L, New England Biolabs) for 16 hours at 37° C. with 1.5 U/μg. T5 exonuclease is used to digest linear dsDNA molecules but not circular dsDNA molecules. The circular dsDNA molecules are enriched using spin columns. Other similar methods may also be used, for instance agarose gel enrichment.

To convert the linear dsDNA molecules to linear, end-closed dsDNA molecules, the linear dsDNA molecules are digested by the restriction enzymes specific to the recognition sequences incorporated on the primer overhangs. Hairpin molecules containing single-stranded sequences complementary to the overhangs are added to the digested DNA, and ligated using T3 DNA ligase (M0317, New England Biolabs) for 1-16 hours at 23-26° C., then heat killed at 80° C. for 30 minutes. Non-circularized DNA and T5 exonuclease are used in the same way as described above for circular dsDNA, and the linear dsDNA molecules are enriched in the same way as described above for circular dsDNA.

Analysis of the composition and the level of purity of the resultant circular dsDNA molecules is performed on an Agilent 5200 Fragment Analyzer using the HS Large Fragment kit (DNF-464). The buffers are prepared according to the manufacturer's specifications. Circular dsDNA molecule samples are diluted in water to a final concentration of 1 ng/μL. For each sample well, 2 μL of the DNA samples are added to 22 μL of marker solution, with one well used for the HS Large Fragment DNA ladder. The samples are run via the instrument controller software using default settings of the HS Large Fragment method.

Sample traces are analyzed using the ProSize Data Analysis Software v4.0.2.7. Peak Analysis conditions for dsDNA are set at the standard conditions of a 'Peak Width (sec)' of 5 and a 'Min. peak height (RFU)' of 50, #Extra Valley Points of 3, and with 'Valley to Valley Baseline?' turned on. Peaks are automatically detected by the software under these conditions, and the desired peak purity is calculated via smear analysis method, with lower molecular weight products starting at 50 nt, and larger molecular weight products ending at 40000 nt.

Example 10: Alternative Method of Preparation of Double-Stranded DNA Incorporating Chemically Modified DNA Nucleobases on One Strand (Hemi-Modified) in a Bidirectional Format This example describes another method for the preparation of circular or linear, end-closed dsDNA molecules comprising a first promoter sequence operably linked to a first effector sequence that comprises chemically modified nucleobases on the sense strand of the first effector sequence, and a second promoter sequence, which is oriented to drive transcription in the opposite direction of the first promoter sequence, operably linked to a second effector sequence that comprises chemically modified nucleobases on the sense strand of the second effector sequence. The first promoter sequence and the second promoter sequence are both comprised in a promoter region.

Figure 7:
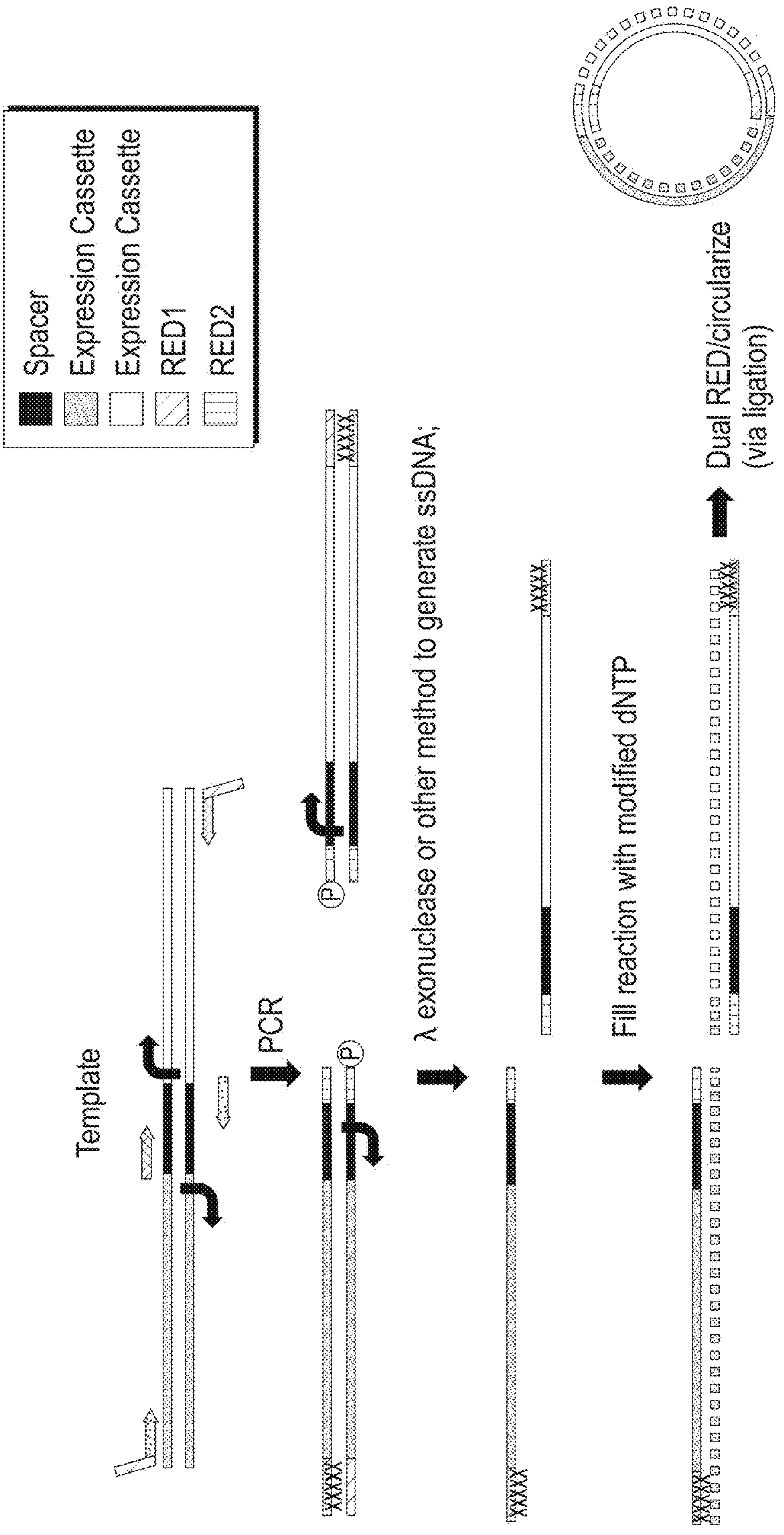
FIG. 7 shows another exemplary method for producing a dsDNA molecule having asymmetrical modification as described herein, using two different restriction enzymes. The template, RED overhangs, primers, promoter sequences, DNA strands, and phosphorothioate bonds are as described for FIG. 6. In brief, the method comprises performing PCR on the template, isolating antisense strands using lambda exonuclease, filling in the single stranded regions with DNA comprising chemically modified nucleotides, digesting with restriction enzyme, and then ligating to form circular dsDNA. This process is described in more detail in Example 10.

The methods in this example are illustrated in FIG. 7.

The same plasmids described in Example 9 (e.g., a single plasmid containing two expression cassettes, or two plasmids each containing one of the expression cassettes) are used for PCR. PCR is performed on each of the two expression cassettes in the same conditions as Example 9, and the enrichment of the PCR amplicons is performed using the same methods as described in Example 9. However, for the primers used for the PCR for the preparation of circular dsDNA molecules, each primer for a given amplification contains a dual restriction enzyme recognition sequence (e.g., BsaI v2-HF, SalI-HF, or EcoRI-HF, New England Biolabs) in which the forward and reverse primer sequence for each expression cassette has different restriction enzyme sequences, which are not complementary to each other, but are complementary to the primer sequences of the other expression cassette such that when ligated together, the expression cassettes are arranged in a manner for which transcription proceeds in the opposite direction for each expression cassette.

For the synthesis of linear, end-closed dsDNA molecules, primers include complementary restriction enzyme sequences on the 3' end of the first expression cassette and the 5' end of the second expression cassette. The 5' end of the first cassette and the 3' end of the second cassette contain different restriction enzyme sites that are not complementary to each other, but which are complementary to hairpin molecule overhangs.

ssDNA precursors are prepared as described in Example 9. The ssDNA precursors are then used to generate dsDNA molecules in a fill reaction. Suitable fill reaction conditions are described in Example 9, with the exception that primers are also added to this fill reaction to allow for amplification. The fill reaction results in two linear dsDNA molecules, each of which has a strand comprising chemically modified nucleobases and a strand that lacks chemically modified nucleobases, the first linear dsDNA molecule comprising the first effector sequence and the second linear dsDNA molecule comprising the second effector sequence.

To convert the two linear dsDNA molecules to a circular dsDNA molecule, each dsDNA molecule sample is digested by both restriction enzymes specific to the recognition sequence incorporated on the primer overhangs. Digested dsDNA molecules are then mixed together in a 1:1 molar ratio at a final concentration of 16 ng/μL and circularized using T3 DNA ligase (M0317, New England Biolabs) for 1-16 hours at 23-26° C., then incubated at 80° C. for 30 minutes to inactivate the ligase. The same methods as described in Example 9 are then used to degrade non-circularized dsDNA molecules and to enrich the circular dsDNA molecules. Analysis of the enriched circular dsDNA molecules is performed as described in Example 9.

To convert the two linear dsDNA molecules to a linear, end-closed dsDNA molecule, each dsDNA molecule sample is digested by the restriction enzyme specific to the recognition sequence incorporated on the primer overhangs. Hairpin molecules containing single-stranded sequences complementary to the overhangs are added to the digested DNA, and ligated using T3 DNA ligase (M0317, New England Biolabs) for 1-16 hours at 23-26° C. The same methods as described in Example 9 are then used to degrade other dsDNA molecules besides the linear, end-closed dsDNA molecules present in the solution, and to enrich the linear, end-closed dsDNA molecules. Analysis of the enriched linear, end-closed dsDNA molecules is performed as described in Example 9.

Figure 8:
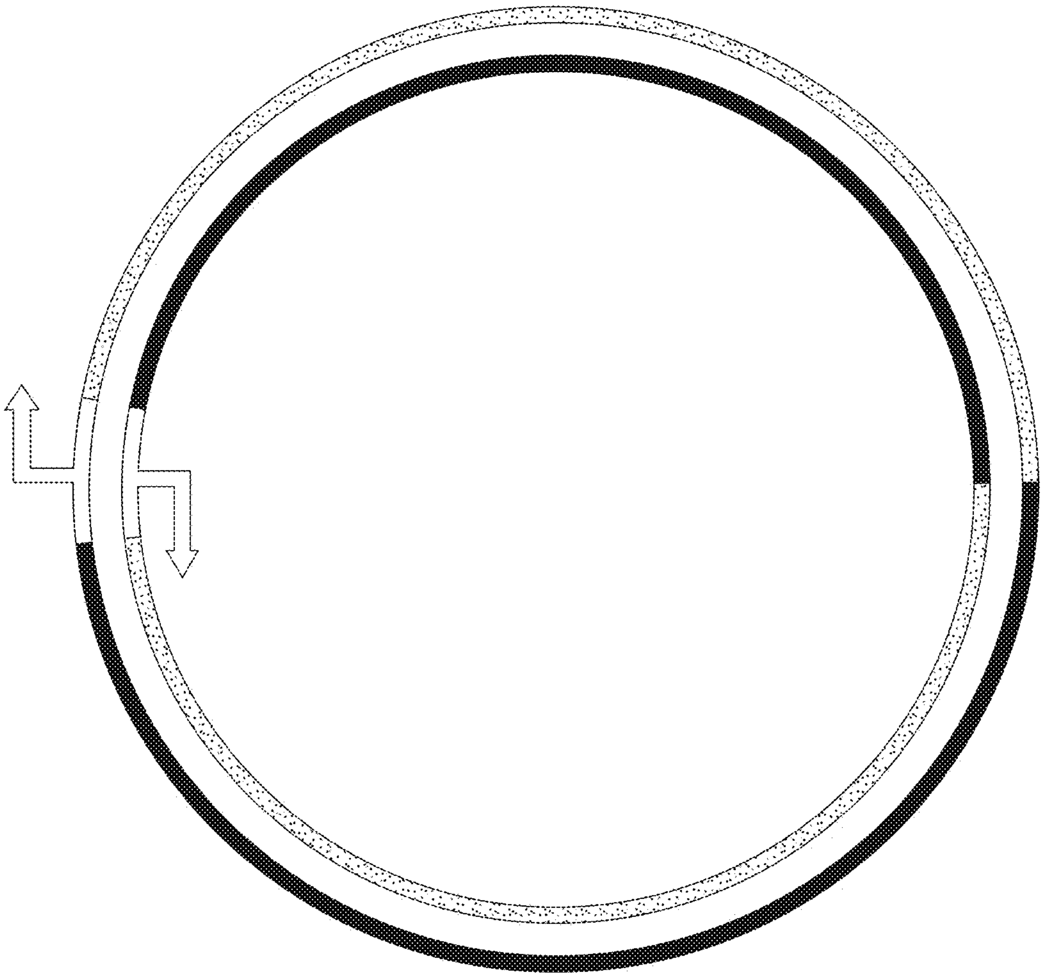
FIG. 8 is an illustration of a circular dsDNA molecule described herein. The promoter region is displayed with arrows at the top of the molecule. The direction of these arrows indicates the direction in which transcription is oriented to occur. The regions of the dsDNA molecule shaded in solid black indicate a portion of DNA that is substantially free of chemically modified nucleobases. The regions of the dsDNA molecule shaded with a dotted pattern indicate a portion of DNA that contains chemically modified nucleobases.
Figure 9:
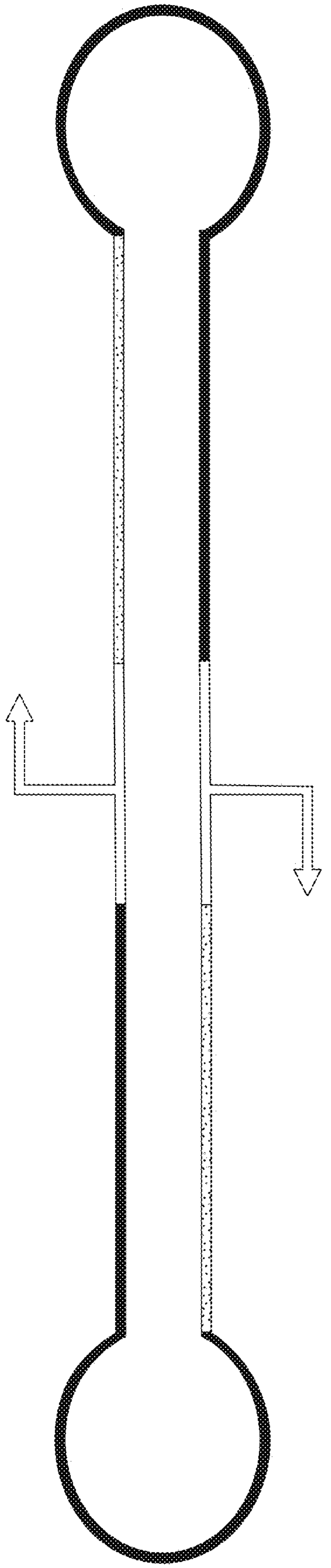
FIG. 9 is an illustration of a linear, end-closed dsDNA molecule described herein. The promoter region is displayed with arrows in the middle of the molecule. The direction of these arrows indicates the direction in which transcription is oriented to occur. The regions of the dsDNA molecule shaded in solid black indicate a portion of DNA that is substantially free of chemically modified nucleobases. The regions of the dsDNA molecule shaded with a dotted pattern indicate a portion of DNA that contains chemically modified nucleobases. The DNA end forms are shown at the end of the molecule as rounded black lines connecting the strands of the DNA molecule.

Illustrations of dsDNA molecules that can be prepared using the methods described in Example 9 and Example 10 are shown in FIG. 8 (circular dsDNA) and FIG. 9 (linear, end-closed dsDNA).

Example 11: Delivery of Naked DNA Molecules

This example describes focused ultrasound (FUS) delivery of an unencapsulated "naked" DNA molecule encoding an exogenous effector to the liver or spleen in mice.

Unencapsulated DNA molecules described herein are prepared in sterile saline and are dosed via bolus (5 mL/kg) intravenous administration to a final dose of between 0.1 and 2 mg/kg into mice. Immediately following, microbubbles (Definity) are administered via IV bolus to a final concentration of 0.5e5-1e7 microbubbles/g body weight. A focused ultrasound transducer with a center frequency of 0.5-2 MHz is positioned such that the ultrasound focus is aligned with the targeted spleen or liver. Ultrasound application begins within 30 seconds after administration of the DNA molecule and microbubbles. The transducer is operated in 10 ms bursts, 0.5 Hz pulse repetition frequency, 0.1-2 MPa peak negative pressure for a total two minute duration.

For DNA molecules that encode luciferase, the successful delivery of DNA molecules can be verified via bioluminescence. Seven days after dosing and FUS application, mice receive an intraperitoneal dose of luciferin (150 mg/kg). Bioluminescence is captured by an In Vivo Imaging System (IVIS) and is quantified using proprietary software.

Example 12: Production of Lipid Nanoparticle-Encapsulated DNA Molecules

This example describes the encapsulation of DNA molecules encoding an exogenous effector into lipid nanoparticles (LNPs) prior to dosing into mice.

LNPs are formulated encapsulating DNA molecules described herein encoding an exogenous effector using standard formulation methods. In brief, the DNA molecules are diluted into citrate buffer (pH 4.0), and a lipid mixture (50% ionizable lipid, 10% DSPC, 38.5% cholesterol and 1.5% DMG-PEG2000 by mole) is dissolved into ethanol. The two solutions are mixed rapidly at a ratio of 3:1 DNA:lipid solution (vol:vol). LNPs are washed and concentrated using Amicon centrifugal filter units (100 kDa, UFC8100, Millipore) before characterization.

Example 13: Delivery of Lipid Nanoparticle-Encapsulated DNA Molecules

This example describes FUS delivery of DNA molecules that are encapsulated in LNPs, as prepared in Example 12, to the liver or spleen in mice.

LNPs encapsulating DNA molecules described herein are prepared in sterile saline and dosed via bolus (5 mL/kg) intravenous administration to a final dose of between 0.1 and 2 mg DNA/kg into mice. Immediately following, microbubbles (Definity) are administered via IV bolus to a final concentration of 0.5e5-1e7 microbubbles/g body weight. A focused ultrasound transducer with a center frequency of 0.5-2 MHz is positioned such that the ultrasound focus is aligned with the targeted spleen or liver. Ultrasound application begins within 30 seconds after administration of DNA molecule and microbubbles. The transducer is operated in 10 ms bursts, 0.5 Hz pulse repetition frequency, 0.1-2 MPa peak negative pressure for a total two minute duration.

For LNPs comprising DNA molecules that encode luciferase, the successful delivery of the DNA molecules can be verified via bioluminescence. Seven days after dosing and FUS application, mice receive an intraperitoneal dose of luciferin (150 mg/kg). Bioluminescence is captured by an In Vivo Imaging System (IVIS) and quantified using proprietary software.

Example 14: Design and Assembly of a Plasmid Template for Production of Double-Stranded DNA (dsDNA) Molecules This example demonstrates the production of a plasmid template for a dsDNA molecule. In this example, a construct template was designed with the following specific sequence components.

```
Promoter UBC:
                                                                    (SEQ ID NO: 1)
5'ggcctccgcgccgggttttggcgcctcccgcgggcgccccctcgtcacggcgagcgctgccacgtcagacgaagggcg
caggagcgtcctgatccttccgcccggacgctcaggacagcggcccgctgctcataagactcggccttagaaccccagtatca
gcagaaggacattttaggacgggacttgggtgactctagggcactggttttctttccagagagcggaacaggcgaggaaaagta
gtcccttctcggcgattctgcggagggatctccgtggggcggtgaacgccgatgattatataaggacgcgccgggtgtggcac
agctagttccgtcgcagccgggatttgggtcgcggttcttgtttgtggatcgctgtgatcgtcacttggtgagtagcgggctgctgg
gctggccggggctttcgtggccgccgggccgctcggtgggacggaagcgtgtggagagattgccaagggctgtagtctgggt
ccgcgagcaaggttgccctgaactgggggttggggggagcgcagcaaaatggcggctgttcccgagtcttgaatggaagacg
cttgtgaggcgggctgtgaggtcgttgaaacaaggtgggggggcatggtgggcggcaagaacccaaggtcttgagccttcgct
aatgcgggaaagctcttattcgggtgagatgggctgggcaccatctggggaccctgacgtgaagtttgtcactgactggagaac
tcggtttgtcgtctgttgcgggggcggcagttatggcggtgccgttgggcagtgcacccgtacctttgggagcgcgcgccctcgt
cgtgtcgtgacgtcacccgttctgttggcttataatgcagggtggggccacctgccggtaggtgtgcggtaggcttttctccgtcg
caggacgcagggttcgggcctagggtaggctctcctgaatcgacaggcgccggacctctggtgaggggagggataagtgag
gcgtcagtttctttggtcggttttatgtacctatcttcttaagtagctgaagctccggttttgaactatgcgctcggggttggcgagtgt
gttttgtgaagtttttaggcaccttttgaaatgtaatcatttgggtcaatatgtaattttcagtgttagacttgtaaattgtccgctaaattc
tggccgtttttggctttttttgttagaca3'

Effector sequence (in this case exemplified by a reporter protein) encoding a dual
reporter protein cassette (NLuc/T2A/eGFP/Double Stop):
                                                                   (SEQ ID NO: 15)
5'
atggtcttcacactcgaagatttcgttggggactggcgacagacagccggctacaacctggaccaagtccttgaacagggaggt
gtgtccagtttgtttcagaatctcggggtgtccgtaactccgatccaaaggattgtcctgagcggtgaaaatgggctgaagatcga
catccatgtcatcatcccgtatgaaggtctgagcggcgaccaaatgggccagatcgaaaaaatttttaaggtggtgtaccctgtgg
atgatcatcactttaaggtgatcctgcactatggcacactggtaatcgacggggttacgccgaacatgatcgactatttcggacgg
ccgtatgaaggcatcgccgtgttcgacggcaaaaagatcactgtaacagggaccctgtggaacggcaacaaaattatcgacga
```

-continued

```
gcgcctgatcaaccccgacggctccctgctgttccgagtaaccatcaacggagtgaccggctggcggctgtgcgaacgcattct
ggcgggctccggcgagggcagaggaagtcttctaacatgcggtgacgtggaggagaatcccggccctgtgagcaagggcg
aggagctgttcaccggggggtgcccatcctggtcgagctggacggcgacgtaaacggccacaagttcagcgtgtccggcga
gggcgagggcgatgccacctacggcaagctgaccctgaagttcatctgcaccaccggcaagctgcccgtgccctggcccacc
ctcgtgaccaccctgacctacggcgtgcagtgcttcagccgctaccccgaccacatgaagcagcacgacttcttcaagtccgcc
atgcccgaaggctacgtccaggagcgcaccatcttcttcaaggacgacggcaactacaagacccgcgccgaggtgaagttcg
agggcgacaccctggtgaaccgcatcgagctgaagggcatcgacttcaaggaggacggcaacatcctggggcacaagctgg
agtacaactacaacagccacaacgtctatatcatggccgacaagcagaagaacggcatcaaggtgaacttcaagatccgccac
aacatcgaggacggcagcgtgcagctcgccgaccactaccagcagaacacccccatcggcgacggccccgtgctgctgccc
gacaaccactacctgagcacccagtccgccctgagcaaagaccccaacgagaagcgcgatcacatggtcctgctggagttcgt
gaccgccgccgggatcactctcggcatggacgagctgtacaagtgatga3'
```

Bovine growth hormone PolyA:

(SEQ ID NO: 3)

```
5'ctgtgccttctagttgccagccatctgttgtttgcccctcccccgtgccttccttgaccctggaaggtgccactcccactgtcctttt
cctaataaaatgaggaaattgcatcgcattgtctgagtaggtgtcattctattctggggggtggggtggggcaggacagcaaggg
ggaggattgggaagacaatagcaggcatgctggggatgcggtgggctctatgg3'
```

A plasmid template was designed with these elements using standard DNA design manipulation software. Once designed, plasmids were prepared according to standard methods for use as a template in PCR amplification.

Example 15: Production of Single-Stranded DNA Molecules as Precursors to Circular Hemi-Modified dsDNA Molecules This example demonstrates preparation of single stranded DNA (ssDNA) molecules, which can be used as precursor material for production of circular, hemi-modified double stranded DNA. To generate the ssDNA precursor, plasmid DNA (2 ng/100 ul PCR reaction), e.g., as described in Example 14 above, was used as a template for PCR amplification using KOD-Multi & Epi-polymerase (TYB-KME-101, Diagnocine). Other commercially available polymerases such as KOD One (TYB-KMM-101, Diagnocine) or KOD Xtreme (Millipore Sigma) may also be used. PCR reaction conditions include:

a. PCR Buffer for KOD FX (TYB-KFX-1B, Diagnocine) at a 1× concentration.
b. Forward and reverse primers at a final concentration of 300 μM.
c. 2 units of KOD-Multi & Epi-polymerase/100 ul PCR reaction For the synthesis of dsDNA molecules by PCR, in addition to containing sequences complementary to the plasmid, primers contained additional sequences useful in downstream processes:

a. Restriction enzyme recognition sequence (e.g. BsaI), used to create sticky ends in the DNA after restriction enzyme digestion and facilitate adapter ligation; and
b. Additional bases to increase restriction enzyme digestion efficiency.
c. Phosphorothioate modifications to block 5'->3' exonuclease activity.

To prepare hemi-modified DNA containing modified nucleotides on the anti-sense strand (che-dU (antisense)):

Forward (SEQ ID NO: 16)

```
T*A*T*A*T*A*T*A*GATATCTATGGTCTCCGCCG
```

Reverse (SEQ ID NO: 17)

```
/5Phos/CACACGTCCCGAGGTCTCCCGGCgccatagagcccaccgcatc
cccag
```

To prepare hemi-modified DNA containing modified nucleotides on the sense strand (che-dU (sense)):

Forward (SEQ ID NO: 18)

```
/5Phos/TATATATAGATATCTATGGTCTCAGAAGgctgcttcgcgatgt
acgggccag
```

Reverse (SEQ ID NO: 8)

```
C*A*C*A*C*G*T*C*CCGAGGTCTCACTTCgccatagagcccaccgcat
ccccag
```

In these sequences, the bases specific for the template are in lower case, the additional bases to create the sticky ends, including the BsaI recognition site, are shown in UPPER CASE, and the phosphorothioate linkages between nucleosides are shown as *.

Thermocycling was performed. For KOD-Multi & Epi-polymerase, the following reaction conditions were used: 1 cycle at 94° C. for 2 minutes, and 40 repeats of the following cycles: 10 seconds at 98° C., 10 seconds at 63° C., and 30 seconds/kb at 68° C., with a final hold at 4° C. The PCR was enriched first through treatment with 0.24 U of Thermolabile Proteinase K (P8111, New England Biolabs) per 1 mL of PCR, incubated at 37° C. for 30-60 minutes, followed by a heat inactivation of 30-60 minutes at 55-80° C. The solution was 0.22 micron filtered and enriched by tangential flow filtration a KR2i system (Repligen) using a 100 kDa cutoff hollow fiber with 14× diavolumes. The PCR DNA was then quantified by Nanodrop (Thermo Scientific).

To generate the single-stranded DNA precursor, PCR DNA containing the 8× phosphorothioate modifications on the 5' side of the reverse primer was digested overnight (~14 hours) at 37° C. in 1× Lambda Exonuclease buffer (B7004S, New England Biolabs), with 5 U/μg of Lambda Exonuclease (M0262, New England Biolabs). To remove residual PCR DNA, the DNA was incubated with DraI endonuclease for 60-120 mins and heat inactivated for 60 mins to 120 mins at 80° C. The ssDNA was 0.22 micron filtered and enriched by tangential flow filtration with a KR2i system (Repligen) using a 30 kDa cutoff hollow fiber with 5% DMSO with 14× diavolumes. The enrichment of the ssDNA precursor was assessed by Agilent UPLC, using a size exclusion chromatography.

Example 16: Production of Circular Hemi-Modified Double-Stranded DNA Molecules Containing Modified Nucleobases in Sense or Antisense Strands This example demonstrates preparation of circular "hemi-modified" dsDNA molecules (cheDNA), i.e., circular dsDNA molecules containing chemically modified nucleobases on a single strand, e.g., sense strand or antisense strand, using ssDNA precursors from Example 15.

KOD-Multi & Epi-polymerase was first heat-activated by incubation at 94° C. for two minutes. Thereafter, 5' second-strand synthesis reactions were set up, consisting of 0.25-2 units of heat-activated KOD-Multi & Epi-polymerase per 250 ng of ssDNA, 25 ng/μL ssDNA, the forward primer from PCR at 300 M, dNTPs to a final concentration of 0.2 mM each, and KOD FX polymerase buffer (1× final concentration). Deoxyuridine triphosphate fully replaced its cognate dTTP at a final concentration of 200 μM in the second-strand synthesis reaction.

Production of the linear, hemi-modified dsDNA entailed isothermal extension of DNA from a primer, not a thermocycling process akin to polymerase chain reaction. To polymerize DNA starting from the primer, reaction mixtures (without the heat-activated KOD-Multi & Epi-polymerase) were brought up to 68° C., at which time the heat-activated KOD-Multi & Epi-polymerase was added to the reaction and the entire solution was thoroughly mixed via tube inversion and shaking. The reaction was then incubated overnight at 68° C. DNA was enriched using standard DNA enrichment columns. Second strand synthesis was confirmed via the Invitrogen E-gel system with 1% EX gels (G401001, Invitrogen). An alternative method of assessing DNA enrichment was determined by the 4200 Tapestation (G2991BA, Agilent) using the Genomic DNA screentape (5067-5366; 5067-5365). Samples were run according to the manufacturer's protocol. Enrichment was determined by automated software detection of the target peak, calculated as a percentage of the total area of all peaks detected by the software.

To generate circular, hemi-modified double-stranded DNA (cheDNA), the linear, hemi-modified double stranded DNA was digested at 80 ng/μL by BsaI v2-HF (R3733, New England Biolabs) at 2.5 U/μg in 1× rCutsmart buffer at 37° C. for >1 hr to create sticky ends. The solution was then diluted to 16 ng/μL in 1×T4 Ligase buffer (B0202, New England Biolabs), and ligated with T3 DNA Ligase (M0317, New England Biolabs) at 20 U/μg at 20° C. for >1 hr. Ligation was confirmed via the Invitrogen E-gel system with 1% EX gels (G401001, Invitrogen). The enzymes were then heat inactivated at >65° C. for 60-120 minutes and allowed to cool to room temperature. To remove unligated DNA, T5 exonuclease (M0663, New England Biolabs) was added to the solution at 0.5 U/μg and incubated at 37° C. for overnight. The persistence of the desired product was confirmed via the Invitrogen E-gel system with 1% EX gels (G401001, Invitrogen). The solution was then run through standard silica DNA enrichment columns to enrich for cheDNA. The cheDNA enrichment was assessed by the 4200 Tapestation (G2991BA, Agilent) using the Genomic DNA screentape (5067-5366; 5067-5365). Samples were run according to the manufacturer's protocol. Enrichment was determined by automated software detection of the target peak, calculated as a percentage of the total area of all peaks detected by the software.

Example 17: Assessment of Reporter Gene Expression In Vitro

This example demonstrates detection and quantification of gene expression using circular hemi-modified dsDNA molecules.

Circular hemi-modified dsDNA molecules comprising canonical uracil nucleobase in the antisense strand, where at least 98% of the thymine or uracil positions in the antisense strand comprise canonical uracil nucleobase, and where the sense strand does not comprise chemically modified nucleobases, were prepared as described in Examples 14-16 above. Circular hemi-modified dsDNA molecules comprising canonical uracil nucleobase in the sense strand, where at least 98% of the thymine or uracil positions in the sense strand comprise canonical uracil nucleobase, and where the antisense strand does not comprise chemically modified nucleobases, were also prepared as described in Examples 14-16 above. Control circular, unmodified dsDNA molecules were prepared as described in Example 5.

The circular hemi-modified dsDNA molecules and controls were administered via lipid transfection (lipofection) into Fa2N cells, as described in Example 5. Expression of the reporter protein eGFP was assayed by flow cytometry 48 hours post-transfection.

Figure 10A:
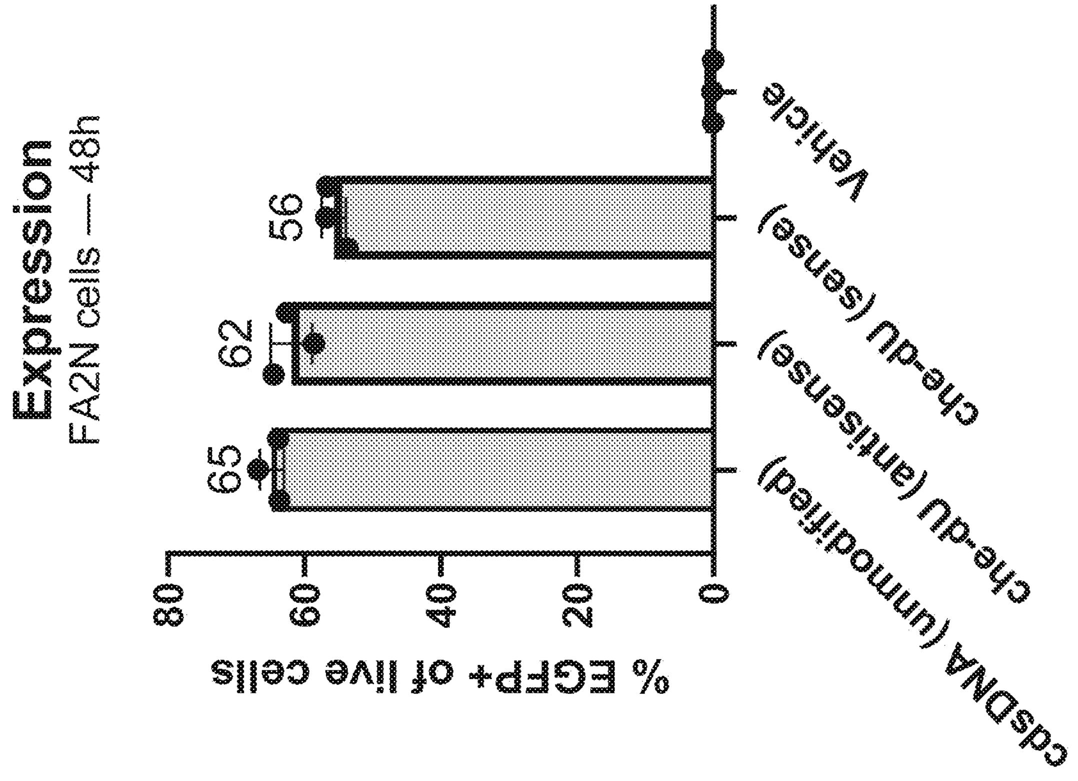
FIGS. 10A-10B are graphs showing the expression of a reporter gene (EGFP) in FA2N cells following transfection of circular dsDNA molecules without chemically modified nucleobases ("cdsDNA (unmodified)"), circular hemi-modified dsDNA molecules containing canonical uracil nucleobase in the antisense strand ("che-dU (antisense)") or sense strand ("che-dU (sense)"), or vehicle.
Figure 10B:
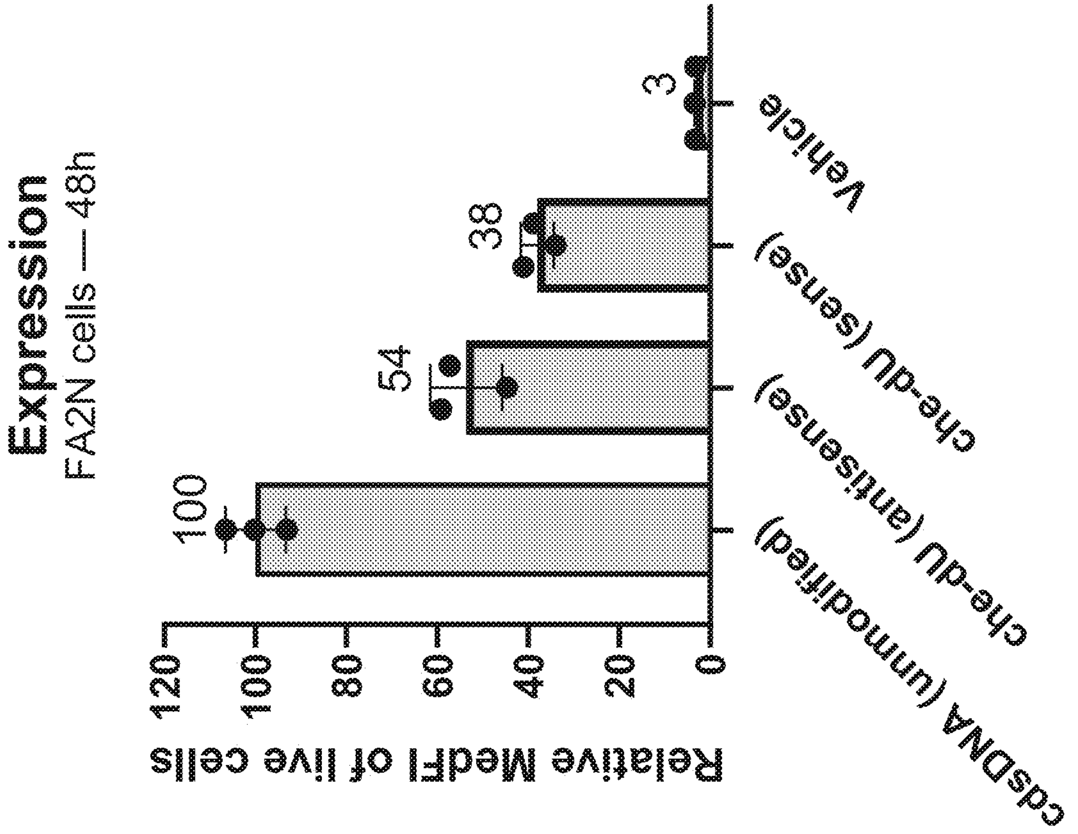

FIGS. 10A-10B show that circular hemi-modified dsDNA molecules comprising canonical uracil nucleobase in either the antisense strand or the sense strand were functional with detectable expression of the reporter protein eGFP. These results demonstrate that circular hemi-modified DNAs with chemically modified nucleobases in either the antisense strand or the sense strand can be efficiently transcribed and ultimately yield a protein product in cells.

Example 18: Assessment of Innate Immune Response in Cells In Vitro

This example demonstrates that circular hemi-modified dsDNA molecules comprising chemically modified nucleobases in the antisense strand or sense strand can reduce the innate immune response of cultured cells compared to control dsDNA.

Circular hemi-modified dsDNA molecules comprising canonical uracil nucleobase in the antisense strand, where at least 98% of the thymine or uracil positions in the antisense strand comprise canonical uracil nucleobase, and where the sense strand does not comprise chemically modified nucleobases, were prepared as described in Examples 14-16 above. Circular hemi-modified dsDNA molecules comprising canonical uracil nucleobase in the sense strand, where at least 98% of the thymine or uracil positions in the sense strand comprise canonical uracil nucleobase, and where the antisense strand does not comprise chemically modified nucleobases, were also prepared as described in Examples 14-16 above. Control circular, unmodified dsDNA molecules were prepared as described in Example 5. The dsDNA molecules were administered to macrophages using the transfection procedures as described in Examples 5-6 above. 6 hours after administration to cells, cGAMP levels were measured using the 2'3'-cyclic GAMP ELISA Kit (Invitrogen, EIAGAMP).

Figure 11:
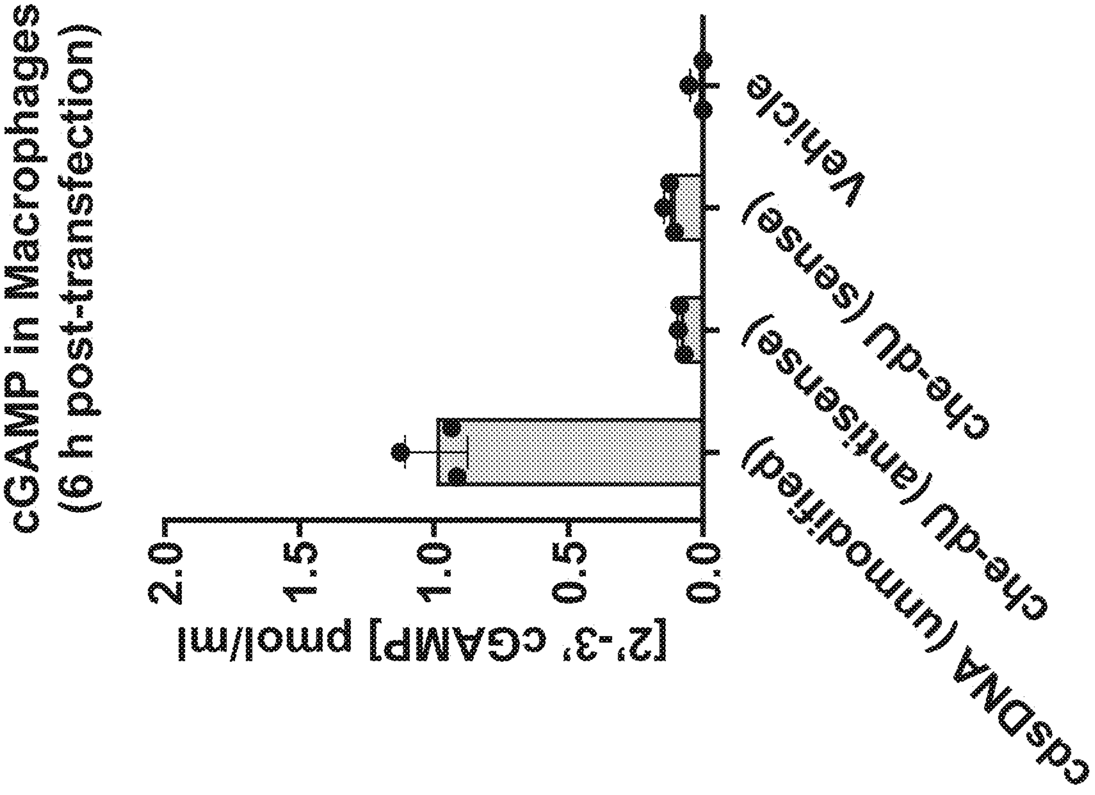
FIG. 11 is a graph showing cGAMP levels of macrophages following transfection of circular dsDNA molecules without chemically modified nucleobases ("cdsDNA (unmodified)"), circular hemi-modified dsDNA molecules containing canonical uracil nucleobase in the antisense strand ("che-dU (antisense)") or sense strand ("che-dU (sense)"), or vehicle. cGAMP levels were assayed 6 hours post-transfection. Y-axis: [2'-3' cGAMP] pmol/ml.

FIG. 11 shows that circular hemi-modified dsDNA molecules with canonical uracil nucleobase in either the antisense or sense strands yielded lower cGAMP levels as compared to control unmodified circular dsDNA.

These results indicate that incorporation of chemically modified nucleobases into either the antisense strand or sense strand of circular dsDNA can reduce the immunogenicity of dsDNA while retaining the capacity to encode a functional protein product.

All publications, patents, and patent applications cited herein are incorporated by reference in their entirety to the same extent as if each individual publication, patent, or patent application was specifically and individually indicated to be incorporated by reference. In the event of a conflict between a term herein and a term in an incorporated reference, the term herein controls.

The invention claimed is:

1. A pharmaceutical composition comprising a lipid nanoparticle (LNP) that comprises a double stranded DNA (dsDNA) molecule, wherein:

(a) the dsDNA molecule is circular;

(b) the dsDNA molecule comprises a first strand and a second strand, wherein:

at least 50% of thymine or uracil positions in the first strand of the dsDNA molecule comprise 5-hydroxymethyluracil, and the second strand is free of chemically modified nucleobases; and (c) the dsDNA molecule comprises an effector sequence that encodes an effector, wherein the effector is selected from the group consisting of: a transcription factor, a chromatin remodeling factor, an antigen, a peptide, a hormone, an enzyme, an antibody, a receptor ligand, a receptor, a clotting factor, and a membrane protein.

2. The pharmaceutical composition of claim 1, wherein the first strand is a sense strand and the second strand is an antisense strand.

3. The pharmaceutical composition of claim 1, wherein the first strand is an antisense strand and the second strand is a sense strand.

4. The pharmaceutical composition of claim 1, wherein the dsDNA molecule further comprises a promoter sequence operably linked to the effector sequence.

5. The pharmaceutical composition of claim 1, wherein the effector is a chimeric antigen receptor (CAR) or a T cell receptor.

6. The pharmaceutical composition of claim 1, wherein at least 75% of thymine or uracil positions in the first strand of the dsDNA molecule comprise 5-hydroxymethyluracil.

7. The pharmaceutical composition of claim 1, wherein at least 90% of thymine or uracil positions in the first strand of the dsDNA molecule comprise 5-hydroxymethyluracil.

8. The pharmaceutical composition of claim 1, wherein the dsDNA molecule has a length of between 500-1000, 1000-2000, 2000-3000, 3000-4000, or 4000-5000 nucleotides.

9. The pharmaceutical composition of claim 1, wherein the dsDNA molecule further comprises one or more additional chemically modified nucleotides that comprise a backbone modification.

10. The pharmaceutical composition of claim 1, wherein the dsDNA molecule further comprises one or more additional chemically modified nucleotides that comprise a chemically modified sugar.

11. The pharmaceutical composition of claim 1, wherein the first strand of the dsDNA molecule further comprises a second type of chemically modified nucleobase.

12. The pharmaceutical composition of claim 1, wherein at least 99% of sugars of the dsDNA molecule are deoxyribose sugars.

13. The pharmaceutical composition of claim 1, wherein the longest stretch of unmodified nucleotides in the first strand is no more than 100 nucleotides.

14. The pharmaceutical composition of claim 1, wherein the dsDNA molecule is resistant to endonuclease digestion.

15. The pharmaceutical composition of claim 1, wherein when the dsDNA molecule is introduced to a cell, the cell exhibits a level of the effector that is at least 80% of the level of the effector in a control cell of the same type that was contacted with an unmodified circular dsDNA molecule having the same sequence as the dsDNA molecule but comprising no chemically modified nucleobases.

16. The pharmaceutical composition of claim 1, wherein when the dsDNA molecule is contacted to a human cell, the cell exhibits a level of cyclic AMP-GMP (cGAMP) that is less than 10% of the level of cGAMP in a control cell of the same type that was contacted with an unmodified circular dsDNA molecule having the same sequence as the dsDNA molecule but comprising no chemically modified nucleobases.

17. The pharmaceutical composition of claim 1, wherein at least 70% by mass of total DNA in the composition is the dsDNA molecule.

18. The pharmaceutical composition of claim 1, which further comprises a protein or a second nucleic acid molecule encoding the protein.

19. The pharmaceutical composition of claim 18, wherein the protein is an enzyme, a DNA-binding protein, an RNA-binding protein, a nuclear protein, a cytoplasmic protein, a kinase, a phosphatase, a structural protein, an antigen, or an antibody.

20. A method of delivering an effector to a target cell or a subject in need thereof, the method comprising:

contacting the target cell with or administering to the subject the pharmaceutical composition of claim 1, thereby delivering the effector to the target cell or the subject.

21. A method of treating a cell, tissue, or subject in need thereof, the method comprising:

administering to the cell, tissue, or subject the pharmaceutical composition of claim 1;

thereby treating the cell, tissue, or subject.

22. The pharmaceutical composition of claim 1, wherein the pharmaceutical composition is free of one or more of: endotoxin, mononucleotides, and protein.

* * * * *

SEQUENCE LISTING

Sequence total quantity: 19
SEQ ID NO: 1 moltype = DNA length = 1211
FEATURE Location/Qualifiers
source 1..1211
mol_type = other DNA
organism = synthetic construct
SEQUENCE: 1
ggcctccgcg ccgggttttg gcgcctcccg cgggcgcccc cctcgtcacg gcgagcgctg 60
ccacgtcaga cgaagggcgc aggagcgtcc tgatccttcc gcccggacgc tcaggacagc 120
ggcccgctgc tcataagact cggccttaga accccagtat cagcagaagg acattttagg 180
acgggacttg ggtgactcta gggcactggt tttctttcca gagagcggaa caggcgagga 240
aaagtagtcc cttctcggcg attctgcgga gggatctccg tggggcggtg aacgccgatg 300
attatataag gacgcgccgg gtgtggcaca gctagttccg tcgcagccgg gatttgggtc 360
gcggttcttg tttgtggatc gctgtgatcg tcacttggtg agtagcgggc tgctgggctg 420
gccggggctt tcgtggccgc cgggccgctc ggtgggacgg aagcgtgtgg agagattgcc 480
aagggctgta gtctgggtcc gcgagcaagg ttgccctgaa ctgggggttg gggggagcgc 540
agcaaaatgg cggctgttcc cgagtcttga atggaagacg cttgtgaggc gggctgtgag 600
gtcgttgaaa caaggtgggg ggcatggtgg gcggcaagaa cccaaggtct tgagcccttc 660
gctaatgcgg gaaagctctt attcgggtga gatgggctgg gcaccatctg gggaccctga 720
cgtgaagttt gtcactgact ggagaactcg gtttgtcgtc tgttgcgggg gcggcagtta 780
tggcggtgcc gttgggcagt gcacccgtac ctttgggagc gcgcgccctc gtcgtgtcgt 840
gacgtcaccc gttctgttgg cttataatgc agggtggggc cacctgccgg taggtgtgcg 900
gtaggctttt ctccgtcgca ggacgcaggg ttcgggccta gggtaggctc tcctgaatcg 960
acaggcgccg gacctctggt gaggggaggg ataagtgagg cgtcagtttc tttggtcggt 1020
tttatgtacc tatcttctta agtagctgaa gctccggttt tgaactatgc gctcggggtt 1080
ggcgagtgtg ttttgtgaag ttttttaggc accttttgaa atgtaatcat ttgggtcaat 1140
atgtaatttt cagtgttaga cttgtaaatt gtccgctaaa ttctggccgt ttttggcttt 1200
tttgttagac a 1211

SEQ ID NO: 2 moltype = DNA length = 2433
FEATURE Location/Qualifiers
source 1..2433
mol_type = other DNA
organism = synthetic construct
SEQUENCE: 2
atggaggacg ccaagaacat caagaagggc cccgccccct tctaccccct ggaggacggc 60
accgccggcg agcagctgca caaggccatg aagcggtacg ccctggtgcc cggcaccatc 120
gccttcaccg acgcccacat cgaggtggac atcacctacg ccgagtactt cgagatgagc 180
gtgcggctgg ccgaggccat gaagcggtac ggcctgaaca ccaaccaccg gatcgtggtg 240
tgcagcgaga acagcctgca gttcttcatg cccgtgctgg gcgccctgtt catcggcgtg 300
gccgtggccc ccgccaacga catctacaac gagcgggagc tgctgaacag catgggcatc 360
agccagccca ccgtggtgtt cgtgagcaag aagggcctgc agaagatcct gaacgtgcag 420
aagaagctgc ccatcatcca gaagatcatc atcatggaca gcaagaccga ctaccagggc 480
ttccagagca tgtacacctt cgtgaccagc cacctgcccc ccggcttcaa cgagtacgac 540
ttcgtgcccg agagcttcga ccgggacaag accatcgccc tgatcatgaa cagcagcggc 600
agcaccggcc tgcccaaggg cgtggccctg ccccaccgga ccgcctgcgt gcggttcagc 660
cacgcccggg accccatctt cggcaaccag atcatccccg acaccgccat cctgagcgtg 720
gtgcccttcc accacggctt cggcatgttc accaccctgg gctacctgat ctgcggcttc 780
cgggtggtgc tgatgtaccg gttcgaggag gagctgttcc tgcggagcct gcaggactac 840
aagatccaga gcgccctgct ggtgcccacc ctgttcagct tcttcgccaa gagcaccctg 900
atcgacaagt acgacctgag caacctgcac gagatcgcca gcggcggcgc ccccctgagc 960
aaggaggtgg gcgaggccgt ggccaagcgg ttccacctgc ccggcatccg gcagggctac 1020
ggcctgaccg aaaccaccag cgccatcctg atcacccccg agggcgacga caagcccggc 1080
gccgtgggca aggtggtgcc cttcttcgag gccaaggtgg tggacctgga caccggcaag 1140
accctgggcg tgaaccagcg gggcgagctg tgcgtgcggg gccccatgat catgagcggc 1200
tacgtgaaca accccgaggc caccaacgcc ctgatcgaca aggacggctg gctgcacagc 1260
ggcgacatcg cctactggga cgaggacgag cacttcttca tcgtggaccg gctgaagagc 1320
ctgatcaagt acaagggcta ccaggtggcc cccgccgagc tggagagcat cctgctgcag 1380
caccccaaca tcttcgacgc cggcgtggcc ggcctgcccg acgacgacgc cggcgagctg 1440
cccgccgccg tggtggtgct ggagcacggc aagaccatga ccgagaagga gatcgtggac 1500
tacgtggcca gccaggtgac caccgccaag aagctgcggg gcggcgtggt gttcgtggac 1560
gaggtgccca agggcctgac cggcaagctg gacgcccgga agatccggga gatcctgatc 1620
aaggccaaga agggcggcaa gatcgccgtg ggctccggcg agggcagagg aagtcttcta 1680
acatgcggtg acgtggagga gaatcccggc cctgtgagca agggcgagga gctgttcacc 1740
ggggtggtgc ccatcctggt cgagctggac ggcgacgtaa acggccacaa gttcagcgtg 1800
tccggcgagg gcgagggcga tgccacctac ggcaagctga ccctgaagtt catctgcacc 1860
accggcaagc tgcccgtgcc ctggcccacc ctcgtgacca ccctgaccta cggcgtgcag 1920
tgcttcagcc gctaccccga ccacatgaag cagcacgact tcttcaagtc cgccatgccc 1980
gaaggctacg tccaggagcg caccatcttc ttcaaggacg acggcaacta caagacccgc 2040
gccgaggtga agttcgaggg cgacaccctg gtgaaccgca tcgagctgaa gggcatcgac 2100
ttcaaggagg acggcaacat cctggggcac aagctggagt acaactacaa cagccacaac 2160
gtctatatca tggccgacaa gcagaagaac ggcatcaagg tgaacttcaa gatccgccac 2220
aacatcgagg acggcagcgt gcagctcgcc gaccactacc agcagaacac ccccatcggc 2280
gacggccccg tgctgctgcc cgacaaccac tacctgagca cccagtccgc cctgagcaaa 2340
gaccccaacg agaagcgcga tcacatggtc ctgctggagt tcgtgaccgc cgccgggatc 2400
actctcggca tggacgagct gtacaagtga tga 2433

SEQ ID NO: 3 moltype = DNA length = 225

-continued

```
FEATURE                Location/Qualifiers
source                 1..225
                       mol_type = genomic DNA
                       organism = Bos sp.
SEQUENCE: 3
ctgtgccttc tagttgccag ccatctgttg tttgcccctc ccccgtgcct tccttgaccc  60
tggaaggtgc cactcccact gtcctttcct aataaaatga ggaaattgca tcgcattgtc  120
tgagtaggtg tcattctatt ctggggggtg gggtggggca ggacagcaag ggggaggatt  180
gggaagacaa tagcaggcat gctggggatg cggtgggctc tatgg                 225

SEQ ID NO: 4           moltype = DNA  length = 72
FEATURE                Location/Qualifiers
source                 1..72
                       mol_type = genomic DNA
                       organism = Simian virus 40
SEQUENCE: 4
ggtgtggaaa gtccccaggc tccccagcag gcagaagtat gcaaagcatg catctcaatt  60
agtcagcaac ca                                                      72

SEQ ID NO: 5           moltype = DNA  length = 133
FEATURE                Location/Qualifiers
source                 1..133
                       mol_type = other DNA
                       organism = synthetic construct
SEQUENCE: 5
gtaagtatca aggttacaag acaggtttaa ggaaaccaat agaaactggg cttgtcgaga  60
cagagaagac tcttgcgttt ctgataggca cctattggtc ttactgacat ccactttgcc  120
tttctctcca cag                                                     133

SEQ ID NO: 6           moltype = DNA  length = 589
FEATURE                Location/Qualifiers
source                 1..589
                       mol_type = genomic DNA
                       organism = Woodchuck hepatitis virus
SEQUENCE: 6
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgc              589

SEQ ID NO: 7           moltype = DNA  length = 47
FEATURE                Location/Qualifiers
source                 1..47
                       mol_type = other DNA
                       organism = synthetic construct
modified_base          1
                       mod_base = OTHER
                       note = 5'-Phosphate modified nucleotide
SEQUENCE: 7
gcgcggtcct tcggtctcag aaggctgctt cgcgatgtac gggccag                47

SEQ ID NO: 8           moltype = DNA  length = 48
FEATURE                Location/Qualifiers
source                 1..48
                       mol_type = other DNA
                       organism = synthetic construct
modified_base          1
                       mod_base = OTHER
                       note = Nucleotide with phosphorothioate linkage
modified_base          2
                       mod_base = OTHER
                       note = Nucleotide with phosphorothioate linkage
modified_base          3
                       mod_base = OTHER
                       note = Nucleotide with phosphorothioate linkage
modified_base          4
                       mod_base = OTHER
                       note = Nucleotide with phosphorothioate linkage
modified_base          5
                       mod_base = OTHER
                       note = Nucleotide with phosphorothioate linkage
modified_base          6
                       mod_base = OTHER
```

```
                         note = Nucleotide with phosphorothioate linkage
modified_base            7
                         mod_base = OTHER
                         note = Nucleotide with phosphorothioate linkage
modified_base            8
                         mod_base = OTHER
                         note = Nucleotide with phosphorothioate linkage
SEQUENCE: 8
cacacgtccc gaggtctcac ttcgccatag agcccaccgc atccccag              48

SEQ ID NO: 9             moltype = DNA  length = 156
FEATURE                  Location/Qualifiers
source                   1..156
                         mol_type = genomic DNA
                         organism = Homo sapiens
SEQUENCE: 9
tataattcac tggaattttt ttgtgtgtat ggtatgacat atgggttccc ttttattttt  60
tacatataaa tatatttccc tgtttttcta aaaaagaaaa agatcatcat tttcccattg  120
taaaatgcca tattttttttc ataggtcact tacata                           156

SEQ ID NO: 10            moltype = DNA  length = 32
FEATURE                  Location/Qualifiers
source                   1..32
                         mol_type = other DNA
                         organism = synthetic construct
SEQUENCE: 10
aattctcctc cccaccttcc ccaccctccc ca                                32

SEQ ID NO: 11            moltype = DNA  length = 10
FEATURE                  Location/Qualifiers
source                   1..10
                         mol_type = other DNA
                         organism = synthetic construct
SEQUENCE: 11
tctcgcgaga                                                         10

SEQ ID NO: 12            moltype = DNA  length = 21
FEATURE                  Location/Qualifiers
source                   1..21
                         mol_type = genomic DNA
                         organism = Simian virus 40
SEQUENCE: 12
cccaagaaga agaggaaagt c                                            21

SEQ ID NO: 13            moltype = DNA  length = 46
FEATURE                  Location/Qualifiers
source                   1..46
                         mol_type = other DNA
                         organism = synthetic construct
SEQUENCE: 13
ctggggactt tccagcctgg ggactttcca gctgggactt tccagg                 46

SEQ ID NO: 14            moltype = DNA  length = 10
FEATURE                  Location/Qualifiers
source                   1..10
                         mol_type = other DNA
                         organism = synthetic construct
SEQUENCE: 14
tatatatata                                                         10

SEQ ID NO: 15            moltype = DNA  length = 1296
FEATURE                  Location/Qualifiers
source                   1..1296
                         mol_type = other DNA
                         organism = synthetic construct
SEQUENCE: 15
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacggctcc ctgctgttcc gagtaaccat caacggagtg  480
accggctggc ggctgtgcga acgcattctg gcgggctccg gcgagggcag aggaagtctt  540
ctaacatgcg gtgacgtgga ggagaatccc ggccctgtga gcaagggcga ggagctgttc  600
accggggtgg tgcccatcct ggtcgagctg gacggcgacg taaacggcca caagttcagc  660
gtgtccggcg agggcgaggg cgatgccacc tacggcaagc tgaccctgaa gttcatctgc  720
accaccggca agctgcccgt gccctggccc accctcgtga ccaccctgac ctacggcgtg  780
```

-continued

```
cagtgcttca gccgctaccc cgaccacatg aagcagcacg acttcttcaa gtccgccatg  840
cccgaaggct acgtccagga gcgcaccatc ttcttcaagg acgacggcaa ctacaagacc  900
cgcgccgagg tgaagttcga gggcgacacc ctggtgaacc gcatcgagct gaagggcatc  960
gacttcaagg aggacggcaa catcctgggg cacaagctgg agtacaacta caacagccac  1020
aacgtctata tcatggccga caagcagaag aacggcatca aggtgaactt caagatccgc  1080
cacaacatcg aggacggcag cgtgcagctc gccgaccact accagcagaa cacccccatc  1140
ggcgacggcc ccgtgctgct gcccgacaac cactacctga gcacccagtc cgccctgagc  1200
aaagacccca acgagaagcg cgatcacatg gtcctgctgg agttcgtgac cgccgccggg  1260
atcactctcg gcatggacga gctgtacaag tgatga                            1296

SEQ ID NO: 16          moltype = DNA  length = 28
FEATURE                Location/Qualifiers
source                 1..28
                       mol_type = other DNA
                       organism = synthetic construct
modified_base          1
                       mod_base = OTHER
                       note = Nucleotide with phosphorothioate linkage
modified_base          2
                       mod_base = OTHER
                       note = Nucleotide with phosphorothioate linkage
modified_base          3
                       mod_base = OTHER
                       note = Nucleotide with phosphorothioate linkage
modified_base          4
                       mod_base = OTHER
                       note = Nucleotide with phosphorothioate linkage
modified_base          5
                       mod_base = OTHER
                       note = Nucleotide with phosphorothioate linkage
modified_base          6
                       mod_base = OTHER
                       note = Nucleotide with phosphorothioate linkage
modified_base          7
                       mod_base = OTHER
                       note = Nucleotide with phosphorothioate linkage
modified_base          8
                       mod_base = OTHER
                       note = Nucleotide with phosphorothioate linkage
SEQUENCE: 16
tatatataga tatctatggt ctccgccg                                     28

SEQ ID NO: 17          moltype = DNA  length = 48
FEATURE                Location/Qualifiers
source                 1..48
                       mol_type = other DNA
                       organism = synthetic construct
modified_base          1
                       mod_base = OTHER
                       note = 5'-Phosphate modified nucleotide
SEQUENCE: 17
cacacgtccc gaggtctccc ggcgccatag agcccaccgc atccccag               48

SEQ ID NO: 18          moltype = DNA  length = 52
FEATURE                Location/Qualifiers
source                 1..52
                       mol_type = other DNA
                       organism = synthetic construct
modified_base          1
                       mod_base = OTHER
                       note = 5'-Phosphate modified nucleotide
SEQUENCE: 18
tatatataga tatctatggt ctcagaaggc tgcttcgcga tgtacgggcc ag          52

SEQ ID NO: 19          moltype = DNA  length = 13
FEATURE                Location/Qualifiers
source                 1..13
                       mol_type = other DNA
                       organism = synthetic construct
misc_difference        7
                       note = a, c, t, g, unknown or other
misc_difference        8
                       note = a, c, t, g, unknown or other
misc_difference        9
                       note = a, c, t, g, unknown or other
SEQUENCE: 19
actayrnnnc ccr                                                     13
```